(12) United States Patent
Brough et al.

(10) Patent No.: US 9,617,560 B2
(45) Date of Patent: *Apr. 11, 2017

(54) SIMIAN (GORILLA) ADENOVIRUS OR ADENOVIRAL VECTORS AND METHODS OF USE

(71) Applicant: GenVec, Inc., Gaithersburg, MD (US)

(72) Inventors: Douglas E. Brough, Gaithersburg, MD (US); Jason G. D. Gall, Germantown, MD (US); Duncan McVey, Derwood, MD (US)

(73) Assignee: GenVec, Inc., Gaithersburg, MD (US)

( * ) Notice: Subject to any disclaimer, the term of this patent is extended or adjusted under 35 U.S.C. 154(b) by 91 days.

This patent is subject to a terminal disclaimer.

(21) Appl. No.: 14/349,470

(22) PCT Filed: Oct. 5, 2012

(86) PCT No.: PCT/US2012/059006
§ 371 (c)(1),
(2) Date: Apr. 3, 2014

(87) PCT Pub. No.: WO2013/052832
PCT Pub. Date: Apr. 11, 2013

(65) Prior Publication Data
US 2014/0314717 A1 Oct. 23, 2014

Related U.S. Application Data

(60) Provisional application No. 61/543,661, filed on Oct. 5, 2011.

(51) Int. Cl.
*C12N 15/86* (2006.01)
*C07K 14/005* (2006.01)
*C12N 7/00* (2006.01)

(52) U.S. Cl.
CPC ............ *C12N 15/86* (2013.01); *C07K 14/005* (2013.01); *C12N 7/00* (2013.01); *C12N 2710/10322* (2013.01); *C12N 2710/10333* (2013.01); *C12N 2710/10343* (2013.01); *C12N 2760/18034* (2013.01); *C12N 2840/60* (2013.01)

(58) Field of Classification Search
None
See application file for complete search history.

(56) References Cited

U.S. PATENT DOCUMENTS

| | | | |
|---|---|---|---|
| 5,837,511 A | 11/1998 | Falck-Pedersen et al. | |
| 5,851,806 A | 12/1998 | Kovesdi et al. | |
| 5,994,106 A | 11/1999 | Kovesdi et al. | |
| 5,994,128 A | 11/1999 | Fallaux et al. | |
| 5,998,205 A | 12/1999 | Hallenbeck et al. | |
| 6,033,908 A | 3/2000 | Bout et al. | |
| 6,127,175 A | 10/2000 | Vigne et al. | |
| 6,225,289 B1 | 5/2001 | Kovesdi et al. | |
| 6,482,616 B1 | 11/2002 | Kovesdi et al. | |
| 6,514,943 B2 | 2/2003 | Kovesdi et al. | |
| 6,551,586 B1 | 4/2003 | Davidson et al. | |
| 6,677,156 B2 | 1/2004 | Brough et al. | |
| 6,682,929 B2 | 1/2004 | Brough et al. | |
| 7,195,896 B2 | 3/2007 | Kovesdi et al. | |
| 8,940,290 B2 | 1/2015 | Roy et al. | |
| 2003/0165820 A1 | 9/2003 | Day et al. | |
| 2004/0136963 A1* | 7/2004 | Wilson ................. C07K 14/005 424/93.2 |
| 2008/0233650 A1 | 9/2008 | Gall et al. | |
| 2011/0223135 A1 | 9/2011 | Roy et al. | |
| 2014/0248307 A1 | 9/2014 | Gall et al. | |
| 2014/0248308 A1 | 9/2014 | McVey et al. | |
| 2014/0271711 A1 | 9/2014 | Brough et al. | |
| 2015/0152434 A1 | 6/2015 | Roy et al. | |
| 2015/0157700 A1 | 6/2015 | Bruder et al. | |

FOREIGN PATENT DOCUMENTS

| | | |
|---|---|---|
| WO | WO 94/28152 A1 | 12/1994 |
| WO | WO 95/02697 A2 | 1/1995 |
| WO | WO 95/16772 A1 | 6/1995 |
| WO | WO 95/34671 A1 | 12/1995 |
| WO | WO 96/22378 A1 | 7/1996 |
| WO | WO 97/00326 A1 | 1/1997 |
| WO | WO 97/12986 A2 | 4/1997 |
| WO | WO 97/21826 A2 | 6/1997 |
| WO | WO 00/00628 A1 | 1/2000 |
| WO | WO 00/34444 A2 | 6/2000 |
| WO | WO 03/020879 A2 | 3/2003 |
| WO | WO 03/022311 A1 | 3/2003 |
| WO | WO 2007/027860 A2 | 3/2007 |
| WO | WO 2008/011609 A2 | 1/2008 |
| WO | WO 2010/051367 A1 | 5/2010 |

(Continued)

OTHER PUBLICATIONS

U.S. Appl. No. 14/403,397, filed Nov. 24, 2014.*
Genbank Accession# KC702815, Gorilla beringei graueri adenovirus 9 isolate GC46 hexon gene, complete cds, Sep. 17, 2013.*
Altschul et al., "Basic Local Alignment Search Tool," *J. Molecular Biol.*, 215(3): 403-410 (1990).
Altschul et al., "Gapped BLAST and PSI-BLAST: a new generation of protein database search programs," *Nucleic Acids Res.*, 25(17): 3389-3402 (1997).
Bai et al., "Mutations that alter an Arg-Gly-Asp (RGD) sequence in the adenovirus type 2 penton base protein abolish its cell-rounding activity and delay virus reproduction in flat cells," *J. Virol.*, 67(9): 5198-5205 (1993).
Biegert et al., "Sequence context-specific profiles for homology searching," *Proc. Natl. Acad. Sci. USA*, 106(10): 3770-3775 (2009).
Boulanger et al., "Characterization of adenovirus protein IX," *J. Gen. Virol.*, 44(3): 783-800 (1979).
Brough et al., "Activation of transgene expression by early region 4 is responsible for a high level of persistent transgene expression from adenovirus vectors in vivo," *J. Virol.*, 71(12): 9206-9213 (1997).
Cartier et al., "Hematopoietic stem cell gene therapy with a lentiviral vector in X-linked adrenoleukodystrophy," *Science*, 326(5954): 818-823 (2009).

(Continued)

*Primary Examiner* — Benjamin P Blumel
(74) *Attorney, Agent, or Firm* — Leydig, Voit & Mayer, Ltd.

(57) ABSTRACT

The invention provides an adenovirus or adenoviral vector characterized by comprising one or more particular nucleic acid sequences or one or more particular amino acid sequences, or portions thereof, pertaining to, for example, an adenoviral pIX protein, DNA polymerase protein, penton protein, hexon protein, and/or fiber protein.

30 Claims, No Drawings

(56) References Cited

FOREIGN PATENT DOCUMENTS

| WO | WO 2011/057248 A2 | 5/2011 |
|---|---|---|
| WO | 2012/021730 A2 | 2/2012 |

OTHER PUBLICATIONS

Cavazzana-Calvo et al., "Gene therapy of human severe combined immunodeficiency (SCID)-X1 disease," Science, 288(5466): 669-672 (2000).
Chen et al., "Persistence in muscle of an adenoviral vector that lacks all viral genes," Proc. Natl. Acad. Sci. USA, 94(5): 1645-1650 (1997).
Chroboczek et al., "The sequence of the genome of adenovirus type 5 and its comparison with the genome of adenovirus type 2," Virology, 186(1): 280-285 (1992).
Crawford-Miksza et al., "Analysis of 15 adenovirus hexon proteins reveals the location and structure of seven hypervariable regions containing serotype-specific residues," J. Virol., 70(3): 1836-1844 (1996).
Curiel et al., "High-efficiency gene transfer mediated by adenovirus coupled to DNA-polylysine complexes," Hum. Gene Ther., 3(2): 147-154 (1992).
Devaux et al., "Structure of adenovirus fibre. I. Analysis of crystals of fibre from adenovirus serotypes 2 and 5 by electron microscopy and X-ray crystallography," J. Molec. Biol., 215(4): 567-588 (1990).
Dey et al., "Molecular epidemiology of adenovirus infection among infants and children with acute gastroenteritis in Dhaka City, Bangladesh," Infect. Genet. Evol., 9(4) 518-522 (2009).
Field et al., "Properties of the adenovirus DNA polymerase," J. Biol. Chem., 259(15): 9487-9495 (1984).
Gall et al., "Construction and characterization of hexon-chimeric adenoviruses: specification of adenovirus serotype," J. Virol., 72(12): 10260-10264 (1998).
Genbank Accession No. ABU95388.1, "hexon, partial [Human adenovirus 9]," (Jun. 2009).
Genbank Accession No. EDA88859.1, "hypothetical protein GOS_1918841, partial [marine metagenome]," (Apr. 2007).
Genbank Accession No. FJ025900.1, "Simian adenovirus 43, complete genome," (Mar. 2012).
Genbank Accession No. FJ025901.1, "Simian adenovirus 45, complete genome," (Mar. 2012).
Genbank Accession No. JN163990.1, "Gorilla gorilla beringei adenovirus 6 hexon gene, partial cds," (Dec. 2011).
Ghosh-Choudhury et al., "Protein IX, a minor component of the human adenovirus capsid, is essential for the packaging of full length genomes," EMBO J., 6(6): 1733-1739 (1987).
Ginsberg et al., "A proposed terminology for the adenovirus antigens and virion morphological subunits," Virology, 28(4): 782-783 (1966).
Goins et al., "Herpes simplex virus vector-mediated gene delivery for the treatment of lower urinary tract pain," Gene Ther., 16(4): 558-569 (2009).
Graham et al., "Characteristics of a human cell line transformed by DNA from human adenovirus type 5," J. Gen. Virol., 36(1): 59-72 (1977).
Green et al., "Evidence for a repeating cross-beta sheet structure in the adenovirus fibre," EMBO J., 2(8): 1357-1365 (1983).
Hacein-Bey-Abina et al., "A serious adverse event after successful gene therapy for X-linked severe combined immunodeficiency," N. Engl. J. Med., 348(3): 255-256 (2003).
Henry et al., "Characterization of the knob domain of the adenovirus type 5 fiber protein expressed in Escherichia coli," J. Virol., 68(8): 5239-5246 (1994).
Horvath et al., "Nonpermissivity of human peripheral blood lymphocytes to adenovirus type 2 infection," J. Virology, 62(1): 341-345 (1988).
Jornvall et al., "The adenovirus hexon protein. The primary structure of the polypeptide and its correlation with the hexon gene," J. Biol. Chem., 256(12): 6181-6186 (1981).
Kannan et al., "Structural and functional diversity of the microbial kinome," PLoS Biol., 5(3) E17 (2007).
Kay et al., "Viral vectors for gene therapy: the art of turning infectious agents into vehicles of therapeutics," Nature Medicine, 7(1): 33-40 (2001).
Kochanek et al., "High-capacity adenoviral vectors for gene transfer and somatic gene therapy," Hum. Gene Ther., 10(15): 2451-2459 (1999).
Lasaro et al., "New insights on adenovirus as vaccine vectors," Molecular Therapy, 17(8): 1333-1339 (2009).
Lutz et al., "The product of the adenovirus intermediate gene IX is a transcriptional activator," J. Virol., 71(7): 5102-5109 (1997).
Mayrhofer et al., "Nonreplicating vaccinia virus vectors expressing the H5 influenza virus hemagglutinin produced in modified Vero cells induce robust protection," J. Virol., 83(10): 5192-5203 (2009).
Mease et al., "Safety, tolerability, and clinical outcomes after intraarticular injection of a recombinant adeno-associated vector containing a tumor necrosis factor antagonist gene: results of a phase 1/2 Study," Journal of Rheumatology, 37(4): 692-703 (2010).
Morsy et al., An adenoviral vector deleted for all viral coding sequences results in enhanced safety and extended expression of a leptin transgene, Proc. Natl. Acad. Sci. USA, 95: 7866-7871 (1998).
NCBI reference sequence AP_000218, "E3 12.5K [Human adenovirus 5]," (Dec. 2008).
NCBI reference sequence AP_000224.1, "Homo sapiens genomic DNA, chromosome 21q21.2, LL56-APP region, clone:B2017A3, complete sequence," (Nov. 1991).
Neumann et al., "Determination of the nucleotide sequence for the penton-base gene of human adenovirus type 5," Gene, 69(1) 153-157 (1988).
Novelli et al., "Deletion analysis of functional domains in baculovirus-expressed adenovirus type 2 fiber," Virology, 185(1): 365-376 (1991).
Roberts et al., "Three-dimensional structure of the adenovirus major coat protein hexon," Science, 232(4754): 1148-1151 (1986).
Roy et al., "Isolation and Characterization of Adenoviruses Persistently Shed from the Gastrointestinal Tract of Non-Human Primates," PLOS Pathogens, 5(7): E1000503, 1-9, (2009).
Rusch et al., "The Sorcerer II Global Ocean Sampling expedition: northwest Atlantic through eastern tropical Pacific," PLoS Biol., 5(3) E77 (2007).
Rux et al., "Structural and phylogenetic analysis of adenovirus hexons by use of high-resolution x-ray crystallographic, molecular modeling, and sequence-based methods," J. Virol., 77(17): 9553-9566 (2003).
Signas et al., Adenovirus 3 Fiber Polypeptide Gene: Implications for the Structure of the Fiber Protein, J. Virol., 53(2): 672-678 (1985).
Silver et al., "Interaction of human adenovirus serotype 2 with human lymphoid cells," Virology, 165(2): 377-387 (1988).
Soding, "Protein homology detection by HMM-HMM comparison," Bioinformatics, 21(7): 951-960 (2005).
Stewart et al., "Image reconstruction reveals the complex molecular organization of adenovirus," Cell, 67(1): 145-154 (1991).
Stewart et al., "Difference imaging of adenovirus: bridging the resolution gap between X-ray crystallography and electron microscopy," EMBO J., 12(7): 2589-99 (1993).
Thomas et al., "Progress and problems with the use of viral vectors for gene therapy," Nature Review Genetics, 4(5): 346-358 (2003).
Van Oostrum et al, "Molecular composition of the adenovirus type 2 virion," J. Virol., 56(2): 439-448 (1985).
Wevers et al., "A novel adenovirus of Western lowland gorillas (Gorilla gorilla gorilla)," J. Virology, 7(1): 1-8 (2010).
Wevers et al., "Novel Adenoviruses in Wild Primates: a High Level of Genetic Diversity and Evidence of Zoonotic Transmissions," J. Virology, 85(20): 10774-10784, (2011).
Yeh et al., "Human adenovirus type 41 contains two fibers," Virus Res., 33(2): 179-198 (1991).
Yooseph et al., "The Sorcerer II Global Ocean Sampling expedition: expanding the universe of protein families," PLoS Biol., 5(3) E16, (2007).
Aubert et al., "Accumulation of Herpes Simplex Virus Type 1 Early and Leaky-Late Proteins Correlates with Apoptosis Prevention in infected Human Hep-2 Cells," J. Virol., 75(2): 1013-1030 (2001).

(56) References Cited

OTHER PUBLICATIONS

Dolan et al., "The genome sequence of herpes simplex virus type 2," J. Virol.72(3): 2010-2021 (1998).
European Patent Office, International Search Report in International Patent Application No.
Genbank Accession No. ABX79578, "UL47 [Human herpesvirus 2]" (Apr. 14, 2009).
Genbank Accession No. CAB06743.1, "major capsid protein [Human herpesvirus 2]" (Nov. 14, 2006).
Genbank Accession No. EDL20708.1, "mCG1048340," (Jun. 2007).
Genbank Accession No. KC702813.1," Gorilla beringei beringei adenovirus 7 isolate GC44 hexon gene, complete cds" (Sep. 2013).
Genbank Accession No. KC702816, "Gorilla beringei beringei adenovirus 7 isolate GC44 DNA polymerase gene, complete cds," (Sep. 2013).
Genbank Accession No. P89442.1, "Major capsid protein" (Nov. 2005).
Genbank Accession No. P89467, "Tegument protien and transactivator of immediate early genes," (Oct. 2006).
Koelle et al., "CD4 T-cell responses to herpes simplex virus type 2 major capsid protein VP5: Comparison with responses to tegument and envelope glycoproteins", J. Virol., 74(23):11422-11425 (2000).
Kohlmann et al., "Protective efficacy and immunogenictiy of an adenoviral vector vaccine encoding the codon-optimized F protein of respiratory syncytial virus," J Virol. 83(23): 12601-12610 (2009).
Muller et al., "Herpes simplex virus type 2 tegument proteins contain subdominant T-cell epitopes detectable in BALB/c mice after DNA immunization and infection", J. Virol., 90 (5): 1153-1163 (2009).
Roy et al., "Generation of an adenoviral vaccine vector based on simian adenovirus 21," Journal of General Virology 87: 2477-2485 (2006).
Subak-Sharpe et al., "HSV Molecular Biology: General Aspects of Herpes Simplex Virus Molecular Biology", Virus Genes, 16(3): 239-251 (1998).
U.S. Appl. No. 14/349,421, filed Apr. 3, 2014.
U.S. Appl. No. 14/349,426, filed Apr. 3, 2014.
U.S. Appl. No. 14/349,735, filed Apr. 4, 2014.
U.S. Appl. No. 14/373,574, filed Jul. 21, 2014.
European Patent Office, Office Action in European Patent Application No. 12775113.9 (Sep. 19, 2016).

\* cited by examiner

SEQUENCE LISTING

```
<160> NUMBER OF SEQ ID NOS: 28

<210> SEQ ID NO 1
<211> LENGTH: 83
<212> TYPE: DNA
<213> ORGANISM: Gorilla beringei graueri

<400> SEQUENCE: 1
ggcgcggcct ctcgcgcgtc tgctcgggat gagaaactga ccgctctgct gcttaaactg      60
gaagacttga cccgggagct ggc                                             83

<210> SEQ ID NO 2
<211> LENGTH: 100
<212> TYPE: DNA
<213> ORGANISM: Gorilla beringei graueri

<400> SEQUENCE: 2
gcttcgtcag ggactcggtg ggcttgcaag aagcaagctt caacgtcttc cagcggccca      60
ccatctcctc caactcccat gccatcttca ggcagatcgc                           100

<210> SEQ ID NO 3
<211> LENGTH: 45
<212> TYPE: DNA
<213> ORGANISM: Gorilla beringei graueri

<400> SEQUENCE: 3
gaggagggcg cacaggaggg cgcgcagaag gacatgaacg atggg                      45

<210> SEQ ID NO 4
<211> LENGTH: 111
<212> TYPE: DNA
<213> ORGANISM: Gorilla beringei graueri

<400> SEQUENCE: 4
tccctggccc ccaagggcgc tcccaattct tgcgagtggg aacaagagga aaatcaggtg      60
gtcgctgcag atgatgaact tgaagatgaa gaagcgcaag ctcaagagga c              111

<210> SEQ ID NO 5
<211> LENGTH: 38
<212> TYPE: DNA
<213> ORGANISM: Gorilla beringei graueri

<400> SEQUENCE: 5
```
tcgagggtat caatgctttg gcagtagcca caggtaag 38

<210> SEQ ID NO 6
<211> LENGTH: 399
<212> TYPE: DNA
<213> ORGANISM: Gorilla beringei graueri

<400> SEQUENCE: 6

| atgagcgaca | ccggcaacag | ctttgatgga | agcatcttta | gccctatct | gacagtgcgc | 60 |
| atgcctcact | gggctggagt | gcgtcagaat | gtgatgggtt | ccaacgtgga | tggacgcccc | 120 |
| gttctgcctt | caaattcgtc | tacaatggcc | tacgcgaccg | tgggaggaac | tccgctggac | 180 |
| gccgcgacct | ccgccgccgc | ctccgccgcc | gccgcgaccg | cgcgcagcat | ggctacggac | 240 |
| ctttacagct | ctttggtggc | gagcggcgcg | gcctctcgcg | cgtctgctcg | ggatgagaaa | 300 |
| ctgaccgctc | tgctgcttaa | actggaagac | ttgacccggg | agctggctca | actgacccag | 360 |
| caggtctcca | gcttgcgtga | gagcagcctt | gcctccccc | | | 399 |

<210> SEQ ID NO 7
<211> LENGTH: 3168
<212> TYPE: DNA
<213> ORGANISM: Gorilla beringei graueri

<400> SEQUENCE: 7

| atggacagct | ccaatgtgcg | cgatgtcgtc | atcaaactcc | gcccgccgag | cgccgagatc | 60 |
| tggacctgcg | gctctcgcgg | cgtggtggtc | tgctccacca | tcgccctcca | ggagacagat | 120 |
| gctggcggcc | agacaaccaa | agtagaagac | caccagccac | acgggacccc | aggcgggggga | 180 |
| cttagattcc | cgctgcgctt | cctcgtcaga | ggtcgccagg | ttcacctcgt | gcaagatata | 240 |
| caacccgtgc | agcgctgcca | gtactgcggt | cgcttttaca | aaagccagca | cgagtgctcg | 300 |
| gcccgcagac | gggacttcta | ctttcaccac | atcaacagcc | aatcctccaa | ctggtggcgg | 360 |
| gagatccagt | tcttcccgat | cggctctcat | cctcgcacgg | agcgcctctt | tgtcacctac | 420 |
| gatgtagaga | cctacacttg | gatgggagcc | tttggcaagc | agctcgtgcc | cttcatgctg | 480 |
| gtcatgaaac | tggggggcaa | cgaggctctg | gtcgccgccg | cgcgcgaccct | cgcccgagag | 540 |
| ctcagatggg | accctggga | gaaagacccc | ctcaccttct | actgcatcac | ccccgaaaag | 600 |
| atggccgtgg | ggcgacagtt | cagaaccttc | cgcgaccgcc | tgcagaccct | catggcccgc | 660 |
| gacctctggc | gatccttcct | ggcggccaac | cctcacttgc | aagactgggc | cctggaggag | 720 |
| cacggcctgg | aatcgcccga | ggagctcacc | tacgaggaac | tcaaaaagct | ccctccatc | 780 |
| aagggccagc | cccgcttttt | ggagctctac | atcgtgggcc | acaacataaa | cggctttgac | 840 |
| gagatcgtcc | tggccgccca | ggtcatcaac | aaccgctcct | cggtcccagg | gccctttcgc | 900 |
| atcaccagaa | acttcatgcc | tcgagcgggg | aagatcctct | tcaatgacct | caccttctcc | 960 |
| ctgcccaacc | cgcgctccaa | aaagcgcacg | gactacaccc | tgtgggaaca | gggcggctgc | 1020 |
| gatgacacag | acttcaaaca | tcaataacctc | aaagtcatgg | tcagggacac | tttcgccctc | 1080 |
| acccacacct | ccctccgcaa | ggcggcgcag | gcctacgcgc | tgcccgtgga | aagggctgt | 1140 |
| tgcccctacc | aggccgtcaa | ccagttctac | atgctaggct | cttaccgttc | ggacacggac | 1200 |
| gggtttcccc | tccaagagta | ctggaaagac | cgcgaagagt | tcgtcctcaa | ccgcgagctg | 1260 |
| tggaaaaaga | agggggagga | taagtatgac | atcatccgcg | agaccctcga | ctactgcgcg | 1320 |
| ctcgacgtcc | aggtcaccgc | cgagctggtg | cacaagctgc | gcgagtccta | cgcctgcttc | 1380 |

```
gtcagggact cggtgggctt gcaagaagca agcttcaacg tcttccagcg gcccaccatc    1440
tcctccaact cccatgccat cttcaggcag atcgccttcc gcgccgagcg cccccagcgc    1500
accaacctcg ggcccaacat gctggccccc tcccacgagc tctatgacta cgtgcgcgcc    1560
agcatccgcg gggggcgctg ctaccccacc tacctcggca tcctcaggga accccctgtac   1620 gtgtatgaca tctgcggcat gtacgcctcc gcgctcaccc accccatgcc ctggggcccg    1680
cccctcaacc cctacgagcg cgcgctcgcc gcccgcgaat ggcagcgggc tctggacatg    1740
caagcttgca agatcgacta cttttgacccg cgcttgctcc ccggggtctt caccatcgac   1800
gcggaccccc caaacgagga ccagctggac cccctacccc ccttctgctc gcgcaagggc    1860
ggccgcctct gctggaccaa cgagcgcctg cgcggcgagg tcgccaccag cgtcgacatg    1920
gtcaccctgc acaaccgagg ctggagggtg cgcctgatcc cagacgagcg caccaccgtc    1980
ttccccgagt ggaagtgcgt ggcccgcgag tacgtgcaac tcaacatcgc ggccaaggag    2040
cgagccgacc gcgacaaaaa ccagaccctg cgctccatcg ccaagctgct ctccaacgcc    2100
ctctacgggt cgttcgccac caagcttgac aacaaaaaaa tagtgttttc tgaccagatg    2160
gacccaggta ccctcaaagg tatcacctcc ggacaggtga acatcaaatc ctcctcattt    2220
ttagaaactg acaacctgag cgctgaggtc atgcccgcct tcgagaggga atacttaccc    2280
cagcagctgg ctctcgcaga cagcgatgcg aagagagtg aagatgaaag ggtgcccacc     2340 ccctttata ccccccgtc gggaaccccc ggtcacgtgt cctacaccta caagccaatc       2400 actttctgg acgcggagga gggggacatg tgcctgcaca ccctggagaa ggtggacccg     2460
ctagtggaca cgaccgcta cccctcccac gtggcctcct tcgtcctggc ctggacgcgg     2520
gccttcgtct cagagtggtc agagtttctc tacgaggagg acagaggcac tccgctggaa    2580
gacaggcccc tgaagtcggt ctacggagac acggacagcc tcttcgtcac cgagaaggga    2640
caccgcctca tggagagccg aggtaagaaa cgcatcaaaa agcatggggg caacctggtt    2700
tttgaccctg accgcccgga gctcacttgg ctggtggaat gcgagacggt ctgcgcttcc    2760
tgcggcgcgg acgcctactc cccagagtcc gtgtttctcg ctcccaagct ctacgccctg    2820
aagagcctgc agtgccccctc gtgcggcgcc acctccaagg gaaagctccg cgccaagggg   2880
cacgccgccg agggtctcga ctacgagacc atggtcaaat gctacctggc cgacgcgcag    2940
ggcgaagagc ggcagcgatt cagcaccagc agaaccagcc tcaagcgcac cctggccagc    3000
gcccaacccg gagcgcaccc cttcaccgtg acccagacca ccctgacgag gaccctgcgc    3060
ccatggaagg acatgactct ggccccgctg gacgccatc ggctggtgcc ctacagcgaa     3120
agccgcccca acccgcgaaa cgaggagatc tgctggatcg agatgccg                 3168

<210> SEQ ID NO 8
<211> LENGTH: 1974
<212> TYPE: DNA
<213> ORGANISM: Gorilla beringei graueri

<400> SEQUENCE: 8
atgcggcgcg cggcgatgtt cgaggagggg cctccccccct cttacgagag cgcgatgggg      60
atttctcctg cggcgcccct gcagcctccc tacgtgcctc ctcggtacct gcaacctaca     120 gggggggagaa atagcatctg ttactctgag ctgcagcccc tgtacgatac caccagactg     180
tacctggtgg acaacaagtc cgcggacgtg gcctccctga actaccagaa cgaccacagc     240 gatttttttga ccacgtgat ccaaaacaac gacttcaccc caaccgaggc cagcactcag     300 accataaaacc tggataacag gtcgaactgg ggcggcgacc tgaagaccat cttgcacacc    360
```

```
aacatgccca acgtgaacga gttcatgttc accaactctt ttaaggcgcg ggtgatggtg      420
gcgcgcgagc agggggaggc gaagtacgag tgggtggact tcacgctgcc cgagggcaac      480
tactcagaga ccatgactct cgacctgatg aacaatgcga tcgtggaaca ctatctgaaa      540
gtgggcaggc agaacggggt gaaggaaagc gatatcgggg tcaagtttga caccagaaac      600
ttccgtctgg gctgggaccc cgtgaccggg ctggtcatgc cggggtcta caccaacgag      660 gcctttcatc ccgacatagt gcttctgccc ggctgtgggg tggacttcac ccagagccgg      720
ctgagcaacc tgctgggcat tcgcaagcgg cagccttttcc aggagggttt caagatcacc      780
tatgaggatc tgaaggggggg caacattccc gcgctccttg atctggacgc ctacgaggag      840
agcttgaaac ccgaggagag cgctggcgac agcggcgaga gtggcgagga caagccggc      900 ggcggtggcg cgcgtcggt agaaaacgaa agtacgcccg cagtggcggc ggacgctgcg      960
gaggtcgagc cggaggccat gcagcaggac gcagaggagg cgcacagga gggcgcgcag     1020 aaggacatga cgatgggga gatcagggga gacacattcg ccacccgggg cgaagaaaaa     1080
gaggcagagg cggcggcggc ggcgacggcg gaggccgaaa ccgaggttga ggcagaggca     1140
gagcccgaga ccgaagttat ggaagacatg aatgatggag aacgtagggg cgacacgttc     1200
gccacccggg gcgaagagaa ggcggcggag gcagaagccg cggctgagga ggcggctgcg     1260
gctgcggcca agactgaggc tgcggctaag gctgaggtcg aagccaatgt tgcggttgag     1320
gctcaggctg aggaggaggc ggcggctgaa gcagttaagg aaaaggccca ggcagagcag     1380
gaagagaaaa aacctgtcat tcaacctcta aagaagata gcaaaaagcg cagttacaac     1440
gtcatcgagg gcagcacctt tacccagtac cgcagctggt acctggcgta caactacggc     1500
gacccggtca aggggggtgcg ctcgtggacc ctgctctgca cgccggacgt cacctgcggc     1560
tccgagcaga tgtactggtc gctgccgaac atgatgcaag acccggtgac cttccgctcc     1620
acgcggcagg ttagcaactt cccggtggtg ggcgccgaac tgctgcccgt gcactccaag     1680 agttttaca acgagcaggc cgtctactcc cagctgatcc gccaggccac ctctctgacc     1740
cacgtgttca tcgctttcc cgagaaccag attttggcgc gccgccggc ccccaccatc     1800 accaccgtga gtgaaaacgt tcctgccctc acagatcacg ggacgctacc gctgcgcaac     1860
agcatctcag gagtccagcg agtgaccatt actgacgcca gacgccggac ctgcccctac     1920
gtttacaagg ccttgggcat agtctcgccg cgcgtcctct ccagtcgcac tttt           1974

<210> SEQ ID NO 9
<211> LENGTH: 2865
<212> TYPE: DNA
<213> ORGANISM: Gorilla beringei graueri

<400> SEQUENCE: 9
atggcgaccc catcgatgat gcctcagtgg tcgtacatgc acatctcggg ccaggacgct       60
tcggagtacc tgagcccggg gctggtgcag ttcgcccgcg ccacagacac ctacttcaac      120
atgagtaaca agttcaggaa ccccactgtg gcgcccaccc acgatgtgac cacggaccgg      180
tcgcagcgcc tgacgctgcg gttcatcccc gtggatcggg aggacaccgc ctactcttac      240
aaggcgcggt tcacgctggc cgtgggcgac aaccgcgtgc tggacatggc ctccacttac      300
tttgacatca gggggggtgct ggacagggggc ccaccttca gccctactc gggtactgcc      360 tacaactccc tggccccccaa gggcgctccc aattcttgcg agtgggaaca agaggaaaat      420
caggtggtcg ctgcagatga tgaacttgaa gatgaagaag cgcaagctca agaggacgcc      480
```

```
ccagctaaaa aaattcatgt atatgcccag gcgcctcttg ctggcgaaaa gattaccaag    540
gatggtttgc aaataggtac tgaagttgta ggagatacat ctaaggacac ttttgcagac    600
aaaacattcc aacccgaacc tcagataggc gagtctcagt ggaacgaggc tgatgccaca    660
gtagcaggag gcagagtctt gaaaaaaacc accctatga accttgcta tggatcctat     720
gccaggccta caaatgccaa cggggtcaa ggaattatgg ttgccaatga caaggagtg     780
ttggagtcta aagtggagat gcaattttt tctaacacta caacccttaa tgcgcgggat     840
ggagctggca atcccgaacc aaaggtggtg ttgtacagtg aagatgtcca cttggaatct    900
cctgacactc atttgtctta caagcccaaa aaggatgatg ttaatgctaa aattatgttg    960
ggtcagcaag ctatggctaa caggcccaac ctcattgctt ttagagataa tttcattgga   1020
ctcatgtact acaacagcac tggtaacatg ggagtgctgg cgggtcaggc ctctcagttg   1080
aatgccgtgg tggacctgca ggatagaaac acagaactgt catatcagct tatgcttgat   1140
tccattgggg atagatccag atacttctcc atgtggaacc aggcagtgga tagctatgac   1200
ccagatgtca gaatcattga aaaccatggt gtcgaggacg agctacccaa ctactgcttc   1260
cctctgggcg gcataggaat tactgatact tatcaaggga tcaaaaatac caatggcaat   1320
ggtcagtgga ccaaagatga tcagttcgcg gaccgtaatg aaatagggt gggaaacaac   1380
ttcgccatgg agatcaacat ccaggccaac ctctggagga acttcctcta tgcgaacgtg   1440
gggctctacc tgccagacaa gctcaagtac aaccccacca cgtggacat ctctgacaac   1500
cccaacacct atgactacat gaacaagcgt gtggtggctc ccggcctggt ggactgcttt   1560
gtcaatgtgg gagccaggtg gtccctggac tacatggaca cgtcaaccc cttcaaccac   1620
caccgcaatg cgggtctgcg ctaccgctcc atgatcctgg gcaacgggcg ctacgtgccc   1680
ttccacattc aggtgcccca gaagttcttt gccatcaaga acctcctcct cctgccgggc   1740
tcctacactt acgagtggaa cttcaggaag gatgtcaaca tggtcctgca gagctctctg   1800
ggcaatgacc ttagggtgga cggggccagc atcaagtttg acagcgtcac cctctatgct   1860
accttcttcc ccatggctca caacaccgcc tccacgctcg aggccatgct gaggaacgac   1920
accaacgacc agtccttcaa tgactacctc tctggggcca catgctcta ccccatcccc   1980
gccaaggcca ccaacgtgcc catctccatt ccctctcgca actgggccgc cttcagaggc   2040
tgggcctttta cccgccttaa gaccaaggaa acccccctccc tgggctcggg ttttgacccc   2100
tactttgtct actcgggatc catcccctac ctggatggca ccttctacct caaccacact   2160
tttaagaaga tatccatcat gtatgactcc tccgtcagct ggcgggcaa tgaccgcctg   2220
ctcaccccca atgagttcga ggtcaagcgc gccgtggacg gcgagggcta caacgtggcc   2280
cagtgcaaca tgaccaagga ctggttcctg gtgcagatgc tggccaacta acacataggc   2340
taccagggct tctacatccc agagagctac aaggacagga tgtactcctt cttcagaaat   2400
ttccaaccca tgagcaggca ggtggtggac gagaccaaat acaaggacta tcaggccatt   2460
ggcatcactc accagcacaa caactcggga ttcgtgggct acctggctcc caccatgcgc   2520
gaggggcagg cctaccccgc caacttcccc tacccgttga taggcaagac cgcggtcgac   2580
agcgtcaccc agaaaaagtt cctctgcgac cgcaccctct ggcgcatccc cttctctagc   2640
aacttcatgt ccatgggtgc gctcacggac ctgggccaga acctgctcta tgccaactcc   2700
gcccatgcgc tggacatgac tttgaggtg gaccccatgg acgagcccac ccttctctat   2760
attgtgtttg aagtgttcga cgtggtcaga gtgcaccagc cgcaccgcgg tgtcatcgag   2820
accgtgtacc tgcgcacgcc cttctcggcc ggcaacgcca ccac               2865
```

<210> SEQ ID NO 10
<211> LENGTH: 1740
<212> TYPE: DNA
<213> ORGANISM: Gorilla beringei graueri

<400> SEQUENCE: 10

```
atgaaacgcg cgagatcgtc tgacgagacc ttcaaccccg tgtacccta cgataccgag        60
atcgctccga cttctgtccc tttccttacc cctcccttg tgtcatccgc aggaatgcaa       120
gaaaatccag ctggggtgct gtccctgcac ttgtcagagc ccttaccac ccacaatggg       180
gccctgactc taaaaatggg gggcggcctg accctggaca aggaagggaa tctcacttcc       240
caaaacatca ccagtgtcga tcccctctc aaaaaaagca gaacaacat cagccttcag        300
accgccgcac cctcgccgt cagctccggg ccctaacac ttttgccac tcccccccta         360
gcggtcagtg gtgacaacct tactgtgcag tctcaggccc ctctcacttt ggaagactca      420
aaactaactc tggccaccaa ggaccccta actgtgtccg aaggcaaact tgtcctagaa       480
acagaggctc cctgcatgc aagtgacagc agcagcctgg gcttagcgt tacggcccca        540
cttagcatta caatgacag cctaggacta gacatgcaag cgcccattag ctctcgagat       600
ggaaaactgg ctctaacagt ggcggccccc ctaactgtgg tcgagggtat caatgctttg     660
gcagtagcca caggtaaggg tattgggcta aatgaaacca cacacacct gcaggcaaaa       720
ctggtcgcac ccctaggctt tgataccaac ggcaacatta agctaagcgt tgcaggaggc      780
atgaggctaa acaataacac actgatacta gatgtaaact acccatttga ggctcaaggc     840
caactgagcc taagagtggg ctcgggccca ctatatgtag attctagtag tcataaccta     900
accattagat gccttagggg attgtatata acatcttcta caaccaaaa cggtctagaa       960
gccaacatta aactaacaag aggccttgtg tatgacggaa atgccatagc agttaatgtt     1020
ggcaaagggc tggaatacag ccctactgac acaacagaaa aacctataca gactaaaata    1080
ggtctaggca tggagtatga taccgaggga gccatgatga caaaactagg ctctggacta   1140
agctttgaca attcaggagc cattgtagtg gaaacaaaa atgatgacag gcttactttg     1200
tggaccacac cggacccatc gcccaactgt cagatctact ctgaaaaaga tgctaaacta   1260
accttggtac tgactaaatg tggcagtcag gttgtaggca cagtatctat tgccgctctt   1320
aaaggtagcc tcgtgccaat cactagtgca atcagtgtgg ttcaggtata cctaaggttt   1380
gatgaaaatg gggtactaat gagtaactct tcacttaatg gcgaatactg gaattttaga   1440
aacgagact caactaatgg cacaccatat acaaacgcag tgggtttcat gcctaatcta    1500
ctggcctatc ctaaaggtca aactacaact gcaaaagta acattgtcag ccaggtctac   1560
atgaatgggg acgatactaa acccatgaca tttacaatca acttcaatgg ccttagtgaa   1620
acagggata ccctgttag taaatattcc atgacattct catggaggtg gccaaatgga    1680
agctacatag gcacaatttt tgtaacaaac tcctttacct tctcctacat cgcccaagaa   1740
```

<210> SEQ ID NO 11
<211> LENGTH: 28
<212> TYPE: PRT
<213> ORGANISM: Gorilla beringei graueri

<400> SEQUENCE: 11

Gly Ala Ala Ser Arg Ala Ser Ala Arg Asp Glu Lys Leu Thr Ala Leu
1               5                   10                  15

Leu Leu Lys Leu Glu Asp Leu Thr Arg Glu Leu Ala

```
                    20                  25

<210> SEQ ID NO 12
<211> LENGTH: 34
<212> TYPE: PRT
<213> ORGANISM: Gorilla beringei graueri

<400> SEQUENCE: 12

Cys Phe Val Arg Asp Ser Val Gly Leu Gln Glu Ala Ser Phe Asn Val
1               5                   10                  15

Phe Gln Arg Pro Thr Ile Ser Ser Asn Ser His Ala Ile Phe Arg Gln
            20                  25                  30

Ile Ala

<210> SEQ ID NO 13
<211> LENGTH: 15
<212> TYPE: PRT
<213> ORGANISM: Gorilla beringei graueri

<400> SEQUENCE: 13

Glu Glu Gly Ala Gln Glu Gly Ala Gln Lys Asp Met Asn Asp Gly
1               5                   10                  15

<210> SEQ ID NO 14
<211> LENGTH: 37
<212> TYPE: PRT
<213> ORGANISM: Gorilla beringei graueri

<400> SEQUENCE: 14

Ser Leu Ala Pro Lys Gly Ala Pro Asn Ser Cys Glu Trp Glu Gln Glu
1               5                   10                  15

Glu Asn Gln Val Val Ala Ala Asp Asp Glu Leu Glu Asp Glu Glu Ala
            20                  25                  30

Gln Ala Gln Glu Asp
        35

<210> SEQ ID NO 15
<211> LENGTH: 15
<212> TYPE: PRT
<213> ORGANISM: Gorilla beringei graueri

<400> SEQUENCE: 15

Val Glu Gly Ile Asn Ala Leu Ala Val Ala Thr Gly Lys Gly Ile
1               5                   10                  15

<210> SEQ ID NO 16
<211> LENGTH: 133
<212> TYPE: PRT
<213> ORGANISM: Gorilla beringei graueri

<400> SEQUENCE: 16

Met Ser Asp Thr Gly Asn Ser Phe Asp Gly Ser Ile Phe Ser Pro Tyr
1               5                   10                  15

Leu Thr Val Arg Met Pro His Trp Ala Gly Val Arg Gln Asn Val Met
            20                  25                  30

Gly Ser Asn Val Asp Gly Arg Pro Val Leu Pro Ser Asn Ser Ser Thr
        35                  40                  45

Met Ala Tyr Ala Thr Val Gly Gly Thr Pro Leu Asp Ala Ala Thr Ser
    50                  55                  60

Ala Ala Ala Ser Ala Ala Ala Thr Ala Arg Ser Met Ala Thr Asp
65                  70                  75                  80
```

```
Leu Tyr Ser Ser Leu Val Ala Ser Gly Ala Ala Ser Arg Ala Ser Ala
                85                  90                  95

Arg Asp Glu Lys Leu Thr Ala Leu Leu Lys Leu Glu Asp Leu Thr
            100                 105                 110

Arg Glu Leu Ala Gln Leu Thr Gln Gln Val Ser Ser Leu Arg Glu Ser
        115                 120                 125

Ser Leu Ala Ser Pro
    130

<210> SEQ ID NO 17
<211> LENGTH: 1056
<212> TYPE: PRT
<213> ORGANISM: Gorilla beringei graueri

<400> SEQUENCE: 17

Met Asp Ser Ser Asn Val Arg Asp Val Val Ile Lys Leu Arg Pro Pro
1               5                   10                  15

Ser Ala Glu Ile Trp Thr Cys Gly Ser Arg Gly Val Val Cys Ser
            20                  25                  30

Thr Ile Ala Leu Gln Glu Thr Asp Ala Gly Gly Gln Thr Thr Lys Val
        35                  40                  45

Glu Asp His Gln Pro His Gly Thr Pro Gly Gly Leu Arg Phe Pro
50                  55                  60

Leu Arg Phe Leu Val Arg Gly Arg Gln Val His Leu Val Gln Asp Ile
65                  70                  75                  80

Gln Pro Val Gln Arg Cys Gln Tyr Cys Gly Arg Phe Tyr Lys Ser Gln
                85                  90                  95

His Glu Cys Ser Ala Arg Arg Arg Asp Phe Tyr Phe His His Ile Asn
            100                 105                 110

Ser Gln Ser Ser Asn Trp Trp Arg Glu Ile Gln Phe Phe Pro Ile Gly
        115                 120                 125

Ser His Pro Arg Thr Glu Arg Leu Phe Val Thr Tyr Asp Val Glu Thr
    130                 135                 140

Tyr Thr Trp Met Gly Ala Phe Gly Lys Gln Leu Val Pro Phe Met Leu
145                 150                 155                 160

Val Met Lys Leu Gly Gly Asn Glu Ala Leu Val Ala Ala Arg Asp
            165                 170                 175

Leu Ala Arg Glu Leu Arg Trp Asp Pro Trp Glu Lys Asp Pro Leu Thr
            180                 185                 190

Phe Tyr Cys Ile Thr Pro Glu Lys Met Ala Val Gly Arg Gln Phe Arg
        195                 200                 205

Thr Phe Arg Asp Arg Leu Gln Thr Leu Met Ala Arg Asp Leu Trp Arg
    210                 215                 220

Ser Phe Leu Ala Ala Asn Pro His Leu Gln Asp Trp Ala Leu Glu Glu
225                 230                 235                 240

His Gly Leu Glu Ser Pro Glu Glu Leu Thr Tyr Glu Glu Leu Lys Lys
                245                 250                 255

Leu Pro Ser Ile Lys Gly Gln Pro Arg Phe Leu Glu Leu Tyr Ile Val
            260                 265                 270

Gly His Asn Ile Asn Gly Phe Asp Glu Ile Val Leu Ala Gln Val
        275                 280                 285

Ile Asn Asn Arg Ser Ser Val Pro Gly Pro Phe Arg Ile Thr Arg Asn
    290                 295                 300

Phe Met Pro Arg Ala Gly Lys Ile Leu Phe Asn Asp Leu Thr Phe Ser
```

```
            305                 310                 315                 320
Leu Pro Asn Pro Arg Ser Lys Lys Arg Thr Asp Tyr Thr Leu Trp Glu
                    325                 330                 335

Gln Gly Gly Cys Asp Asp Thr Asp Phe Lys His Gln Tyr Leu Lys Val
                340                 345                 350

Met Val Arg Asp Thr Phe Ala Leu Thr His Thr Ser Leu Arg Lys Ala
            355                 360                 365

Ala Gln Ala Tyr Ala Leu Pro Val Glu Lys Gly Cys Cys Pro Tyr Gln
        370                 375                 380

Ala Val Asn Gln Phe Tyr Met Leu Gly Ser Tyr Arg Ser Asp Thr Asp
385                 390                 395                 400

Gly Phe Pro Leu Gln Glu Tyr Trp Lys Asp Arg Glu Phe Val Leu
                405                 410                 415

Asn Arg Glu Leu Trp Lys Lys Gly Glu Asp Lys Tyr Asp Ile Ile
                420                 425                 430

Arg Glu Thr Leu Asp Tyr Cys Ala Leu Asp Val Gln Val Thr Ala Glu
            435                 440                 445

Leu Val His Lys Leu Arg Glu Ser Tyr Ala Cys Phe Val Arg Asp Ser
        450                 455                 460

Val Gly Leu Gln Glu Ala Ser Phe Asn Val Phe Gln Arg Pro Thr Ile
465                 470                 475                 480

Ser Ser Asn Ser His Ala Ile Phe Arg Gln Ile Ala Phe Arg Ala Glu
                485                 490                 495

Arg Pro Gln Arg Thr Asn Leu Gly Pro Asn Met Leu Ala Pro Ser His
                500                 505                 510

Glu Leu Tyr Asp Tyr Val Arg Ala Ser Ile Arg Gly Arg Cys Tyr
            515                 520                 525

Pro Thr Tyr Leu Gly Ile Leu Arg Glu Pro Leu Tyr Val Tyr Asp Ile
        530                 535                 540

Cys Gly Met Tyr Ala Ser Ala Leu Thr His Pro Met Pro Trp Gly Pro
545                 550                 555                 560

Pro Leu Asn Pro Tyr Glu Arg Ala Leu Ala Ala Arg Glu Trp Gln Arg
                565                 570                 575

Ala Leu Asp Met Gln Ala Cys Lys Ile Asp Tyr Phe Asp Pro Arg Leu
            580                 585                 590

Leu Pro Gly Val Phe Thr Ile Asp Ala Asp Pro Pro Asn Glu Asp Gln
        595                 600                 605

Leu Asp Pro Leu Pro Pro Phe Cys Ser Arg Lys Gly Gly Arg Leu Cys
610                 615                 620

Trp Thr Asn Glu Arg Leu Arg Gly Glu Val Ala Thr Ser Val Asp Met
                630                 635                 640

Val Thr Leu His Asn Arg Gly Trp Arg Val Arg Leu Ile Pro Asp Glu
            645                 650                 655

Arg Thr Thr Val Phe Pro Glu Trp Lys Cys Val Ala Arg Glu Tyr Val
        660                 665                 670

Gln Leu Asn Ile Ala Ala Lys Glu Arg Ala Asp Arg Asp Lys Asn Gln
            675                 680                 685

Thr Leu Arg Ser Ile Ala Lys Leu Leu Ser Asn Ala Leu Tyr Gly Ser
        690                 695                 700

Phe Ala Thr Lys Leu Asp Asn Lys Lys Ile Val Phe Ser Asp Gln Met
705                 710                 715                 720

Asp Pro Gly Thr Leu Lys Gly Ile Thr Ser Gly Gln Val Asn Ile Lys
                725                 730                 735
```

Ser Ser Ser Phe Leu Glu Thr Asp Asn Leu Ser Ala Glu Val Met Pro
                740                 745                 750

Ala Phe Glu Arg Glu Tyr Leu Pro Gln Gln Leu Ala Leu Ala Asp Ser
            755                 760                 765

Asp Ala Glu Glu Ser Glu Asp Glu Arg Val Pro Thr Pro Phe Tyr Thr
        770                 775                 780

Pro Pro Ser Gly Thr Pro Gly His Val Ser Tyr Thr Tyr Lys Pro Ile
785                 790                 795                 800

Thr Phe Leu Asp Ala Glu Gly Asp Met Cys Leu His Thr Leu Glu
                805                 810                 815

Lys Val Asp Pro Leu Val Asp Asn Asp Arg Tyr Pro Ser His Val Ala
                820                 825                 830

Ser Phe Val Leu Ala Trp Thr Arg Ala Phe Val Ser Glu Trp Ser Glu
            835                 840                 845

Phe Leu Tyr Glu Glu Asp Arg Gly Thr Pro Leu Glu Asp Arg Pro Leu
        850                 855                 860

Lys Ser Val Tyr Gly Asp Thr Asp Ser Leu Phe Val Thr Glu Lys Gly
865                 870                 875                 880

His Arg Leu Met Glu Ser Arg Gly Lys Lys Arg Ile Lys Lys His Gly
                885                 890                 895

Gly Asn Leu Val Phe Asp Pro Asp Arg Pro Glu Leu Thr Trp Leu Val
                900                 905                 910

Glu Cys Glu Thr Val Cys Ala Ser Cys Gly Ala Asp Ala Tyr Ser Pro
            915                 920                 925

Glu Ser Val Phe Leu Ala Pro Lys Leu Tyr Ala Leu Lys Ser Leu Gln
        930                 935                 940

Cys Pro Ser Cys Gly Ala Thr Ser Lys Gly Lys Leu Arg Ala Lys Gly
945                 950                 955                 960

His Ala Ala Glu Gly Leu Asp Tyr Glu Thr Met Val Lys Cys Tyr Leu
                965                 970                 975

Ala Asp Ala Gln Gly Glu Glu Arg Gln Arg Phe Ser Thr Ser Arg Thr
                980                 985                 990

Ser Leu Lys Arg Thr Leu Ala Ser Ala Gln Pro Gly Ala His Pro Phe
            995                 1000                1005

Thr Val Thr Gln Thr Thr Leu Thr Arg Thr Leu Arg Pro Trp Lys
        1010                1015                1020

Asp Met Thr Leu Ala Pro Leu Asp Ala His Arg Leu Val Pro Tyr
    1025                1030                1035

Ser Glu Ser Arg Pro Asn Pro Arg Asn Glu Glu Ile Cys Trp Ile
    1040                1045                1050

Glu Met Pro
    1055

<210> SEQ ID NO 18
<211> LENGTH: 658
<212> TYPE: PRT
<213> ORGANISM: Gorilla beringei graueri

<400> SEQUENCE: 18

Met Arg Arg Ala Ala Met Phe Glu Glu Gly Pro Pro Ser Tyr Glu
1               5                   10                  15

Ser Ala Met Gly Ile Ser Pro Ala Ala Pro Leu Gln Pro Pro Tyr Val
            20                  25                  30

Pro Pro Arg Tyr Leu Gln Pro Thr Gly Gly Arg Asn Ser Ile Cys Tyr

```
                35                  40                  45
Ser Glu Leu Gln Pro Leu Tyr Asp Thr Thr Arg Leu Tyr Leu Val Asp
 50                  55                  60

Asn Lys Ser Ala Asp Val Ala Ser Leu Asn Tyr Gln Asn Asp His Ser
 65                  70                  75                  80

Asp Phe Leu Thr Thr Val Ile Gln Asn Asn Asp Phe Thr Pro Thr Glu
                 85                  90                  95

Ala Ser Thr Gln Thr Ile Asn Leu Asp Asn Arg Ser Asn Trp Gly Gly
                100                 105                 110

Asp Leu Lys Thr Ile Leu His Thr Asn Met Pro Asn Val Asn Glu Phe
            115                 120                 125

Met Phe Thr Asn Ser Phe Lys Ala Arg Val Met Val Ala Arg Glu Gln
            130                 135                 140

Gly Glu Ala Lys Tyr Glu Trp Val Asp Phe Thr Leu Pro Glu Gly Asn
145                 150                 155                 160

Tyr Ser Glu Thr Met Thr Leu Asp Leu Met Asn Asn Ala Ile Val Glu
                165                 170                 175

His Tyr Leu Lys Val Gly Arg Gln Asn Gly Val Lys Glu Ser Asp Ile
            180                 185                 190

Gly Val Lys Phe Asp Thr Arg Asn Phe Arg Leu Gly Trp Asp Pro Val
            195                 200                 205

Thr Gly Leu Val Met Pro Gly Val Tyr Thr Asn Glu Ala Phe His Pro
210                 215                 220

Asp Ile Val Leu Leu Pro Gly Cys Gly Val Asp Phe Thr Gln Ser Arg
225                 230                 235                 240

Leu Ser Asn Leu Leu Gly Ile Arg Lys Arg Gln Pro Phe Gln Glu Gly
                245                 250                 255

Phe Lys Ile Thr Tyr Glu Asp Leu Lys Gly Gly Asn Ile Pro Ala Leu
            260                 265                 270

Leu Asp Leu Asp Ala Tyr Glu Glu Ser Leu Lys Pro Glu Glu Ser Ala
            275                 280                 285

Gly Asp Ser Gly Glu Ser Gly Glu Gln Ala Gly Gly Gly Gly
            290                 295                 300

Ala Ser Val Glu Asn Glu Ser Thr Pro Ala Val Ala Ala Asp Ala Ala
305                 310                 315                 320

Glu Val Glu Pro Glu Ala Met Gln Gln Asp Ala Glu Glu Gly Ala Gln
                325                 330                 335

Glu Gly Ala Gln Lys Asp Met Asn Asp Gly Glu Ile Arg Gly Asp Thr
            340                 345                 350

Phe Ala Thr Arg Gly Glu Glu Lys Glu Ala Glu Ala Ala Ala Ala Ala
            355                 360                 365

Thr Ala Glu Ala Glu Thr Glu Val Glu Ala Glu Ala Glu Pro Glu Thr
            370                 375                 380

Glu Val Met Glu Asp Met Asn Asp Gly Glu Arg Arg Gly Asp Thr Phe
385                 390                 395                 400

Ala Thr Arg Gly Glu Glu Lys Ala Ala Glu Ala Glu Ala Ala Ala Glu
                405                 410                 415

Glu Ala Ala Ala Ala Ala Lys Thr Glu Ala Ala Lys Ala Glu
            420                 425                 430

Val Glu Ala Asn Val Ala Val Glu Ala Gln Ala Glu Glu Glu Ala Ala
            435                 440                 445

Ala Glu Ala Val Lys Glu Lys Ala Gln Ala Glu Gln Glu Glu Lys Lys
            450                 455                 460
```

-continued

```
Pro Val Ile Gln Pro Leu Lys Glu Asp Ser Lys Lys Arg Ser Tyr Asn
465                 470                 475                 480

Val Ile Glu Gly Ser Thr Phe Thr Gln Tyr Arg Ser Trp Tyr Leu Ala
            485                 490                 495

Tyr Asn Tyr Gly Asp Pro Val Lys Gly Val Arg Ser Trp Thr Leu Leu
        500                 505                 510

Cys Thr Pro Asp Val Thr Cys Gly Ser Glu Gln Met Tyr Trp Ser Leu
    515                 520                 525

Pro Asn Met Met Gln Asp Pro Val Thr Phe Arg Ser Thr Arg Gln Val
530                 535                 540

Ser Asn Phe Pro Val Val Gly Ala Glu Leu Leu Pro Val His Ser Lys
545                 550                 555                 560

Ser Phe Tyr Asn Glu Gln Ala Val Tyr Ser Gln Leu Ile Arg Gln Ala
                565                 570                 575

Thr Ser Leu Thr His Val Phe Asn Arg Phe Pro Glu Asn Gln Ile Leu
            580                 585                 590

Ala Arg Pro Pro Ala Pro Thr Ile Thr Thr Val Ser Glu Asn Val Pro
        595                 600                 605

Ala Leu Thr Asp His Gly Thr Leu Pro Leu Arg Asn Ser Ile Ser Gly
    610                 615                 620

Val Gln Arg Val Thr Ile Thr Asp Ala Arg Arg Thr Cys Pro Tyr
625                 630                 635                 640

Val Tyr Lys Ala Leu Gly Ile Val Ser Pro Arg Val Leu Ser Ser Arg
                645                 650                 655

Thr Phe

<210> SEQ ID NO 19
<211> LENGTH: 955
<212> TYPE: PRT
<213> ORGANISM: Gorilla beringei graueri

<400> SEQUENCE: 19

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Asn Met Ser Asn Lys Phe Arg Asn Pro
        35                  40                  45

Thr Val Ala Pro Thr His Asp Val Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
        115                 120                 125

Ala Pro Asn Ser Cys Glu Trp Glu Gln Glu Asn Gln Val Val
    130                 135                 140

Ala Asp Asp Glu Leu Glu Asp Glu Glu Ala Gln Ala Gln Gln Asp Ala
145                 150                 155                 160

Pro Ala Lys Lys Ile His Val Tyr Ala Gln Ala Pro Leu Ala Gly Glu
                165                 170                 175
```

-continued

Lys Ile Thr Lys Asp Gly Leu Gln Ile Gly Thr Glu Val Val Gly Asp
            180                 185                 190

Thr Ser Lys Asp Thr Phe Ala Asp Lys Thr Phe Gln Pro Glu Pro Gln
            195                 200                 205

Ile Gly Glu Ser Gln Trp Asn Glu Ala Asp Ala Thr Val Ala Gly Gly
210                 215                 220

Arg Val Leu Lys Lys Thr Thr Pro Met Arg Pro Cys Tyr Gly Ser Tyr
225                 230                 235                 240

Ala Arg Pro Thr Asn Ala Asn Gly Gly Gln Gly Ile Met Val Ala Asn
            245                 250                 255

Glu Gln Gly Val Leu Glu Ser Lys Val Glu Met Gln Phe Phe Ser Asn
            260                 265                 270

Thr Thr Thr Leu Asn Ala Arg Asp Gly Ala Gly Asn Pro Glu Pro Lys
            275                 280                 285

Val Val Leu Tyr Ser Glu Asp Val His Leu Glu Ser Pro Asp Thr His
            290                 295                 300

Leu Ser Tyr Lys Pro Lys Lys Asp Val Asn Ala Lys Ile Met Leu
305                 310                 315                 320

Gly Gln Gln Ala Met Ala Asn Arg Pro Asn Leu Ile Ala Phe Arg Asp
            325                 330                 335

Asn Phe Ile Gly Leu Met Tyr Tyr Asn Ser Thr Gly Asn Met Gly Val
            340                 345                 350

Leu Ala Gly Gln Ala Ser Gln Leu Asn Ala Val Val Asp Leu Gln Asp
            355                 360                 365

Arg Asn Thr Glu Leu Ser Tyr Gln Leu Met Leu Asp Ser Ile Gly Asp
            370                 375                 380

Arg Ser Arg Tyr Phe Ser Met Trp Asn Gln Ala Val Asp Ser Tyr Asp
385                 390                 395                 400

Pro Asp Val Arg Ile Ile Glu Asn His Gly Val Glu Asp Glu Leu Pro
            405                 410                 415

Asn Tyr Cys Phe Pro Leu Gly Gly Ile Gly Ile Thr Asp Thr Tyr Gln
            420                 425                 430

Gly Ile Lys Asn Thr Asn Gly Asn Gly Gln Trp Thr Lys Asp Asp Gln
            435                 440                 445

Phe Ala Asp Arg Asn Glu Ile Gly Val Gly Asn Asn Phe Ala Met Glu
450                 455                 460

Ile Asn Ile Gln Ala Asn Leu Trp Arg Asn Phe Leu Tyr Ala Asn Val
465                 470                 475                 480

Gly Leu Tyr Leu Pro Asp Lys Leu Lys Tyr Asn Pro Thr Asn Val Asp
            485                 490                 495

Ile Ser Asp Asn Pro Asn Thr Tyr Asp Tyr Met Asn Lys Arg Val Val
            500                 505                 510

Ala Pro Gly Leu Val Asp Cys Phe Val Asn Val Gly Ala Arg Trp Ser
            515                 520                 525

Leu Asp Tyr Met Asp Asn Val Asn Pro Phe Asn His Arg Asn Ala
            530                 535                 540

Gly Leu Arg Tyr Arg Ser Met Ile Leu Gly Asn Gly Arg Tyr Val Pro
545                 550                 555                 560

Phe His Ile Gln Val Pro Gln Lys Phe Phe Ala Ile Lys Asn Leu Leu
            565                 570                 575

Leu Leu Pro Gly Ser Tyr Thr Tyr Glu Trp Asn Phe Arg Lys Asp Val
            580                 585                 590

-continued

Asn Met Val Leu Gln Ser Ser Leu Gly Asn Asp Leu Arg Val Asp Gly
            595                 600                 605

Ala Ser Ile Lys Phe Asp Ser Val Thr Leu Tyr Ala Thr Phe Phe Pro
610                 615                 620

Met Ala His Asn Thr Ala Ser Thr Leu Glu Ala Met Leu Arg Asn Asp
625                 630                 635                 640

Thr Asn Asp Gln Ser Phe Asn Asp Tyr Leu Ser Gly Ala Asn Met Leu
                645                 650                 655

Tyr Pro Ile Pro Ala Lys Ala Thr Asn Val Pro Ile Ser Ile Pro Ser
            660                 665                 670

Arg Asn Trp Ala Ala Phe Arg Gly Trp Ala Phe Thr Arg Leu Lys Thr
        675                 680                 685

Lys Glu Thr Pro Ser Leu Gly Ser Gly Phe Asp Pro Tyr Phe Val Tyr
690                 695                 700

Ser Gly Ser Ile Pro Tyr Leu Asp Gly Thr Phe Tyr Leu Asn His Thr
705                 710                 715                 720

Phe Lys Lys Ile Ser Ile Met Tyr Asp Ser Ser Val Ser Trp Pro Gly
                725                 730                 735

Asn Asp Arg Leu Leu Thr Pro Asn Glu Phe Glu Val Lys Arg Ala Val
            740                 745                 750

Asp Gly Glu Gly Tyr Asn Val Ala Gln Cys Asn Met Thr Lys Asp Trp
        755                 760                 765

Phe Leu Val Gln Met Leu Ala Asn Tyr Asn Ile Gly Tyr Gln Gly Phe
770                 775                 780

Tyr Ile Pro Glu Ser Tyr Lys Asp Arg Met Tyr Ser Phe Phe Arg Asn
785                 790                 795                 800

Phe Gln Pro Met Ser Arg Gln Val Val Asp Glu Thr Lys Tyr Lys Asp
                805                 810                 815

Tyr Gln Ala Ile Gly Ile Thr His Gln His Asn Asn Ser Gly Phe Val
            820                 825                 830

Gly Tyr Leu Ala Pro Thr Met Arg Glu Gly Gln Ala Tyr Pro Ala Asn
        835                 840                 845

Phe Pro Tyr Pro Leu Ile Gly Lys Thr Ala Val Asp Ser Val Thr Gln
850                 855                 860

Lys Lys Phe Leu Cys Asp Arg Thr Leu Trp Arg Ile Pro Phe Ser Ser
865                 870                 875                 880

Asn Phe Met Ser Met Gly Ala Leu Thr Asp Leu Gly Gln Asn Leu Leu
                885                 890                 895

Tyr Ala Asn Ser Ala His Ala Leu Asp Met Thr Phe Glu Val Asp Pro
            900                 905                 910

Met Asp Glu Pro Thr Leu Leu Tyr Ile Val Phe Glu Val Phe Asp Val
        915                 920                 925

Val Arg Val His Gln Pro His Arg Gly Val Ile Glu Thr Val Tyr Leu
930                 935                 940

Arg Thr Pro Phe Ser Ala Gly Asn Ala Thr Thr
945                 950                 955

<210> SEQ ID NO 20
<211> LENGTH: 580
<212> TYPE: PRT
<213> ORGANISM: Gorilla beringei graueri

<400> SEQUENCE: 20

Met Lys Arg Ala Arg Ser Ser Asp Glu Thr Phe Asn Pro Val Tyr Pro
1               5                   10                  15

```
Tyr Asp Thr Glu Ile Ala Pro Thr Ser Val Pro Phe Leu Thr Pro Pro
            20                  25                  30

Phe Val Ser Ser Ala Gly Met Gln Glu Asn Pro Ala Gly Val Leu Ser
            35                  40                  45

Leu His Leu Ser Glu Pro Leu Thr Thr His Asn Gly Ala Leu Thr Leu
        50                  55                  60

Lys Met Gly Gly Gly Leu Thr Leu Asp Lys Glu Gly Asn Leu Thr Ser
65                  70                  75                  80

Gln Asn Ile Thr Ser Val Asp Pro Pro Leu Lys Lys Ser Lys Asn Asn
                85                  90                  95

Ile Ser Leu Gln Thr Ala Ala Pro Leu Ala Val Ser Ser Gly Ala Leu
                100                 105                 110

Thr Leu Phe Ala Thr Pro Pro Leu Ala Val Ser Gly Asp Asn Leu Thr
            115                 120                 125

Val Gln Ser Gln Ala Pro Leu Thr Leu Glu Asp Ser Lys Leu Thr Leu
130                 135                 140

Ala Thr Lys Gly Pro Leu Thr Val Ser Glu Gly Lys Leu Val Leu Glu
145                 150                 155                 160

Thr Glu Ala Pro Leu His Ala Ser Asp Ser Ser Leu Gly Leu Ser
                165                 170                 175

Val Thr Ala Pro Leu Ser Ile Asn Asn Asp Ser Leu Gly Leu Asp Met
            180                 185                 190

Gln Ala Pro Ile Ser Ser Arg Asp Gly Lys Leu Ala Leu Thr Val Ala
            195                 200                 205

Ala Pro Leu Thr Val Val Glu Gly Ile Asn Ala Leu Ala Val Ala Thr
            210                 215                 220

Gly Lys Gly Ile Gly Leu Asn Glu Thr Asn Thr His Leu Gln Ala Lys
225                 230                 235                 240

Leu Val Ala Pro Leu Gly Phe Asp Thr Asn Gly Asn Ile Lys Leu Ser
                245                 250                 255

Val Ala Gly Gly Met Arg Leu Asn Asn Asn Thr Leu Ile Leu Asp Val
                260                 265                 270

Asn Tyr Pro Phe Glu Ala Gln Gly Gln Leu Ser Leu Arg Val Gly Ser
            275                 280                 285

Gly Pro Leu Tyr Val Asp Ser Ser Ser His Asn Leu Thr Ile Arg Cys
        290                 295                 300

Leu Arg Gly Leu Tyr Ile Thr Ser Ser Asn Asn Gln Asn Gly Leu Glu
305                 310                 315                 320

Ala Asn Ile Lys Leu Thr Arg Gly Leu Val Tyr Asp Gly Asn Ala Ile
                325                 330                 335

Ala Val Asn Val Gly Lys Gly Leu Glu Tyr Ser Pro Thr Asp Thr Thr
            340                 345                 350

Glu Lys Pro Ile Gln Thr Lys Ile Gly Leu Gly Met Glu Tyr Asp Thr
            355                 360                 365

Glu Gly Ala Met Met Thr Lys Leu Gly Ser Gly Leu Ser Phe Asp Asn
            370                 375                 380

Ser Gly Ala Ile Val Val Gly Asn Lys Asn Asp Asp Arg Leu Thr Leu
385                 390                 395                 400

Trp Thr Thr Pro Asp Pro Ser Pro Asn Cys Gln Ile Tyr Ser Glu Lys
                405                 410                 415

Asp Ala Lys Leu Thr Leu Val Leu Thr Lys Cys Gly Ser Gln Val Val
            420                 425                 430
```

Gly Thr Val Ser Ile Ala Ala Leu Lys Gly Ser Leu Val Pro Ile Thr
            435                 440                 445

Ser Ala Ile Ser Val Val Gln Val Tyr Leu Arg Phe Asp Glu Asn Gly
        450                 455                 460

Val Leu Met Ser Asn Ser Ser Leu Asn Gly Glu Tyr Trp Asn Phe Arg
465                 470                 475                 480

Asn Gly Asp Ser Thr Asn Gly Thr Pro Tyr Thr Asn Ala Val Gly Phe
                485                 490                 495

Met Pro Asn Leu Leu Ala Tyr Pro Lys Gly Gln Thr Thr Thr Ala Lys
            500                 505                 510

Ser Asn Ile Val Ser Gln Val Tyr Met Asn Gly Asp Asp Thr Lys Pro
        515                 520                 525

Met Thr Phe Thr Ile Asn Phe Asn Gly Leu Ser Glu Thr Gly Asp Thr
    530                 535                 540

Pro Val Ser Lys Tyr Ser Met Thr Phe Ser Trp Arg Trp Pro Asn Gly
545                 550                 555                 560

Ser Tyr Ile Gly His Asn Phe Val Thr Asn Ser Phe Thr Phe Ser Tyr
                565                 570                 575

Ile Ala Gln Glu
            580

<210> SEQ ID NO 21
<211> LENGTH: 37211
<212> TYPE: DNA
<213> ORGANISM: Gorilla beringei graueri

<400> SEQUENCE: 21

```
catcatcaat aatataccttt attttggatt gtggccaata tgataatgag gtgggcgggg      60
agaggcgggg cggtgacgt aggacgcgcg agtaggggttg ggaggtgtgg cggaagtgtg     120
gcatttgcaa gtgggaggag ctcacatgca agcttccgtc gcggaaaatg tgacgttttt     180
gatgagcgcc gcctacctcc ggaagtgcca atttttcgcgc gcttttcacc ggatatcgta     240
gtaattttgg gcgggaccat gtaagatttg gccatttttcg cgcgaaaagt gaaacgggga     300
agtgaaaact gaataatagg gcgttagtca tagtgcgtaa tatttaccga gggccgaggg     360
acttttgaccg attacgtgga ggactcgccc aggtgttttt tacgtgaatt tccgcgttcc     420
gggtcaaagt ctccgttttta ttgtcaccgt catttgacgc ggagggtatt taaacccgct     480
gcgctcctca agaggccact cttgagtgcc agcgagaaga gttttctcct ctgctccgct     540
tcggtgatcg aaaaatgaga cacatagcct gcactccggg tcttttgtcc ggtcgggcgg     600
cggccgagct tttggacgct tgatcaatg atgtcctgag cgatgatttt ccgtctacta     660
cccactttag cccacctact cttcacgaac tgtacgatct ggatgtactg gtggatgtga     720
acgatcccaa cgaggaggcg gtttctgcgt ttttttccga gtctgcgctg ttggccgctc     780
aggagggatt tgacctacac actccgccgc ctatttttaga gtctccgctg ccggagccca     840
gtggtatacc ttatatgcct gaactgcttc ccgaagtggt agacctgacc tgccacgagc     900
ctggctttcc gcccagcgac gatgatggtg agccttttgt tttagacttt gctgagatac     960
ctgggcacgg ttgcaggtct tgtgcatatc atcagagggt taccggagac ccgaggtta    1020
agtgttcgct gtgctatatg aggatgacct cttccttttat ctacagtaag ttttttgtcta    1080
ggtgggcttt tgggtaggtg ggttttgtgt cagaacaggt gtaaacgttg cttgtgtttt    1140
ttgtacctgt aggtccggtg tccgagccag accggagcc cgaccgcgat ccgagccgg    1200
atcccgagcc tcctcgtagg gcaagaaaat taccttctat tctgtgcaag tctaagacac    1260
```

```
ctgtgaggac cagcgaggcg gacagcaccg actctggcac ttctacctct cctcctgaaa    1320
ttcacccagt ggttcctctg ggtatacata gacctgttgc tgttagagtt tgcgggcgac    1380
gctctgcagt agagtgcatt gaggacttgc ttcacgaacc cgaggaacct ttggacttga    1440
gcgttaaacg ccctaggcaa taaacccac  ctaagtaata aacccacct  aagtaataaa    1500 ccctgccgcc cttggttatt gagatgacgc ccaatgtttg cttttgaatg acttcatgtg    1560
tgtaataaaa gtgagtgtga tcataggtct cttgtttgtc tgggcggggc ttaagggtat    1620
ataagtctct tggggctaaa cttggttaca cttgacccca atggaggcgt gggggtgctt    1680
ggaggagttt gcgacgtgc  gccgtttgct ggacgagagc tctagcaata cctatactat    1740
ttggaggtat ctgtggggct ctactcaggc caagttggtc tccagaatta agcaggatta    1800
caagtgcgat tttgaagagc tttttagttc ctgcggtgag cttttgcaat ccttgaatct    1860
gggccatcag gctattttcc aggaaaaggt tctctcgact ttggattttt ccactcccgg    1920
gcgcaccgcc gcttgtgtgg cttttgtgtc ttttgtgcaa gataaatgga gcaggagac   1980 ccacctgagt cacggctacg tactggattt catggcgatg gctcttgga  gggcttacaa   2040 caaatggaag attcagaagg aactgtacgg ttccgcccta cgtcgtccac ttctgtcgcg    2100 acagggctg  aggtttcccg accatcggca gcatcagaat ctggaagacg agtcggagga    2160
gcgagcggag gagaagatca gcttgagagc cggcctggac cctcctcagg aggaatgaat   2220
ctcccgcagg tggttgacct gtttccagaa ctgagacggg tcctgactat cagggaggat    2280 ggtcagttg  tgaagaagtt taagaggat  cggggtgagg gagatgatga ggcggctagc    2340
aatttagctt ttagtctgat gactcgccac cgaccggaat gtattaccta tcagcagatt    2400
aaggagagtg tgccaacga  gctggatctt ttgggtcaga agtatagcat agaacagctt    2460
accacttact ggcttcagcc tggggatgat tgggaagagc cgatcagggt gtatgcaaag    2520
gtggccctgc ggcccgattg caagtataag attactaagt tggttaatat tagaaactgc    2580
tgctatattt ctgggaacgg ggccgaagtg gagatagata ctcaggacag ggtggctttt    2640
aggtgttgca tgataaacat gtggcccggg atactgggga tggatggggt ggtattcatg    2700
aatgtgaggt ttacgggccc caactttaat ggcacggtgt tcatgggcaa caccaacttg    2760
ctcctgcatg gtgcgagttt ctatgggttt aataacacct gtatagaggc ctggaccgat    2820
gtaaaggttc gaggttgttc cttttatagc tgttggaagg cggtggtgtg tcgccctaaa    2880 agcagggggtt ctgtgaaaaa atgcttgttt gaaaggtgca ccttaggcat cctctctgag    2940
ggcaactcca gggtgcgcca taatgtggct tcgaactgcg gttgcttcat gcaagtgaag    3000
ggggtgagcg ttatcaagca taactcggtg tgtggaaact gcgaggatcg cgcctcccag    3060
atgctgacct gctttgatgg caactgtcac ctgttgaaga ccattcatat aagcagccac    3120
cccagaaagg cctggcccgt gtttgagcat aacatcttga cccgctgctc cttgcatctg    3180
ggggtcagga ggggtatgtt cctgccttac cagtgtaact ttagccacac taaaatcctg    3240
ctggaacccg agtgcatgac caaggtcagc ctgaatggtg tgtttgatgt gactctgaaa    3300
atctggaagg tgctgaggta tgatgagacc aggaccaggt gccgaccctg cgagtgcggc    3360
ggcaagcaca tgagaaatca gcctgtgatg ttggatgtga ccgaggagct taggcctgac    3420
catctggtgc tggcctgcac cagggccgag tttgggtcta gcgatgagga taccgattga    3480
ggtgggtaag gtgggcgtgg ctagaagggt gggggcgtgta taaattgggg gtctaagggt    3540
ctctctgttt tgtcttgcaa cagccgccgc catgagcgac accggcaaca gctttgatgg    3600
```

```
aagcatctttagccccatatctgacagtgcgcatgcctcactgggctggagtgcgtcagaa      3660
tgtgatgggttccaacgtggatggacgcccgcttctgccttcaaattcgtctacaatggc      3720
ctacgcgaccgtgggaggaactccgctggacgccgcgacctccgccgccgcctccgccgc      3780
cgccgcgaccgcgcgcagcatggctacggaccttttacagctctttggtggcgagcggcgc     3840
ggcctctcgcgcgtctgctcgggatgagaaactgaccgctctgctgcttaaactggaaga      3900
cttgacccgggagctggctcaactgacccagcaggtctccagcttgcgtgagagcagcct      3960
tgcctcccctaatggcccataatataaataaaagccagtctgtttggataagcaagtg        4020
tatgttcttatttaactctccgcgcgcgtaagcccgggaccagcggtctcggtcgttt        4080
agggtgcggtggattctttcaacacgtggtacaggtggctctggatgtttagatacatg      4140
ggcatgagtccatccctgggtggaggtagcaccactgcagagcttcgtgctcgggggtg      4200
gtgttgtatatgatccagtcgtagcaggagcgctgggcgtggtgctgaaaaatgtcctta    4260
agcaagaggcttatagctagggggaggccttggtgtaagtgtttacaaatctgctcagt       4320
tgggaggggtgcatccggggggatataatgtgcatcttggactggatttttaggttggct    4380
atgttcccaccccagatccctctgggattcatgttgtgcaggaccaccagcacggtatat    4440
ccagtacacttgggaaattttatcgtggagcttagacgggaatgcatgaagaacttggag    4500
acgcccttgtggcctcccagattttccatacattcgtccatgatgatggaatgggcccg     4560
tgggaagctgcctgagcaaaatgtttctggatcgctcacatcgtagttatgttccagg       4620
gtgaggtcatcataggacatcttacaaatcggggggcggagggtcccggactggggatg      4680
atggtgccctcgggcccggggcgtagttcccctcacagatctgcatctccaggcttttc      4740
atttcagagggagggatcatatccacctgcggagcgatgaaaaacacagtttctggcgca    4800
ggggagattaactgggatgagagcaggtttctgagcagctgtgactttccacagccggtg    4860
ggcccatatatcacgcctataccggctgcagctggtagttaagagagctgcagctgccg      4920
tcctcccggagcaggggggccacctcgttcagcatatccctgacgtggatgttctccctg    4980
accaattccgccagaaggcgctcgccgcccagcgaaagcagctcttgcaaggaagcaaaa    5040
ttttttcagcggttttaggccgtcggccgtggcatgttttttcagcgtctgggtcagcagt    5100
tccagtctgtcccacagctcggtgatgtgctctacggcatctcgatccagcagatctcct    5160
cgtttcgcggttggggcggcttttcgctgtagggcaccagccgatgggcgtccagcgggg    5220
ccagagtcatgtccttccatgggcgcagggtcctcgtcagggtggtctgggtcacggtga    5280
aggggtgcgctccgggttgggcgctggccagggtgcgcttgaggctggttctgctggtgc    5340
tgaatcgctgccgctcttcgccctgcgcgtcggccaggtagcatttgaccatggtctcgt    5400
agtcgagacctcggcggcgtgcccctttggcgcggagcttcccttggagtggcgccgc      5460
acgagggcactgcaggctcttcagggcgtagagcttgggagcgagaaacacggactctg      5520
gggagtaggcgtccgcgccgcaggaagcgcgacgtctcgcattccaccagccaagtga       5580
gctccgggcgtcagggtcaaaaccaggttgccccatgcttttttgatgcgtttcttac       5640
ctcggctctccatgaggcggtgtcccttctcggtgacgaagaggctgtccgtgtctccgt    5700
agaccgacttcaggggcctgtcttccagcggagtgcctctgtcctcctcgtagagaaact    5760
ctgaccactctgagacgaaggccgcgtccaggccaggacgaaggaggccacgtgggagg      5820
ggtagcggtcgttgtccactagcgggtccaccttctccaggtgtgcaggcacatgtccc      5880
cctcctccgcgtccagaaaagtgattggctgtaggtgtaggacacgtgaccggggggttc      5940
ccgacgggggggtataaaaggggtggcacccctttcatcttcactctctccgcatcgc      6000
```

-continued

```
tgtctgcgag agccagctgc tggggtaagt attccctctc gaaggcgggc atgacctcag    6060
cgctcaggtt gtcagtttct aaaaatgagg aggatttgat gttcacctgt ccggaggtga    6120
tacctttgag ggtacctggg tccatctggt cagaaaacac tatttttttg ttgtcaagct    6180
tggtggcgaa cgacccgtag agggcgttgg agagcagctt ggcgatggag cgcagggtct    6240
ggttttgtc gcggtcggct cgctccttgg ccgcgatgtt gagttgcacg tactcgcggg     6300
ccacgcactt ccactcgggg aagacggtgg tgcgctcgtc tgggatcagg cgcaccctcc    6360
agcctcggtt gtgcagggtg accatgtcga cgctggtggc gacctcgccg cgcaggcgct    6420
cgttggtcca gcagaggcgg ccgcccttgc gcgagcagaa ggggggtagg gggtccagct    6480
ggtcctcgtt tgggggtcc gcgtcgatgg tgaagacccc ggggagcaag cgcgggtcaa     6540
agtagtcgat cttgcaagct tgcatgtcca gagcccgctg ccattcgcgg gcggcgagcg    6600
cgcgctcgta ggggttgagg ggcgggcccc agggcatggg gtgggtgagc gcggaggcgt    6660
acatgccgca gatgtcatac acgtacaggg gttccctgag gatgccgagg taggtggggt    6720
agcagcgccc cccgcggatg ctggcgcgca cgtagtcata gagctcgtgg gagggggcca    6780
gcatgttggg cccgaggttg gtgcgctggg ggcgctcggc gcggaaggcg atctgcctga    6840
agatggcatg ggagttggag gagatggtgg gccgctggaa gacgttgaag cttgcttctt    6900
gcaagcccac cgagtccctg acgaagcagg cgtaggactc gcgcagcttg tgcaccagct    6960
cggcggtgac ctggacgtcg agcgcgcagt agtcgagggt ctcgcggatg atgtcatact    7020
tatcctcccc cttctttttc cacagctcgc ggttgaggac gaactcttcg cggtcttttcc   7080
agtactcttg gaggggaaac ccgtccgtgt ccgaacggta agagcctagc atgtagaact    7140
ggttgacggc ctggtagggg caacagccct tctccacggg cagcgcgtag gcctgcgccg    7200
ccttgcggag ggaggtgtgg gtgagggcga aagtgtccct gaccatgact ttgaggtatt    7260
gatgtttgaa gtctgtgtca tcgcagccgc cctgttccca cagggtgtag tccgtgcgct    7320
ttttggagcg cgggttgggc agggagaagg tgaggtcatt gaagaggatc ttccccgctc    7380
gaggcatgaa gtttctggtg atgcgaaagg gccctgggac cgaggagcgg ttgttgatga    7440
cctgggcggc caggacgatc tcgtcaaagc cgtttatgtt gtggcccacg atgtagagct    7500
ccaaaaagcg gggctggccc ttgatggagg ggagcttttt gagttcctcg taggtgagct    7560
cctcgggcga ttccaggccg tgctcctcca gggcccagtc ttgcaagtga gggttggccg    7620
ccaggaagga tcgccagagg tcgcgggcca tgggtctg caggcggtcg cggaaggttc      7680
tgaactgtcg ccccacggcc atcttttcgg gggtgatgca gtagaaggtg aggggtctt    7740
tctcccaggg gtcccatctg agctctcggg cgaggtcgcg cgcggcggcg accagagcct    7800
cgttgccccc cagtttcatg accagcatga agggcacgag ctgcttgcca aaggctccca    7860
tccaagtgta ggtctctaca tcgtaggtga caaagaggcg ctccgtgcga ggatgagagc    7920
cgatcgggaa gaactggatc tcccgccacc agttggagga ttggctgttg atgtggtgaa    7980
agtagaagtc ccgtctgcgg gccgagcact cgtgctggct tttgtaaaag cgaccgcagt    8040
actggcagcg ctgcacgggt tgtatatctt gcacgaggtg aacctggcga cctctgacga    8100
ggaagcgcag cgggaatcta agtcccccgc ctggggtccc gtgtggctgg tggtcttcta    8160
ctttggttgt ctggccgcca gcatctgtct cctggagggc gatggtggag cagaccacca    8220
cgccgcgaga gccgcaggtc cagatctcgg cgctcggcgg gcggagtttg atgacgacat    8280
cgcgcacatt ggagctgtcc atggtctcca gctcccgcgg cggcaggtca gctgggagtt    8340
```

```
cctggaggtt cacctcgcag agacgggtca aggcgcgggc agtgttgaga tggtatctga    8400
tttcaagggg cgtgttggcg gcggagtcga tggcttgcag gaggccgcag ccccggggg     8460 ccacgatggt tccccgcggg gcgcgagggg aggcggaagc tgggggtgtg ttcagaagcg    8520
gtgacgcggg cgggcccccg gaggtagggg gggttccggc cccacaggca tgggcggcag   8580
gggcacgtct tcgccgcgcg cgggcagggg ctggtgctgg ctccgaagag cgcttgcgtg   8640
cgcgacgacg cgacggttgg tgtcctgtat ctgacgcctc tgagtgaaga ccacgggtcc   8700
cgtgaccttg aacctgaaag agagttcgac agaatcaatc tcggcatcgt tgacagcggc   8760
ctggcgcagg atctcctgca cgtcgcccga gttgtcctgg taggcgatct ctgccatgaa   8820
ctgctcgatc tcttcttcct ggagatctcc tcgtccggcg cgctccacgg tggccgccag   8880
gtcgttggag atgcgaccca tgagctgcga gaaggcgttg agcccgccct cgttccagac   8940
ccggctgtag accacgcccc cctcggcgtt gcgggcgcgc atgaccacct gggccaggtt   9000
gagctccacg tgtcgcgtga agacggcgta gttgcgcagg cgctggaaaa ggtagttcag   9060
ggtggtggcg gtgtgctcgg cgacgaagaa gtacatgacc cagcgccgca acgtggattc   9120
attgatgtcc cccaaggcct ccaggcgctc catggcctcg tagaagtcca cggcgaagtt   9180
gaaaaactgg gagttgcgag cggacacggt caactcctcc tccagaagac ggatgagctc   9240
ggcgacagtg tcgcgcacct cgcgctcgaa ggccacgggg ggcgcttctt cctcttccac   9300
ctcttcttcc atgatcgctt cttcttcttc ctcagccggg acgggagggg gcggcggcgg   9360
cgggggaggg gcgcggcggc ggcggcggcg caccgggagg cggtcgatga agcgctcgat   9420
catctccccc cgcatgcggc gcatggtctc ggtgacggcg cggccgttct cccggggcg    9480 cagctcgaag acgccgcctc tcatctcgcc gcggggcggg cggccgtgag gtagcgagac   9540
ggcgctgact atgcatctta acaattgctg tgtaggtaca ccgccgaggg acctgattga   9600
gtccagatcc accggatccg aaaacctttg gaggaaagcg tctatccagt cgcagtcgca   9660
aggtaggctg agcaccgtgg cgggcggggg cgggtctgga gagttcctgg cggagatgct   9720
gctgatgatg taattaaagt aggcggtctt gagaaggcgg atggtggaca ggagcaccat   9780
gtctttgggt ccggcctgtt ggatgcggag gcggtcggcc atgccccagg cctcgttctg   9840
acaccggcgc aggtctttgt agtagtcttg catgagtctt tccaccggca cctcttctcc   9900
ttcctcttct ccatctcgcc ggtggttttct cgcgccgccc atgcgcgtga ccccaaagcc   9960
cctgagcggc tgcagcaggg ccaggtcggc gaccacgcgc tcggccaaga tggcctgctg   10020
cacctgagtg agggtcctct cgaagtcatc catgtccacg aagcggtggt aggcgcccgt   10080
gttgatggtg taggtgcagt tggccatgac ggaccagttg acggtctggt gtcccggctg   10140
cgagagctcc gtgtaccgca ggcgcgagaa ggcgcgggaa tcgaacacgt agtcgttgca   10200
agtccgcacc agatactggt agcccaccag gaagtgcggc ggaggttggc gatagagggg   10260
ccagcgctgg gtggcggggg cgccgggcgc caggttttcc agcatgaggc ggtggtatcc   10320
gtagatgtac ctggacatcc aggtgatgcc ggcggcggtg tggtggcgc gcgcgtagtc    10380 gcggacccgg ttccagatgt ttcgcagggg cgagaagtgt tccatggtcg gcacgctctg   10440
gccggtgagg cgcgcgcagt cgttgacgct ctatacacac acaaaaacga aagcgtttac   10500
agggctttcg ttctgtagcc tggaggaaag taaatgggtt gggttgcggt gtgccccggt   10560
tcgagaccaa gctgagctcg gccggctgaa gccgcagcta acgtggtatt ggcagtcccg   10620
tctcgaccca ggcctgtat cctccaggat acggtcgaga gccctttgc tttcttggcc    10680 aagcgcccgt ggcgcgatct gggatagatg gtcgcgatga gaggacaaaa gcggctcgct   10740
```

```
tccgtagtct ggagaaacaa tcgccagggt tgcgttgcgg cgtacccgg  ttcgagcccc   10800 tatgcggct  tgaatcggcc ggaaccgcgg ctaacgaggg ccgtggcagc cccgtcctca   10860
ggaccccgcc agccgacttc tccagttacg ggagcgagcc ccttttgttt tttatttttt   10920
agatgcatcc cgtgctgcgg cagatgcgcc cctcgcccg  gccgatcag  cagcagcaac   10980 agcaggcatg cagaccccc  tctccccttt ccgcccggt  caccacggcc gcggcggccg   11040
tgtcgggcgc ggggggcgcg ctggagtcag atgagccacc gcggcggcga cctaggcagt   11100
atctggactt ggaagagggc gagggactgg cgcggctggg ggcgaactct ccagagcgcc   11160
acccgcgggt gcagttgaaa agggacgcgc gcgaggcgta cctgccgcgg cagaacctgt   11220
ttcgcgaccg cggggggcgag agcccgagg  agatgcgaga ctgcaggttc caagcggggc   11280
gcgagctgcg gcgcgggctg gacagacagc gcctgctgcg cgaggaggac tttgagcccg   11340
acacgcagac gggcatcagc ccgcgcgcg  cgcacgtagc cgcggccgac ctggtgaccg   11400
cctacgagca gacggtgaac caggagcgca acttccaaaa gagcttcaac aaccacgtgc   11460
gcacgctggt ggcgcgcgag gaggtgaccc tgggtctcat gcatctgtgg gacctggtgg   11520
aggcgatcgt gcagaacccc agcagcaagc ccctgaccgc gcagctgttc ctggtggtgc   11580
agcacagcag ggacaacgag gccttcaggg aggcgctgct gaacatcacc gagccggagg   11640
ggcgctggct cctggacctg ataaacatcc tgcagagcat agtggtgcag gagcgcagcc   11700
tgagcctggc cgagaaggtg gcggccatca actactctat gctgagcctg ggcaagttct   11760
acgcccgcaa gatctacaag accccctacg tgcccataga caaggaggtg aagatagaca   11820
gcttctacat gcgcatggcg ctgaaggtgc tgaccctgag cgacgacctg ggagtgtacc   11880
gcaacgagcg catccacaag gccgtgagcc ccagccggcg gcgcgagctg agcgaccgcg   11940
agctgatgca cagtctgcag cgcgcgctga ccggcgcggg cgagggcgac agggaggtcg   12000
agtcctactt cgacatgggg gccgacctgc actggcagcc gagccgccgc gccctggagg   12060 cggcggggc  gtacggcggc cccctggcgg ccgatgacca ggaagaggag gactatgagc   12120
tagaggaggg cgagtacctg gaggactgac ctggctggtg gtgttttggt atagatgcaa   12180
gatccgaacg tggcggaccc ggcggtccgg gcggcgctgc aaagccagcc gtccggcatt   12240
aactcctctg acgactgggc cgcggccatg ggtcgcatca tggccctgac cgcgcgcaac   12300
cccgaggctt tcaggcagca gcctcaggcc aaccggctgg cggccatctt ggaagcggta   12360
gtgcccgcgc gctccaaccc cacccacgag aaggtgctgg ccatagtcaa cgcgctggcg   12420
gagagcaggg ccatccgcgc ggacgaggcc ggactggtgt acgatgcgct gctgcagcgg   12480
gtggcgcggt acaacagcgg caacgtgcag accaacctgg accgcctggt gacggacgtg   12540 cgcgaggcc  tggcgcagcg cgagcgcttg catcaggacg gtaacctggg ctcgctggtg   12600
gcgctaaacg ccttcctcag cacccagccg gccaacgtac cgcgggggca ggaggactac   12660
accaactttt tgagcgcgct gcggctgatg gtgaccgagg tccctcagag cgaggtgtac   12720
cagtcggggc ccgactactt cttccagacc agcagacagg gcttgcaaac cgtgaacctg   12780
agccaggctt tcaagaacct gcgggggctg tggggagtga aggcgcccac cggcgaccgg   12840
gctacggtgt ccagcctgct aaccccccaac tcgcgcctgc tgctgctgct gatcgcgccc   12900
ttcacggaca gcgggagcgt ctcgcgggag acctatctgg gccacctgct gacgctgtac   12960
cgcgaggcca tcgggcaggc gcaggtggac gagcacacct tccaagagat caccagcgtg   13020
agccacgcgc tggggcagga ggacacgggc agcctgcagg cgaccctgaa ctacctgctg   13080
```

```
accaacaggc ggcagaagat tcccacgctg cacagcctga cccaggagga ggagcgcatc   13140
ttgcgctacg tgcagcagag cgtgagcctg aacctgatgc gcgacggcgt gacgcccagc   13200
gtggcgctgg acatgaccgc gcgcaacatg gaaccgggca tgtacgcctc ccaccggccg   13260
ttcatcaacc gcctgatgga ctacttgcat cgggcggcgg ccgtgaaccc cgagtacttc   13320
actaatgcca ttctgaatcc ccactggatg cccccctccgg gtttctacaa cggggacttt   13380
gaggtgcccg aggtcaacga cgggttcctc tgggatgaca tggatgacag tgtgttctca   13440
cccaacccgc tgcgcgccgc gtctctgcga ttgaaggagg gctctgacag ggaaggaccg   13500
agaagtctgg cctcctccct ggctctggga gcggtgggcg ccacgggcgc ggcggcgcgg   13560
ggcagtagcc ccttccccag cctggcagac tctctgaaca gcgggcgggt gagcaggccc   13620
cgcttgctag gcgaggagga gtatctgaac aactccctgc tgcagcccgc gagggacaag   13680
aacgctcagc ggcagcagtt tcccaacaat gggatagaga gcctggtgga caagatgtcc   13740
agatggaaga cgtatgcgca ggagtacaag gagtgggagg accgccagcc gcggcccttg   13800
ccgcccccta ggcagcgctg gcagcggcgc gcgtccaacc gccgctggag gcaggggccc   13860
gaggacgatg atgactctgc agatgacagc agcgtgttgg acctgggcgg gagcgggaac   13920 ccctttttcgc acctgcgccc acgcctgggc aagatgtttt aaaagaaaaa aaaaaaataa   13980
aactcaccaa ggccatggcg acgagcgttg gttttttgtt cccttcctta gtatgcggcg   14040
cgcggcgatg ttcgaggagg ggcctccccc ctcttacgag agcgcgatgg ggatttctcc   14100
tgcggcgccc ctgcagcctc cctacgtgcc tcctcggtac ctgcaaccta cagggggag   14160 aaatagcatc tgttactctg agctgcagcc cctgtacgat accaccagac tgtacctggt   14220
ggacaacaag tccgcggacg tggcctccct gaactaccag aacgaccaca gcgatttttt   14280
gaccacggtg atccaaaaca acgacttcac cccaaccgag gccagcactc agaccataaa   14340
cctggataac aggtcgaact ggggcggcga cctgaagacc atcttgcaca ccaacatgcc   14400
caacgtgaac gagttcatgt tcaccaactc ttttaaggcg cgggtgatgg tggcgcgcga   14460
gcagggggag gcgaagtacg agtgggtgga cttcacgctg cccgagggca actactcaga   14520
gaccatgact ctcgacctga tgaacaatgc gatcgtggaa cactatctga agtgggcag   14580 gcagaacggg gtgaaggaaa gcgatatcgg ggtcaagttt gacaccagaa acttccgtct   14640
gggctgggac cccgtgaccg ggctggtcat gccgggggtc tacaccaacg aggccttttca   14700 tcccgacata gtgcttctgc ccggctgtgg ggtggacttc acccagagcc ggctgagcaa   14760
cctgctgggc attcgcaagc ggcagccttt ccaggagggt ttcaagatca cctatgagga   14820
tctgaagggg ggcaacattc ccgcgctcct tgatctggac gcctacgagg agagcttgaa   14880
acccgaggag agcgctggcg acagcggcga gagtggcgag gagcaagccg gcggcggtgg   14940
cggcgcgtcg gtagaaaacg aaagtacgcc cgcagtggcg gcggacgctg cggaggtcga   15000 gccgaggcc atgcagcagg acgcagagga gggcgcacag gagggcgcgc agaaggacat   15060
gaacgatggg gagatcaggg gagacacatt cgccacccgg ggcgaagaaa agaggcaga   15120 ggcggcggcg gcggcgacgg cggaggccga aaccgaggtt gaggcagagg cagagcccga   15180
gaccgaagtt atgaagaca tgaatgatgg agaacgtagg ggcgacacgt tcgccacccg   15240
gggcgaagag aaggcggcgg aggcagaagc cgcggctgag gaggcggctg cggctgcggc   15300
caagactgag gctgcggcta aggctgaggt cgaagccaat gttgcggttg aggctcaggc   15360
tgaggaggag gcggcggctg aagcagttaa ggaaaaggcc caggcagagc aggaagagaa   15420
aaaacctgtc attcaaccctc taaaagaaga tagcaaaaag cgcagttaca acgtcatcga   15480
```

```
gggcagcacc tttacccagt accgcagctg gtacctggcg tacaactacg gcgacccggt   15540 caaggggggtg cgctcgtgga ccctgctctg cacgccggac gtcacctgcg gctccgagca   15600
gatgtactgg tcgctgccga acatgatgca agacccggtg accttccgct ccacgcggca   15660
ggttagcaac ttcccggtgg tgggcgccga actgctgccc gtgcactcca agagttttta   15720
caacgagcag gccgtctact cccagctgat ccgccaggcc acctctctga cccacgtgtt   15780
caatcgcttt cccgagaacc agattttggc gcgcccgccg gccccacca tcaccaccgt   15840 gagtgaaaac gttcctgccc tcacagatca cgggacgcta ccgctgcgca acagcatctc   15900
aggagtccag cgagtgacca ttactgacgc cagacgccgg acctgcccct acgtttacaa   15960
ggccttgggc atagtctcgc cgcgcgtcct ctccagtcgc acttttaaa acacatctac   16020 ccacacgttc caaaatcatg tccgtactca tctcacccag caacaacacc ggctggggggc   16080 tgcgcgcgcc cagcaagatg tttggagggg cgaggaagcg ctccgaccag caccctgtgc   16140
gcgtgcgcgg ccactaccgc gcgccctggg gagcgcacaa gcgcgggcgc acagggcgca   16200
ccactgtgga cgacgtcatt gactccgtag tggagcaagc gcgccactac acacccggcg   16260
cgccgaccgc ccccgccgtg tccaccgtgg accaggcgat cgaaagcgtg gtacagggcg   16320
cgcggcacta tgccaacctt aaaagtcgcc gccgccgcgt ggcccgccgc catcgccgga   16380
gaccccgggc caccgccgcc gcgcgcctta ctaaggctct gctcaggcgc gccaggcgaa   16440
ctggccaccg ggccgccatg agggccgcac ggcgggctgc cgctgccgca agcgccgtgg   16500
ccccgcgggc acgaaggcgc gcggccgccg ccgccgccgc cgccatttcc agcttggcct   16560
cgacgcggcg cggtaacata tactgggtgc gcgactcggt aaccggcacg cgggtacccg   16620
tgcgctttcg ccccccgcgg aattagcaca agacaacata cacactgagt ctcctgctgt   16680
tgtgtatccc agcggcgacc gtcagcagcg gcgacatgtc caagcgcaaa attaaagaag   16740
agatgctcca ggtcatcgcg ccggagatct atgggccccc gaagaaggag gaggatgatt   16800
acaagccccg caagctaaag cgggtcaaaa agaaaaagaa agatgatgat gatgacgagg   16860
cggtggagtt tgtccgccgc atggcaccca ggcgccccgt gcagtggaag gccggcgcg   16920 tgcagcgcgt tttgcgcccc ggcaccgcgg tggtcttcac gcccggcgag cgctccacgc   16980
gcactttcaa gcgggtgtac gatgaggtgt acggcgacga ggacctgttg gagcaggcca   17040
accagcgctt tgggggagttt gcatatggga acggccccg cgagagtcta aaagaggacc   17100
tgctggcgct accgctggac gagggcaatc ccaccccgag tctgaagccg gtaaccctgc   17160
aacaggtgct gcctttgagc gcgcccagcg agcataagcg agggttgaag cgcgaaggcc   17220
gggacctggc gccccaccgtg cagttgatgg tgcccaagcg gcagaagctg gaggacgtgc   17280
tggagaaaat gaaagtagag cccggggatcc agcccgagat caaggtccgc cccatcaagc   17340
aggtggcgcc cggcgtggga gtccagaccg tggacgttag gattcccacg gaggagatgg   17400
aaacccaaac cgccactccc tcttcggcgg ccagcgccac caccggcacc gcttcggtag   17460
aggtgcagac ggaccctgg ctacccgcca ccgctgttgc cgccgccgcc cccgttcgc   17520 gcgggcgcaa gagaaattat ccagcggcca gcgcgctcat gccccagtac gcactgcatc   17580
catccatcgc gcccaccccc ggctaccgcg ggtactcgta ccgcccgcgc agatcagccg   17640
gcactcgcgg ccgccgccgc cgtgcgacca caaccagccg ccgccgtcgc cgccgccgcc   17700
agccagtgct gaccccgtg tctgtaagga aggtggctcg ctcggggagc acgctggtgg   17760
tgcccagagc gcgctaccac cccagcatcg tttaaagccg gtctctgtat ggttcttgca   17820
```

```
gatatggccc tcacttgtcg cctccgcttc ccggtgccgg gataccgagg aagaactcac  17880
cgccgcagag gcatggcggg cagcggtctc cgcggcggcc gtcgccatcg ccggcgcgca  17940
aaaagcaggc gcatgcgcgg cggtgtgctg cctctgctaa tcccgctaat cgccgcggcg  18000
atcggtgccg tacccgggat cgcctccgtg gccctgcagg cgtcccagaa acgttgactc  18060
ttgcaacctt gcaagcttgc attttttgga ggaaaaataa aaaagtcta gactctcacg  18120 ctcgcttggt cctgtgacta ttttgtagaa aaaagatgga agacatcaac tttgcgtcgc  18180
tggccccgcg tcacggctcg cgcccgttca tgggagactg gacagatatc ggcaccagca  18240
atatgagcgg tggcgccttc agctggggca gtctgtggag cggccttaaa aattttggtt  18300
ccaccattaa gaactatggc aacaaagcgt ggaacagcag cacgggccag atgctgagag  18360
acaagttgaa agagcagaac ttccaggaga aggtggcgca gggcctggcc tctggcatca  18420
gcggggtggt ggacatagct aaccaggccg tgcagaaaaa gataaacagt catctggacc  18480
cccgtcctca ggtggaggaa atgcctccag cgatggagac ggtgtctccc gagggcaaag  18540
gcgaaaagcg cccgcggccc gacagagaag agacctggt gtcacacacc gaggagccgc  18600
cctcttacga ggaggcagtc aaggccggcc tgcccaccac tcgccccata gcccccatgg  18660
ccaccggtgt ggtgggccac aggcaacaca ctcccgcaac actagatctg ccccgccgt  18720 ccgagccgcc gcgccagcca aaggcggcga cggtgcccgc tccctccact tccgccgcca  18780
acagagtgcc cctgcgccgc gccgagcg ccccgggc ctcgcgagtt agcggcaact  18840
ggcagagcac actgaacagc atcgtgggcc tgggagtgag gagtgtgaag cgccgccgtt  18900
gctactgaat gagcaagcta gctaacgtgt tgtatgtgtg tatgcgtcct atgtcgccgc  18960
cagaggagct gttgagccgc cggcgccgtc tgcactccag cgaatttcaa gatggcgacc  19020
ccatcgatga tgcctcagtg gtcgtacatg cacatctcgg gccaggacgc ttcggagtac  19080
ctgagccccg ggctggtgca gttcgcccgc gccacagaca cctacttcaa catgagtaac  19140
aagttcagga accccactgt ggcgcccacc cacgatgtga ccacggaccg gtcgcagcgc  19200
ctgacgctgc ggttcatccc cgtggatcgg gaggacaccg cctactctta caggcgcgg  19260 ttcacgctgg ccgtgggcga caaccgcgtg ctggacatgg cctccactta ctttgacatc  19320
aggggggtgc tggacagggg ccccaccttc aagccctact cgggtactgc ctacaactcc  19380
ctggccccca agggcgctcc caattcttgc gagtgggaac aagaggaaaa tcaggtggtc  19440
gctgcagatg atgaacttga agatgaagaa gcgcaagctc aagaggacgc cccagctaaa  19500
aaaattcatg tatatgccca ggcgcctctt gctggcgaaa agattaccaa ggatggtttg  19560
caaataggta ctgaagttgt aggagataca tctaaggaca cttttgcaga caaaacattc  19620
caacccgaac ctcagatagg cgagtctcag tggaacgagg ctgatgccac agtagcagga  19680
ggcagagtct tgaaaaaaac caccccctatg agaccttgct atggatccta tgccaggcct  19740
acaaatgcca acgggggtca aggaattatg gttgccaatg aacaaggagt gttggagtct  19800
aaagtggaga tgcaattttt ttctaacact acaacccctta atgcgcggga tggagctggc  19860
aatcccgaac caaggtggt gttgtacagt gaagatgtcc acttggaatc tcctgacact  19920
catttgtctt acaagcccaa aaaggatgat gttaatgcta aaattatgtt gggtcagcaa  19980
gctatggcta acaggcccaa cctcattgct tttagagata atttcattgg actcatgtac  20040
tacaacagca ctggtaacat gggagtgctg gcgggtcagg cctctcagtt gaatgccgtg  20100
gtggacctgc aggatagaaa cacagaactg tcatatcagc ttatgcttga ttccattggg  20160
gatagatcca gatacttctc catgtggaac caggcagtgg atagctatga cccagatgtc  20220
```

```
agaatcattg aaaaccatgg tgtcgaggac gagctaccca actactgctt ccctctgggc   20280
ggcataggaa ttactgatac ttatcaaggg atcaaaaata ccaatggcaa tggtcagtgg   20340
accaaagatg atcagttcgc ggaccgtaat gaaatagggg tgggaaacaa cttcgccatg   20400
gagatcaaca tccaggccaa cctctggagg aacttcctct atgcgaacgt ggggctctac   20460
ctgccagaca agctcaagta caaccccacc aacgtggaca tctctgacaa ccccaacacc   20520
tatgactaca tgaacaagcg tgtggtggct cccggcctgg tggactgctt tgtcaatgtg   20580
ggagccaggt ggtccctgga ctacatggac aacgtcaacc ccttcaacca ccaccgcaat   20640
gcgggtctgc gctaccgctc catgatcctg ggcaacgggc gctacgtgcc cttccacatt   20700
caggtgcccc agaagttctt tgccatcaag aacctcctcc tcctgccggg ctcctacact   20760
tacgagtgga acttcaggaa ggatgtcaac atggtcctgc agagctctct gggcaatgac   20820
cttagggtgg acggggccag catcaagttt gacagcgtca ccctctatgc taccttcttc   20880
cccatggctc acaacaccgc ctccacgctc gaggccatgc tgaggaacga caccaacgac   20940
cagtccttca tgactacct ctctgggcc aacatgctct accccatccc cgccaaggcc   21000
accaacgtgc ccatctccat tccctctcgc aactgggccg ccttcagagg ctgggccttt   21060
acccgcctta agaccaagga aaccccctcc ctgggctcgg ttttgaccc ctactttgtc   21120 tactcgggat ccatcccta cctggatggc accttctacc tcaaccacac ttttaagaag   21180
atatccatca tgtatgactc ctccgtcagc tggccgggca atgaccgcct gctcaccccc   21240
aatgagttcg aggtcaagcg cgccgtggac ggcgagggct acaacgtggc ccagtgcaac   21300
atgaccaagg actggttcct ggtgcagatg ctggccaact acaacatagg ctaccagggc   21360
ttctacatcc cagagagcta caaggacagg atgtactcct tcttcagaaa tttccaaccc   21420
atgagcaggc aggtggtgga cgagaccaaa tacaaggact atcaggccat ggcatcact   21480 caccagcaca caactcggg attcgtgggc tacctggctc ccaccatgcg cgaggggcag   21540
gcctaccccg ccaacttccc ctacccgttg ataggcaaga ccgcggtcga cagcgtcacc   21600
cagaaaaagt tcctctgcga ccgcacctc tggcgcatcc ccttctctag caacttcatg   21660
tccatgggtg cgctcacgga cctgggccag aacctgctct atgccaactc cgcccatgcg   21720
ctggacatga cttttgaggt ggaccccatg gacgagccca cccttctcta tattgtgttt   21780
gaagtgttcg acgtggtcag agtgcaccag ccgcaccgcg tgtcatcga ccgtgtac   21840 ctgcgcacgc ccttctcggc cggcaacgcc accacctaag agacagcgc cgccgcctgc   21900 atgacgggtt ccaccgagca agagctcagg gccatcgcca gagacctggg atgcggaccc   21960
tattttttgg gcacctatga caaacgcttc ccgggcttca tctcccgaga caagctcgcc   22020
tgcgccatcg tcaacacggc cgcgcgcgag accgggggcg tgcactggct ggcctttggc   22080
tgggacccgc gctccaaaac ctgctacctc ttcgacccct tggcttctc cgatcagcgc   22140 ctcagacaga tctatgagtt tgagtacgag gggctgctgc ccgcagcgc gcttgcctcc   22200 tcgcccgacc gctgcatcac ccttgagaag tccaccgaga ccgtgcaggg gccccactcg   22260
gccgcctgcg gtctcttctg ctgcatgttt ttgcacgcct ttgtgcgctg gccccagagt   22320
cccatggatc gcaaccccac catgaacttg ctcaaggag tgcccaacgc catgctccag   22380
agcccccagg tccagcccac cctgcgccac aaccaggaac agctctaccg cttcctggag   22440
cgccactccc cctacttccg cagtcacagc gcgcacatcc gggggccac ctctttctgc   22500 cacttgcaac aaaacatgca agacggaaaa tgatgtacag ctcgctttt aataaatgta   22560
```

```
aagactgtgc actttatttta tacacgggct ctttctggtt atttattcaa caccgccgtc   22620
gccatctaga aatcgaaagg gttctgccgc gcgtcgccgt gcgccacggg cagagacacg   22680
ttgcgatact ggaagcggct cgcccacttg aactcgggca ccaccatgcg gggcagtggc   22740
tcctcgggga agttctcgcc ccacaggdtg cgggtcagct gcagcgcgct caggaggtcg   22800
ggagccgaga tcttgaagtc gcagttgggg ccggaaccct gcgcgcgcga gttgcggtac   22860
acggggttgc agcactggaa caccagcagg gccggattac gcacgctggc cagcaggctc   22920
tcgtcgctga tcatgtcgct gtccagatcc tccgcgttgc tcagggcgaa tggggtcatc   22980
ttgcagacct gcctgcccag gaaaggcggc agcccgggct tgccgttgca gtcgcagcgc   23040
aggggcatca gcaggtgccc gtggcccgtc tgcgcctgcg ggtacagcgc gcgcatgaag   23100
gcttcgatct gcctgaaagc cacctgcgtc ttggctccct ccgaaaagaa catcccacag   23160
gacttgctgg agaactggtt cgcgggacag ctggcatcgt gcaggcagca gcgcgcgtcg   23220
gtgttggcga tctgcaccac gttgcgaccc caccggttct tcactatctt ggccttggaa   23280
gcctgctcct tcagcgcgcg ctggccgttc tcgctggtca catccatctc tatcacctgc   23340
tccttgttga tcatgtttgt cccgtgcaga cacttcaggt cgccctccgt ctgggtgcag   23400
cggtgctccc acagcgcgca accggtgggc tcccaatttt tgtgggtcac cccgcgtag   23460 gcctgcaggt aggcctgcaa gaagcgcccc atcatggcca caaaggtctt ctggctcgta   23520
aaggtcagct gcaggccgcg atgctcttcg ttcagccagg tcttgcagat ggcggccagc   23580
gcctcggtct gctcgggcag catcctaaaa tttgtcttca ggtcgttatc cacgtggtac   23640
ttgtccatca tggcgcgcgc cgcctccatg cccttctccc aggcggacac catgggcagg   23700
cttagggggt ttatcacttc caccggcgag gacaccgtac tttcgatttc ttcttcctcc   23760
ccctcttccc ggcgcgcgcc cacgctgctg cgcgctctca ccgcctgcac caaggggtcg   23820
tcttcaggca agcgccgcac cgagcgcttg ccgcccttga cctgcttaat cagcaccggc   23880
gggttgctga agcccaccat ggtcagctcc gcctgctctt cttcgtcttc gctgtctacc   23940
actatctctg gggaagggct ctccgctct cggcggtgc gcttcttttt tttcttggga   24000
gcagccgtga cggagtccgc cacggcgacg gaggtcgagg gcgtggggct gggggtgcgc   24060
ggtaccaggg cctcgtcgcc ctcggactct tcctctgact ccaggcggcg gcggagacgc   24120
ttctttgggg gcgcgcgcgt cagcggcggc ggagacgggg acgggacgg ggacgggacg   24180 ccctccacag ggggtggtct tcgcgcagac ccgcggccgc gctcgggggt cttttcgagc   24240
tggtcttggt cccgactggc cattgtatcc tcctcctcct aggcagagag acataaggag   24300
tctatcatgc aagtcgagaa ggaggagagc ttaaccaccc cctctgagac cgccgatgcg   24360
cccgccgtcg ccgtcgcccc cgctgccgcc gacgcgcccg ccacccgag cgacaccccc   24420 gcggaccccc cagccgacgc acccctgttc gaggaagcgg ccgtggagca ggacccgggc   24480
tttgtctcgg cagaggagga tttgcgagag gaggaggata aggagaagaa gccctcagtg   24540
ccaaaagatg ataaagagca agacgagcac gacgcagatg cacaccaggg tgaagtcggg   24600
cggggggacg gagggcatga cggcgccgac tacctagacg aagggaacga cgtgctcttg   24660
aagcacctgc atcgtcagtg cgccatcgtt tgcgacgctc tgcaggagcg cagcgaagtg   24720
cccctcagcg tggcggaggt cagccacgcc tacgagctca gcctcttctc ccccgggtg   24780 ccccccccgcc gccgcgaaaa cggcacatgc gagcccaacc cgcgcctcaa cttctacccc   24840
gcctttgtgt tgcccgaggt cctggccacc tatcacatct tctttcaaaa ttgcaagatc   24900
cccctctcgt gccgcgccaa ccgtagccgc gccgataaga tgctggccct gcgccagggc   24960
```

| | | |
|---|---|---|
| gaccacatac ctgatatcgc cgctttggaa gatgtgccaa agatcttcga gggtctgggt | 25020 |
| cgcaacgaga agcgggcagc aaactctctg caacaggaaa acagcgaaaa tgagagtcac | 25080 |
| accgggtac tggtggagct cgagggcgac aacgcccgcc tggcggtggt caagcgcagc | 25140 |
| atcgaggtca cccactttgc ctaccccgcg ctcaacctgc cccccaaagt catgaacgcg | 25200 |
| gccatggacg ggctgatcat gcgccgcggc cggcccctcg ctccagatgc aaacttgcat | 25260 |
| gaggagaccg aggacggcca gcccgtggtc agcgacgagc agctggcgcg ctggctggag | 25320 |
| accgcggacc ccgccgaact ggaggagcgg cgcaagatga tgatggccgc ggtgctggtc | 25380 |
| accgtagagc tggagtgtct gcagcgcttc ttcggcgacc ccgagatgca gagaaaggtc | 25440 |
| gaggagaccc tgcactacac cttccgccag ggctacgtgc gccaggcttg caagatctcc | 25500 |
| aacgtgagc tcagcaacct ggtgtcctac ctgggcatct tgcatgagaa ccgcctcggg | 25560 |
| cagagcgtgc tgcactccac cctgcgcggg gaggcgcgcc gcgactacgt gcgcgactgc | 25620 |
| gtttacctct tcctctgcta cacctggcag acggccatgg gggtctggca gcagtgcctg | 25680 |
| gaggagcgca acctcaagga gctggagaag ctcctgcagc gcgcgctcaa agacctctgg | 25740 |
| acgggctaca acgagcgctc ggtggccgcc gcgctggccg acctcatctt ccccgagcgc | 25800 |
| ctgctcaaaa ccctccagca ggggctgccc gacttcacca gccaaagcat gttgcaaaac | 25860 |
| ttcaggaact ttatcctgga gcgttctggc atcctacccg ccacctgctg cgccctgccc | 25920 |
| agcgactttg tccccctcgt gtaccgcgag tgccccccgc cgctgtgggg tcactgctac | 25980 |
| ctgttccaac tggccaacta cctgtcctac cacgcggacc tcatggagga ctccagcggc | 26040 |
| gagggctca tggagtgcca ctgccgctgc aacctctgca cgccccaccg ctccctggtc | 26100 |
| tgcaacaccc aactgctcag cgagagtcag attatcggta ccttcgagct acagggtccg | 26160 |
| tcctcctcag acgagaagtc cgcggctccg ggctaaaac tcactccggg gctgtggact | 26220 |
| tccgcctacc tgcgcaaatt tgtacctgaa gactaccacg cccacgagat caggttttac | 26280 |
| gaagaccaat cccgcccgcc caaggcggag ctgaccgcct gcgtcatcac ccagggcgag | 26340 |
| atcctaggcc aattgcaagc catccaaaaa gcccgccaag atttttttgct gagaaagggt | 26400 |
| cgggggggtgt atctggaccc ccagtcgggt gaggagctca accggttcc cccgctgccg | 26460 |
| ccgccgcggg accttgcttc ccaggataag catcgccatg gctcccagaa agaagcagca | 26520 |
| gcggccgcca ctgccgccac cccacatgct ggaggaagag gaggaatact gggacagtca | 26580 |
| ggcagaggag gtttcggacg aggaggagcc ggagacggag atggaagagt gggaggagga | 26640 |
| cagcttagac gaggaggctt ccgaagccga agaggcagag gcaacaccgt cacccctcgg | 26700 |
| cgcagccccc tcgcaggcgc ccccgaagtc cgctcccagc atcagcagca acagcagcgc | 26760 |
| tataacctcc gctcctccac cgccgcgacc cacgccgac cgcagaccca accgtagatg | 26820 |
| ggacaccacc ggaaccgggg ccggtaagtc ctccgggaga ggcaagcaag cgcagcgcca | 26880 |
| aggctaccgc tcgtggcgcg ctcacaagaa cgccatagtc gcttgcttgc aagactgcgg | 26940 |
| ggggaacatc tccttcgccc gccgcttcct gctcttccac cacggtgtgg ccttcccccg | 27000 |
| taacgtcctg cattactacc gtcatctcta cagcccctac tgcggcggca gtgagccaga | 27060 |
| gacggtcggc ggcggcggcg gcgcccgttt cggcgcctag gaagacccag ggcaagactt | 27120 |
| cagccaagaa actcgcggcg gccgcggcga acgcggtcgc gggggccctg cgcctgacgg | 27180 |
| tgaacgaacc cctgtcgacc cgcgaactga gaaaccgaat cttccccact ctctatgcca | 27240 |
| tcttccagca gagcagaggg caggatcagg aactgaaagt aaaaaacagg tctctgcgct | 27300 |

```
ccctcacccg cagctgtctg tatcacaaga gcgaagacca gcttcggcgc acgctggagg    27360
acgctgaggc actcttcagc aaatactgcg cgctcactct taaggactag ctccgcgccc    27420
ttctcgaatt taggcgggaa cgcctacgtc atcgcagcgc cgccgtcatg agcaaggaca    27480
ttcccacgcc atacatgtgg agctatcagc cgcagatggg actcgcggcg ggcgcctccc    27540
aagactactc cacccgcatg aactggctca gtgccggccc acacatgatc tcacaggtta    27600
atgatatccg cacccatcga aaccaaatat tggtggagca ggcggcaatt accaccacgc    27660
cccgcaataa tcccaacccc agggagtggc ccgcgtccct ggtgtatcag gaaattcccg    27720
gccccaccac cgtactactt ccgcgtgatt cccaggccga agtccaaatg actaactcag    27780
gggcgcagct cgcgggcggc tgtcgtcaca gggtgcggcc tcctcgccag ggtataactc    27840
acctggagat ccgaggcaga ggtattcagc tcaacgacga gtcggtgagc tcctcgctcg    27900
gtctaagacc tgacgggacc ttccagatag ccggagccgg ccgatcttcc ttcacgcccc    27960
gccaggcgta cctgactctg cagagctcgt cctcggcgcc gcgctcgggc ggcatcggga    28020
ctctccagtt cgtgcaggag tttgtgccct cggtctactt caaccccttc tcgggctctc    28080
ccggtcgcta cccggaccag ttcatctcga actttgacgc cgcgagggac tcggtggacg    28140
gctacgactg aatgtcgggt ggacccggtg cagagcaact tcgcctgaag cacctcgacc    28200
actgccgccg ccctcagtgc tttgcccgct gtcagaccgg tgagttccag tacttttccc    28260
tgcccgactc gcacccggac ggccggcgc acggggtgcg cttttcatc ccgagtcagg    28320 tgcgctctac cctaatcagg gagtttaccg cccgtcccct actggcggag ttggaaaagg    28380
ggccttctat cctaaccatt gcctgcatct gctctaaccc tggattgcac caagatcttt    28440
gctgtcattt gtgtgctgag tataataaag gctgagatca gaatctactc gggctcctgt    28500
cgccatcctg tcaacgccac cgtccaagcc cggcccgatc agcccgaggt gaacctcacc    28560
tgcggtctgc accggcgcct gaggaaatac ctagcttggt actacaacag cactcccttt    28620
gtggtttaca acagctttga ccaggacggg gtctcactga gggataacct ctcgaacctg    28680
agctactcca tcaggaagaa cagcacccctc gagctacttc ctccttacct gcccgggact    28740
taccagtgtg tcaccggtcc ctgcacccac acccacctgt tgatcgtaaa cgactctctt    28800
ccgagaacag acctcaataa ctcctcttcg cagttcccca gaacaggagg tgagctcagg    28860
aaacccgggg taagaagggg tggacaagag ttaacacttg tggggtttct ggtgtatgtg    28920
acgctggtgg tggctctttt gattaaggct tttccttcca tgtctgaact ctccctcttt    28980
tatgaacaac tcgactagtg ctaacgggac cctacccaac gaatcgggat tgaatatcgg    29040
taaccaggtt gcagtttcac ttttgattac cttcatagtc ctcttcctgc tagtgctgtc    29100
gcttctgtgc ctgcggatcg ggggctgctg catccacgtt tatatctggt gctggctgtt    29160
tagaaggttc ggagaccatc gcaggtagaa taaacatgct gctgcttacc ctctttgtcc    29220
tggcgctggc cgccagctgc caagcctttt ccgaggctga cttatagag ccccagtgta    29280 acgtgacttt taaagcccat gcacagcgtt gtcatactat aatcaaatgt gccaccgaac    29340
acgatgaata ccttatccag tataaagata aatcacacaa agtggcactt gttgacatct    29400
ggaaacccga agacccttg gaatacaatg tgaccgtttt ccagggtgac ctcttcaaaa    29460
tttacaatta cactttccca tttgaccaga tgtgtgactt tgtcatgtac atggaaaagc    29520
agcacaagct gtggcctccg actccccagg gctgtgtgga aaatccaggc tctttctgca    29580
tgatctctct ctgtgtaact gtgctggcac taatactcac gcttttgtat atcagattta    29640
aatcaaggca aagcttcatc gatgaaaaga aaatgcctta aacgctttca cgcttgattg    29700
```

```
ctaacaccgg gttttatcc gcagaatgat tggaatcacc ctactaatca cctccctcct    29760
tgcgattgcc catgggttgg aacgaatcga agccctgtg ggggccaatg ttaccctggt    29820
ggggcctgtc ggcaatgcta cattaatgtg ggaaaaatat actaaaaatc aatgggtctc    29880
ttactgcact aacaaaaaca gccacaagcc cagagccatc tgcgatgggc aaaatctaac    29940
cttgattgat gttcaaatgc tggatgcggg ctactattat gggcagctgg gtacaatgat    30000
taattactgg agaccccaca agattacat gctccacgta gtaaagggtc cccttagcag     30060
cccacccact accacctcta ctaccccac taccaccact actcccacca ccagcactgc     30120
cgcccagcct cctcatagca gaacaaccac ttttatcaat tccaagtccc actcccccca    30180
cattgccggc gggccctccg cctcagactc cgagaccacc gagatctgct tctgcaaatg    30240
ctctgacgcg tttgctgagg atttggaaga ccacgaggaa gatgagcatg acttcgcaga    30300
tgcatgccag gcatcagagg cagaagcgct gccggtggcc ctcaaacagt atgcagaccc    30360
ccacaccacc cccaaccttc ctccaccttc ccagaagcca agtttcctgg gggaaaatga    30420
aactctgcct ctctccatac tcgctctgac atctgttgct atgttgaccg ctctgctggt    30480
gcttctatgc tctatatgct acctgatctg ctgcagaaag aaaaaatctc acggccatgc    30540
tcaccagccc ctcatgcact tcccttaccc tccagagctg ggcgaccaca aactttaagt    30600
ctgcagtaac tatctgccca tcccttgtca gtcgacagcg atgagcccca ctaatctaac    30660
ggcctctgga cttacaacat cgtctcttaa tgagaccacc gctcctcaag acctgtacga    30720
tggtgtctcc gcgctggtta accagtggga tcacctgggc atatggtggc tcctcatagg    30780
agcagtgacc ctgtgcctaa tcctggtctg gatcatctgc tgcatcaaaa gcagaagacc    30840
caggcggcgg cccatctaca ggccctttgt catcacacct gaagatgatg atgacaccac    30900
ttccaggctg cagaggctaa agcagctact cttctctttt acagcatggt aaattgaatc    30960
atgcctcgca ttttcatcta cttgtctctc cttccacttt ttctgggctc ttctacattg    31020
gccgctgtgt cccacatcga ggtagactgc ctcacgccct tcacagtcta cctgcttttc    31080
ggctttgtca tctgcacctt tgtctgcagc gttatcactg tagtgatctg cttcatacag    31140
tgcatcgact acgtctgcgt gcgggtggct tactttagac accacccca gtatcgcaac    31200 agggacatag cggctctcct aagacttgtt taaaatcatg gccaaattaa ctgtgattgg    31260
tcttctgatc atctgctgcg tcctagccgc gattgggact caagctccta ccaccaccag    31320
cgctcccaga aagagacatg tatcctgcag cttcaagcgt ccctggaata tacccaatg     31380 ctttactgat gaacctgaaa tctctttggc ttggtacttc agcgtcaccg cccttcttat    31440
cttctgcagt acggttattg cccttgccat ctaccccttcc cttgacctgg ctggaatgc     31500 tgtcaactct atggaatatc ccaccttccc agaaccagac ctgccagacc tggttgttct    31560
aaacgcgttt cctcctcctg ctcccgttca aaatcagttt cgccctccgt ccccacgcc     31620 cactgaggtc agctactta atctaacagg cggagatgac tgaaaaccta gacctagaaa    31680
tggacggtct ctgcagcgag caacgcacac tagagaggcg ccggcaaaaa gagctcgagc    31740
gtcttaaaca agagctccaa gacgcggtgg ccatacacca gtgcaaaaaa ggtgtcttct    31800
gtctggtaaa acaggccacg ctcacctatg aaaaacagg tgcacccac cgcctaggat       31860 acaagctgcc cacacagcgc cagaagttcg ccctcatgat aggcgaacaa cccatcaccg    31920
tgacccagca ctccgtggag acagaaggct gcatacacgc tccctgtagg ggcgctgact    31980
gcctctacac cttgatcaaa accctctgcg gtctcagaga cctcatccct tttaattaat    32040
```

```
cataactgta atcaataaaa aatcacttac ttgaaatctg atagcaagcc tctgtccaat   32100
tttttcagca acacttcctt cccctcctcc caactctggt actctaggcg cctcctagct   32160
gcaaacttcc tccacagtct gaagggaatg tcagattcct cctcctgtcc ctccgcaccc   32220
acgatcttca tgttgttgca gatgaaacgc gcgagatcgt ctgacgagac cttcaacccc   32280
gtgtacccct acgataccga gatcgctccg acttctgtcc ctttccttac ccctcccttt   32340
gtgtcatccg caggaatgca agaaaatcca gctggggtgc tgtccctgca cttgtcagag   32400 cccccttacca cccacaatgg ggccctgact ctaaaaatgg ggggcggcct gaccctggac   32460
aaggaaggga atctcacttc ccaaaacatc accagtgtcg atcccctct caaaaaagc    32520 aagaacaaca tcagccttca gaccgccgca cccctcgccg tcagctccgg ggccctaaca   32580 cttttttgcca ctccccccct agcggtcagt ggtgacaacc ttactgtgca gtctcaggcc   32640
cctctcactt tggaagactc aaaactaact ctggccacca aaggacccct aactgtgtcc   32700
gaaggcaaac ttgtcctaga acagaggct cccctgcatg caagtgacag cagcagcctg    32760
ggccttagcg ttacggcccc acttagcatt aacaatgaca gcctaggact agacatgcaa   32820
gcgcccatta gctctcgaga tggaaaactg gctctaacag tggcggcccc cctaactgtg   32880
gtcgagggta tcaatgcttt ggcagtagcc acaggtaagg gtattgggct aaatgaaacc   32940
aacacacacc tgcaggcaaa actggtcgca cccctaggct ttgataccaa cggcaacatt   33000
aagctaagcg ttgcaggagg catgaggcta acaataaca cactgatact agatgtaaac    33060
tacccatttg aggctcaagg ccaactgagc ctaagagtgg gctcgggccc actatatgta   33120
gattctagta gtcataacct aaccattaga tgccttaggg gattgtatat aacatcttct   33180
aacaaccaaa acggtctaga agccaacatt aaactaacaa gaggccttgt gtatgacgga   33240
aatgccatag cagttaatgt tggcaaaggg ctggaataca gccctactga cacaacagaa   33300
aaacctatac agactaaaat aggtctaggc atggagtatg ataccgaggg agccatgatg   33360
acaaaactag gctctggact aagctttgac aattcaggag ccattgtagt gggaaacaaa   33420
aatgatgaca ggcttacttt gtggaccaca ccggacccat cgcccaactg tcagatctac   33480
tctgaaaaag atgctaaaact aaccttggta ctgactaaat gtggcagtca ggttgtaggc   33540
acagtatcta ttgccgctct taaaggtagc ctcgtgccaa tcactagtgc aatcagtgtg   33600
gttcaggtat acctaaggtt tgatgaaaat ggggtactaa tgagtaactc ttcacttaat   33660
ggcgaatact ggaattttag aaacggagac tcaactaatg gcacaccata tacaaacgca   33720
gtgggtttca tgcctaatct actggcctat cctaaaggtc aaactacaac tgcaaaaagt   33780
aacattgtca gccaggtcta catgaatggg gacgatacta aacccatgac atttacaatc   33840
aacttcaatg gccttagtga aacaggggat acccctgtta gtaaatattc catgacattc   33900
tcatggaggt ggccaaatgg aagctacata gggcacaatt ttgtaacaaa ctccttttacc   33960 ttctcctaca tcgcccaaga ataaagaaag cacagagatg cttgtttttg atttcaaaat   34020
tgtgtgcttt tatttatttt cagcttacag tatttccagt agtcattcaa ataaagctta   34080
atcaaactgc atgagaaccc ttccacatag cttaaattag caccagtgca aatggagaaa   34140
aatcaacata cctttttta tccagatatc agagaactct agtggtcagt tttccccac    34200 cctcccagct cacagaatac acagtccttt cccccggct ggctttaaac aacactatct   34260
cattggtaac agacatattc ttaggtgtaa taatccacac ggtctcttgg cgggccaaac   34320
gctggtcggt gatgttaata aactccccag gcagctcttt caagttcacg tcgctgtcca   34380
actgctgaag cgctcgcggc tccgactgcg cctctagcgg aggcaacggc aacacccgat   34440
```

```
ccttgatcta taaaggagta gagtcataat cccccataag aatagggcgg tgatgcagca   34500
acaaggcgcg cagcaactcc tgccgccgcc tctccgtacg gcaggaatgc aacggcgtgg   34560
tggtctcctc cgtgataatc cgcaccgctc gcagcatcag catcctcgtc ctccgggcac   34620
agcagcgcat cctgatctca ctgagatcgg cgcagtaagt gcagcacaaa accaagatgt   34680
tatttaagat cccacagtgc aaagcactgt acccaaagct catggcggga aggacagccc   34740
ccacgtgacc atcataccag atcctcaggt aaatcaaatg acgacctctc ataaacacgc   34800
tggacatgta catcacctcc ttgggcatgt gctgattcac cacctctcga taccacaagc   34860
atcgctgatt aattaaagac ccctcgagca ccatcctaaa ccaggaagcc agcacctgac   34920
cccccgccag gcactgcagg gaccccggtg aatcgcagtg gcagtgaaga ctccagcgct   34980
cgtagccgtg aacctagag ctggtcatta tatccacatt ggcacaacac agacacactt   35040
tcatacactt tttcatgatt agcagctcct ctctagtcag gaccatatcc caaggaatca   35100
cccactcttg aatcaaggta aatcccacac agcagggcag gcctctcaca taactcacgt   35160
tatgcatagt gagcgtgtcg caatctggaa ataccggatg atcttccatc accgaagccc   35220
gggtctccgt ctcaaaggga ggtaaacggt ccctcgtgta gggacagtgg cgggataatc   35280
gagatcgtgt tgaacgtaga gtcatgccaa agggaacagc ggacgtactc atatttcctc   35340
cagcagaacc aagtgcgcgc gtggcagcta tccctgcgtc ttctgtctcg ccgcctgccc   35400
cgttcggtgt agtagttgta atacagccac tccctgagac cgtcaaggcg ctccctggcg   35460
tccggatcta tgacaacacc gtcctgcagc gccgccctga tgacatccac caccgtagag   35520
tatgccaagc ccagccagga aatgcattca ctttgacagc gagagatagg aggagcgggg   35580
agagatggaa gaaccatgat agtaaagaga acttttattc caatcgatct tctaagatat   35640
caaagtggag atctataaga tgacactggt ctcctccgct gagtcgatca aaaataacag   35700
ctaaaccaca aacaacacga ttggtcaaat gctccacaag ggcctgcagc ataaaattgc   35760
ctcggaactc caccgcaagc ataacatcaa agccaccgcc tctatcgtga tcaagaataa   35820
aaaccccaca gctatccacc agacccatat agttttcatc tctccatcgt gaaaaaagat   35880
ttacaagctc ctcctttaaa tcacctccaa ccaattgaaa aagttgaacc agaccgccct   35940
ccaccttcat tttcagcaag cgtatcatga ttgcaaaaat tcaggctcct cagacacctg   36000
tataagattg agaagcggaa cgttaacatc gatgtttcgc tcgcgtaaat cacgcctcag   36060
tgcaagcata atataatccc acaggtcgga gcggatcagc gaggacacct ccccgccagg   36120
aaccaactca acggagccta tgctgattat aatacgcata ttcggagcta tgctaaccag   36180
cacggccccc aaataggcgt actgcatagg cggcgacaaa aagtgaacag tttgggttaa   36240
aaaatcaggc aaacactcgc gcaaaaaagc aagaacatca taaccatgct catgcaaata   36300
gatgcaagta agctcaggaa caaccacaga aaaatgcaca atttttctct caaacatgac   36360
tgcgagccct gcaaaaaata aaaagaaac attacacaag agtagcctgt cttacgatgg   36420
gatagactac tctaaccaac ataagacggg ccacaacatc gcccgcgtgg ccataaaaaa   36480
aattgtccgt gtgattaaaa agaagcacag atagctggcc agtcatatcc ggagtcatca   36540
cgtgtgaacc cgtgtagacc cccggggttgg acacatcggc caaagaaaga aagcggccaa   36600
tgtacccagg aggaattata acactaagac gaagatacaa cagaataacc ccatgagggg   36660
gaataacaaa gttagtaggt gaataaaaac gataaacacc cgaaactccc tcctgcgtag   36720
gcaaaatagc accctccccct tccaaaacaa catatagcgc ttccacagca gccatgacaa   36780
```

```
aagactcaaa acactcaaaa gactcagtct taccaggaaa ataaaagcac tctcacagca   36840
ccagcactaa tcagagtgtg aagagggcca agtgccgaac gagtatatat aggaataaaa   36900
aatgacgtaa atgtgtaaag gtcagaaaac gcccagaaaa atacacagac caacgcccga   36960
aacgaaaacc cgcgaaaaaa tacccagaac ttcctcaaca accgccactt ccgctttctc   37020
acggtacgtc acttccgcaa gaaaagcaaa actacatttc ccacatgtgt aaaaacgaaa   37080
ccccgcccct tgtaaccgcc cacaacttac atcatcaaaa cgtaaactcc tacgtcaccc   37140
gccccgcctc tccccgccca cctcattatc atattggcca caatccaaaa taaggtatat   37200
tattgatgat g                                                        37211

<210> SEQ ID NO 22
<211> LENGTH: 37213
<212> TYPE: DNA
<213> ORGANISM: Gorilla beringei graueri

<400> SEQUENCE: 22
catcatcaat aatataccct attttggatt gtggccaata tgataatgag gtgggcgggg     60
agaggcgggg cggtgacgt aggacgcgcg agtagggttg ggaggtgtgg cggaagtgtg    120
gcatttgcaa gtgggaggag ctcacatgca agcttccgtc gcggaaaatg tgacgttttt    180
gatgagcgcc gcctacctcc ggaagtgcca attttcgcgc gcttttcacc ggatatcgta    240
gtaattttgg gcgggaccat gtaagatttg gccattttcg cgcgaaaagt gaaacgggga    300
agtgaaaact gaataatagg gcgttagtca tagtgcgtaa tatttaccga gggccgaggg    360
actttgaccg attacgtgga ggactcgccc aggtgttttt tacgtgaatt ccgcgttcc     420 gggtcaaagt ctccgttttta ttgtcaccgt catttgacgc ggagggtatt taaacccgct    480
gcgctcctca agaggccact cttgagtgcc agcgagaaga gttttctcct ctgctccgct    540
tcggtgatcg aaaaatgaga cacatagcct gcactccggg tcttttgtcc ggtcgggcgg    600
cggccgagct tttggacgct tgatcaatg atgtcctgag cgatgatttt ccgtctacta    660
cccactttag cccacctact cttcacgaac tgtacgatct ggatgtactg gtggatgtga    720
acgatcccaa cgaggaggcg gtttctgcgt tttttcccga gtctgcgctg ttggccgctc    780
aggagggatt tgacctacac actccgccgc ctatttttaga gtctccgctg ccggagccca    840
gtggtatacc ttatatgcct gaactgcttc ccgaagtggt agacctgacc tgccacgagc    900
ctggctttcc gcccagcgac gatgatggtg agccttttgt tttagacttt gctgagatac    960
ctgggcacgg ttgcaggtct tgtgcatatc atcagagggt taccgagac cccgaggtta   1020 agtgttcgct gtgctatatg aggatgacct cttcctttat ctacagtaag ttttttgtcta   1080 ggtgggcttt tgggtaggtg ggttttgtgt cagaacaggt gtaaacgttg cttgtgtttt   1140
ttgtacctgt aggtccggtg tccgagccag accggagcc cgaccgcgat cccgagccgg   1200
atcccgagcc tcctcgtagg gcaagaaaat taccttctat tctgtgcaag tctaagacac   1260
ctgtgaggac cagcgaggcg gacagcaccg actctggcac ttctacctct cctcctgaaa   1320
ttcacccagt ggttcctctg ggtatacata gacctgttgc tgttagagtt tgcgggcgac   1380
gctctgcagt agagtgcatt gaggacttgc ttcacgaacc cgaggaacct ttggacttga   1440
gcgttaaacg ccctaggcaa taaaccccac ctaagtaata aaccccacct aagtaataaa   1500
ccctgccgcc cttggttatt gagatgacgc ccaatgtttg cttttgaatg acttcatgtg   1560
tgtaataaaa gtgagtgtga tcataggtct cttgtttgtc tgggcggggc ttaagggtat   1620
ataagtctct tggggctaaa cttggttaca cttgacccca atggaggcgt gggggtgctt   1680
```

```
ggaggagttt gcggacgtgc gccgtttgct ggacgagagc tctagcaata cctatactat   1740
ttggaggtat ctgtggggct ctactcaggc caagttggtc tccagaatta agcaggatta   1800
caagtgcgat tttgaagagc ttttagttc  ctgcggtgag cttttgcaat ccttgaatct   1860
gggccatcag gctattttcc aggaaaaggt tctctcgact ttggattttt ccactcccgg   1920
gcgcaccgcc gcttgtgtgg cttttgtgtc ttttgtgcaa gataaatgga gcgaggagac   1980
ccacctgagt cacggctacg tactggattt catggcgatg gctctttgga gggcttacaa   2040
caaatggaag attcagaagg aactgtacgg ttccgcccta cgtcgtccac ttctgtcgcg   2100 acagggggctg aggtttcccg accatcggca gcatcagaat ctggaagacg agtcggagga  2160
gcgagcggag gagaagatca gcttgagagc cggcctggac cctcctcagg aggaatgaat   2220
ctcccgcagg tggttgacct gtttccagaa ctgagacggg tcctgactat cagggaggat   2280
ggtcagtttg tgaagaagtt taagagggat cggggtgagg gagatgatga ggcggctagc   2340
aatttagctt ttagtctgat gactcgccac cgaccggaat gtattaccta tcagcagatt   2400
aaggagagtt gtgccaacga gctggatctt ttgggtcaga agtatagcat agaacagctt   2460
accacttact ggcttcagcc tggggatgat tgggaagagg cgatcagggt gtatgcaaag   2520
gtggccctgc ggcccgattg caagtataag attactaagt tggttaatat tagaaactgc   2580
tgctatattt ctgggaacgg ggccgaagtg gagatagata ctcaggacag ggtggctttt   2640
aggtgttgca tgataaacat gtggcccggg atactgggga tggatggggt ggtattcatg   2700
aatgtgaggt ttacgggccc caactttaat ggcacggtgt tcatgggcaa caccaacttg   2760
ctcctgcatg gtgcgagttt ctatgggttt aataacacct gtatagaggc ctggaccgat   2820
gtaaaggttc gaggttgttc cttttatagc tgttggaagg cggtggtgtg tcgccctaaa   2880 agcagggggtt ctgtgaaaaa atgcttgttt gaaaggtgca ccttaggcat cctctctgag  2940
ggcaactcca gggtgcgcca taatgtggct tcgaactgcg gttgcttcat gcaagtgaag   3000
ggggtgagcg ttatcaagca taactcggtg tgtggaaact gcgaggatcg cgcctcccag   3060
atgctgacct gctttgatgg caactgtcac ctgttgaaga ccattcatat aagcagccac   3120
cccagaaagg cctggcccgt gtttgagcat aacatcttga cccgctgctc cttgcatctg   3180
ggggtcagga ggggtatgtt cctgccttac cagtgtaact ttagccacac taaaatcctg   3240
ctggaacccg agtgcatgac caaggtcagc ctgaatggtg tgtttgatgt gactctgaaa   3300
atctggaagg tgctgaggta tgatgagacc aggaccaggt gccgaccctg cgagtgcggc   3360
ggcaagcaca tgagaaatca gcctgtgatg ttggatgtga ccgaggagct taggcctgac   3420
catctggtgc tggcctgcac cagggccgag tttgggtcta gcgatgagga taccgattga   3480
ggtgggtaag gtgggcgtgg ctagaagggt ggggcgtgta taattggggg gtctaagggt   3540
ctctctgttt tgtcttgcaa cagccgccgc catgagcgac accggcaaca gctttgatgg   3600
aagcatcttt agcccctatc tgacagtgcg catgcctcac tgggctggag tgcgtcagaa   3660
tgtgatgggt tccaacgtgg atggacgccc cgttctgcct tcaaattcgt ctacaatggc   3720
ctacgcgacc gtgggaggaa ctccgctgga cgccgcgacc tccgccgccg cctccgccgc   3780
cgccgcgacc gcgcgcagca tggctacgga ccttacagc  tctttggtgg cgagcggcgc   3840
ggcctctcgc gcgtctgctc gggatgagaa actgaccgct ctgctgctta aactggaaga   3900
cttgacccgg gagctggctc aactgaccca gcaggtctcc agcttgcgtg agagcagcct   3960
tgcctccccc taatggccca taatataaat aaaagccagt ctgtttggat taagcaagtg   4020
```

```
tatgttctttt atttaactct ccgcgcgcgg taagcccggg accagcggtc tcggtcgttt    4080
agggtgcggt ggattctttc caacacgtgg tacaggtggc tctggatgtt tagatacatg    4140
ggcatgagtc catccctggg gtggaggtag caccactgca gagcttcgtg ctcggggggtg    4200
gtgttgtata tgatccagtc gtagcaggag cgctgggcgt ggtgctgaaa aatgtcctta    4260
agcaagaggc ttatagctag ggggaggccc ttggtgtaag tgtttacaaa tctgctcagt    4320
tgggagggggt gcatccgggg ggatataatg tgcatcttgg actggatttt taggttggct    4380
atgttcccac ccagatccct tctgggattc atgttgtgca ggaccaccag cacggtatat    4440
ccagtacact tgggaaattt atcgtggagc ttagacggga atgcatggaa gaacttggag    4500
acgcccttgt ggcctcccag attttccata cattcgtcca tgatgatggc aatgggcccg    4560
tgggaagctg cctgagcaaa aatgtttctg ggatcgctca catcgtagtt atgttccagg    4620
gtgaggtcat cataggacat cttacaaat cggggggcgga gggtcccgga ctggggggatg    4680
atggtgccct cgggcccccgg ggcgtagttc ccctcacaga tctgcatctc ccaggctttc    4740
atttcagagg gagggatcat atccacctgc ggagcgatga aaaacacagt ttctggcgca    4800
ggggagatta actgggatga gagcaggttt ctgagcagct gtgactttcc acagccggtg    4860
ggcccatata tcacgcctat caccggctgc agctggtagt taagagagct gcagctgccg    4920
tcctcccgga gcagggggc cacctcgttc agcatatccc tgacgtggat gttctccctg    4980
accaattccg ccagaaggcg ctcgccgccc agcgaaagca gctcttgcaa ggaagcaaaa    5040
ttttcagcg gttttaggcc gtcggccgtg ggcatgtttt tcagcgtctg ggtcagcagt    5100
tccagtctgt cccacagctc ggtgatgtgc tctacggcat ctcgatccag cagatctcct    5160
cgtttcgcgg gttggggcgg ctttcgctgt agggcaccag ccgatgggcg tccagcgggg    5220
ccagagtcat gtccttccat gggcgcaggg tcctcgtcag ggtggtctgg gtcacggtga    5280
aggggtgcgc tccgggttgg gcgctggcca gggtgcgctt gaggctggtt ctgctggtgc    5340
tgaatcgctg ccgctcttcg ccctgcgcgt cggccaggta gcatttgacc atggtctcgt    5400
agtcgagacc ctcggcggcg tgcccccttgg cgcggagctt tcccttggag gtggcgccgc    5460
acgaggggca ctgcaggctc ttcagggcgt agagcttggg agcgagaaac acggactctg    5520
gggagtaggc gtccgcgccg caggaagcgc agaccgtctc gcattccacc agccaagtga    5580
gctccgggcg gtcagggtca aaaaccaggt tgccccatg ctttttgatg cgtttcttac    5640
ctcggctctc catgaggcgg tgtcccttct cggtgacgaa gaggctgtcc gtgtctccgt    5700
agaccgactt caggggcctg tcttccagcg gagtgcctct gtcctcctcg tagagaaact    5760
ctgaccactc tgagacgaag gcccgcgtcc aggccaggac gaaggaggcc acgtgggagg    5820
ggtagcggtc gttgtccact agcgggtcca ccttctccag ggtgtgcagg cacatgtccc    5880
cctcctccgc gtccagaaaa gtgattggct tgtaggtgta ggacacgtga ccgggggttc    5940
ccgacggggg ggtataaaag ggggtgggca ccctttcatc ttcactctct tccgcatcgc    6000
tgtctgcgag agccagctgc tggggtaagt attccctctc gaaggcgggc atgacctcag    6060
cgctcaggtt gtcagtttct aaaaatgagg aggatttgat gttcacctgt ccggaggtga    6120
tacctttgag ggtacctggg tccatctggt cagaaaacac tatttttttg ttgtcaagct    6180
tggtggcgaa cgacccgtag agggcgttgg agagcagctt ggcgatggag cgcagggtct    6240
ggttttttgtc gcggtcggct cgctccttgg ccgcgatgtt gagttgcacg tactcgcggg    6300
ccacgcactt ccactcgggg aagacggtgg tgcgctcgtc tgggatcagg cgcaccctcc    6360
agcctcggtt gtgcagggtg accatgtcga cgctggtggc gacctcgccg cgcaggcgct    6420
```

```
cgttggtcca gcagaggcgg ccgcccttgc gcgagcagaa ggggggtagg gggtccagct   6480
ggtcctcgtt tgggggtcc gcgtcgatgg tgaagacccc ggggagcaag cgcgggtcaa   6540
agtagtcgat cttgcaagct tgcatgtcca gagcccgctg ccattcgcgg gcggcgagcg   6600
cgcgctcgta ggggttgagg ggcgggcccc agggcatggg gtgggtgagc gcggaggcgt   6660
acatgccgca gatgtcatac acgtacaggg gttccctgag gatgccgagg taggtggggt   6720
agcagcgccc cccgcggatg ctggcgcgca cgtagtcata gagctcgtgg gaggggccca   6780
gcatgttggg cccgaggttg gtgcgctggg ggcgctcggc gcggaaggcg atctgcctga   6840
agatggcatg ggagttggag gagatggtgg gccgctggaa gacgttgaag cttgcttctt   6900
gcaagcccac cgagtccctg acgaagcagg cgtaggactc gcgcagcttg tgcaccagct   6960
cggcggtgac ctggacgtcg agcgcgcagt agtcgagggt ctcgcggatg atgtcatact   7020
tatcctcccc cttctttttc cacagctcgc ggttgaggac gaactcttcg cggtctttcc   7080
agtactcttg gaggggaaac ccgtccgtgt ccgaacggta agagcctagc atgtagaact   7140
ggttgacggc ctggtagggg caacagccct tctccacggg cagcgcgtag gcctgcgccg   7200
ccttgcggag ggaggtgtgg gtgagggcga aagtgtccct gaccatgact ttgaggtatt   7260
gatgtttgaa gtctgtgtca tcgcagccgc cctgttccca cagggtgtag tccgtgcgct   7320
ttttggagcg cgggttgggc agggagaagg tgaggtcatt gaagaggatc ttccccgctc   7380
gaggcatgaa gtttctggtg atgcgaaagg gccctgggac cgaggagcgg ttgttgatga   7440
cctgggcggc caggacgatc tcgtcaaagc cgtttatgtt gtggcccacg atgtagagct   7500
ccaaaaagcg gggctggccc ttgatggagg ggagcttttt gagttcctcg taggtgagct   7560
cctcgggcga ttccaggccg tgctcctcca ggggcccagtc ttgcaagtga gggttggccg   7620
ccaggaagga tcgccagagg tcgcgggcca tgagggtctg caggcggtcg cggaaggttc   7680
tgaactgtcg ccccacggcc atcttttcgg gggtgatgca gtagaaggtg aggggtctt   7740 tctcccaggg gtcccatctg agctctcggg cgaggtcgcg cgcggcggcg accagagcct   7800 cgttgcccccc cagtttcatg accagcatga agggcacgag ctgcttgcca aaggctccca   7860
tccaagtgta ggtctctaca tcgtaggtga caaagaggcg ctccgtgcga ggatgagagc   7920
cgatcgggaa gaactggatc tcccgccacc agttggagga ttggctgttg atgtggtgaa   7980
agtagaagtc ccgtctgcgg gccgagcact cgtgctggct tttgtaaaag cgaccgcagt   8040
actggcagcg ctgcacgggt tgtatatctt gcacgaggtg aacctggcga cctctgacga   8100
ggaagcgcag cggaatcta agtccccgc ctggggtccc gtgtggctgg tggtcttcta   8160
ctttggttgt ctggccgcca gcatctgtct cctggagggc gatggtggag cagaccacca   8220
cgccgcgaga gccgcaggtc cagatctcgg cgctcggcgg gcgagtttg atgacgacat   8280 cgcgcacatt ggagctgtcc atggtctcca gctcccgcgg cggcaggtca gctgggagtt   8340
cctggaggtt cacctcgcag agacgggtca aggcgcgggc agtgttgaga tggtatctga   8400
tttcaagggg cgtgttggcg gcggagtcga tggcttgcag gaggccgcag ccccgggggg   8460
ccacgatggt tccccgcggg gcgcgagggg aggcggaagc tgggggtgtg ttcagaagcg   8520
gtgacgcggc cgggcccccg gaggtagggg gggttccggc cccacaggca tgggcggcag   8580
gggcacgtct tcgccgcgcg cgggcagggg ctggtgctgg ctccgaagag cgcttgcgtg   8640
cgcgacgacg cgacggttgg tgtcctgtat ctgacgcctc tgagtgaaga ccacgggtcc   8700
cgtgaccttg aacctgaaag agagttcgac agaatcaatc tcggcatcgt tgacagcggc   8760
```

```
ctggcgcagg atctcctgca cgtcgcccga gttgtcctgg taggcgatct ctgccatgaa    8820
ctgctcgatc tcttcttcct ggagatctcc tcgtccggcg cgctccacgg tggccgccag    8880
gtcgttggag atgcgaccca tgagctgcga gaaggcgttg agcccgccct cgttccagac    8940
ccggctgtag accacgcccc cctcggcgtt gcgggcgcgc atgaccacct gggccaggtt    9000
gagctccacg tgtcgcgtga agacggcgta gttgcgcagg cgctggaaaa ggtagttcag    9060
ggtggtggcg gtgtgctcgg cgacgaagaa gtacatgacc cagcgccgca acgtggattc    9120
attgatgtcc cccaaggcct ccaggcgctc catggcctcg tagaagtcca cggcgaagtt    9180
gaaaaactgg gagttgcgag cggacacggt caactcctcc tccagaagac ggatgagctc    9240
ggcgacagtg tcgcgcacct cgcgctcgaa ggccacgggg ggcgcttctt cctcttccac    9300
ctcttcttcc atgatcgctt cttcttcttc ctcagccggg acgggagggg gcggcggcgg    9360
cgggggaggg gcgcggcggc ggcggcggcg caccgggagg cggtcgatga agcgctcgat    9420
catctccccc cgcatgcggc gcatggtctc ggtgacggcg cggccgttct cccggggcg    9480 cagctcgaag acgccgcctc tcatctcgcc gcggggcggg cggccgtgag gtagcgagac    9540
ggcgctgact atgcatctta acaattgctg tgtaggtaca ccgccgaggg acctgattga    9600
gtccagatcc accggatccg aaaaccttg gaggaaagcg tctatccagt cgcagtcgca    9660
aggtaggctg agcaccgtgg cgggcggggg cgggtctgga gagttcctgg cggagatgct    9720
gctgatgatg taattaaagt aggcggtctt gagaaggcgg atggtggaca ggagcaccat    9780
gtctttgggt ccggcctgtt ggatgcggag gcggtcggcc atgccccagg cctcgttctg    9840
acaccggcgc aggtctttgt agtagtcttg catgagtctt tccaccggca cctcttctcc    9900
ttcctcttct ccatctcgcc ggtggtttct cgcgccgccc atgcgcgtga ccccaaagcc    9960
cctgagcggc tgcagcaggg ccaggtcggc gaccacgcgc tcggccaaga tggcctgctg   10020
cacctgagtg agggtcctct cgaagtcatc catgtccacg aagcggtggt aggcgcccgt   10080
gttgatggtg taggtgcagt tggccatgac ggaccagttg acggtctggt gtcccggctg   10140
cgagagctcc gtgtaccgca ggcgcgagaa ggcgcgggaa tcgaacacgt agtcgttgca   10200
agtccgcacc agatactggt agcccaccag gaagtgcggc ggaggttggc gatagagggg   10260
ccagcgctgg gtggcggggg cgccgggcgc caggttttcc agcatgaggc ggtggtatcc   10320
gtagatgtac ctggacatcc aggtgatgcc ggcggcggtg gtggtggcgc gcgcgtagtc   10380
gcggacccgg ttccagatgt ttcgcagggg cgagaagtgt tccatggtcg gcacgctctg   10440
gccggtgagg cgcgcgcagt cgttgacgct ctatacacac acaaaaacga aagcgtttac   10500
agggctttcg ttctgtagcc tggaggaaag taaatgggtt gggttgcggt gtgccccggt   10560
tcgagaccaa gctgagctcg gccggctgaa gccgcagcta acgtggtatt ggcagtcccg   10620
tctcgaccca ggccctgtat cctccaggat acggtcgaga gcccttttgc tttcttggcc   10680
aagcgcccgt ggcgcgatct gggatagatg gtcgcgatga gaggacaaaa gcggctcgct   10740
tccgtagtct ggagaaacaa tcgccagggt tgcgttgcgg cgtaccccgg ttcgagcccc   10800
tatggcggct tgaatcggcc ggaaccgcgg ctaacgaggg ccgtggcagc cccgtcctca   10860
ggaccccgcc agccgacttc tccagttacg ggagcgagcc ccttttgttt tttatttttt   10920
agatgcatcc cgtgctgcgg cagatgcgcc cctcgccccg gcccgatcag cagcagcaac   10980
agcaggcatg cagaccccccc tctcccctttt ccgccccggt caccacggcc gcggcggccg   11040
tgtcgggcgc gggggggcgcg ctggagtcag atgagccacc gcggcggcga cctaggcagt   11100
atctggactt ggaagagggc gagggactgg cgcggctggg ggcgaactct ccagagcgcc   11160
```

```
acccgcgggt gcagttgaaa agggacgcgc gcgaggcgta cctgccgcgg cagaacctgt    11220
ttcgcgaccg cggggggcgag gagcccgagg agatgcgaga ctgcaggttc caagcggggc    11280
gcgagctgcg gcgcgggctg gacagacagc gcctgctgcg cgaggaggac tttgagcccg    11340
acacgcagac gggcatcagc cccgcgcgcg cgcacgtagc cgcggccgac ctggtgaccg    11400
cctacgagca gacggtgaac caggagcgca acttccaaaa gagcttcaac aaccacgtgc    11460
gcacgctggt ggcgcgcgag gaggtgaccc tgggtctcat gcatctgtgg gacctggtgg    11520
aggcgatcgt gcagaacccc agcagcaagc ccctgaccgc gcagctgttc ctggtggtgc    11580
agcacagcag ggacaacgag gccttcaggg aggcgctgct gaacatcacc gagccggagg    11640
ggcgctggct cctggacctg ataaacatcc tgcagagcat agtggtgcag gagcgcagcc    11700
tgagcctggc cgagaaggtg gcggccatca actactctat gctgagcctg ggcaagttct    11760
acgcccgcaa gatctacaag acccccctacg tgcccataga caaggaggtg aagatagaca    11820
gcttctacat gcgcatggcg ctgaaggtgc tgaccctgag cgacgacctg ggagtgtacc    11880
gcaacgagcg catccacaag gccgtgagcg ccagccggcg gcgcgagctg agcgaccgcg    11940
agctgatgca cagtctgcag cgcgcgctga ccggcgcggg cgagggcgac agggaggtcg    12000
agtcctactt cgacatgggg gccgacctgc actggcagcc gagccgccgc gccctggagg    12060
cggcgggggc gtacgcggc cccctggcgg ccgatgacca ggaagaggag gactatgagc    12120
tagaggaggg cgagtacctg gaggactgac ctggctggtg gtgttttggt atagatgcaa    12180
gatccgaacg tggcggaccc ggcggtccgg gcggcgctgc aaagccagcc gtccggcatt    12240
aactcctctg acgactgggc cgcggccatg ggtcgcatca tggccctgac cgcgcgcaac    12300
cccgaggctt tcaggcagca gcctcaggcc aaccggctgg cggccatctt ggaagcggta    12360
gtgcccgcgc gctccaaccc cacccacgag aaggtgctgg ccatagtcaa cgcgctggcg    12420
gagagcaggg ccatccgcgc ggacgaggcc ggactggtgt acgatgcgct gctgcagcgg    12480
gtggcgcggt acaacagcgg caacgtgcag accaacctgg accgcctggt gacggacgtg    12540
cgcgaggccg tggcgcagcg cgagcgcttg catcaggacg gtaacctggg ctcgctggtg    12600
gcgctaaacg ccttcctcag cacccagccg gccaacgtac cgcggggca ggaggactac    12660 accaactttt tgagcgcgct gcggctgatg gtgaccgagg tccctcagag cgaggtgtac    12720
cagtcggggc ccgactactt cttccagacc agcagacagg gcttgcaaac cgtgaacctg    12780
agccaggctt tcaagaacct gcgggggctg tggggagtga aggcgcccac cggcgaccgg    12840
gctacggtgt ccagcctgct aacccccaac tcgcgcctgc tgctgctgct gatcgcgccc    12900
ttcacggaca gcgggagcgt ctcgcgggag acctatctgg ccacctgct gacgctgtac    12960 cgcgaggcca tcgggcaggc gcaggtggac gagcacacct tccaagagat caccagcgtg    13020
agccacgcgc tggggcagga ggacacgggc agcctgcagg cgaccctgaa ctacctgctg    13080
accaacaggc ggcagaagat tcccacgctg cacagcctga cccaggagga ggagcgcatc    13140
ttgcgctacg tgcagcagag cgtgagcctg aacctgatgc gcgacggcgt gacgcccagc    13200
gtggcgctgg acatgaccgc gcgcaacatg gaaccgggca tgtacgcctc ccaccggccg    13260
ttcatcaacc gcctgatgga ctacttgcat cgggcggcgc ccgtgaaccc cgagtacttc    13320
actaatgcca ttctgaatcc ccactggatg cccctccgg gtttctacaa cggggacttt    13380
gaggtgcccg aggtcaacga cgggttcctc tgggatgaca tggatgacag tgtgttctca    13440
cccaacccgc tgcgcgccgc gtctctgcga ttgaaggagg gctctgacag ggaaggaccg    13500
```

```
agaagtctgg cctcctccct ggctctggga gcggtgggcg ccacgggcgc ggcggcgcgg   13560
ggcagtagcc ccttccccag cctggcagac tctctgaaca gcgggcgggt gagcaggcc    13620
cgcttgctag gcgaggagga gtatctgaac aactccctgc tgcagcccgc gagggacaag   13680
aacgctcagc ggcagcagtt tcccaacaat gggatagaga gcctggtgga caagatgtcc   13740
agatggaaga cgtatgcgca ggagtacaag gagtgggagg accgccagcc gcggcccttg   13800
ccgcccccta ggcagcgctg gcagcggcgc gcgtccaacc gccgctggag gcaggggccc   13860
gaggacgatg atgactctgc agatgacagc agcgtgttgg acctgggcgg gagcgggaac   13920
cccttttcgc acctgcgccc acgcctgggc aagatgtttt aaaagaaaaa aaaaaaata    13980
aaactcacca aggccatggc gacgagcgtt ggttttttgt tcccttcctt agtatgcggc   14040
gcgcggcgat gttcgaggag gggcctcccc cctcttacga gagcgcgatg gggatttctc   14100
ctgcggcgcc cctgcagcct ccctacgtgc ctcctcggta cctgcaacct acaggggga   14160
gaaatagcat ctgttactct gagctgcagc ccctgtacga taccaccaga ctgtacctgg   14220
tggacaacaa gtccgcggac gtggcctccc tgaactacca gaacgaccac agcgattttt   14280
tgaccacggt gatccaaaac aacgacttca ccccaaccga ggccagcact cagaccataa   14340
acctggataa caggtcgaac tggggcggcg acctgaagac catcttgcac accaacatgc   14400
ccaacgtgaa cgagttcatg ttcaccaact cttttaaggc gcgggtgatg gtggcgcgcg   14460
agcagggggga ggcgaagtac gagtgggtgg acttcacgct gcccgagggc aactactcag   14520
agaccatgac tctcgacctg atgaacaatg cgatcgtgga acactatctg aaagtgggca   14580
ggcagaacgg ggtgaaggaa agcgatatcg gggtcaagtt tgacaccaga aacttccgtc   14640
tgggctggga ccccgtgacc gggctggtca tgccggggt ctacaccaac gaggccttc    14700
atcccgacat agtgcttctg cccggctgtg gggtggactt cacccagagc cggctgagca   14760
acctgctggg cattcgcaag cggcagcctt ccaggaggg tttcaagatc acctatgagg   14820
atctgaaggg gggcaacatt cccgcgctcc ttgatctgga cgcctacgag gagagcttga   14880
aacccgagga gagcgctggc gacagcggcg agagtggcga ggagcaagcc ggcggcggtg   14940
gcggcgcgtc ggtagaaaac gaaagtacgc ccgcagtggc ggcggacgct gcggaggtcg   15000
agccggaggc catgcagcag gacgcagagg agggcgcaca ggagggcgcg cagaaggaca   15060
tgaacgatgg ggagatcagg ggagacacat tcgccacccg gggcgaagaa aaagaggcag   15120
aggcggcggc ggcggcgacg gcggaggccg aaaccgaggt tgaggcagag gcagagcccg   15180
agaccgaagt tatggaagac atgaatgatg gagaacgtag gggcgacacg ttcgccaccc   15240
ggggcgaaga gaaggcggcg gaggcagaag ccgcggctga ggaggcggct gcggctgcgg   15300
ccaagactga ggctgcggct aaggctgagg tcgaagccaa tgttgcggtt gaggctcagg   15360
ctgaggagga ggcggcggct gaagcagtta aggaaaaggc ccaggcagag caggaagaga   15420
aaaaacctgt cattcaacct ctaaaagaag atagcaaaaa gcgcagttac aacgtcatcg   15480
agggcagcac ctttacccag taccgcagct ggtacctggc gtacaactac ggcgacccgg   15540
tcaaggggggt gcgctcgtgg accctgctct gcacgccgga cgtcacctgc ggctccgagc   15600
agatgtactg gtcgctgccg aacatgatgc aagaccggt gaccttccgc tccacgcggc   15660
aggttagcaa cttccgggtg gtgggcgccg aactgctgcc cgtgcactcc aagagttttt   15720
acaacgagca ggccgtctac tcccagctga tccgccaggc cacctctctg acccacgtgt   15780
tcaatcgctt tcccgagaac cagattttgg cgcgcccgcc ggcccccacc atcaccaccg   15840
tgagtgaaaa cgttcctgcc ctcacagatc acgggacgct accgctgcgc aacagcatct   15900
```

```
caggagtcca gcgagtgacc attactgacg ccagacgccg gacctgcccc tacgtttaca   15960
aggccttggg catagtctcg ccgcgcgtcc tctccagtcg cacttttttaa aacacatcta   16020 cccacacgtt ccaaaatcat gtccgtactc atctcaccca gcaacaacac cggctggggg   16080
ctgcgcgcgc ccagcaagat gtttggaggg gcgaggaagc gctccgacca gcaccctgtg   16140
cgcgtgcgcg gccactaccg cgcgccctgg ggagcgcaca agcgcgggcg cacagggcgc   16200
accactgtgg acgacgtcat tgactccgta gtggagcaag cgcgccacta cacacccggc   16260
gcgccgaccg cccccgccgt gtccaccgtg gaccaggcga tcgaaagcgt ggtacagggc   16320
gcgcggcact atgccaacct taaaagtcgc cgccgccgcg tgcccgccg ccatcgccgg    16380 agaccccggg ccaccgccgc cgcgcgcctt actaaggctc tgctcaggcg cgccaggcga   16440
actggccacc gggccgccat gagggccgca cggcgggctg ccgctgccgc aagcgccgtg   16500
gccccgcggg cacgaaggcg cgcggccgcc gccgccgccg ccgccatttc cagcttggcc   16560
tcgacgcggc gcggtaacat atactgggtg cgcgactcgg taaccggcac gcgggtaccc   16620
gtgcgctttc gccccccgcg gaattagcac aagacaacat acacactgag tctcctgctg   16680
ttgtgtatcc cagcggcgac cgtcagcagc ggcgacatgt ccaagcgcaa aattaaagaa   16740
gagatgctcc aggtcatcgc gccggagatc tatgggcccc cgaagaagga ggaggatgat   16800
tacaagcccc gcaagctaaa gcgggtcaaa aagaaaaaga aagatgatga tgatgacgag   16860
gcggtggagt ttgtccgccg catggcaccc aggcgccccg tgcagtggaa gggccggcgc   16920
gtgcagcgcg ttttgcgccc cggcaccgcg gtggtcttca cgcccggcga gcgctccacg   16980
cgcactttca agcgggtgta cgatgaggtg tacgcgacg aggacctgtt ggagcaggcc    17040
aaccagcgct tgggggagtt tgcatatggg aaacggcccc gcgagagtct aaaagaggac   17100
ctgctggcgc taccgctgga cgagggcaat cccaccccga gtctgaagcc ggtaaccctg   17160
caacaggtgc tgcctttgag cgcgcccagc gagcataagc gagggttgaa gcgcgaaggc   17220
ggggacctgg cgcccaccgt gcagttgatg gtgcccaagc ggcagaagct ggaggacgtg   17280
ctggagaaaa tgaaagtaga gcccgggatc cagcccgaga tcaaggtccg ccccatcaag   17340
caggtggcgc ccgcgtggg agtccagacc gtggacgtta ggattccac ggaggagatg     17400 gaaacccaaa ccgccactcc ctcttcggcg gccagcgcca ccaccggcac cgcttcggta   17460
gaggtgcaga cggaccctg gctacccgcc accgctgttg ccgccgccgc ccccgttcg    17520 cgcgggcgca agagaaatta tccagcggcc agcgcgctca tgcccagta cgcactgcat    17580 ccatccatcg cgcccacccc cggctaccgc gggtactcgt accgcccgcg cagatcagcc   17640
ggcactcgcg gccgccgccg ccgtgcgacc acaaccagcc gccgccgtcg ccgccgccgc   17700
cagccagtgc tgaccccgt gtctgtaagg aaggtggctc gctcggggag cacgctggtg    17760
gtgcccagag cgcgctacca ccccagcatc gtttaaagcc ggtctctgta tggttcttgc   17820
agatatggcc ctcacttgtc gcctccgctt cccggtgccg ggataccgag gaagaactca   17880
ccgccgcaga ggcatggcgg gcagcggtct ccgcggcggc cgtcgccatc gccggcgcgc   17940
aaaaagcagg cgcatgcgcg gcggtgtgct gcctctgcta atcccgctaa tcgccgcggc   18000
gatcggtgcc gtacccggga tcgcctccgt ggccctgcag gcgtcccaga acgttgact   18060 cttgcaacct tgcaagcttg catttttttgg aggaaaaaat aaaaaagtc tagactctca   18120 cgctcgcttg gtcctgtgac tatttttgtag aaaaagatg gaagcatca actttgcgtc    18180 gctggccccg cgtcacggct cgcgcccgtt catgggagac tggacagata tcggcaccag   18240
```

```
caatatgagc ggtggcgcct tcagctgggg cagtctgtgg agcggcctta aaaattttgg   18300
ttccaccatt aagaactatg caacaaagc gtggaacagc agcacgggcc agatgctgag     18360
agacaagttg aaagagcaga acttccagga aaggtggcg cagggcctgg cctctggcat     18420
cagcggggtg gtggacatag ctaaccaggc cgtgcagaaa aagataaaca gtcatctgga    18480
cccccgtcct caggtggagg aaatgcctcc agcgatggag acggtgtctc ccgagggcaa    18540
aggcgaaaag cgcccgcggc ccgacagaga agagaccctg gtgtcacaca ccgaggagcc    18600
gccctcttac gaggaggcag tcaaggccgg cctgcccacc actcgcccca tagcccccat    18660
ggccaccggt gtggtgggcc acaggcaaca cactcccgca acactagatc tgcccccgcc    18720
gtccgagccg ccgcgccagc caaaggcggc gacggtgccc gctccctcca cttccgccgc    18780
caacagagtg cccctgcgcc gcgcgcgag cggcccccgg gcctcgcgag ttagcggcaa     18840
ctggcagagc acactgaaca gcatcgtggg cctgggagtg aggagtgtga agcgccgccg    18900
ttgctactga atgagcaagc tagctaacgt gttgtatgtg tgtatgcgtc ctatgtcgcc    18960
gccagaggag ctgttgagcc gccggcgccg tctgcactcc agcgaatttc aagatggcga    19020
ccccatcgat gatgcctcag tggtcgtaca tgcacatctc gggccaggac gcttcggagt    19080
acctgagccc cgggctggtg cagttcgccc gcgccacaga cacctacttc aacatgagta    19140
acaagttcag gaaccccact gtggcgccca ccacgatgt gaccacggac cggtcgcagc     19200
gcctgacgct gcggttcatc cccgtggatc gggaggacac cgcctactct tacaaggcgc    19260
ggttcacgct ggccgtgggc gacaaccgcg tgctggacat ggcctccact tactttgaca    19320
tcaggggggt gctggacagg ggccccacct caagcccta ctcgggtact gcctacaact    19380
ccctggcccc caagggcgct cccaattctt gcgagtggga acaagaggaa atcaggtgg    19440 tcgctgcaga tgatgaactt gaagatgaag aagcgcaagc tcaagaggac gccccagcta   19500
aaaaaattca tgtatatgcc caggcgcctc ttgctggcga aaagattacc aaggatggtt    19560
tgcaaatagg tactgaagtt gtaggagata catctaagga cacttttgca gacaaaaacat   19620 tccaacccga acctcagata ggcgagtctc agtggaacga ggctgatgcc acagtagcag    19680
gaggcagagt cttgaaaaaa accaccccta tgagaccttg ctatggatcc tatgccaggc    19740
ctacaaatgc caacgggggt caaggaatta tggttgccaa tgaacaagga gtgttggagt    19800
ctaaagtgga gatgcaattt ttttctaaca ctacaaccct taatgcgcgg gatgagctg     19860 gcaatcccga accaaaggtg gtgttgtaca gtgaagatgt ccacttggaa tctcctgaca    19920
ctcatttgtc ttacaagccc aaaaaggatg atgttaatgc taaaattatg ttgggtcagc    19980
aagctatggc taacaggccc aacctcattg cttttagaga taatttcatt ggactcatgt    20040
actacaacag cactggtaac atgggagtgc tggcgggtca ggcctctcag ttgaatgccg    20100
tggtggacct gcaggataga aacacagaac tgtcatatca gcttatgctt gattccattg    20160
gggatagatc cagatacttc tccatgtgga accaggcagt ggatagctat gacccagatg    20220
tcagaatcat tgaaaaccat ggtgtcgagg acagctacc caactactgc ttccctctgg    20280
gcggcatagg aattactgat acttatcaag ggatcaaaaa taccaatggc aatggtcagt    20340
ggaccaaaga tgatcagttc gcggaccgta atgaaatagg ggtgggaaac aacttcgcca    20400
tggagatcaa catccaggcc aacctctgga ggaacttcct ctatgcgaac gtgggctct    20460 acctgccaga caagctcaag tacaacccca ccaacgtgga catctctgac aaccccaaca    20520
cctatgacta catgaacaag cgtgtggtgg ctccccggcct ggtggactgc tttgtcaatg    20580
tgggagccag gtggtccctg gactacatgg acaacgtcaa ccccttcaac caccaccgca    20640
```

```
atgcgggtct gcgctaccgc tccatgatcc tgggcaacgg gcgctacgtg cccttccaca   20700
ttcaggtgcc ccagaagttc tttgccatca agaacctcct cctcctgccg ggctcctaca   20760
cttacgagtg gaacttcagg aaggatgtca acatggtcct gcagagctct ctgggcaatg   20820
accttagggg ggacggggcc agcatcaagt ttgacagcgt caccctctat gctaccttct   20880
tccccatggc tcacaacacc gcctccacgc tcgaggccat gctgaggaac gacaccaacg   20940
accagtcctt caatgactac ctctctgggg ccaacatgct ctaccccatc cccgccaagg   21000
ccaccaacgt gcccatctcc attccctctc gcaactgggc cgccttcaga ggctgggcct   21060
ttacccgcct taagaccaag gaaaccccct ccctgggctc gggttttgac ccctactttg   21120
tctactcggg atccatcccc tacctggatg gcaccttcta cctcaaccac acttttaaga   21180
agatatccat catgtatgac tcctccgtca gctggccggg caatgaccgc ctgctcaccc   21240
ccaatgagtt cgaggtcaag cgcgccgtgg acggcgaggg ctacaacgtg gcccagtgca   21300
acatgaccaa ggactggttc ctggtgcaga tgctggccaa ctacaacata ggctaccagg   21360
gcttctacat cccagagagc tacaaggaca ggatgtactc cttcttcaga aatttccaac   21420
ccatgagcag gcaggtggtg gacgagacca aatacaagga ctatcaggcc attggcatca   21480
ctcaccagca caacaactcg ggattcgtgg gctacctggc tcccaccatg cgcgaggggc   21540
aggcctaccc cgccaacttc ccctacccgt tgataggcaa gaccgcggtc gacagcgtca   21600
cccagaaaaa gttcctctgc gaccgcaccc tctggcgcat cccccttctct agcaacttca   21660
tgtccatggg tgcgctcacg gacctgggcc agaacctgct ctatgccaac tccgcccatg   21720
cgctggacat gacttttgag gtggacccca tggacgagcc caccttctct atattgtgt   21780
ttgaagtgtt cgacgtggtc agagtgcacc agccgcaccg cggtgtcatc gagaccgtgt   21840
acctgcgcac gcccttctcg gccggcaacg ccaccaccta aggagacagc gccgccgcct   21900
gcatgacggg ttccaccgag caagagctca gggccatcgc cagagacctg ggatgcggac   21960
cctattttt gggcacctat gacaaacgct tcccgggctt catctcccga gacaagctcg   22020
cctgcgccat cgtcaacacg gccgcgcgcg agaccggggg cgtgcactgg ctggcctttg   22080
gctgggaccc gcgctccaaa acctgctacc tcttcgaccc ctttggcttc tccgatcagc   22140
gcctcagaca gatctatgag tttgagtacg aggggctgct cgccgcagc gcgcttgcct   22200
cctcgcccga ccgctgcatc acccttgaga agtccaccga gccgtgcag gggccccact   22260
cggccgcctg cggtctcttc tgctgcatgt ttttgcacgc cttgtgcgc tggccccaga   22320
gtcccatgga tcgcaacccc accatgaact tgctcaaggg agtgcccaac gccatgctcc   22380
agagccccca ggtccagccc accctgcgcc acaaccagga acagctctac cgcttcctgg   22440
agcgccactc cccctacttc gcagtcaca gcgcgcacat ccgggggggcc acctctttct   22500
gccacttgca acaaaacatg caagacggaa aatgatgtac agctcgcttt ttaataaatg   22560
taaagactgt gcactttatt tatacacggg ctctttctgg ttatttattc aacaccgccg   22620
tcgccatcta gaaatcgaaa gggttctgcc gcgcgtcgcc gtgcgccacg ggcagagaca   22680
cgttgcgata ctggaagcgg ctcgcccact tgaactcggg caccaccatg cggggcagtg   22740
gctcctcggg gaagttctcg ccccacaggg tgcgggtcag ctgcagcgcg ctcaggaggt   22800
cgggagccga gatcttgaag tcgcagttgg ggccggaacc ctgcgcgcgc gagttgcggt   22860
acacgggggtt gcagcactgg aacaccagca gggccggatt acgcacgctg gccagcaggc   22920
tctcgtcgct gatcatgtcg ctgtccagat cctccgcgtt gctcagggcg aatggggtca   22980
```

```
tcttgcagac ctgcctgccc aggaaaggcg gcagcccggg cttgccgttg cagtcgcagc   23040 gcagggcat cagcaggtgc ccgtggcccg tctgcgcctg cgggtacagc gcgcgcatga    23100
aggcttcgat ctgcctgaaa gccacctgcg tcttggctcc ctccgaaaag aacatcccac   23160
aggacttgct ggagaactgg ttcgcgggac agctggcatc gtgcaggcag cagcgcgcgt   23220
cggtgttggc gatctgcacc acgttgcgac cccaccggtt cttcactatc ttggccttgg   23280
aagcctgctc cttcagcgcg cgctggccgt tctcgctggt cacatccatc tctatcacct   23340
gctccttgtt gatcatgttt gtcccgtgca gacacttcag gtcgccctcc gtctgggtgc   23400
agcggtgctc ccacagcgcg caaccggtgg gctcccaatt tttgtgggtc accccgcgt    23460 aggcctgcag gtaggcctgc aagaagcgcc ccatcatggc cacaaaggtc ttctggctcg   23520
taaaggtcag ctgcaggccg cgatgctctt cgttcagcca ggtcttgcag atggcggcca   23580
gcgcctcggt ctgctcgggc agcatcctaa aatttgtctt caggtcgtta ccacgtggt    23640 acttgtccat catggcgcgc gccgcctcca tgcccttctc ccaggcggac accatgggca   23700
ggcttagggg gtttatcact tccaccggcg aggacaccgt actttcgatt tcttcttcct   23760
ccccctcttc ccggcgcgcg cccacgctgc tgcgcgctct caccgcctgc accaaggggt   23820
cgtcttcagg caagcgccgc accgagcgct tgccgccctt gacctgctta atcagcaccg   23880
gcgggttgct gaagcccacc atggtcagct ccgcctgctc ttcttcgtct tcgctgtcta   23940
ccactatctc tggggaaggg cttctccgct ctgcggcgt gcgcttcttt ttttcttgg    24000 gagcagccgt gacggagtcc gccacggcga cggaggtcga gggcgtgggg ctggggtgc    24060 gcggtaccag ggcctcgtcg ccctcggact cttcctctga ctccaggcgg cggcggagac   24120
gcttctttgg gggcgcgcgc gtcagcggcg gcggagacgg ggacggggac ggggacggga   24180
cgccctccac agggggtggt cttcgcgcag accgcggcc gcgctcgggg gtcttttcga    24240
gctggtcttg gtcccgactg gccattgtat cctcctcctc ctaggcagag agacataagg   24300
agtctatcat gcaagtcgag aaggaggaga gcttaaccac cccctctgag accgccgatg   24360
cgcccgccgt cgccgtcgcc cccgctgccg ccgacgcgcc cgccacaccg agcgacaccc   24420
ccgcggaccc cccagccgac gcaccccctgt tcgaggaagc ggccgtggag caggacccgg   24480
gctttgtctc ggcagaggag gatttgcgag aggaggagga taaggagaag aagccctcag   24540
tgccaaaaga tgataaagag caagacgagc acgacgcaga tgcacaccag ggtgaagtcg   24600
ggcgggggga cggagggcat gacggcgccg actacctaga cgaagggaac gacgtgctct   24660
tgaagcacct gcatcgtcag tgcgccatcg tttgcgacgc tctgcaggag cgcagcgaag   24720 tgccctcag cgtggcggag gtcagccacg cctacgagct cagcctcttc tccccccggg   24780 tgccccccg ccgccgcgaa aacggcacat gcgagcccaa cccgcgcctc aacttctacc    24840
ccgcctttgt ggtgcccgag gtcctggcca cctatcacat cttctttcaa aattgcaaga   24900
tccccctctc gtgccgcgcc aacgtagcc gcgccgataa gatgctggcc ctgcgccagg    24960
gcgaccacat acctgatatc gccgctttgg aagatgtgcc aaagatcttc gagggtctgg   25020
gtcgcaacga gaagcgggca gcaaactctc tgcaacagga aaacagcgaa aatgagagtc   25080
acaccggggt actggtggag ctcgagggcg acaacgcccg cctggcggtg tcaagcgca    25140 gcatcgaggt cacccacttt gcctaccccg cgctcaacct gccccccaaa gtcatgaacg   25200
cggccatgga cgggctgatc atgcgccgcg gccggcccct cgctccagat gcaaacttgc   25260
atgaggagac cgaggacggc cagcccgtgg tcagcgacga gcagctggcg cgctggctgg   25320
agaccgcgga ccccgccgaa ctggaggagc ggcgcaagat gatgatggcc gcggtgctgg   25380
```

```
tcaccgtaga gctggagtgt ctgcagcgct tcttcggcga ccccgagatg cagagaaagg    25440
tcgaggagac cctgcactac accttccgcc agggctacgt gcgccaggct tgcaagatct    25500
ccaacgtgga gctcagcaac ctggtgtcct acctgggcat cttgcatgag aaccgcctcg    25560
ggcagagcgt gctgcactcc accctgcgcg gggaggcgcg ccgcgactac gtgcgcgact    25620
gcgtttacct cttcctctgc tacacctggc agacggccat gggggtctgg cagcagtgcc    25680
tggaggagcg caacctcaag gagctggaga agctcctgca gcgcgcgctc aaagacctct    25740
ggacgggcta caacgagcgc tcggtggccg ccgcgctggc cgacctcatc ttccccgagc    25800
gcctgctcaa aaccctccag caggggctgc ccgacttcac cagccaaagc atgttgcaaa    25860
acttcaggaa cttatccctg gagcgttctg gcatcctacc cgccacctgc tgcgccctgc    25920
ccagcgactt tgtcccccctc gtgtaccgcg agtgccccccc gccgctgtgg ggtcactgct    25980
acctgttcca actggccaac tacctgtcct accacgcgga cctcatggag gactccagcg    26040
gcgaggggct catggagtgc cactgccgct gcaacctctg cacgcccccac cgctccctgg    26100 tctgcaacac ccaactgctc agcgagagtc agattatcgg taccttcgag ctacagggtc    26160
cgtcctcctc agacgagaag tccgcggctc cggggctaaa actcactccg gggctgtgga    26220
cttccgccta cctgcgcaaa tttgtacctg aagactacca cgcccacgag atcaggtttt    26280
acgaagacca atcccgcccg cccaaggcgg agctgaccgc ctgcgtcatc acccagggcg    26340
agatcctagg ccaattgcaa gccatccaaa aagcccgcca agatttttg ctgagaaagg    26400 gtcgggggt gtatctggac ccccagtcgg gtgaggagct caacccggtt ccccccgctgc    26460 cgccgccgcg ggaccttgct tcccaggata agcatcgcca tggctcccag aaagaagcag    26520
cagcggccgc cactgccgcc accccacatg ctggaggaag aggaggaata ctgggacagt    26580
caggcagagg aggtttcgga cgaggaggag ccggagacgg agatggaaga gtgggaggag    26640
gacagcttag acgaggaggc ttccgaagcc gaagaggcag acgcaacacc gtcaccctcg    26700
gccgcagccc cctcgcaggc gccccccgaag tccgctccca gcatcagcag caacagcagc    26760
gctataacct ccgctcctcc accgccgcga cccacggccg accgcagacc caaccgtaga    26820
tgggacacca ccggaaccgg ggccggtaag tcctccggga gaggcaagca agcgcagcgc    26880
caaggctacc gctcgtggcg cgctcacaag aacgccatag tcgcttgctt gcaagactgc    26940
ggggggaaca tctccttcgc ccgccgcttc ctgctcttcc accacggtgt ggccttcccc    27000
cgtaacgtcc tgcattacta ccgtcatctc tacagcccct actgcggcgg cagtgagcca    27060
gagacggtcg gcggcggcgg cggcgcccgt ttcggcgcct aggaagaccc agggcaagac    27120
ttcagccaag aaactcgcgg cggccgcggc gaacgcggtc gcggggggccc tgcgcctgac    27180 ggtgaacgaa cccctgtcga cccgcgaact gagaaaccga atcttcccca ctctctatgc    27240
catcttccag cagagcagag ggcaggatca ggaactgaaa gtaaaaaaca ggtctctgcg    27300
ctccctcacc cgcagctgtc tgtatcacaa gagcgaagac cagcttcggc gcacgctgga    27360
ggacgctgag gcactcttca gcaaatactg cgcgctcact cttaaggact agctccgcgc    27420
ccttctcgaa tttaggcggg aacgcctacg tcatcgcagc gccgccgtca tgagcaagga    27480
cattcccacg ccatacatgt ggagctatca gccgcagatg ggactcgcgg cgggcgcctc    27540
ccaagactac tccacccgca tgaactggct cagtgccggc ccacacatga tctcacaggt    27600
taatgatatc cgcaccccatc gaaaccaaat attggtggag caggcggcaa ttaccaccac    27660
gccccgcaat aatcccaacc ccagggagtg gcccgcgtcc ctggtgtatc aggaaattcc    27720
```

```
cggccccacc accgtactac ttccgcgtga ttcccaggcc gaagtccaaa tgactaactc    27780
aggggcgcag ctcgcgggcg gctgtcgtca cagggtgcgg cctcctcgcc agggtataac    27840
tcacctggag atccgaggca gaggtattca gctcaacgac gagtcggtga gctcctcgct    27900
cggtctaaga cctgacggga ccttccagat agccggagcc ggccgatctt ccttcacgcc    27960
ccgccaggcg tacctgactc tgcagagctc gtcctcggcg ccgcgctcgg gcggcatcgg    28020
gactctccag ttcgtgcagg agtttgtgcc ctcggtctac ttcaaccoct tctcgggctc    28080 tcccggtcgc tacccggacc agttcatctc gaactttgac gccgcgaggg actcggtgga    28140
cggctacgac tgaatgtcgg gtggacccgg tgcagagcaa cttcgcctga agcacctcga    28200
ccactgccgc cgccctcagt gctttgcccg ctgtcagacc ggtgagttcc agtactttc    28260 cctgcccgac tcgcacccgg acggcccggc gcacggggtg cgcttttcca tcccgagtca    28320
ggtgcgctct accctaatca gggagtttac cgcccgtccc ctactggcgg agttggaaaa    28380
ggggccttct atcctaacca ttgcctgcat ctgctctaac cctggattgc accaagatct    28440
ttgctgtcat ttgtgtgctg agtataataa aggctgagat cagaatctac tcgggctcct    28500
gtcgccatcc tgtcaacgcc accgtccaag cccggcccga tcagcccgag gtgaacctca    28560
cctgcggtct gcaccggcgc ctgaggaaat acctagcttg gtactacaac agcactcct    28620 ttgtggttta caacagcttt gaccaggacg gggtctcact gagggataac ctctcgaacc    28680
tgagctactc catcaggaag aacagcaccc tcgagctact cctccttac ctgcccggga    28740 cttaccagtg tgtcaccggt ccctgcaccc acacccacct gttgatcgta aacgactctc    28800
ttccgagaac agacctcaat aactcctctt cgcagttccc cagaacagga ggtgagctca    28860
ggaaaccccg ggtaagaag ggtggacaag agttaacact tgtggggttt ctggtgtatg    28920
tgacgctggt ggtggctctt ttgattaagg cttttccttc catgtctgaa ctctccctct    28980
tttatgaaca actcgactag tgctaacggg accctaccca acgaatcggg attgaatatc    29040
ggtaaccagg ttgcagtttc acttttgatt accttcatag tcctcttcct gctagtgctg    29100
tcgcttctgt gcctgcggat cggggggctgc tgcatccacg tttatatctg gtgctggctg    29160
tttagaaggt tcggagacca tcgcaggtag aataaacatg ctgctgctta ccctctttgt    29220
cctggcgctg gccgccagct gccaagcctt ttccgaggct gactttatag agccccagtg    29280
taacgtgact tttaaagccc atgcacagcg ttgtcatact ataatcaaat gtgccaccga    29340
acacgatgaa taccttatcc agtataaaga taaatcacac aaagtggcac ttgttgacat    29400
ctggaaaccc gaagacccctt tggaatacaa tgtgaccgtt ttccagggtg acctcttcaa    29460
aatttacaat tacactttcc catttgacca gatgtgtgac tttgtcatgt acatggaaaa    29520
gcagcacaag ctgtggcctc cgactcccca gggctgtgtg gaaatccag gctctttctg    29580 catgatctct ctctgtgtaa ctgtgctggc actaatactc acgcttttgt atatcagatt    29640
taaatcaagg caaagcttca tcgatgaaaa gaaaatgcct taaacgcttt cacgcttgat    29700
tgctaacacc gggttttat ccgcagaatg attggaatca ccctactaat cacctccctc    29760
cttgcgattg cccatgggtt ggaacgaatc gaagcccctg tggggccaa tgttaccctg    29820 gtggggcctg tcggcaatgc tacattaatg tgggaaaaat atactaaaaa tcaatgggtc    29880
tcttactgca ctaacaaaaa cagccacaag cccagagcca tctgcgatgg gcaaaatcta    29940
accttgattg atgttcaaat gctggatgcg ggctactatt atgggcagct gggtacaatg    30000
attaattact ggagacccca caaagattac atgctccacg tagtaaaggg tccccttagc    30060
agcccaccca ctaccacctc tactaccccc actaccacca ctactcccac caccagcact    30120
```

```
gccgcccagc ctcctcatag cagaacaacc actttatca attccaagtc ccactccccc    30180
cacattgccg gcgggccctc cgcctcagac tccgagacca ccgagatctg cttctgcaaa    30240
tgctctgacg cctttgctga ggatttggaa gaccacgagg aagatgagca tgacttcgca    30300
gatgcatgcc aggcatcaga ggcagaagcg ctgccggtgg ccctcaaaca gtatgcagac    30360
ccccacacca cccccaacct tcctccacct tcccagaagc caagtttcct gggggaaaat    30420
gaaactctgc ctctctccat actcgctctg acatctgttg ctatgttgac cgctctgctg    30480
gtgcttctat gctctatatg ctacctgatc tgctgcagaa agaaaaaatc tcacggccat    30540
gctcaccagc ccctcatgca cttcccttac cctccagagc tgggcgacca caaacttaa     30600 gtctgcagta actatctgcc catcccttgt cagtcgacag cgatgagccc cactaatcta    30660
acggcctctg gacttacaac atcgtctctt aatgagacca ccgctcctca agacctgtac    30720
gatggtgtct ccgcgctggt taaccagtgg gatcacctgg gcatatggtg gctcctcata    30780
ggagcagtga ccctgtgcct aatcctggtc tggatcatct gctgcatcaa aagcagaaga    30840
cccaggcggc ggcccatcta caggcccttt gtcatcacac ctgaagatga tgatgacacc    30900
acttccaggc tgcagaggct aaagcagcta ctcttctctt ttacagcatg gtaaattgaa    30960
tcatgcctcg cattttcatc tacttgtctc tccttccact ttttctgggc tcttctacat    31020
tggccgctgt gtcccacatc gaggtagact gcctcacgcc cttcacagtc tacctgcttt    31080
tcggctttgt catctgcacc tttgtctgca gcgttatcac tgtagtgatc tgcttcatac    31140
agtgcatcga ctacgtctgc gtgcgggtgg cttactttag acaccacccc cagtatcgca    31200
acagggacat agcggctctc ctaagacttg tttaaaatca tggccaaatt aactgtgatt    31260
ggtcttctga tcatctgctg cgtcctagcc gcgattggga ctcaagctcc taccaccacc    31320
agcgctccca gaaagagaca tgtatcctgc agcttcaagc gtccctggaa tataccccaa    31380
tgctttactg atgaacctga aatctctttg gcttggtact tcagcgtcac cgccttctt    31440 atcttctgca gtacggttat tgcccttgcc atctaccctt cccttgacct gggctggaat    31500
gctgtcaact ctatggaata tcccaccttc ccagaaccag acctgccaga cctggttgtt    31560
ctaaacgcgt ttcctcctcc tgctcccgtt caaaatcagt ttcgccctcc gtcccccacg    31620
cccactgagg tcagctactt taatctaaca ggcggagatg actgaaaacc tagacctaga    31680
aatggacggt ctctgcagcg agcaacgcac actagagagg cgccggcaaa aagagctcga    31740
gcgtcttaaa caagagctcc aagacgcggt ggccatacac cagtgcaaaa aaggtgtctt    31800
ctgtctggta aaacaggcca cgctcaccta tgaaaaaaca ggtgacaccc accgcctagg    31860
atacaagctg cccacacagc gccagaagtt cgccctcatg ataggcgaac aacccatcac    31920
cgtgacccag cactccgtgg agacagaagg ctgcatacac gctccctgta ggggcgctga    31980
ctgcctctac accttgatca aaaccctctg cggtctcaga gacctcatcc ctttaatta     32040 atcataactg taatcaataa aaaatcactt acttgaaatc tgatagcaag cctctgtcca    32100 atttttcag caacacttcc ttcccctcct cccaactctg gtactctagg cgcctcctag    32160
ctgcaaactt cctccacagt ctgaagggaa tgtcagattc ctcctcctgt ccctccgcac    32220
ccacgatctt catgttgttg cagatgaaac gcgcagatc gtctgacgag accttcaacc     32280
ccgtgtaccc ctacgatacc gagatcgctc cgacttctgt cccttcctt accccctcct    32340 ttgtgtcatc cgcaggaatg caagaaaatc cagctgggt gctgtccctg cacttgtcag    32400
agccccttac cacccacaat ggggccctga ctctaaaaat gggggcggc ctgaccctgg     32460
```

```
acaaggaagg gaatctcact tcccaaaaca tcaccagtgt cgatcccect ctcaaaaaaa   32520 gcaagaacaa catcagcctt cagaccgccg caccectcgc cgtcagctcc ggggccctaa   32580 cacttttgc cactcccccc ctagcggtca gtggtgacaa ccttactgtg cagtctcagg    32640 ccctctcac tttggaagac tcaaaactaa ctctggccac caaaggaccc ctaactgtgt    32700
ccgaaggcaa acttgtccta gaaacagagg ctccectgca tgcaagtgac agcagcagcc   32760
tgggccttag cgttacggcc ccacttagca ttaacaatga cagcctagga ctagacatgc   32820
aagcgcccat tagctctcga gatggaaaac tggctctaac agtggcggcc ccctaactg    32880 tggtcgaggg tatcaatgct ttggcagtag ccacaggtaa gggtattggg ctaaatgaaa   32940
ccaacacaca cctgcaggca aaactggtcg caccectagg ctttgatacc aacggcaaca   33000
ttaagctaag cgttgcagga ggcatgaggc taaacaataa cactgata ctagatgtaa     33060 actacccatt tgaggctcaa ggccaactga gcctaagagt gggctcgggc ccactatatg   33120
tagattctag tagtcataac ctaaccatta gatgccttag gggattgtat ataacatctt   33180
ctaacaacca aaacggtcta gaagccaaca ttaaactaac aagaggcctt gtgtatgacg   33240
gaaatgccat agcagttaat gttggcaaag ggctggaata cagccctact gacacaacag   33300
aaaaacctat acagactaaa ataggtctag gcatggagta tgataccgag ggagccatga   33360
tgacaaaact aggctctgga ctaagctttg acaattcagg agccattgta gtgggaaaca   33420
aaaatgatga caggcttact ttgtggacca caccggaccc atcgcccaac tgtcagatct   33480
actctgaaaa agatgctaaa ctaaccttgg tactgactaa atgtggcagt caggttgtag   33540
gcacagtatc tattgccgct cttaaaggta gcctcgtgcc aatcactagt gcaatcagtg   33600
tggttcaggt atacctaagg tttgatgaaa atggggtact aatgagtaac tcttcactta   33660
atggcgaata ctggaatttt agaaacggag actcaactaa tggcacacca tatacaaacg   33720
cagtgggttt catgcctaat ctactggcct atcctaaagg tcaaactaca actgcaaaaa   33780
gtaacattgt cagccaggtc tacatgaatg gggacgatac taaacccatg acatttacaa   33840
tcaacttcaa tggccttagt gaaacagggg ataccectgt tagtaaatat tccatgacat   33900
tctcatggag gtggccaaat ggaagctaca tagggcacaa ttttgtaaca aactccttta   33960
ccttctccta catcgcccaa gaataaagaa agcacagaga tgcttgtttt tgatttcaaa   34020
attgtgtgct tttatttatt ttcagcttac agtatttcca gtagtcattc aaataaagct   34080
taatcaaact gcatgagaac ccttccacat agcttaaatt agcaccagtg caaatggaga   34140
aaaatcaaca taccttttttt tatccagata tcagagaact ctagtggtca gtttccccc    34200 accctcccag ctcacagaat acacagtcct ttccccccgg ctggctttaa acaacactat   34260
ctcattggta acagacatat tcttaggtgt aataatccac acggtctctt ggcgggccaa   34320
acgctggtcg gtgatgttaa taaactcccc aggcagctct ttcaagttca cgtcgctgtc   34380
caactgctga agcgctcgcg gctccgactg cgcctctagc ggaggcaacg gcaacacccg   34440
atccttgatc tataaaggag tagagtcata atccccccata agaatagggc ggtgatgcag   34500
caacaaggcg cgcagcaact cctgccgccg cctctccgta cggcaggaat gcaacggcgt   34560
ggtggtctcc tccgtgataa tccgcaccgc tcgcagcatc agcatcctcg tcctccgggc   34620
acagcagcgc atcctgatct cactgagatc ggcgcagtaa gtgcagcaca aaaccaagat   34680
gttatttaag atcccacagt gcaaagcact gtacccaaag ctcatggcgg aaggacagc    34740 ccccacgtga ccatcatacc agatcctcag gtaaatcaaa tgacgacctc tcataaacac   34800
gctggacatg tacatcacct ccttgggcat gtgctgattc accacctctc gataccacaa   34860
```

```
gcatcgctga ttaattaaag accoctcgag caccatccta aaccaggaag ccagcacctg   34920
accccccgcc aggcactgca gggacccogg tgaatcgcag tggcagtgaa gactccagcg   34980
ctcgtagccg tgaaccatag agctggtcat tatatccaca ttggcacaac acagacacac   35040
tttcatacac tttttcatga ttagcagctc ctctctagtc aggaccatat cccaaggaat   35100
cacccactct tgaatcaagg taaatcccac acagcagggc aggcctctca cataactcac   35160
gttatgcata gtgagcgtgt cgcaatctgg aaataccgga tgatcttcca tcaccgaagc   35220
ccgggtctcc gtctcaaagg gaggtaaacg gtccctcgtg tagggacagt ggcgggataa   35280
tcgagatcgt gttgaacgta gagtcatgcc aaagggaaca gcggacgtac tcatatttcc   35340
tccagcagaa ccaagtgcgc gcgtggcagc tatccctgcg tcttctgtct cgccgcctgc   35400
cccgttcggt gtagtagttg taatacagcc actccctgag accgtcaagg cgctccctgg   35460
cgtccggatc tatgacaaca ccgtcctgca gcgccgccct gatgacatcc accaccgtag   35520
agtatgccaa gccagccag gaaatgcatt cactttgaca gcgagagata ggaggagcgg   35580
ggagagatgg aagaaccatg atagtaaaga gaacttttat tccaatcgat cttctaagat   35640
atcaaagtgg agatctataa gatgacactg gtctcctccg ctgagtcgat caaaaataac   35700
agctaaacca caaacaacac gattggtcaa atgctccaca agggcctgca gcataaaatt   35760
gcctcggaac tccaccgcaa gcataacatc aaagccaccg cctctatcgt gatcaagaat   35820
aaaaacccca cagctatcca ccagacccat atagttttca tctctccatc gtgaaaaaag   35880
atttacaagc cctcccttta aatcacctcc aaccaattga aaagttgaa ccagaccgcc   35940 ctccaccttc atttcagca gcgtatcat gattgcaaaa attcaggctc ctcagacacc   36000
tgtataagat tgagaagcgg aacgttaaca tcgatgtttc gctcgcgtaa atcacgcctc   36060
agtgcaagca taatataatc ccacaggtcg gagcggatca gcgaggacac ctccccgcca   36120
ggaaccaact caacggagcc tatgctgatt ataatacgca tattcggagc tatgctaacc   36180
agcacggccc ccaaataggc gtactgcata ggcggcgaca aaaagtgaac agtttgggtt   36240
aaaaaatcag gcaaacactc gcgcaaaaaa gcaagaacat cataaccatg ctcatgcaaa   36300
tagatgcaag taagctcagg aacaaccaca gaaaaatgca caattttcct ctcaaacatg   36360
actgcgagcc ctgcaaaaaa taaaaagaa acattacaca agagtagcct gtcttacgat   36420
gggatagact actctaacca acataagacg ggccacaaca tcgcccgcgt ggccataaaa   36480
aaaattgtcc gtgtgattaa aaagaagcac agatagctgg ccagtcatat ccggagtcat   36540
cacgtgtgaa cccgtgtaga cccccgggtt ggacacatcg gccaagaaa gaaagcggcc   36600 aatgtaccca ggaggaatta taacactaag acgaagatac aacagaataa ccccatgagg   36660
gggaataaca aagttagtag gtgaataaaa acgataaaca cccgaaactc cctcctgcgt   36720
aggcaaaata gcaccctccc cttccaaaac aacatatagc gcttccacag cagccatgac   36780
aaaagactca aaacactcaa aagactcagt cttaccagga aataaaagc actctcacag   36840 caccagcact aatcagagtg tgaagagggc caagtgccga acgagtatat ataggaataa   36900
aaaatgacgt aaatgtgtaa aggtcagaaa acgcccagaa aaatacacag accaacgccc   36960
gaaacgaaaa cccgcgaaaa aatacccaga acttcctcaa caaccgccac ttccgctttc   37020
tcacggtacg tcacttccgc aagaaaagca aaactacatt tcccacatgt gtaaaaacga   37080
aaccccgccc cttgtaaccg cccacaactt acatcatcaa aacgtaaact cctacgtcac   37140
ccgccccgcc tctccccgcc cacctcatta tcatattggc cacaatccaa aataaggtat   37200
```
attattgatg atg 37213

<210> SEQ ID NO 23
<211> LENGTH: 37195
<212> TYPE: DNA
<213> ORGANISM: Gorilla beringei graueri

<400> SEQUENCE: 23

```
ataatatacc ttattttgga ttgtggccaa tatgataatg aggtgggcgg ggagaggcgg      60
ggcgggtgac gtaggacgcg cgagtagggt tgggaggtgt ggcggaagtg tggcatttgc     120
aagtgggagg agctcacatg caagcttccg tcgcggaaaa tgtgacgttt ttgatgagcg     180
ccgcctacct ccggaagtgc caattttcgc gcgcttttca ccggatatcg tagtaatttt     240
gggcgggacc atgtaagatt tggccatttt cgcgcgaaaa gtgaaacggg gaagtgaaaa     300
ctgaataata gggcgttagt catagtgcgt aatatttacc gagggccgag ggactttgac     360
cgattacgtg gaggactcgc ccaggtgttt tttacgtgaa tttccgcgtt ccgggtcaaa     420
gtctccgttt tattgtcacc gtcatttgac gcggagggta tttaaacccg ctgcgctcct     480
caagaggcca ctcttgagtg ccagcgagaa gagttttctc ctctgctccg cttcggtgat     540
cgaaaaatga gacacatagc ctgcactccg ggtcttttgt ccggtcgggc ggcggccgag     600
cttttggacg ctttgatcaa tgatgtcctg agcgatgatt ttccgtctac tacccacttt     660
agcccaccta ctcttcacga actgtacgat ctggatgtac tggtggatgt gaacgatccc     720
aacgaggagg cggtttctgc gttttttccc gagtctgcgc tgttggccgc tcaggaggga     780
tttgacctac acactccgcc gcctatttta gagtctccgc tgccggagcc cagtggtata     840
ccttatatgc ctgaactgct tcccgaagtg gtagacctga cctgccacga gcctggcttt     900
ccgcccagcg acgatgatgg tgagcctttt gttttagact ttgctgagat acctgggcac     960
ggttgcaggt cttgtgcata tcatcagagg gttaccggag accccgaggt taagtgttcg    1020
ctgtgctata tgaggatgac ctcttccttt atctacagta agttttttgtc taggtgggct    1080
tttgggtagg tgggttttgt gtcagaacag gtgtaaacgt tgcttgtgtt ttttgtacct    1140
gtaggtccgt tgtccgagcc agacccggag cccgaccgcg atcccgagcc ggatcccgag    1200
cctcctcgta gggcaagaaa attaccttct attctgtgca agtctaagac acctgtgagg    1260
accagcgagg cggacagcac cgactctggc acttctacct ctcctcctga aattcaccca    1320
gtggttcctc tgggtataca tagacctgtt gctgttagag tttgcgggcg acgctctgca    1380
gtagagtgca ttgaggactt gcttcacgaa cccgaggaac ctttggactt gagcgttaaa    1440
cgccctaggc aataaacccc acctaagtaa taaaccccac ctaagtaata aaccctgccg    1500
cccttggtta ttgagatgac gcccaatgtt tgcttttgaa tgacttcatg tgtgtaataa    1560
aagtgagtgt gatcataggt ctcttgtttg tctgggcggg gcttaagggt atataagtct    1620
cttggggcta aacttggtta cacttgaccc caatggaggc gtggggtgc ttggaggagt    1680
ttgcggacgt gcgccgtttg ctggacgaga gctctagcaa tacctatact atttggaggt    1740
atctgtgggg ctctactcag gccaagttgg tctccagaat taagcaggat tacaagtgcg    1800
attttgaaga gcttttttagt tcctgcggtg agcttttgca atccttgaat ctgggccatc    1860
aggctatttt ccaggaaaag gttctctcga ctttggattt ttccactccc gggcgcaccg    1920
ccgcttgtgt ggcttttgtg tcttttgtgc aagataaatg gagcgaggag acccacctga    1980
gtcacgccta cgtactggat ttcatggcga tggctctttg gagggcttac aacaaatgga    2040
agattcagaa ggaactgtac ggttccgccc tacgtcgtcc acttctgtcg cgacaggggc    2100
```

-continued

```
tgaggtttcc cgaccatcgg cagcatcaga atctggaaga cgagtcggag gagcgagcgg    2160
aggagaagat cagcttgaga gccggcctgg accctcctca ggaggaatga atctcccgca    2220
ggtggttgac ctgttccag aactgagacg ggtcctgact atcagggagg atggtcagtt     2280
tgtgaagaag tttaagaggg atcggggtga gggagatgat gaggcggcta gcaatttagc    2340
ttttagtctg atgactcgcc accgaccgga atgtattacc tatcagcaga ttaaggagag    2400
ttgtgccaac gagctggatc ttttgggtca gaagtatagc atagaacagc ttaccactta    2460
ctggcttcag cctggggatg attgggaaga ggcgatcagg gtgtatgcaa aggtggccct    2520
gcggcccgat tgcaagtata agattactaa gttggttaat attagaaact gctgctatat    2580
ttctgggaac ggggccgaag tggagataga tactcaggac agggtggctt taggtgttg     2640 catgataaac atgtggcccg ggatactggg gatggatggg gtggtattca tgaatgtgag    2700
gtttacgggc cccaacttta atggcacggt gttcatgggc aacaccaact tgctcctgca    2760
tggtgcgagt ttctatgggt ttaataacac ctgtatagag gcctggaccg atgtaaaggt    2820
tcgaggttgt tcctttata gctgttggaa ggcggtggtg tgtcgcccta aaagcagggg      2880
ttctgtgaaa aaatgcttgt ttgaaaggtg caccttaggc atcctctctg agggcaactc    2940
cagggtgcgc cataatgtgg cttcgaactg cggttgcttc atgcaagtga aggggggtgag   3000 cgttatcaag cataactcgg tgtgtggaaa ctgcgaggat cgcgcctccc agatgctgac    3060
ctgctttgat ggcaactgtc acctgttgaa gaccattcat ataagcagcc accccagaaa    3120
ggcctggccc gtgtttgagc ataacatctt gacccgctgc tccttgcatc tgggggtcag    3180
gaggggtatg ttcctgcctt accagtgtaa ctttagccac actaaaatcc tgctggaacc    3240
cgagtgcatg accaaggtca gcctgaatgg tgtgtttgat gtgactctga aaatctggaa    3300
ggtgctgagg tatgatgaga ccaggaccag gtgccgaccc tgcgagtgcg gcggcaagca    3360
catgagaaat cagcctgtga tgttggatgt gaccgaggag cttaggcctg accatctggt    3420
gctggcctgc accagggccg agtttgggtc tagcgatgag gataccgatt gaggtgggta    3480
aggtgggcgt ggctagaagg gtggggcgtg tataaattgg gggtctaagg gtctctctgt    3540
tttgtcttgc aacagccgcc gccatgagcg acaccggcaa cagctttgat ggaagcatct    3600
ttagccccta tctgacagtg cgcatgcctc actgggctgg agtgcgtcag aatgtgatgg    3660
gttccaacgt ggatggacgc cccgttctgc cttcaaattc gtctacaatg gcctacgcga    3720
ccgtgggagg aactccgctg gacgccgcga cctccgccgc cgcctccgcc gccgccgcga    3780
ccgcgcgcag catggctacg gaccttacag gctctttggt ggcgagcggc gcggcctctc    3840
gcgcgtctgc tcgggatgag aaactgaccg ctctgctgct taaactggaa gacttgaccc    3900
gggagctggc tcaactgacc cagcaggtct ccagcttgcg tgagagcagc cttgcctccc    3960
cctaatggcc cataatataa ataaaagcca gtctgtttgg attaagcaag tgtatgttct    4020
ttatttaact ctccgcgcgc ggtaagcccg ggaccagcgg tctcggtcgt ttagggtgcg    4080
gtggattctt ccaacacgt ggtacaggtg gctctggatg tttagataca tgggcatgag     4140
tccatccctg gggtggaggt agcaccactg cagagcttcg tgctcgggg tggtgttgta     4200 tatgatccag tcgtagcagg agcgctgggc gtggtgctga aaaatgtcct taagcaagag    4260
gcttatagct agggggaggc ccttggtgta agtgtttaca aatctgctca gttgggaggg    4320
gtgcatccgg ggggatataa tgtgcatctt ggactggatt tttaggttgg ctatgttccc    4380
acccagatcc cttctgggat tcatgttgtg caggaccacc agcacggtat atccagtaca    4440
```

```
cttgggaaat ttatcgtgga gcttagacgg gaatgcatgg aagaacttgg agacgccctt     4500
gtggcctccc agattttcca tacattcgtc catgatgatg gcaatgggcc cgtgggaagc     4560
tgcctgagca aaaatgtttc tgggatcgct cacatcgtag ttatgttcca gggtgaggtc     4620
atcataggac atctttacaa atcggggcg gagggtcccg gactggggga tgatggtgcc     4680
ctcgggcccc gggcgtagt tcccctcaca gatctgcatc tcccaggctt tcatttcaga     4740
gggagggatc atatccacct gcggagcgat gaaaaacaca gtttctggcg caggggagat     4800
taactgggat gagagcaggt ttctgagcag ctgtgacttt ccacagccgg tgggcccata     4860
tatcacgcct atcaccggct gcagctggta gttaagagag ctgcagctgc cgtcctcccg     4920
gagcaggggg gccacctcgt tcagcatatc cctgacgtgg atgttctccc tgaccaattc     4980
cgccagaagg cgctcgccgc ccagcgaaag cagctcttgc aaggaagcaa aattttcag      5040 cggttttagg ccgtcggccg tgggcatgtt tttcagcgtc tgggtcagca gttccagtct     5100
gtcccacagc tcggtgatgt gctctacggc atctcgatcc agcagatctc ctcgtttcgc     5160 gggttgggc ggctttcgct gtagggcacc agccgatggg cgtccagcgg ggccagagtc      5220
atgtccttcc atgggcgcag ggtcctcgtc agggtggtct gggtcacggt gaaggggtgc     5280
gctccgggtt gggcgctggc cagggtgcgc ttgaggctgg ttctgctggt gctgaatcgc     5340
tgccgctctt cgccctgcgc gtcggccagg tagcatttga ccatggtctc gtagtcgaga     5400
ccctcggcgg cgtgccccctt ggcgcggagc tttcccttgg aggtggcgcc gcacgagggg    5460
cactgcaggc tcttcagggc gtagagcttg ggagcgagaa acacggactc tggggagtag    5520
gcgtccgcgc cgcaggaagc gcagaccgtc tcgcattcca ccagccaagt gagctccggg    5580
cggtcagggt caaaaccag gttgccccca tgcttttga tgcgtttctt acctcggctc       5640
tccatgagcc ggtgtccctt ctcggtgacg aagaggctgt ccgtgtctcc gtagaccgac    5700
ttcaggggcc tgtcttccag cggagtgcct ctgtcctcct cgtagagaaa ctctgaccac    5760
tctgagacga aggcccgcgt ccaggccagg acgaaggagg ccacgtggga ggggtagcgg    5820
tcgttgtcca ctagcgggtc caccttctcc agggtgtgca ggcacatgtc cccctcctcc    5880
gcgtccagaa aagtgattgg cttgtaggta taggacacgt gaccgggggt tcccgacggg    5940
ggggtataaa aggggggtggg caccctttca tcttcactct cttccgcatc gctgtctgcg    6000
agagccagct gctgggtaa gtattccctc tcgaaggcgg gcatgacctc agcgctcagg     6060
ttgtcagttt ctaaaaatga ggaggatttg atgttcacct gtccggaggt gatacctttg    6120
agggtacctg ggtccatctg gtcagaaaac actattttt tgttgtcaag cttggtggcg     6180
aacgacccgt agagggcgtt ggagagcagc ttggcgatgg agcgcagggt ctggtttttg    6240
tcgcggtcgg ctcgctcctt ggccgcgatg ttgagttgca cgtactcgcg ggccacgcac    6300
ttccactcgg ggaagacggt ggtgcgctcg tctgggatca ggcgcaccct ccagcctcgg    6360
ttgtgcaggg tgaccatgtc gacgctggtg gcgacctcgc cgcgcaggcg ctcgttggtc    6420
cagcagaggc ggccgccctt gcgcgagcag aaggggggta gggggtccag ctggtcctcg    6480 tttgggggt ccgcgtcgat ggtgaagacc ccggggagca agcgcgggtc aaagtagtcg     6540
atcttgcaag cttgcatgtc cagagcccgc tgccattcgc gggcggcgag cgcgcgctcg    6600 tagggggttga gggcgggcc ccagggcatg gggtgggtga gcgcggaggc gtacatgccg    6660
cagatgtcat acacgtacag gggttccctg aggatgccga ggtaggtggg gtagcagcgc    6720
cccccgcgga tgctggcgcg cacgtagtca tagagctcgt gggaggggc cagcatgttg     6780 ggcccgaggt tggtgcgctg ggggcgctcg gcgcggaagg cgatctgcct gaagatggca    6840
```

```
tgggagttgg aggagatggt gggccgctgg aagacgttga agcttgcttc ttgcaagccc      6900
accgagtccc tgacgaagca ggcgtaggac tcgcgcagct tgtgcaccag ctcggcggtg      6960
acctggacgt cgagcgcgca gtagtcgagg gtctcgcgga tgatgtcata cttatcctcc      7020
cccttctttt tccacagctc gcggttgagg acgaactctt cgcggtcttt ccagtactct      7080 tgagggaa acccgtccgt gtccgaacgg taagagccta gcatgtagaa ctggttgacg       7140
gcctggtagg ggcaacagcc cttctccacg ggcagcgcgt aggcctgcgc cgccttgcgg      7200
agggaggtgt gggtgagggc gaaagtgtcc ctgaccatga ctttgaggta ttgatgtttg      7260
aagtctgtgt catcgcagcc gccctgttcc cacagggtg agtccgtgcg cttttttggag      7320 cgcgggttgg gcaggagaa ggtgaggtca ttgaagagga tcttccccgc tcgaggcatg       7380
aagtttctgg tgatgcgaaa gggccctggg accgaggagc ggttgttgat gacctgggcg      7440
gccaggacga tctcgtcaaa gccgtttatg ttgtggccca cgatgtagag ctccaaaaag      7500
cggggctggc ccttgatgga ggggagcttt ttgagttcct cgtaggtgag ctcctcgggc      7560
gattccaggc cgtgctcctc cagggcccag tcttgcaagt gagggttggc cgccaggaag      7620
gatcgccaga ggtcgcgggc catgagggtc tgcaggcggt cgcggaaggt tctgaactgt      7680
cgccccacgg ccatctttc gggggtgatg cagtagaagg tgaggggtc tttctcccag        7740 gggtccatc tgagctctcg ggcgaggtcg cgcgcggcgg cgaccagagc ctcgttgccc       7800
cccagtttca tgaccagcat gaagggcacg agctgcttgc caaaggctcc catccaagtg     7860
taggtctcta catcgtaggt gacaaagagg cgctccgtgc gaggatgaga gccgatcggg     7920
aagaactgga tctcccgcca ccagttggag gattggctgt tgatgtggtg aaagtagaag     7980
tcccgtctgc gggccgagca ctcgtgctgg cttttgtaaa agcgaccgca gtactggcag    8040
cgctgcacgg gttgtatatc ttgcacgagg tgaacctggc gacctctgac gaggaagcgc     8100
agcgggaatc taagtccccc gcctgggtc ccgtgtggct ggtggtcttc tactttggtt      8160
gtctggccgc cagcatctgt ctcctggagg gcgatggtgg agcagaccac cacgccgcga     8220
gagccgcagg tccagatctc ggcgctcggc gggcggagtt tgatgacgac atcgcgcaca     8280
ttggagctgt ccatggtctc cagctcccgc ggcggcaggt cagctgggag ttcctggagg     8340
ttcacctcgc agacgcgggt caaggcgcgg gcagtgttga gatggtatct gatttcaagg    8400
ggcgtgttgg cggcggagtc gatggcttgc aggaggccgc agccccgggg ggccacgatg     8460
gttccccgcg gggcgcgagg ggaggcggaa gctgggggtg tgttcagaag cggtgacgcg     8520
ggcgggcccc cggaggtagg gggggttccg gccccacagg catgggcggc aggggcacgt     8580
cttcgccgcg cgcgggcagg ggctggtgct ggctccgaag agcgcttgcg tgcgcgacga     8640
cgcgacggtt ggtgtcctgt atctgacgcc tctgagtgaa gaccacgggt cccgtgacct     8700
tgaacctgaa agagagttcg acagaatcaa tctcggcatc gttgacagcg gcctggcgca     8760
ggatctcctg cacgtcgccc gagttgtcct ggtaggcgat ctctgccatg aactgctcga    8820
tctcttcttc ctggagatct cctcgtccgg cgcgctccac ggtggccgcc aggtcgttgg     8880
agatgcgacc catgagctgc gagaaggcgt tgagcccgcc ctcgttccag acccggctgt     8940
agaccacgcc ccctcggcg ttgcgggcgc gcatgaccac ctgggccagg ttgagctcca     9000
cgtgtcgcgt gaagacggcg tagttgcgca ggcgctggaa aaggtagttc agggtggtgg    9060
cggtgtgctc ggcgacgaag aagtacatga cccagcgccg caacgtggat tcattgatgt     9120
cccccaaggc ctccaggcgc tccatggcct cgtagaagtc cacggcgaag ttgaaaaact    9180
```

```
gggagttgcg agcggacacg gtcaactcct cctccagaag acggatgagc tcggcgacag    9240
tgtcgcgcac ctcgcgctcg aaggccacgg ggggcgcttc ttcctcttcc acctcttctt    9300
ccatgatcgc ttcttcttct tcctcagccg ggacgggagg gggcggcggc ggcggggggag   9360
gggcgcggcg gcggcggcgg cgcaccggga ggcggtcgat gaagcgctcg atcatctccc    9420
cccgcatgcg gcgcatggtc tcggtgacgg cgcggccgtt ctcccggggg cgcagctcga    9480
agacgccgcc tctcatctcg ccgcggggcg ggcggccgtg aggtagcgag acggcgctga    9540
ctatgcatct taacaattgc tgtgtaggta caccgccgag ggacctgatt gagtccagat    9600
ccaccggatc cgaaaacctt tggaggaaag cgtctatcca gtcgcagtcg caaggtaggc    9660
tgagcaccgt ggcgggcggg ggcgggtctg gagagttcct ggcggagatg ctgctgatga    9720
tgtaattaaa gtaggcggtc ttgagaaggc ggatggtgga caggagcacc atgtctttgg    9780
gtccggcctg ttggatgcgg aggcggtcgg ccatgcccca ggcctcgttc tgacaccggc    9840
gcaggtcttt gtagtagtct tgcatgagtc tttccaccgg cacctcttct ccttcctctt    9900
ctccatctcg ccggtggttt ctcgcgccgc ccatgcgcgt gaccccaaag cccctgagcg    9960
gctgcagcag ggccaggtcg cgaccacgc gctcggccaa gatggcctgc tgcacctgag    10020
tgagggtcct ctcgaagtca tccatgtcca cgaagcggtg gtaggcgccc gtgttgatgg    10080
tgtaggtgca gttggccatg acggaccagt tgacggtctg gtgtcccggc tgcgagagct    10140
ccgtgtaccg caggcgcgag aaggcgcggg aatcgaacac gtagtcgttg caagtccgca    10200
ccagatactg gtagcccacc aggaagtgcg gcggaggttg gcgatagagg ggccagcgct    10260
gggtggcggg ggcgccgggc gccaggtttt ccagcatgag gcggtggtat ccgtagatgt    10320
acctggacat ccaggtgatg ccggcggcgg tggtggtggc gcgcgcgtag tcgcggaccc    10380
ggttccagat gtttcgcagg ggcgagaagt gttccatggt cggcacgctc tggccggtga    10440
ggcgcgcgca gtcgttgacg ctctatacac acacaaaaac gaaagcgttt acagggcttt    10500
cgttctgtag cctggaggaa agtaaatggg ttggttgcg gtgtgccccg gttcgagacc    10560
aagctgagct cggccggctg aagccgcagc taacgtggta ttggcagtcc cgtctcgacc    10620
caggccctgt atcctccagg atacggtcga gagccctttt gctttcttgg ccaagcgccc    10680
gtggcgcgat ctgggataga tggtcgcgat gagaggacaa aagcggctcg cttccgtagt    10740
ctggagaaac aatcgccagg gttgcgttgc ggcgtacccc ggttcgagcc cctatgcgg    10800
cttgaatcgg ccggaaccgc ggctaacgag ggccgtggca gccccgtcct caggaccccg    10860
ccagccgact tctccagtta cgggagcgag cccctttttgt tttttatttt ttagatgcat   10920
cccgtgctgc ggcagatgcg cccctcgccc cggcccgatc agcagcagca acagcaggca    10980
tgcagacccc cctctcccct ttccgccccg gtcaccacgg ccgcggcggc cgtgtcgggc    11040
gcgggggggcg cgctggagtc agatgagcca ccgcggcggc gacctaggca gtatctggac    11100
ttggaagagg gcgagggact ggcgcggctg ggggcgaact ctccagagcg ccaccgcgg    11160
gtgcagttga aaagggacgc gcgcgaggcg tacctgccgc ggcagaacct gtttcgcgac    11220
cgcggggggcg aggagcccga ggagatgcga gactgcaggt tccaagcggg gcgcgagctg    11280
cggcgcgggc tggacagaca gcgcctgctg cgcgaggagg actttgagcc cgacacgcag    11340
acgggcatca gccccgcgcg cgcgcacgta gccgcggccg acctggtgac cgcctacgag    11400
cagacggtga accaggagcg caacttccaa aagagcttca acaaccacgt gcgcacgctg    11460
gtggcgcgcg aggaggtgac cctggtgtctc atgcatctgt gggacctggt ggaggcgatc    11520
gtgcagaacc ccagcagcaa gccccctgacc gcgcagctgt tcctggtggt gcagcacagc    11580
```

```
agggacaacg aggccttcag ggaggcgctg ctgaacatca ccgagccgga ggggcgctgg    11640
ctcctggacc tgataaacat cctgcagagc atagtggtgc aggagcgcag cctgagcctg    11700
gccgagaagg tggcggccat caactactct atgctgagcc tgggcaagtt ctacgcccgc    11760
aagatctaca agaccccta cgtgcccata gacaaggagg tgaagataga cagcttctac     11820
atgcgcatgg cgctgaaggt gctgacccctg agcgacgacc tgggagtgta ccgcaacgag   11880
cgcatccaca aggccgtgag cgccagccgg cggcgcgagc tgagcgaccg cgagctgatg    11940
cacagtctgc agcgcgcgct gaccggcgcg ggcgagggcg acaggaggt cgagtcctac     12000 ttcgacatgg gggccgacct gcactggcag ccgagccgcc gcgccctgga ggcggcgggg    12060
gcgtacggcg gccccctggc ggccgatgac caggaagagg aggactatga gctagaggag    12120
ggcgagtacc tggaggactg acctggctgg tggtgttttg gtatagatgc aagatccgaa    12180
cgtggcggac ccggcggtcc gggcggcgct gcaaagccag ccgtccggca ttaactcctc    12240
tgacgactgg gccgcggcca tgggtcgcat catggccctg accgcgcgca accccgaggc    12300
tttcaggcag cagcctcagg ccaaccggct ggcggccatc ttggaagcgg tagtgcccgc    12360
gcgctccaac cccacccacg agaaggtgct ggccatagtc aacgcgctgg cggagagcag    12420
ggccatccgc gcggacgagg ccggactggt gtacgatgcg ctgctgcagc gggtggcgcg    12480
gtacaacagc ggcaacgtgc agaccaacct ggaccgcctg gtgacggacg tgcgcgaggc    12540
cgtggcgcag cgcgagcgct tgcatcagga cggtaacctg ggctcgctgg tggcgctaaa    12600
cgccttcctc agcacccagc cggccaacgt accgcggggg caggaggact acaccaactt    12660
tttgagcgcg ctgcggctga tggtgaccga ggtccctcag agcgaggtgt accagtcggg    12720
gcccgactac ttcttccaga ccagcagaca gggcttgcaa accgtgaacc tgagccaggc    12780
tttcaagaac ctgcgggggc tgtggggagt gaaggcgccc accggcgacc gggctacggt    12840
gtccagcctg ctaaccccca actcgcgcct gctgctgctg ctgatcgcgc ccttcacgga    12900
cagcgggagc gtctcgcggg agacctatct gggccacctg ctgacgctgt accgcgaggc    12960
catcgggcag gcgcaggtgg acgagcacac cttccaagag atcaccagcg tgagccacgc    13020
gctggggcag gaggacacgg gcagcctgca ggcgaccctg aactacctgc tgaccaacag    13080
gcggcagaag attcccacgc tgcacagcct gacccaggag gaggagcgca tcttgcgcta    13140
cgtgcagcag agcgtgagcc tgaacctgat gcgcgacggc gtgacgccca gcgtggcgct    13200
ggacatgacc gcgcgcaaca tggaaccggg catgtacgcc tcccaccggc cgttcatcaa    13260
ccgcctgatg gactacttgc atcgggcggc ggccgtgaac cccgagtact tcactaatgc    13320
cattctgaat ccccactgga tgccccctcc gggtttctac aacggggact ttgaggtgcc    13380
cgaggtcaac gacgggttcc tctgggatga catggatgac agtgtgttct cacccaaccc    13440
gctgcgcgcc gcgtctctgc gattgaagga gggctctgac agggaaggac cgagaagtct    13500
ggcctcctcc ctggctctgg gagcggtggg cgccacgggc gcggcggcgc ggggcagtag    13560
ccccttcccc agcctggcag actctctgaa cagcgggcgg gtgagcaggc ccgcttgct     13620 aggcgaggag gagtatctga caaactccct gctgcagccc gcgagggaca agaacgctca    13680
gcggcagcag tttcccaaca atgggatgga gagcctggtg acaagatgt ccagatgaa     13740 gacgtatgcg caggagtaca aggagtggga ggaccgccag ccgcggccct tgccgcccc     13800 taggcagcgc tggcagcggc gcgcgtccaa ccgccgctgg aggcagggc ccgaggacga    13860 tgatgactct gcagatgaca gcagcgtgtt ggacctgggc gggagcggga accccttttc    13920
```

```
gcacctgcgc ccacgcctgg gcaagatgtt ttaaaagaaa aaaaaaaaat aaaactcacc   13980
aaggccatgg cgacgagcgt tggttttttg ttcccttcct tagtatgcgg cgcgcggcga   14040
tgttcgagga ggggcctccc ccctcttacg agagcgcgat ggggatttct cctgcggcgc   14100
ccctgcagcc tccctacgtg cctcctcggt acctgcaacc tacaggggg agaaatagca    14160 tctgttactc tgagctgcag cccctgtacg ataccaccag actgtacctg gtggacaaca   14220
agtccgcgga cgtggcctcc ctgaactacc agaacgacca cagcgatttt ttgaccacgg   14280
tgatccaaaa caacgacttc accccaaccg aggccagcac tcagaccata aacctggata   14340
acaggtcgaa ctggggcggc gacctgaaga ccatcttgca caccaacatg cccaacgtga   14400
acgagttcat gttcaccaac tcttttaagg cgcgggtgat ggtggcgcgc gagcagggggg  14460 aggcgaagta cgagtgggtg gacttcacgc tgcccgaggg caactactca gagaccatga   14520
ctctcgacct gatgaacaat gcgatcgtgg aacactatct gaaagtgggc aggcagaacg   14580
gggtgaagga aagcgatatc ggggtcaagt ttgacaccag aaacttccgt ctgggctggg   14640
accccgtgac cgggctggtc atgccggggg tctacaccaa cgaggccttt catcccgaca   14700
tagtgcttct gcccggctgt ggggtggact tcacccagag ccggctgagc aacctgctgg   14760
gcattcgcaa gcggcagcct ttccaggagg gtttcaagat cacctatgag gatctgaagg   14820
ggggcaacat tcccgcgctc cttgatctgg acgcctacga ggagagcttg aaacccgagg   14880
agagcgctgg cgacagcggc gagagtggcg aggagcaagc cggcggcggt ggcggcgcgt   14940
cggtagaaaa cgaaagtacg cccgcagtgg cggcggacgc tgcggaggtc gagccggagg   15000
ccatgcagca ggacgcagag gagggcgcac aggaggcgc gcagaaggac atgaacgatg    15060
gggagatcag gggagacaca ttcgccaccc ggggcgaaga aaagaggca gaggcggcgg    15120 cggcggcgac ggcggaggcc gaaaccgagg ttgaggcaga ggcagagccc gagaccgaag   15180
ttatggaaga catgaatgat ggagaacgta ggggcgacac gttcgccacc cggggcgaag   15240
agaaggcggc ggaggcagaa gccgcggctg aggaggcggc tgcggctgcg gccaagactg   15300
aggctgcggc taaggctgag gtcgaagcca atgttgcggt tgaggctcag gctgaggagg   15360
aggcggcggc tgaagcagtt aaggaaaagg cccaggcaga gcaggaagag aaaaaacctg   15420
tcattcaacc tctaaaagaa gatagcaaaa agcgcagtta acgtcatc gagggcagca    15480 cctttaccca gtaccgcagc tggtacctgg cgtacaacta cggcgacccg gtcaaggggg   15540
tgcgctcgtg gaccctgctc tgcacgccgg acgtcacctg cggctccgag cagatgtact   15600
ggtcgctgcc gaacatgatg caagacccgg tgaccttccg ctccacgcgg caggttagca   15660
acttcccggt ggtgggcgcc gaactgctgc ccgtgcactc caagagtttt tacaacgagc   15720
aggccgtcta ctcccagctg atccgccagg ccacctctct gacccacgtg ttcaatcgct   15780
ttcccgagaa ccagattttg gcgcgcccgc cggccccac catcaccacc gtgagtgaaa    15840
acgttcctgc cctcacagat cacgggacgc taccgctgcg caacagcatc tcaggagtcc   15900
agcgagtgac cattactgac gccagacgcc ggaccctgcc ctacgtttac aaggccttgg   15960
gcatagtctc gccgcgcgtc ctctccagtc gcacttttta aaacacatct acccacacgt   16020
tccaaaatca tgtccgtact catctcaccc agcaacaaca ccggctgggg gctgcgcgcg   16080
cccagcaaga tgtttggagg ggcgaggaag cgctccgacc agcaccctgt gcgcgtgcgc   16140
ggccactacc gcgcgccctg gggagcgcac aagcgcgggc gcacagggcg caccactgtg   16200
gacgacgtca ttgactccgt agtggagcaa gcgcgccact acacacccgg cgcgccgacc   16260
gcccccgccg tgtccaccgt ggaccaggcg atcgaaagcg tggtacaggg cgcgcggcac   16320
```

```
tatgccaacc ttaaaagtcg ccgccgccgc gtggcccgcc gccatcgccg gagaccccgg   16380
gccaccgccg ccgcgcgcct tactaaggct ctgctcaggc gcgccaggcg aactggccac   16440
cgggccgcca tgagggccgc acggcgggct gccgctgccg caagcgccgt ggccccgcgg   16500
gcacgaaggc gcgcggccgc cgccgccgcc gccgccattt ccagcttggc ctcgacgcgc   16560
cgcggtaaca tatactgggt gcgcgactcg gtaaccggca cgcgggtacc cgtgcgcttt   16620
cgccccccgc ggaattagca caagacaaca tacacactga gtctcctgct gttgtgtatc   16680
ccagcggcga ccgtcagcag cggcgacatg tccaagcgca aaattaaaga agagatgctc   16740
caggtcatcg cgccggagat ctatgggccc ccgaagaagg aggaggatga ttacaagccc   16800
cgcaagctaa agcgggtcaa aaagaaaaag aaagatgatg atgatgacga ggcggtggag   16860
tttgtccgcc gcatggcacc caggcgcccc gtgcagtgga agggccggcg cgtgcagcgc   16920
gttttgcgcc ccggcaccgc ggtggtcttc acgcccggcg agcgctccac gcgcactttc   16980
aagcgggtgt acgatgaggt gtacggcgac gaggacctgt tggagcaggc caaccagcgc   17040
tttggggagt ttgcatatgg gaaacggccc cgcgagagtc taaaagagga cctgctggcg   17100
ctaccgctgg acgagggcaa tcccaccccg agtctgaagc cggtaaccct gcaacaggtg   17160
ctgcctttga gcgcgcccag cgagcataag cgagggttga agcgcgaagg cggggacctg   17220
gcgcccaccg tgcagttgat ggtgcccaag cggcagaagc tggaggacgt gctggagaaa   17280
atgaaagtag agcccgggat ccagcccgag atcaaggtcc gccccatcaa gcaggtggcg   17340
cccggcgtgg gagtccagac cgtggacgtt aggattccca cggaggagat ggaaacccaa   17400
accgccactc cctcttcggc ggccagcgcc accaccggca ccgcttcggt agaggtgcag   17460 acggaccccct ggctacccgc caccgctgtt gccgccgccg cccccgttc gcgcgggcgc   17520 aagagaaatt atccagcggc cagcgcgctc atgcccagt acgcactgca tccatccatc   17580
gcgcccaccc ccggctaccg cgggtactcg taccgcccgc gcagatcagc cggcactcgc   17640
ggccgccgcc gccgtgcgac cacaaccagc cgccgccgtc gccgccgccg ccagccagtg   17700 ctgaccccccg tgtctgtaag gaaggtggct cgctcgggga gcacgctggt ggtgcccaga   17760
gcgcgctacc accccagcat cgtttaaagc cggtctctgt atggttcttg cagatatggc   17820
cctcacttgt cgcctccgct tcccggtgcc gggataccga ggaagaactc accgccgcag   17880
aggcatggcg ggcagcggtc tccgcggcgg ccgtcgccat cgccggcgcg caaaaagcag   17940
gcgcatgcgc ggcggtgtgc tgcctctgct aatcccgcta atcgccgcgg cgatcggtgc   18000
cgtacccggg atcgcctccg tggccctgca ggcgtcccag aaacgttgac tcttgcaacc   18060
ttgcaagctt gcattttttg gaggaaaaat aaaaaaagtc tagactctca cgctcgcttg   18120
gtcctgtgac tattttgtag aaaaaagatg aagacatca actttgcgtc gctggccccg   18180
cgtcacggct cgcgcccgtt catgggagac tggacagata tcggcaccag caatatgagc   18240
ggtggcgcct tcagctgggg cagtctgtgg agcggcctta aaaattttgg ttccaccatt   18300
aagaactatg gcaacaaagc gtggaacagc agcacgggcc agatgctgag agacaagttg   18360
aaagagcaga acttccagga gaaggtggcg cagggcctgg cctctggcat cagcggggtg   18420
gtggacatag ctaaccaggc cgtgcagaaa agataaaca gtcatctgga ccccgtcct   18480 caggtggagg aaatgcctcc agcgatggag acggtgtctc ccgagggcaa aggcgaaaag   18540
cgcccgcggc ccgacagaga agagaccctg gtgtcacaca ccgaggagcc gccctcttac   18600
gaggaggcag tcaaggccgg cctgcccacc actcgcccca tagcccccat ggccaccggt   18660
```

```
gtggtgggcc acaggcaaca cactcccgca acactagatc tgcccccgcc gtccgagccg  18720
ccgcgccagc caaaggcggc gacggtgccc gctccctcca cttccgccgc caacagagtg  18780
cccctgcgcc gcgccgcgag cggcccccgg gcctcgcgag ttagcggcaa ctggcagagc  18840
acactgaaca gcatcgtggg cctgggagtg aggagtgtga agcgccgccg ttgctactga  18900
atgagcaagc tagctaacgt gttgtatgtg tgtatgcgtc ctatgtcgcc gccagaggag  18960
ctgttgagcc gccggcgccg tctgcactcc agcgaatttc aagatggcga ccccatcgat  19020
gatgcctcag tggtcgtaca tgcacatctc gggccaggac gcttcggagt acctgagccc  19080
cgggctggtg cagttcgccc gcgccacaga cacctacttc aacatgagta acaagttcag  19140
gaaccccact gtggcgccca cccacgatgt gaccacggac cggtcgcagc gcctgacgct  19200
gcggttcatc cccgtggatc gggaggacac cgcctactct tacaaggcgc ggttcacgct  19260
ggccgtgggc gacaaccgcg tgctggacat ggcctccact tactttgaca tcagggggt  19320 gctggacagg ggccccacct tcaagcccta ctcgggtact gcctacaact ccctggcccc  19380
caagggcgct cccaattctt gcgagtggga acaagaggaa aatcaggtgg tcgctgcaga  19440
tgatgaactt gaagatgaag aagcgcaagc tcaagaggac gccccagcta aaaaaattca  19500
tgtatatgcc caggcgcctc ttgctggcga aaagattacc aaggatggtt tgcaaatagg  19560
tactgaagtt gtaggagata catctaagga cacttttgca gacaaaacat tccaacccga  19620
acctcagata ggcgagtctc agtggaacga ggctgatgcc acagtagcag gaggcagagt  19680
cttgaaaaaa accacccta tgagaccttg ctatggatcc tatgccaggc ctacaaatgc  19740
caacgggggt caaggaatta tggttgccaa tgaacaagga gtgttggagt ctaaagtgga  19800
gatgcaattt ttttctaaca ctacaaccct taatgcgcgg gatggagctg gcaatcccga  19860
accaaaggtg gtgttgtaca gtgaagatgt ccacttggaa tctcctgaca ctcatttgtc  19920
ttacaagccc aaaaaggatg atgttaatgc taaaattatg ttgggtcagc aagctatggc  19980
taacaggccc aacctcattg cttttagaga taatttcatt ggactcatgt actacaacag  20040
cactggtaac atgggagtgc tggcgggtca ggcctctcag ttgaatgccg tggtggacct  20100
gcaggataga aacacagaac tgtcatatca gcttatgctt gattccattg gggatagatc  20160
cagatacttc tccatgtgga accaggcagt ggatagctat gacccagatg tcagaatcat  20220
tgaaaaccat ggtgtcgagg acgagctacc caactactgc ttccctctgg gcggcatagg  20280
aattactgat acttatcaag ggatcaaaaa taccaatggc aatggtcagt ggaccaaaga  20340
tgatcagttc gcggaccgta atgaaatagg ggtgggaaac aacttcgcca tggagatcaa  20400
catccaggcc aacctctgga ggaacttcct ctatgcgaac gtggggctct acctgccaga  20460
caagctcaag tacaacccca ccaacgtgga catctctgac aaccccaaca cctatgacta  20520
catgaacaag cgtgtggtgg ctcccggcct ggtggactgc tttgtcaatg tgggagccag  20580
gtggtccctg gactacatgg acaacgtcaa ccccttcaac caccaccgca atgcgggtct  20640
gcgctaccgc tccatgatcc tgggcaacgg cgcgtacgtg cccttccaca ttcaggtgcc  20700
ccagaagttc tttgccatca gaacctcct cctcctgccg ggctcctaca cttacgagtg  20760
gaacttcagg aaggatgtca acatggtcct gcagagctct ctgggcaatg accttagggt  20820
ggacggggcc agcatcaagt tgacagcgt caccctctat gctaccttct tccccatggc  20880
tcacaacacc gcctccacgc tcgaggccat gctgaggaac gacaccaacg accagtcctt  20940
caatgactac ctctctgggg ccaacatgct ctacccatc cccgcaagg ccaccaacgt  21000 gcccatctcc attccctctc gcaactgggc cgccttcaga ggctgggcct ttaccgcct  21060
```

```
taagaccaag gaaaccccct ccctgggctc gggttttgac ccctactttg tctactcggg   21120
atccatcccc tacctggatg gcaccttcta cctcaaccac acttttaaga agatatccat   21180
catgtatgac tcctccgtca gctggccggg caatgaccgc ctgctcaccc ccaatgagtt   21240
cgaggtcaag cgcgccgtgg acggcgaggg ctacaacgtg gcccagtgca acatgaccaa   21300
ggactggttc ctggtgcaga tgctggccaa ctacaacata ggctaccagg gcttctacat   21360
cccagagagc tacaaggaca ggatgtactc cttcttcaga aatttccaac ccatgagcag   21420
gcaggtggtg gacgagacca aatacaagga ctatcaggcc attggcatca ctcaccagca   21480
caacaactcg ggattcgtgg gctacctggc tcccaccatg cgcgaggggc aggcctaccc   21540
cgccaacttc ccctacccgt tgataggcaa gaccgcggtc gacagcgtca cccagaaaaa   21600
gttcctctgc gaccgcaccc tctggcgcat cccccttctct agcaacttca tgtccatggg   21660
tgcgctcacg gacctgggcc agaacctgct ctatgccaac tccgcccatg cgctggacat   21720
gacttttgag gtggacccca tggacgagcc caccccttctc tatattgtgt ttgaagtgtt   21780
cgacgtggtc agagtgcacc agccgcaccg cggtgtcatc gagaccgtgt acctgcgcac   21840
gcccttctcg gccggcaacg ccaccaccta aggagacagc gccgccgcct gcatgacggg   21900
ttccaccgag caagagctca gggccatcgc cagagacctg ggatgcggac cctatttttt   21960
gggcacctat gacaaacgct tcccgggctt catctcccga gacaagctcg cctgcgccat   22020
cgtcaacacg gccgcgcgcg agaccggggg cgtgcactgg ctggcctttg gctgggaccc   22080
gcgctccaaa acctgctacc tcttcgaccc ctttggcttc tccgatcagc gcctcagaca   22140
gatctatgag tttgagtacg aggggctgct gcgccgcagc gcgcttgcct cctcgcccga   22200
ccgctgcatc acccttgaga agtccaccga gaccgtgcag gggccccact cggccgcctg   22260
cggtctcttc tgctgcatgt ttttgcacgc ctttgtgcgc tggccccaga gtcccatgga   22320
tcgcaacccc accatgaact tgctcaaggg agtgcccaac gccatgctcc agagccccca   22380
ggtccagccc accctgcgcc acaaccagga acagctctac cgcttcctgg agcgccactc   22440
cccctacttc cgcagtcaca gcgcgcacat ccggggggcc acctctttct gccacttgca   22500
acaaaacatg caagacggaa aatgatgtac agctcgcttt ttaataaatg taaagactgt   22560
gcactttatt tatacacggg ctctttctgg ttatttattc aacaccgccg tcgccatcta   22620
gaaatcgaaa gggttctgcc gcgcgtcgcc gtgcgcacg ggcagagaca cgttgcgata   22680
ctggaagcgg ctcgcccact tgaactcggg caccaccatg cggggcagtg gctcctcggg   22740
gaagttctcg ccccacaggg tgcgggtcag ctgcagcgcg ctcaggaggt cgggagccga   22800
gatcttgaag tcgcagttgg ggccggaacc ctgcgcgcgc gagttgcggt acacggggtt   22860
gcagcactgg aacaccagca gggccggatt acgcacgctg gccagcaggc tctcgtcgct   22920
gatcatgtcg ctgtccagat cctccgcgtt gctcagggcg aatgggtca tcttgcagac   22980
ctgcctgccc aggaaaggcg gcagcccggg cttgccgttg cagtcgcagc gcaggggcat   23040
cagcaggtgc ccgtggcccg tctgcgcctg cgggtacagc gcgcgcatga aggcttcgat   23100
ctgcctgaaa gccacctgcg tcttggctcc ctccgaaaag aacatcccac aggacttgct   23160
ggagaactgg ttcgcgggac agctggcatc gtgcaggcag cagcgcgcgt cggtgttggc   23220
gatctgcacc acgttgcgac cccaccggtt cttcactatc ttggccttgg aagcctgctc   23280
cttcagcgcg cgctggccgt tctcgctggt cacatccatc tctatcacct gctccttgtt   23340
gatcatgttt gtcccgtgca gacacttcag gtcgccctcc gtctgggtgc agcggtgctc   23400
```

```
ccacagcgcg caaccggtgg gctcccaatt tttgtgggtc accccgcgt aggcctgcag    23460 gtaggcctgc aagaagcgcc ccatcatggc cacaaaggtc ttctggctcg taaaggtcag    23520
ctgcaggccg cgatgctctt cgttcagcca ggtcttgcag atggcggcca gcgcctcggt    23580
ctgctcgggc agcatcctaa aatttgtctt caggtcgtta ccacgtggt acttgtccat    23640 catggcgcgc gccgcctcca tgcccttctc ccaggcggac accatgggca ggcttagggg    23700
gtttatcact tccaccggcg aggacaccgt actttcgatt tcttcttcct ccccctcttc    23760
ccggcgcgcg cccacgctgc tgcgcgctct caccgcctgc accaaggggt cgtcttcagg    23820
caagcgccgc accgagcgct tgccgccctt gacctgctta atcagcaccg gcgggttgct    23880
gaagcccacc atggtcagct ccgcctgctc ttcttcgtct tcgctgtcta ccactatctc    23940
tggggaaggg cttctccgct ctgcggcggt gcgcttcttt tttttcttgg gagcagccgt    24000
gacggagtcc gccacggcga cggaggtcga gggcgtgggg ctggggggtgc gcggtaccag    24060 ggcctcgtcg ccctcggact cttcctctga ctccaggcgg cggcggagac gcttctttgg    24120
gggcgcgcgc gtcagcggcg gcggagacgg ggacggggac ggggacggga cgccctccac    24180 aggggggtggt cttcgcgcag acccgcggcc gcgctcgggg gtcttttcga gctggtcttg    24240
gtcccgactg gccattgtat cctcctcctc ctaggcagag agacataagg agtctatcat    24300
gcaagtcgag aaggaggaga gcttaaccac ccctctgag accgcgatg cgcccgccgt    24360 cgccgtcgcc cccgctgccg ccgacgcgcc cgccacaccg agcgacaccc ccgcggaccc    24420
cccagccgac gcacccctgt tcgaggaagc ggccgtggag caggacccgg gctttgtctc    24480
ggcagaggag gatttgcgag aggaggagga taaggagaag aagccctcag tgccaaaaga    24540
tgataaagag caagacgagc acgacgcaga tgcacaccag ggtgaagtcg ggcggggga    24600 cggagggcat gacggcgccg actacctaga cgaagggaac gacgtgctct tgaagcacct    24660
gcatcgtcag tgcgccatcg tttgcgacgc tctgcaggag cgcagcgaag tgcccctcag    24720
cgtggcggag gtcagccacg cctacgagct cagcctcttc tccccccggg tgcccccccg    24780
ccgccgcgaa aacggcacat gcgagcccaa cccgcgcctc aacttctacc ccgcctttgt    24840
ggtgcccgag gtcctggcca cctatcacat cttctttcaa aattgcaaga tccccctctc    24900
gtgccgcgcc aaccgtagcc gcgccgataa gatgctggcc ctgcgccagg gcgaccacat    24960
acctgatatc gccgctttgg aagatgtgcc aaagatcttc gagggtctgg gtcgcaacga    25020
gaagcgggca gcaaactctc tgcaacagga aaacagcgaa aatgagagtc acaccggggt    25080
actggtggag ctcgagggcg acaacgcccg cctggcggtg gtcaagcgca gcatcgaggt    25140
cacccacttt gcctaccccg cgctcaacct gccccccaaa gtcatgaacg cggccatgga    25200
cgggctgatc atgcgccgcg gccggcccct cgctccagat gcaaacttgc atgaggagac    25260
cgaggacggc cagcccgtgg tcagcgacga gcagctggcg cgctggctgg agaccgcgga    25320
ccccgccgaa ctggaggagc ggcgcaagat gatgatggcc gcggtgctgg tcaccgtaga    25380
gctggagtgt ctgcagcgct tcttcggcga ccccgagatg cagagaaagg tcgaggagac    25440
cctgcactac accttccgcc agggctacgt gcgccaggct tgcaagatct ccaacgtgga    25500
gctcagcaac ctggtgtcct acctgggcat cttgcatgag aaccgcctcg gcagagcgt    25560 gctgcactcc accctgcgcg gggaggcgcg ccgcgactac gtgcgcgact cgtttacct    25620 cttcctctgc tacacctggc agacggccat gggggtctgg cagcagtgcc tggaggagcg    25680
caacctcaag gagctggaga agctcctgca gcgcgcgctc aaaagacctct ggacgggcta    25740 caacgagcgc tcggtggccg ccgcgctggc cgacctcatc ttccccgagc gcctgctcaa    25800
```

```
aaccctccag caggggctgc ccgacttcac cagccaaagc atgttgcaaa acttcaggaa    25860
ctttatcctg gagcgttctg gcatcctacc cgccacctgc tgcgccctgc ccagcgactt    25920 tgtcccctc gtgtaccgcg agtgccccc gccgctgtgg ggtcactgct acctgttcca      25980
actggccaac tacctgtcct accacgcgga cctcatggag gactccagcg gcgaggggct    26040
catggagtgc cactgccgct gcaacctctg cacgccccac cgctccctgg tctgcaacac    26100
ccaactgctc agcgagagtc agattatcgg taccttcgag ctacagggtc cgtcctcctc    26160
agacgagaag tccgcggctc cggggctaaa actcactccg gggctgtgga cttccgccta    26220
cctgcgcaaa tttgtacctg aagactacca cgcccacgag atcaggtttt acgaagacca    26280
atcccgcccg cccaaggcgg agctgaccgc ctgcgtcatc acccagggcg agatcctagg    26340
ccaattgcaa gccatccaaa aagcccgcca agatttttg ctgagaaagg gtcgggggt      26400 gtatctggac ccccagtcgg gtgaggagct caacccggtt ccccgctgc cgccgccgcg     26460 ggaccttgct tccaggata agcatcgcca tggctcccag aaagaagcag cagcggccgc     26520
cactgccgcc accccacatg ctggaggaag aggaggaata ctgggacagt caggcagagg    26580
aggtttcgga cgaggaggag ccggagacgg agatggaaga gtgggaggag acagcttag     26640 acgaggaggc ttccgaagcc gaagaggcag acgcaacacc gtcaccctcg gccgcagccc    26700
cctcgcaggc gccccgaag tccgctccca gcatcagcag caacagcagc gctataacct     26760
ccgctcctcc accgccgcga cccacggccg accgcagacc caaccgtaga tgggacacca    26820
ccggaaccgg ggccggtaag tcctccggga gaggcaagca agcgcagcgc caaggctacc    26880
gctcgtggcg cgctcacaag aacgccatag tcgcttgctt gcaagactgc gggggaaca    26940 tctccttcgc ccgccgcttc ctgctcttcc accacggtgt ggccttcccc cgtaacgtcc   27000
tgcattacta ccgtcatctc tacagcccct actgcggcgg cagtgagcca gagacggtcg   27060
gcggcggcgg cggcgcccgt ttcggcgcct aggaagaccc agggcaagac ttcagccaag    27120
aaactcgcgg cggccgcggc gaacgcggtc gcgggggccc tgcgcctgac ggtgaacgaa    27180
cccctgtcga cccgcgaact gagaaaccga atcttcccca ctctctatgc catcttccag    27240
cagagcagag ggcaggatca ggaactgaaa gtaaaaaaca ggtctctgcg ctccctcacc    27300
cgcagctgtc tgtatcacaa gagcgaagac cagcttcggc gcacgctgga ggacgctgag    27360
gcactcttca gcaaatactg cgcgctcact cttaaggact agctccgcgc ccttctcgaa    27420
tttaggcggg aacgcctacg tcatcgcagc gccgccgtca tgagcaagga cattcccacg    27480
ccatacatgt ggagctatca gccgcagatg ggactcgcgg cgggcgcctc ccaagactac    27540
tccacccgca tgaactggct cagtgccggc ccacacatga tctcacaggt taatgatatc    27600
cgcacccatc gaaaccaaat attggtggag caggcggcaa ttaccaccac gccccgcaat    27660
aatcccaacc ccagggagtg gcccgcgtcc ctggtgtatc aggaaattcc cggccccacc    27720
accgtactac ttccgcgtga ttcccaggcc gaagtccaaa tgactaactc aggggcgcag    27780
ctcgcgggcg gctgtcgtca cagggtgcgg cctcctcgcc agggtataac tcacctggag    27840
atccgaggca gaggtattca gctcaacgac gagtcggtga gctcctcgct cggtctaaga    27900
cctgacggga ccttccagat agccggagcc ggccgatctt ccttcacgcc ccgccaggcg    27960
tacctgactc tgcagagctc gtcctcggcg ccgcgctcgg gcggcatcgg gactctccag    28020
ttcgtgcagg agtttgtgcc ctcggtctac ttcaacccct tctcgggctc tcccggtcgc    28080
tacccggacc agttcatctc gaactttgac gccgcgaggg actcggtgga cggctacgac    28140
```

```
tgaatgtcgg gtggacccgg tgcagagcaa cttcgcctga agcacctcga ccactgccgc    28200
cgccctcagt gctttgcccg ctgtcagacc ggtgagttcc agtacttttc cctgcccgac    28260
tcgcacccgg acggcccggc gcacggggtg cgcttttcca tcccgagtca ggtgcgctct    28320
accctaatca gggagtttac cgcccgtccc ctactggcgg agttggaaaa ggggccttct    28380
atcctaacca ttgcctgcat ctgctctaac cctggattgc accaagatct ttgctgtcat    28440
ttgtgtgctg agtataataa aggctgagat cagaatctac tcgggctcct gtcgccatcc    28500
tgtcaacgcc accgtccaag cccggcccga tcagcccgag gtgaacctca cctgcggtct    28560
gcaccggcgc ctgaggaaat acctagcttg gtactacaac agcactccct tgtggttta    28620 caacagcttt gaccaggacg gggtctcact gagggataac ctctcgaacc tgagctactc    28680
catcaggaag aacagcaccc tcgagctact tcctccttac ctgcccggga cttaccagtg    28740
tgtcaccggt ccctgcaccc acacccacct gttgatcgta aacgactctc ttccgagaac    28800
agacctcaat aactcctctt cgcagttccc cagaacagga ggtgagctca ggaaaccccg    28860
ggtaaagaag ggtggacaag agttaacact tgtggggttt ctggtgtatg tgacgctggt    28920
ggtggctctt ttgattaagg cttttccttc catgtctgaa ctctccctct tttatgaaca    28980
actcgactag tgctaacggg accctaccca acgaatcggg attgaatatc ggtaaccagg    29040
ttgcagtttc acttttgatt accttcatag tcctcttcct gctagtgctg tcgcttctgt    29100
gcctgcggat cggggctgc tgcatccacg tttatatctg gtgctggctg tttagaaggt    29160
tcggagacca tcgcaggtag aataaacatg ctgctgctta ccctctttgt cctggcgctg    29220
gccgccagct gccaagcctt ttccgaggct gactttatag agcccagtg taacgtgact    29280 tttaaagccc atgcacagcg ttgtcatact ataatcaaat gtgccaccga acacgatgaa    29340
taccttatcc agtataaaga taaatcacac aaagtggcac ttgttgacat ctggaaaccc    29400
gaagacccct tggaatacaa tgtgaccgtt ttccagggtg acctcttcaa aatttacaat    29460
tacactttcc catttgacca gatgtgtgac tttgtcatgt acatggaaaa gcagcacaag    29520
ctgtggcctc cgactcccca gggctgtgtg gaaaatccag gctcttctg catgatctct    29580 ctctgtgtaa ctgtgctggc actaatactc acgcttttgt atatcagatt taaatcaagg    29640
caaagcttca tcgatgaaaa gaaaatgcct taaacgcttt cacgcttgat tgctaacacc    29700
gggtttttat ccgcagaatg attggaatca ccctactaat cacctccctc cttgcgattg    29760
cccatgggtt ggaacgaatc gaagccctg tggggccaa tgttaccctg gtggggcctg    29820
tcggcaatgc tacattaatg tgggaaaaat atactaaaaa tcaatgggtc tcttactgca    29880
ctaacaaaaa cagccacaag cccagagcca tctgcgatgg gcaaaatcta accttgattg    29940
atgttcaaat gctggatgcg ggctactatt atgggcagct gggtacaatg attaattact    30000 ggagaccca caaagattac atgctccacg tagtaaaggg tccccttagc agcccaccca    30060
ctaccacctc tactacccc actaccacca ctactcccac caccagcact gccgcccagc    30120
ctcctcatag cagaacaacc acttttatca attccaagtc ccactccccc cacattgccg    30180
gcgggccctc cgcctcagac tccgagacca ccgagatctg cttctgcaaa tgctctgacg    30240
cctttgctga ggatttggaa gaccacgagg aagatgagca tgacttcgca gatgcatgcc    30300
aggcatcaga ggcagaagcg ctgccggtgg ccctcaaaca gtatgcagac ccccacacca    30360
cccccaacct tcctccacct tcccagaagc caagtttcct ggggggaaat gaaactctgc    30420
ctctctccat actcgctctg acatctgttg ctatgttgac cgctctgctg gtgcttctat    30480
gctctatatg ctacctgatc tgctgcagaa agaaaaaatc tcacggccat gctccaccagc   30540
```

-continued

```
ccctcatgca cttcccttac cctccagagc tgggcgacca caaactttaa gtctgcagta    30600
actatctgcc catcccttgt cagtcgacag cgatgagccc cactaatcta acggcctctg    30660
gacttacaac atcgtctctt aatgagacca ccgctcctca agacctgtac gatggtgtct    30720
ccgcgctggt taaccagtgg gatcacctgg gcatatggtg gctcctcata ggagcagtga    30780
ccctgtgcct aatcctggtc tggatcatct gctgcatcaa aagcagaaga cccaggcggc    30840
ggcccatcta caggcccttt gtcatcacac ctgaagatga tgatgacacc acttccaggc    30900
tgcagaggct aaagcagcta ctcttctctt ttacagcatg gtaaattgaa tcatgcctcg    30960
cattttcatc tacttgtctc tccttccact tttctgggc tcttctacat tggccgctgt    31020
gtcccacatc gaggtagact gcctcacgcc cttcacagtc tacctgcttt tcggcttttgt   31080
catctgcacc tttgtctgca gcgttatcac tgtagtgatc tgcttcatac agtgcatcga    31140
ctacgtctgc gtgcgggtgg cttactttag acaccacccc cagtatcgca acagggacat    31200
agcggctctc ctaagacttg tttaaaatca tggccaaatt aactgtgatt ggtcttctga    31260
tcatctgctg cgtcctagcc gcgattggga ctcaagctcc taccaccacc agcgctccca    31320
gaaagagaca tgtatcctgc agcttcaagc gtccctggaa tatacccca tgctttactg    31380
atgaacctga aatctctttg gcttggtact tcagcgtcac cgcccttctt atcttctgca    31440
gtacggttat tgcccttgcc atctacccctt cccttgacct gggctggaat gctgtcaact    31500
ctatggaata tcccaccttc ccagaaccag acctgccaga cctggttgtt ctaaacgcgt    31560
ttcctcctcc tgctcccgtt caaaatcagt ttcgccctcc gtcccccacg cccactgagg    31620
tcagctactt taatctaaca ggcggagatg actgaaaacc tagacctaga aatggacggt    31680
ctctgcagcg agcaacgcac actagagagg cgccggcaaa aagagctcga gcgtcttaaa    31740
caagagctcc aagacgcggt ggccatacac cagtgcaaaa aaggtgtctt ctgtctggta    31800
aaacaggcca cgctcaccta tgaaaaaaca ggtgacaccc accgcctagg atacaagctg    31860
cccacacagc gccagaagtt cgccctcatg ataggcgaac aacccatcac cgtgacccag    31920
cactccgtgg agacagaagg ctgcatacac gctcccctgta ggggcgctga ctgcctctac    31980
accttgatca aaaccctctg cggtctcaga gacctcatcc cttttaatta atcataactg    32040
taatcaataa aaaatcactt acttgaaatc tgatagcaag cctctgtcca atttttttcag    32100
caacacttcc ttccctcct cccaactctg gtactctagg cgcctcctag ctgcaaactt    32160
cctccacagt ctgaagggaa tgtcagattc ctcctcctgt ccctccgcac ccacgatctt    32220
catgttgttg cagatgaaac gcgcgagatc gtctgacgag accttcaacc ccgtgtaccc    32280
ctacgatacc gagatcgctc cgacttctgt ccctttcctt accctccct ttgtgtcatc    32340
cgcaggaatg caagaaaatc cagctggggt gctgtccctg cacttgtcag agcccttac    32400
cacccacaat ggggccctga ctctaaaaat ggggggcggc ctgaccctgg acaaggaagg    32460
gaatctcact tcccaaaaca tcaccagtgt cgatcccccct ctcaaaaaaa gcaagaacaa    32520
catcagcctt cagaccgccg caccctcgc cgtcagctcc ggggccctaa cactttttgc    32580
cactccccc ctagcggtca gtggtgacaa ccttactgtg cagtctcagg ccctctcac    32640
tttggaagac tcaaaactaa ctctggccac caaaggaccc ctaactgtgt ccgaaggcaa    32700
acttgtccta gaaacagagg ctcccctgca tgcaagtgac agcagcagcc tgggccttag    32760
cgttacggcc ccacttagca ttaacaatga cagcctagga ctagacatgc aagcgcccat    32820
tagctctcga gatggaaaac tggctctaac agtggcggcc cccctaactg tggtcgaggg    32880
```

```
tatcaatgct ttggcagtag ccacaggtaa gggtattggg ctaaatgaaa ccaacacaca    32940
cctgcaggca aaactggtcg caccccctagg ctttgatacc aacggcaaca ttaagctaag    33000
cgttgcagga ggcatgaggc taaacaataa cacactgata ctagatgtaa actacccatt    33060
tgaggctcaa ggccaactga gcctaagagt gggctcgggc ccactatatg tagattctag    33120
tagtcataac ctaaccatta gatgccttag gggattgtat ataacatctt ctaacaacca    33180
aaacggtcta gaagccaaca ttaaactaac aagaggcctt gtgtatgacg gaaatgccat    33240
agcagttaat gttggcaaag ggctggaata cagccctact gacacaacag aaaaacctat    33300
acagactaaa ataggtctag gcatggagta tgataccgag ggagccatga tgacaaaact    33360
aggctctgga ctaagctttg acaattcagg agccattgta gtgggaaaca aaaatgatga    33420
caggcttact ttgtggacca caccggaccc atcgcccaac tgtcagatct actctgaaaa    33480
agatgctaaa ctaaccttgg tactgactaa atgtggcagt caggttgtag gcacagtatc    33540
tattgccgct cttaaaggta gcctcgtgcc aatcactagt gcaatcagtg tggttcaggt    33600 ataccctaagg tttgatgaaa atggggtact aatgagtaac tcttcactta atggcgaata    33660
ctggaatttt agaaacggag actcaactaa tggcacacca tatacaaacg cagtgggttt    33720
catgcctaat ctactggcct atcctaaagg tcaaactaca actgcaaaaa gtaacattgt    33780
cagccaggtc tacatgaatg gggacgatac taaacccatg acatttacaa tcaacttcaa    33840
tggccttagt gaaacagggg ataccccctgt tagtaaatat tccatgacat tctcatggag    33900
gtggccaaat ggaagctaca tagggcacaa ttttgtaaca aactcctttaa ccttctccta    33960 catcgcccaa gaataaagaa agcacagaga tgcttgtttt tgattttcaaa attgtgtgct    34020 tttattatt ttcagcttac agtatttcca gtagtcattc aaataaagct taatcaaact    34080
gcatgagaac ccttccacat agcttaaatt agcaccagtg caaatggaga aaaatcaaca    34140
tacctttttt tatccagata tcagagaact ctagtggtca gttttccccc accctcccag    34200
ctcacagaat acacagtcct ttcccccccgg ctggcttttaa acaacactat ctcattggta    34260
acagacatat tcttaggtgt aataatccac acggtctctt ggcgggccaa acgctggtcg    34320
gtgatgttaa taaactcccc aggcagctct ttcaagttca cgtcgctgtc caactgctga    34380
agcgctcgcg gctccgactg cgcctctagc ggaggcaacg gcaacacccg atccttgatc    34440
tataaaggag tagagtcata atcccccata agaatagggc ggtgatgcag caacaaggcg    34500
cgcagcaact cctgccgccg cctctccgta cggcaggaat gcaacggcgt ggtggtctcc    34560
tccgtgataa tccgcaccgc tcgcagcatc agcatcctcg tcctccgggc acagcagcgc    34620
atcctgatct cactgagatc ggcgcagtaa gtgcagcaca aaaccaagat gttatttaag    34680
atcccacagt gcaaagcact gtacccaaag ctcatggcgg gaaggacagc ccccacgtga    34740
ccatcatacc agatcctcag gtaaatcaaa tgacgacctc tcataaacac gctggacatg    34800
tacatcacct ccttgggcat gtgctgattc accacctctc gataccacaa gcatcgctga    34860
ttaattaaag accccctcgag caccatccta aaccaggaag ccagcacctg accccccgcc    34920
aggcactgca gggaccccgg tgaatcgcag tggcagtgaa gactccagcg ctcgtagccg    34980
tgaaccatag agctggtcat tatatccaca ttggcacaac acagacacac tttcatacac    35040
tttttcatga ttagcagctc ctctctagtc aggaccatat cccaaggaat cacccactct    35100
tgaatcaagg taaatcccac acagcagggc aggcctctca cataactcac gttatgcata    35160
gtgagcgtgt cgcaatctgg aaataccgga tgatcttcca tcaccgaagc ccgggtctcc    35220
gtctcaaagg gaggtaaacg gtccctcgtg tagggacagt ggcgggataa tcgagatcgt    35280
```

```
gttgaacgta gagtcatgcc aaagggaaca gcggacgtac tcatatttcc tccagcagaa    35340
ccaagtgcgc gcgtggcagc tatccctgcg tcttctgtct cgccgcctgc cccgttcggt    35400
gtagtagttg taatacagcc actccctgag accgtcaagg cgctccctgg cgtccggatc    35460
tatgacaaca ccgtcctgca gcgccgccct gatgacatcc accaccgtag agtatgccaa    35520
gcccagccag gaaatgcatt cactttgaca gcgagagata ggaggagcgg ggagagatgg    35580
aagaaccatg atagtaaaga gaactttat tccaatcgat cttctaagat atcaaagtgg      35640
agatctataa gatgacactg gtctcctccg ctgagtcgat caaaaataac agctaaacca    35700
caaacaacac gattggtcaa atgctccaca agggcctgca gcataaaatt gcctcggaac    35760
tccaccgcaa gcataacatc aaagccaccg cctctatcgt gatcaagaat aaaaacccca    35820
cagctatcca ccagacccat atagttttca tctctccatc gtgaaaaaag atttacaagc    35880
tcctcctta  aatcacctcc aaccaattga aaaagttgaa ccagaccgcc ctccaccttc    35940
attttcagca agcgtatcat gattgcaaaa attcaggctc ctcagacacc tgtataagat    36000
tgagaagcgg aacgttaaca tcgatgtttc gctcgcgtaa atcacgcctc agtgcaagca    36060
taatataatc ccacaggtcg gagcggatca gcgaggacac ctccccgcca ggaaccaact    36120
caacggagcc tatgctgatt ataatacgca tattcggagc tatgctaacc agcacggccc    36180
ccaaataggc gtactgcata ggcggcgaca aaaagtgaac agtttgggtt aaaaaatcag    36240
gcaaacactc gcgcaaaaaa gcaagaacat cataaccatg ctcatgcaaa tagatgcaag    36300
taagctcagg aacaaccaca gaaaaatgca caattttttct ctcaaacatg actgcgagcc    36360
ctgcaaaaaa taaaaaagaa acattacaca agagtagcct gtcttacgat gggatagact    36420
actctaacca acataagacg ggccacaaca tcgcccgcgt ggccataaaa aaaattgtcc    36480
gtgtgattaa aaagaagcac agatagctgg ccagtcatat ccggagtcat cacgtgtgaa    36540
cccgtgtaga cccccgggtt ggacacatcg gccaaagaaa gaaagcggcc aatgtaccca    36600
ggaggaatta taacactaag acgaagatac aacagaataa cccatgagg gggaataaca     36660
aagttagtag gtgaataaaa acgataaaca cccgaaactc cctcctgcgt aggcaaaata    36720
gcaccctccc cttccaaaac aacatatagc gcttccacag cagccatgac aaaagactca    36780
aaacactcaa aagactcagt cttaccagga aataaaagc actctcacag caccagcact      36840
aatcagagtg tgaagagggc caagtgccga acgagtatat ataggaataa aaaatgacgt    36900
aaatgtgtaa aggtcagaaa acgcccagaa aaatacacag accaacgccc gaaacgaaaa    36960
cccgcgaaaa aatacccaga acttcctcaa caaccgccac ttccgctttc tcacggtacg    37020
tcacttccgc aagaaaagca aaactacatt tcccacatgt gtaaaaacga aaccccgccc    37080
cttgtaaccg cccacaactt acatcatcaa aacgtaaact cctacgtcac ccgccccgcc    37140
tctccccgcc cacctcatta tcatattggc cacaatccaa aataaggtat attat         37195
```

<210> SEQ ID NO 24
<211> LENGTH: 37197
<212> TYPE: DNA
<213> ORGANISM: Gorilla beringei graueri

<400> SEQUENCE: 24

```
ataatatacc ttattttgga ttgtggccaa tatgataatg aggtgggcgg ggagaggcgg      60
ggcgggtgac gtaggacgcg cgagtagggt tgggaggtgt ggcggaagtg tggcatttgc     120
aagtgggagg agctcacatg caagcttccg tcgcggaaaa tgtgacgttt ttgatgagcg     180
```

-continued

| | |
|---|---|
| ccgcctacct ccggaagtgc caattttcgc gcgcttttca ccggatatcg tagtaatttt | 240 |
| gggcgggacc atgtaagatt tggccatttt cgcgcgaaaa gtgaaacggg aagtgaaaa | 300 |
| ctgaataata gggcgttagt catagtgcgt aatatttacc gagggccgag ggactttgac | 360 |
| cgattacgtg gaggactcgc ccaggtgttt tttacgtgaa tttccgcgtt ccgggtcaaa | 420 |
| gtctccgttt tattgtcacc gtcatttgac gcggagggta tttaaacccg ctgcgctcct | 480 |
| caagaggcca ctcttgagtg ccagcgagaa gagttttctc ctctgctccg cttcggtgat | 540 |
| cgaaaaatga gacacatagc ctgcactccg ggtctttttgt ccggtcgggc ggcggccgag | 600 |
| cttttggacg ctttgatcaa tgatgtcctg agcgatgatt ttccgtctac tacccacttt | 660 |
| agcccaccta ctcttcacga actgtacgat ctggatgtac tggtggatgt gaacgatccc | 720 |
| aacgaggagg cggtttctgc gttttttccc gagtctgcgc tgttggccgc tcaggaggga | 780 |
| tttgacctac acactccgcc gcctatttta gagtctccgc tgccggagcc cagtggtata | 840 |
| ccttatatgc ctgaactgct tcccgaagtg gtagacctga cctgccacga gcctggcttt | 900 |
| ccgcccagcg acgatgatgg tgagcctttt gttttagact ttgctgagat acctgggcac | 960 |
| ggttgcaggt cttgtgcata tcatcagagg gttaccggag accccgaggt taagtgttcg | 1020 |
| ctgtgctata tgaggatgac ctcttccttt atctacagta agttttttgtc taggtgggct | 1080 |
| tttgggtagg tgggttttgt gtcagaacag gtgtaaacgt tgcttgtgtt ttttgtacct | 1140 |
| gtaggtccgg tgtccgagcc agacccggag cccgaccgcg atcccgagcc ggatcccgag | 1200 |
| cctcctcgta gggcaagaaa attaccttct attctgtgca agtctaagac acctgtgagg | 1260 |
| accagcgagg cggacagcac cgactctggc acttctacct ctcctcctga aattcaccca | 1320 |
| gtggttcctc tgggtataca tagacctgtt gctgttagag tttgcgggcg acgctctgca | 1380 |
| gtagagtgca ttgaggactt gcttcacgaa cccgaggaac ctttggactt gagcgttaaa | 1440 |
| cgccctaggc aataaacccc acctaagtaa taaaccccac ctaagtaata aaccctgccg | 1500 |
| cccttggtta ttgagatgac gcccaatgtt tgcttttgaa tgacttcatg tgtgtaataa | 1560 |
| aagtgagtgt gatcataggt ctcttgtttg tctgggcggg gcttaagggt atataagtct | 1620 |
| cttgggcta aacttggtta cacttgaccc caatggaggc gtggggtgc ttggaggagt | 1680 |
| ttgcggacgt gcgccgtttg ctggacgaga gctctagcaa tacctatact atttggaggt | 1740 |
| atctgtgggg ctctactcag gccaagttgg tctccagaat taagcaggat tacaagtgcg | 1800 |
| attttgaaga gcttttttagt tcctgcggtg agcttttgca atccttgaat ctgggccatc | 1860 |
| aggctatttt ccaggaaaag gttctctcga ctttggatt ttccactccc gggcgcaccg | 1920 |
| ccgcttgtgt ggcttttgtg tcttttgtgc aagataaatg gagcgaggag acccacctga | 1980 |
| gtcacggcta cgtactggat ttcatggcga tggctctttg gagggcttac aacaaatgga | 2040 |
| agattcagaa ggaactgtac ggttccgccc tacgtcgtcc acttctgtcg cgacaggggc | 2100 |
| tgaggtttcc cgaccatcgg cagcatcaga atctggaaga cgagtcggag gagcgagcgg | 2160 |
| aggagaagat cagcttgaga gccggcctgg accctcctca ggaggaatga atctcccgca | 2220 |
| ggtggttgac ctgttccag aactgagacg ggtcctgact atcagggagg atggtcagtt | 2280 |
| tgtgaagaag tttaagaggg atcggggtga gggagatgat gaggcggcta gcaatttagc | 2340 |
| ttttagtctg atgactcgcc accgaccgga atgtattacc tatcagcaga ttaaggagag | 2400 |
| ttgtgccaac gagctggatc tttttgggtca gaagtatagc atagaacagc ttaccactta | 2460 |
| ctggcttcag cctggggatg attgggaaga ggcgatcagg gtgtatgcaa aggtggccct | 2520 |
| gcggcccgat tgcaagtata agattactaa gttggttaat attagaaact gctgctatat | 2580 |

```
ttctgggaac ggggccgaag tggagataga tactcaggac agggtggctt ttaggtgttg    2640
catgataaac atgtggcccg ggatactggg gatggatggg gtggtattca tgaatgtgag    2700
gtttacgggc cccaacttta atggcacggt gttcatgggc aacaccaact tgctcctgca    2760
tggtgcgagt ttcatgggt ttaataacac ctgtatagag gcctggaccg atgtaaaggt    2820
tcgaggttgt tccttttata gctgttggaa ggcggtggtg tgtcgcccta aaagcagggg    2880
ttctgtgaaa aaatgcttgt ttgaaaggtg caccttaggc atcctctctg agggcaactc    2940
cagggtgcgc cataatgtgg cttcgaactg cggttgcttc atgcaagtga aggggggtgag   3000 cgttatcaag cataactcgg tgtgtggaaa ctgcgaggat cgcgcctccc agatgctgac    3060
ctgctttgat ggcaactgtc acctgttgaa gaccattcat ataagcagcc accccagaaa    3120
ggcctggccc gtgtttgagc ataacatctt gacccgctgc tccttgcatc tgggggtcag    3180 gagggtatg ttcctgcctt accagtgtaa ctttagccac actaaaatcc tgctggaacc     3240
cgagtgcatg accaaggtca gcctgaatgg tgtgtttgat gtgactctga aaatctggaa    3300
ggtgctgagg tatgatgaga ccaggaccag gtgccgaccc tgcgagtgcg gcggcaagca    3360
catgagaaat cagcctgtga tgttggatgt gaccgaggag cttaggcctg accatctggt    3420
gctggcctgc accagggccg agtttgggtc tagcgatgag gataccgatt gaggtgggta    3480
aggtgggcgt ggctagaagg gtggggcgtg tataaattgg gggtctaagg gtctctctgt    3540
tttgtcttgc aacagccgcc gccatgagcg acaccggcaa cagctttgat ggaagcatct    3600
ttagccccta tctgacagtg cgcatgcctc actgggctgg agtgcgtcag aatgtgatgg    3660
gttccaacgt ggatggacgc cccgttctgc cttcaaattc gtctacaatg gcctacgcga    3720
ccgtgggagg aactccgctg gacgccgcga cctccgccgc cgcctccgcc gccgccgcga    3780
ccgcgcgcag catggctacg gacctttaca gctctttggt ggcgagcggc gcggcctctc    3840
gcgcgtctgc tcgggatgag aaactgaccg ctctgctgct taaactgaa gacttgaccc      3900 gggagctggc tcaactgacc cagcaggtct ccagcttgcg tgagagcagc cttgcctccc    3960
cctaatggcc cataatataa ataaaagcca gtctgtttgg attaagcaag tgtatgttct    4020
ttatttaact ctccgcgcgc ggtaagcccg ggaccagcgg tctcggtcgt ttagggtgcg    4080
gtggattctt tccaacacgt ggtacaggtg gctctggatg tttagataca tgggcatgag    4140
tccatccctg gggtggaggt agcaccactg cagagcttcg tgctcggggg tggtgttgta    4200
tatgatccag tcgtagcagg agcgctgggc gtggtgctga aaaatgtcct taagcaagag    4260
gcttatagct aggggggaggc ccttggtgta agtgtttaca aatctgctca gttgggaggg    4320
gtgcatccgg ggggatataa tgtgcatctt ggactggatt tttaggttgg ctatgttccc    4380
acccagatcc cttctgggat tcatgttgtg caggaccacc agcacggtat atccagtaca    4440
cttgggaaat ttatcgtgga gcttagacgg gaatgcatgg aagaacttgg agacgccctt    4500
gtggcctccc agatttttcca tacattcgtc catgatgatg gcaatgggcc cgtgggaagc    4560
tgcctgagca aaaatgtttc tgggatcgct cacatcgtag ttatgttcca gggtgaggtc    4620
atcataggac atctttacaa atcggggggcg gagggtcccg gactggggga tgatggtgcc    4680
ctcgggcccc ggggcgtagt tcccctcaca gatctgcatc tcccaggctt tcatttcaga    4740
gggagggatc atatccacct gcggagcgat gaaaaacaca gtttctggcg caggggagat    4800
taactgggat gagagcaggt ttctgagcag ctgtgacttt ccacagccgg tgggcccata    4860
tatcacgcct atcaccggct gcagctggta gttaagagag ctgcagctgc cgtcctcccg    4920
```

-continued

```
gagcaggggg gccacctcgt tcagcatatc cctgacgtgg atgttctccc tgaccaattc      4980
cgccagaagg cgctcgccgc ccagcgaaag cagctcttgc aaggaagcaa aattttttcag     5040 cggttttagg ccgtcggccg tgggcatgtt tttcagcgtc tgggtcagca gttccagtct     5100
gtcccacagc tcggtgatgt gctctacggc atctcgatcc agcagatctc ctcgtttcgc     5160 gggttgggc ggctttcgct gtagggcacc agccgatggg cgtccagcgg ggccagagtc     5220
atgtccttcc atgggcgcag ggtcctcgtc agggtggtct gggtcacggt gaaggggtgc     5280
gctccgggtt gggcgctggc cagggtgcgc ttgaggctgg ttctgctggt gctgaatcgc     5340
tgccgctctt cgccctgcgc gtcggccagg tagcatttga ccatggtctc gtagtcgaga     5400
ccctcggcgg cgtgccctt ggcgcggagc tttcccttgg aggtggcgcc gcacgagggg     5460
cactgcaggc tcttcagggc gtagagcttg ggagcgagaa acacggactc tgggagtag     5520 gcgtccgcgc cgcaggaagc gcagaccgtc tcgcattcca ccagccaagt gagctccggg     5580
cggtcagggt caaaaaccag gttgccccca tgcttttga tgcgtttctt acctcggctc     5640 tccatgagc ggtgtccctt ctcggtgacg aagaggctgt ccgtgtctcc gtagaccgac      5700
ttcaggggcc tgtcttccag cggagtgcct ctgtcctcct cgtagagaaa ctctgaccac     5760
tctgagacga aggcccgcgt ccaggccagg acgaaggagg ccacgtggga ggggtagcgg     5820
tcgttgtcca ctagcgggtc caccttctcc agggtgtgca ggcacatgtc cccctcctcc     5880
gcgtccagaa aagtgattgg cttgtaggtg taggacacgt gaccgggggt tcccgacggg     5940
ggggtataaa aggggtggg cacccttcca tcttcactct cttccgcatc gctgtctgcg     6000
agagccagct gctgggtaa gtattccctc tcgaaggcgg gcatgacctc agcgctcagg     6060
ttgtcagttt ctaaaaatga ggaggatttg atgttcacct gtccggaggt gatacctttg     6120
agggtacctg ggtccatctg gtcagaaaac actattttt tgttgtcaag cttggtggcg     6180
aacgacccgt agagggcgtt ggagagcagc ttggcgatgg agcgcagggt ctggtttttg     6240
tcgcggtcgc ctcgctcctt ggccgcgatg ttgagttgca cgtactcgcg ggccacgcac     6300
ttccactcgg ggaagacggt ggtgcgctcg tctgggatca ggcgcaccct ccagcctcgg     6360
ttgtgcaggg tgaccatgtc gacgctggtg gcgacctcgc cgcgcaggcg ctcgttggtc     6420
cagcagaggc ggccgcccct gcgcgagcag aaggggggta gggggtccag ctggtcctcg     6480 tttgggggt ccgcgtcgat ggtgaagacc ccggggagca agcgcgggtc aaagtagtcg     6540
atcttgcaag cttgcatgtc cagagcccgc tgccattcgc gggcggcgag cgcgcgctcg     6600
taggggttga gggcgggcc ccagggcatg gggtgggtga gcgcggaggc gtacatgccg     6660
cagatgtcat acacgtacag gggttccctg aggatgccga ggtaggtggg gtagcagcgc     6720 ccccgcgga tgctggcgcg cacgtagtca tagagctcgt gggagggggc cagcatgttg     6780
ggcccgaggt tggtgcgctg ggggcgctcg gcgcggaagg cgatctgcct gaagatggca     6840
tgggagttgg aggagatggt gggcgctgg aagacgttga agcttgcttc ttgcaagccc     6900
accgagtccc tgacgaagca ggcgtaggac tcgcgcagct tgtgcaccag ctcggcggtg     6960
acctggacgt cgagcgcgca gtagtcgagg gtctcgcgga tgatgtcata cttatcctcc     7020
cccttctttt tccacagctc gcggttgagg acgaactctt cgcggtcttt ccagtactct     7080 tggagggaa acccgtccgt gtccgaacgg taagagccta gcatgtagaa ctggttgacg     7140
gcctggtagg ggcaacagcc cttctccacg ggcagcgcgt aggcctgcgc cgccttgcgg     7200
agggaggtgt gggtgagggc gaaagtgtcc ctgaccatga ctttgaggta ttgatgtttg     7260
aagtctgtgt catcgcagcc gccctgttcc cacagggtgt agtccgtgcg cttttttggag     7320
```

```
cgcggggttgg gcagggagaa ggtgaggtca ttgaagagga tcttccccgc tcgaggcatg   7380
aagtttctgg tgatgcgaaa gggccctggg accgaggagc ggttgttgat gacctgggcg   7440
gccaggacga tctcgtcaaa gccgtttatg ttgtggccca cgatgtagag ctccaaaaag   7500
cggggctggc ccttgatgga ggggagcttt ttgagttcct cgtaggtgag ctcctcgggc   7560
gattccaggc cgtgctcctc cagggcccag tcttgcaagt gagggttggc cgccaggaag   7620
gatcgccaga ggtcgcgggc catgagggtc tgcaggcgt cgcggaaggt tctgaactgt   7680
cgccccacgg ccatcttttc ggggtgatg cagtagaagg tgaggggtc tttctcccag   7740 gggtcccatc tgagctctcg ggcgaggtcg cgcgcggcgg cgaccagagc ctcgttgccc   7800
cccagtttca tgaccagcat gaagggcacg agctgcttgc caaaggctcc catccaagtg   7860
taggtctcta catcgtaggt gacaaagagg cgctccgtgc gaggatgaga gccgatcggg   7920
aagaactgga tctcccgcca ccagttggag gattggctgt tgatgtggtg aaagtagaag   7980
tcccgtctgc gggccgagca ctcgtgctgg cttttgtaaa agcgaccgca gtactggcag   8040
cgctgcacgg gttgtatatc ttgcacgagg tgaacctggc gacctctgac gaggaagcgc   8100
agcgggaatc taagtcccccc gcctggggtc ccgtgtggct ggtggtcttc tactttggtt   8160
gtctggccgc cagcatctgt ctcctggagg gcgatggtgg agcagaccac cacgccgcga   8220
gagccgcagg tccagatctc ggcgctcggc gggcggagtt tgatgacgac atcgcgcaca   8280
ttggagctgt ccatggtctc cagctcccgc ggcggcaggt cagctgggag ttcctggagg   8340
ttcacctcgc agagacgggt caaggcgcgg gcagtgttga gatggtatct gatttcaagg   8400
ggcgtgttgg cggcggagtc gatggcttgc aggaggccgc agccccgggg ggccacgatg   8460
gttccccgcg gggcgcgagg ggaggcggaa gctgggggtg tgttcagaag cggtgacgcg   8520
ggcgggcccc cggaggtagg gggggttccg gccccacagg catgggcggc aggggcacgt   8580
cttcgccgcg cgcgggcagg ggctggtgct ggctccgaag agcgcttgcg tgcgcgacga   8640
cgcgacggtt ggtgtcctgt atctgacgcc tctgagtgaa gaccacgggt cccgtgacct   8700
tgaacctgaa agagagttcg acagaatcaa tctcggcatc gttgacacgcg gcctggcgca   8760 ggatctcctg cacgtcgccc gagttgtcct ggtaggcgat ctctgccatg aactgctcga   8820
tctcttcttc ctggagatct cctcgtccgg cgcgctccac ggtggccgcc aggtcgttgg   8880
agatgcgacc catgagctgc gagaaggcgt tgagcccgcc ctcgttccag acccggctgt   8940
agaccacgcc ccctcggcg ttgcgggcgc gcatgaccac ctgggccagg ttgagctcca   9000
cgtgtcgcgt gaagacggcg tagttgcgca ggcgctggaa aaggtagttc agggtggtgg   9060
cggtgtgctc ggcgacgaag aagtacatga cccagcgccg caacgtggat tcattgatgt   9120
cccccaaggc ctcaggcgc tccatggcct cgtagaagtc cacggcgaag ttgaaaaact   9180
gggagttgcg agcggacacg gtcaactcct cctccagaag acggatgagc tcggcgacag   9240
tgtcgcgcac ctcgcgctcg aaggccacgg ggggcgcttc ttcctcttcc acctcttctt   9300
ccatgatcgc ttcttcttct tcctcagccg ggacgggagg gggcggcggc ggcggggag   9360 gggcgcggcg gcggcggcgg cgcaccggga ggcggtcgat gaagcgctcg atcatctccc   9420
cccgcatgcg gcgcatggtc tcggtgacgg cgcggccgtt ctcccggggg cgcagctcga   9480
agacgccgcc tctcatctcg ccgcggggcg ggcggccgtg aggtagcgag acggcgctga   9540
ctatgcatct taacaattgc tgtgtaggta caccgccgag ggacctgatt gagtccagat   9600
ccaccggatc cgaaaacctt tggaggaaag cgtctatcca gtcgcagtcg caaggtaggc   9660
```

```
tgagcaccgt ggcgggcggg ggcgggtctg gagagttcct ggcggagatg ctgctgatga    9720
tgtaattaaa gtaggcggtc ttgagaaggc ggatggtgga caggagcacc atgtctttgg    9780
gtccggcctg ttggatgcgg aggcggtcgg ccatgcccca ggcctcgttc tgacaccggc    9840
gcaggtcttt gtagtagtct tgcatgagtc tttccaccgg cacctcttct ccttcctctt    9900
ctccatctcg ccggtggttt ctcgcgccgc ccatgcgcgt gaccccaaag cccctgagcg    9960
gctgcagcag ggccaggtcg gcgaccacgc gctcggccaa gatggcctgc tgcacctgag   10020
tgagggtcct ctcgaagtca tccatgtcca cgaagcggtg gtaggcgccc gtgttgatgg   10080
tgtaggtgca gttggccatg acggaccagt tgacggtctg gtgtcccggc tgcgagagct   10140
ccgtgtaccg caggcgcgag aaggcgcggg aatcgaacac gtagtcgttg caagtccgca   10200
ccagatactg gtagcccacc aggaagtgcg gcggaggttg gcgatagagg ggccagcgct   10260
gggtggcggg ggcgccgggc gccaggtttt ccagcatgag gcggtggtat ccgtagatgt   10320
acctggacat ccaggtgatg ccggcggcgg tggtggtggc gcgcgcgtag tcgcggaccc   10380
ggttccagat gtttcgcagg ggcgagaagt gttccatggt cggcacgctc tggccggtga   10440
ggcgcgcgca gtcgttgacg ctctatacac acacaaaaac gaaagcgttt acagggcttt   10500
cgttctgtag cctggaggaa agtaaatggg ttgggttgcg gtgtgccccg gttcgagacc   10560
aagctgagct cggccggctg aagccgcagc taacgtggta ttggcagtcc cgtctcgacc   10620
caggccctgt atcctccagg atacggtcga gagccctttt gctttcttgg ccaagcgccc   10680
gtggcgcgat ctgggataga tggtcgcgat gagaggacaa aagcggctcg cttccgtagt   10740
ctggagaaac aatcgccagg gttgcgttgc ggcgtacccc ggttcgagcc cctatggcgg   10800
cttgaatcgg ccggaaccgc ggctaacgag ggccgtggca gccccgtcct caggaccccg   10860
ccagccgact tctccagtta cgggagcgag ccccttttgt tttttatttt ttagatgcat   10920
cccgtgctgc ggcagatgcg cccctcgccc cggcccgatc agcagcagca acagcaggca   10980
tgcagacccc cctctcccct ttccgccccg gtcaccacgg ccgcggcggc cgtgtcgggc   11040
gcggggggcg cgctggagtc agatgagcca ccgcggcggc gacctaggca gtatctggac   11100
ttggaagagg gcgagggact ggcgcggctg ggggcgaact ctccagagcg ccacccgcgg   11160
gtgcagttga aaagggacgc gcgcgaggcg tacctgccgc ggcagaacct gtttcgcgac   11220
cgcgggggcg aggagcccga ggagatgcga gactgcaggt tccaagcggg gcgcgagctg   11280
cggcgcgggc tggacagaca gcgcctgctg cgcgaggagg actttgagcc cgacacgcag   11340
acgggcatca gccccgcgcg cgcgcacgta gccgcggccg acctggtgac cgcctacgag   11400
cagacggtga accaggagcg caacttccaa aagagcttca caaccacgt gcgcacgctg   11460
gtggcgcgcg aggaggtgac cctgggtctc atgcatctgt gggacctggt ggaggcgatc   11520
gtgcagaacc ccagcagcaa gccccctgacc gcgcagctgt tcctggtggt gcagcacagc   11580
agggacaacg aggccttcag ggaggcgctg ctgaacatca ccgagccgga ggggcgctgg   11640
ctcctggacc tgataaacat cctgcagagc atagtggtgc aggagcgcag cctgagcctg   11700
gccgagaagg tggcggccat caactactct atgctgagcc tgggcaagtt ctacgcccgc   11760
aagatctaca agaccccccta cgtgcccata gacaaggagg tgaagataga cagcttctac   11820
atgcgcatgg cgctgaaggt gctgaccctg agcgacgacc tgggagtgta ccgcaacgag   11880
cgcatccaca aggccgtgag cgccagccgg ggcgcgagc tgagcgaccg cgagctgatg   11940
cacagtctgc agcgcgcgct gaccggcgcg ggcgagggca caggaggt cgagtcctac   12000
ttcgacatgg gggccgacct gcactggcag ccgagccgcc gcgccctgga ggcggcgggg   12060
```

```
gcgtacggcg ccccctggc ggccgatgac caggaagagg aggactatga gctagaggag    12120
ggcgagtacc tggaggactg acctggctgg tggtgttttg gtatagatgc aagatccgaa    12180
cgtggcggac ccggcggtcc gggcggcgct gcaaagccag ccgtccggca ttaactcctc    12240
tgacgactgg gccgcggcca tgggtcgcat catgggcctg accgcgcgca accccgaggc    12300
tttcaggcag cagcctcagg ccaaccggct ggcggccatc ttggaagcgg tagtgcccgc    12360
gcgctccaac cccacccacg agaaggtgct ggccatagtc aacgcgctgg cggagagcag    12420
ggccatccgc gcggacgagg ccggactggt gtacgatgcg ctgctgcagc gggtggcgcg    12480
gtacaacagc ggcaacgtgc agaccaacct ggaccgcctg gtgacggacg tgcgcgaggc    12540
cgtggcgcag cgcgagcgct tgcatcagga cggtaacctg ggctcgctgg tggcgctaaa    12600
cgccttcctc agcacccagc cggccaacgt accgcggggg caggaggact acaccaactt    12660
tttgagcgcg ctgcggctga tggtgaccga ggtccctcag agcgaggtgt accagtcggg    12720
gcccgactac ttcttccaga ccagcagaca gggcttgcaa accgtgaacc tgagccaggc    12780
tttcaagaac ctgcggggc tgtggggagt gaaggcgccc accggcgacc gggctacggt    12840
gtccagcctg ctaaccccca actcgcgcct gctgctgctg ctgatcgcgc ccttcacgga    12900
cagcgggagc gtctcgcggg agacctatct gggccacctg ctgacgctgt accgcgaggc    12960
catcgggcag gcgcaggtgg acgagcacac cttccaagag atcaccagcg tgagccacgc    13020
gctggggcag gaggacacgg gcagcctgca ggcgaccctg aactacctgc tgaccaacag    13080
gcggcagaag attcccacgc tgcacagcct gacccaggag gaggagcgca tcttgcgcta    13140
cgtgcagcag agcgtgagcc tgaacctgat gcgcgacggc gtgacgccca gcgtggcgct    13200
ggacatgacc gcgcgcaaca tggaaccggg catgtacgcc tcccaccggc cgttcatcaa    13260
ccgcctgatg gactacttgc atcgggcggc ggccgtgaac cccgagtact tcactaatgc    13320
cattctgaat ccccactgga tgccccctcc gggtttctac aacgggact ttgaggtgcc    13380 cgaggtcaac gacgggttcc tctgggatga catggatgac agtgtgttct cacccaaccc    13440
gctgcgcgcc gcgtctctgc gattgaagga gggctctgac agggaaggac cgagaagtct    13500
ggcctcctcc ctgctctctg gagcggtggg cgccacgggc gcggcggcgc ggggcagtag    13560
cccctttccc agcctggcag actctctgaa cagcgggcgg gtgagcaggc cccgcttgct    13620
aggcgaggag gagtatctga caactccct gctgcagccc gcgagggaca agaacgctca    13680
gcggcagcag tttcccaaca atgggataga gagcctggtg gacaagatgt ccagatggaa    13740
gacgtatgcg caggagtaca aggagtggga ggaccgccag ccgcggccct tgccgccccc    13800
taggcagcgc tggcagcggc gcgcgtccaa ccgccgctgg aggcaggggc ccgaggacga    13860
tgatgactct gcagatgaca gcagcgtgtt ggacctgggc gggagcggga accccttttc    13920
gcacctgcgc ccacgcctgg gcaagatgtt ttaaaagaaa aaaaaaaaaa taaaactcac    13980
caaggccatg gcgacgagcg ttggtttttt gttcccttcc ttagtatgcg gcgcgcggcg    14040
atgttcgagg aggggcctcc cccctcttac gagagcgcga tggggatttc tcctgcggcg    14100
cccctgcagc ctccctacgt gcctcctcgg tacctgcaac ctacaggggg gagaaatagc    14160
atctgttact ctgagctgca gccctgtac gataccacca gactgtacct ggtggacaac    14220
aagtccgcgg acgtggcctc cctgaactac cagaacgacc acagcgattt tttgaccacg    14280
gtgatccaaa acaacgactt cacccccaacc gaggccagca ctcagaccat aaacctggat    14340
aacaggtcga actggggcgg cgacctgaag accatcttgc acaccaacat gcccaacgtg    14400
```

```
aacgagttca tgttcaccaa ctcttttaag gcgcgggtga tggtggcgcg cgagcagggg    14460
gaggcgaagt acgagtgggt ggacttcacg ctgcccgagg gcaactactc agagaccatg    14520
actctcgacc tgatgaacaa tgcgatcgtg aacactatc tgaaagtggg caggcagaac     14580 gggggtgaagg aaagcgatat cggggtcaag tttgacacca gaaacttccg tctgggctgg    14640
gaccccgtga ccgggctggt catgccgggg gtctacacca acgaggcctt tcatcccgac    14700
atagtgcttc tgcccggctg tggggtggac ttcacccaga gccggctgag caacctgctg    14760
ggcattcgca agcggcagcc tttccaggag ggtttcaaga tcacctatga ggatctgaag    14820
gggggcaaca ttcccgcgct ccttgatctg gacgcctacg aggagagctt gaaacccgag    14880
gagagcgctg gcgacagcgg cgagagtggc gaggagcaag ccggcggcgg tggcggcgcg    14940
tcggtagaaa acgaaagtac gcccgcagtg gcggcggacg ctgcggaggt cgagccggag    15000
gccatgcagc aggacgcaga ggaggggcgca caggagggcg cgcagaagga catgaacgat    15060
ggggagatca ggggagacac attcgccacc cggggcgaag aaaaagaggc agaggcggcg    15120
gcggcggcga cggcggaggc cgaaaccgag gttgaggcag aggcagagcc cgagaccgaa    15180
gttatggaag acatgaatga tggagaacgt aggggcgaca cgttcgccac ccggggcgaa    15240
gagaaggcgc cggaggcaga agccgcggct gaggaggcgc ctgcggctgc ggccaagact    15300
gaggctgcgg ctaaggctga ggtcgaagcc aatgttgcgg ttgaggctca ggctgaggag    15360
gaggcggcgg ctgaagcagt taaggaaaag gcccaggcag agcaggaaga gaaaaaacct    15420
gtcattcaac ctctaaaaga agatagcaaa aagcgcagtt acaacgtcat cgagggcagc    15480
acctttaccc agtaccgcag ctggtacctg gcgtacaact acggcgaccc ggtcaagggg    15540
gtgcgctcgt ggaccctgct ctgcacgccg gacgtcacct gcggctccga gcagatgtac    15600
tggtcgctgc cgaacatgat gcaagacccg gtgaccttcc gctccacgcg gcaggttagc    15660
aacttcccgg tggtgggcgc cgaactgctg cccgtgcact ccaagagttt ttacaacgag    15720
caggccgtct actcccagct gatccgccag gccacctctc tgacccacgt gttcaatcgc    15780
tttcccgaga accagatttt ggcgcgcccg ccggcccca ccatcaccac cgtgagtgaa     15840
aacgttcctg ccctcacaga tcacgggacg ctaccgctgc gcaacagcat ctcaggagtc    15900
cagcgagtga ccattactga cgccagacgc cggacctgcc cctacgttta caaggccttg    15960
ggcatagtct cgccgcgcgt cctctccagt cgcactttt aaaacacatc tacccacacg     16020
ttccaaaatc atgtccgtac tcatctcacc cagcaacaac accggctggg ggctgcgcgc    16080
gcccagcaag atgtttggag gggcgaggaa gcgctccgac cagcaccctg tgcgcgtgcg    16140
cggccactac cgcgcgccct ggggagcgca caagcgcggg cgcacagggc gcaccactgt    16200
ggacgacgtc attgactccg tagtggagca agcgcgccac tacacacccg gcgcgccgac    16260
cgcccccgcc gtgtccaccg tggaccaggc gatcgaaagc gtggtacagg gcgcgcggca    16320
ctatgccaac cttaaaagtc gccgccgccg cgtggcccgc cgccatcgcc ggagaccccg    16380
ggccaccgcc gccgcgcgcc ttactaaggc tctgctcagg cgcgccaggc gaactggcca    16440
ccgggccgcc atgagggccg cacggcgggc tgccgctgcc gcaagcgccg tggccccgcg    16500
ggcacgaagg cgcgcggccg ccgccgccgc cgccgccatt tccagcttgg cctcgacgcg    16560
gcgcggtaac atatactggg tgcgcgactc ggtaaccggc acgcgggtac ccgtgcgctt    16620 tcgcccccg cggaattagc acaagacaac atacacactg agtctcctgc tgttgtgtat     16680
cccagcggcg accgtcagca gcggcgacat gtccaagcgc aaaattaaag aagagatgct    16740
ccaggtcatc gcgccggaga tctatgggcc cccgaagaag gaggaggatg attacaagcc    16800
```

-continued

```
ccgcaagcta aagcgggtca aaaagaaaaa gaaagatgat gatgatgacg aggcggtgga   16860
gtttgtccgc cgcatggcac ccaggcgccc cgtgcagtgg aagggccggc gcgtgcagcg   16920
cgttttgcgc cccggcaccg cggtggtctt cacgcccggc gagcgctcca cgcgcacttt   16980
caagcgggtg tacgatgagg tgtacggcga cgaggacctg ttggagcagg ccaaccagcg   17040
ctttggggag tttgcatatg gaaacggcc ccgcgagagt ctaaagagg acctgctggc    17100
gctaccgctg gacgagggca atcccacccc gagtctgaag ccggtaaccc tgcaacaggt   17160
gctgcctttg agcgcgccca gcgagcataa gcgagggttg aagcgcgaag gcggggacct   17220
ggcgcccacc gtgcagttga tggtgcccaa gcggcagaag ctggaggacg tgctggagaa   17280
aatgaaagta gagcccggga tccagcccga gatcaaggtc cgccccatca gcaggtggc   17340
gcccggcgtg ggagtccaga ccgtggacgt taggattccc acggaggaga tggaaaccca   17400
aaccgccact ccctcttcgg cggccagcgc caccaccggc accgcttcgg tagaggtgca   17460
gacgaccccc tggctacccg ccaccgctgt tgccgccgcc gccccccgtt cgcgcgggcg   17520
caagagaaat tatccagcgg ccagcgcgct catgccccag tacgcactgc atccatccat   17580
cgcgcccacc cccggctacc gcgggtactc gtaccgcccg cgcagatcag ccggcactcg   17640
cggccgccgc cgccgtgcga ccacaaccag ccgccgccgt cgccgccgcc gccagccagt   17700
gctgaccccc gtgtctgtaa ggaaggtggc tcgctcgggg agcacgctgg tggtgcccag   17760
agcgcgctac caccccagca tcgtttaaag ccggtctctg tatggttctt gcagatatgg   17820
ccctcacttg tcgcctccgc ttcccggtgc cgggataccg aggaagaact caccgccgca   17880
gaggcatggc gggcagcggt ctccgcggcg gccgtcgcca tcgccggcgc gcaaaaagca   17940
ggcgcatgcg cggcggtgtg ctgcctctgc taatcccgct aatcgccgcg gcgatcggtg   18000
ccgtacccgg gatcgcctcc gtggccctgc aggcgtccca gaaacgttga ctcttgcaac   18060
cttgcaagct tgcattttt ggaggaaaaa ataaaaaaag tctagactct cacgctcgct   18120
tggtcctgtg actattttgt agaaaaaaga tggaagacat caactttgcg tcgctggccc   18180
cgcgtcacgg ctcgcgcccg ttcatgggag actggacaga tatcggcacc agcaatatga   18240
gcggtggcgc cttcagctgg ggcagtctgt ggagcggcct taaaaatttt ggttccacca   18300
ttaagaacta tggcaacaaa gcgtggaaca gcagcacggg ccagatgctg agagacaagt   18360
tgaaagagca gaacttccag gagaaggtgg cgcagggcct ggcctctggc atcagcgggg   18420
tggtggacat agctaaccag gccgtgcaga aaaagataaa cagtcatctg gaccccgtc    18480
ctcaggtgga ggaaatgcct ccagcgatgg agacggtgtc tcccgagggc aaaggcgaaa   18540
agcgcccgcg gcccgacaga gaagagaccc tggtgtcaca caccgaggag ccgccctctt   18600
acgaggaggc agtcaaggcc ggcctgccca ccactcgccc catagccccc atggccaccg   18660
gtgtggtggg ccacaggcaa cacactcccg caacactaga tctgcccccg ccgtccgagc   18720
cgccgcgcca gccaaaggcg cgacggtgc ccgctccctc cacttccgcc gccaacagag    18780
tgccctgcg ccgcgccgcg agcggccccc gggcctcgcg agttagcggc aactggcaga    18840
gcacactgaa cagcatcgtg ggcctgggag tgaggagtgt gaagcgccgc cgttgctact   18900
gaatgagcaa gctagctaac gtgttgtatg tgtgtatgcg tcctatgtcg ccgccagagg   18960
agctgttgag ccgccggcgc cgtctgcact ccagcgaatt tcaagatggc gaccccatcg   19020
atgatgcctc agtggtcgta catgcacatc tcgggccagg acgcttcgga gtacctgagc   19080
cccgggctgg tgcagttcgc ccgcgccaca gacacctact tcaacatgag taacaagttc   19140
```

```
aggaacccca ctgtggcgcc cacccacgat gtgaccacgg accggtcgca gcgcctgacg   19200
ctgcggttca tccccgtgga tcgggaggac accgcctact cttacaaggc gcggttcacg   19260
ctggccgtgg gcgacaaccg cgtgctggac atggcctcca cttactttga catcaggggg   19320
gtgctggaca ggggccccac cttcaagccc tactcgggta ctgcctacaa ctccctggcc   19380
cccaagggcg ctcccaattc ttgcgagtgg gaacaagagg aaaatcaggt ggtcgctgca   19440
gatgatgaac ttgaagatga agaagcgcaa gctcaagagg acgccccagc taaaaaaatt   19500
catgtatatg cccaggcgcc tcttgctggc gaaaagatta ccaaggatgg tttgcaaata   19560
ggtactgaag ttgtaggaga tacatctaag gacacttttg cagacaaaac attccaaccc   19620
gaacctcaga taggcgagtc tcagtggaac gaggctgatg ccacagtagc aggaggcaga   19680
gtcttgaaaa aaaccacccc tatgagacct tgctatggat cctatgccag gcctacaaat   19740
gccaacgggg gtcaaggaat tatggttgcc aatgaacaag gagtgttgga gtctaaagtg   19800
gagatgcaat tttttctaa cactacaacc cttaatgcgc gggatggagc tggcaatccc   19860
gaaccaaagg tggtgttgta cagtgaagat gtccacttgg aatctcctga cactcatttg   19920
tcttacaagc ccaaaaagga tgatgttaat gctaaaatta tgttgggtca gcaagctatg   19980
gctaacaggc ccaacctcat tgcttttaga gataatttca ttggactcat gtactacaac   20040
agcactggta acatgggagt gctggcgggt caggcctctc agttgaatgc cgtggtggac   20100
ctgcaggata gaaacacaga actgtcatat cagcttatgc ttgattccat tggggataga   20160
tccagatact tctccatgtg gaaccaggca gtggatagct atgacccaga tgtcagaatc   20220
attgaaaacc atggtgtcga ggacgagcta cccaactact gcttccctct gggcggcata   20280
ggaattactg atacttatca agggatcaaa ataccaatgc aatggtca gtggaccaaa   20340 gatgatcagt tcgcggaccg taatgaaata ggggtgggaa caacttcgc catggagatc   20400 aacatccagg ccaacctctg gaggaacttc ctctatgcga acgtggggct ctacctgcca   20460
gacaagctca gtacaacccc caccaacgtg gacatctctg acaaccccaa cacctatgac   20520
tacatgaaca gcgtgtggt ggctcccggc ctggtggact gctttgtcaa tgtgggagcc   20580
aggtggtccc tggactacat ggacaacgtc aacccttca accaccaccg caatgcgggt   20640
ctgcgctacc gctccatgat cctgggcaac gggcgctacg tgcccttcca cattcaggtg   20700
ccccagaagt tctttgccat caagaacctc tcctcctgc cgggctccta cacttacgag   20760
tggaacttca ggaaggatgt caacatggtc ctgcagagct ctctgggcaa tgaccttagg   20820
gtggacgggg ccagcatcaa gtttgacagc gtcaccctct atgctaccct cttccccatg   20880
gctcacaaca ccgcctccac gctcgaggcc atgctgagga acgacaccaa cgaccagtcc   20940
ttcaatgact acctctctgg ggccaacatg ctctacccca tccccgccaa ggccaccaac   21000
gtgcccatct ccattccctc tcgcaactgg gccgccttca gaggctgggc ctttacccgc   21060
cttaagacca aggaaacccc ctccctgggc tcgggttttg accctacttt tgtctactcg   21120
ggatccatcc cctacctgga tggcacctc tacctcaacc acacttttaa gaagatatcc   21180
atcatgtatg actcctccgt cagctggccg ggcaatgacc gcctgctcac ccccaatgag   21240
ttcgaggtca gcgcgccgt ggacggcgag ggctacaacg tgcccagtg caacatgacc   21300 aaggactggt tcctggtgca gatgctggcc aactacaaca taggctacca gggcttctac   21360
atcccagaga gctacaagga caggatgtac tccttcttca gaaatttcca acccatgagc   21420
aggcaggtgg tggacgagac caaatacaag gactatcagg ccattggcat cactcaccag   21480
cacaacaact cgggattcgt gggctacctg gctcccacca tgcgcgaggg gcaggcctac   21540
```

```
cccgccaact tcccctaccc gttgataggc aagaccgcgg tcgacagcgt cacccagaaa   21600
aagttcctct gcgaccgcac cctctggcgc atcccctttct ctagcaactt catgtccatg   21660
ggtgcgctca cggacctggg ccagaacctg ctctatgcca actccgccca tgcgctggac   21720
atgacttttg aggtggaccc catggacgag cccacccttc tctatattgt gtttgaagtg   21780
ttcgacgtgg tcagagtgca ccagccgcac cgcggtgtca tcgagaccgt gtacctgcgc   21840
acgcccttct cggccggcaa cgccaccacc taaggagaca gcgccgccgc ctgcatgacg   21900
ggttccaccg agcaagagct cagggccatc gccagagacc tgggatgcgg accctatttt   21960
ttgggcacct atgacaaacg cttcccgggc ttcatctccc gagacaagct cgcctgcgcc   22020
atcgtcaaca cggccgcgcg cgagaccggg ggcgtgcact ggctggcctt tggctgggac   22080
ccgcgctcca aaacctgcta cctcttcgac ccctttggct tctccgatca gcgcctcaga   22140
cagatctatg agtttgagta cgaggggctg ctgcgccgca gcgcgcttgc ctcctcgccc   22200
gaccgctgca tcaccccttga gaagtccacc gagaccgtgc aggggcccca ctcggccgcc   22260
tgcggtctct tctgctgcat gtttttgcac gcctttgtgc gctggcccca gagtcccatg   22320
gatcgcaacc ccaccatgaa cttgctcaag ggagtgccca acgccatgct ccagagcccc   22380
caggtccagc ccaccctgcg ccacaaccag gaacagctct accgcttcct ggagcgccac   22440
tccccctact tccgcagtca cagcgcgcac atccggggg ccacctcttt ctgccacttg   22500
caacaaaaca tgcaagacgg aaaatgatgt acagctcgct ttttaataaa tgtaaagact   22560
gtgcacttta tttatacacg ggctctttct ggttatttat tcaacaccgc cgtcgccatc   22620
tagaaatcga aagggttctg ccgcgcgtcg ccgtgcgcca cgggcagaga cacgttgcga   22680
tactggaagc ggctcgccca cttgaactcg ggcaccacca tgcggggcag tggctcctcg   22740
gggaagttct cgccccacag ggtgcgggtc agctgcagcg cgctcaggag gtcgggagcc   22800
gagatcttga agtcgcagtt gggccggaa ccctgcgcgc gcgagttgcg gtacacgggg   22860
ttgcagcact ggaacaccag cagggccgga ttacgcacg tggccagcag gctctcgtcg   22920
ctgatcatgt cgctgtccag atcctccgcg ttgctcaggg cgaatggggt catcttgcag   22980
acctgcctgc ccaggaaagg cggcagcccg ggcttgccgt tgcagtcgca gcgcaggggc   23040
atcagcaggt gcccgtggcc cgtctgcgcc tgcgggtaca gcgcgcgcat gaaggcttcg   23100
atctgcctga aagccaccctg cgtcttggct ccctccgaaa agaacatccc acaggacttg   23160
ctggagaact ggttcgcggg acagctggca tcgtgcaggc agcagcgcgc gtcggtgttg   23220
gcgatctgca ccacgttgcg accccaccgg ttcttcacta tcttggcctt ggaagcctgc   23280
tccttcagcg cgcgctggcc gttctcgctg gtcacatcca tctctatcac ctgctccttg   23340
ttgatcatgt ttgtcccgtg cagacacttc aggtcgccct ccgtctgggt gcagcggtgc   23400
tcccacagcg cgcaaccggt gggctcccaa ttttttgtggg tcaccccgc gtaggcctgc   23460 aggtaggcct gcaagaagcg ccccatcatg gccacaaagg tcttctggct cgtaaaggtc   23520
agctgcaggc cgcgatgctc ttcgttcagc caggtcttgc agatggcggc cagcgcctcg   23580
gtctgctcgg gcagcatcct aaaatttgtc ttcaggtcgt tatccacgtg gtacttgtcc   23640
atcatggcgc gcgccgcctc catgcccttc tcccaggcgg acaccatggg caggcttagg   23700
gggtttatca cttccaccgg cgaggacacc gtactttcga tttcttcttc ctcccctct   23760 tcccggcgcg cgcccacgct gctgcgcgct ctcaccgcct gcaccaaggg gtcgtcttca   23820
ggcaagcgcc gcaccgagcg cttgccgccc ttgacctgct taatcagcac cggcgggttg   23880
```

```
ctgaagccca ccatggtcag ctccgcctgc tcttcttcgt cttcgctgtc taccactatc   23940
tctggggaag ggcttctccg ctctgcggcg gtgcgcttct ttttttttctt gggagcagcc   24000 gtgacggagt ccgccacggc gacggaggtc gagggcgtgg ggctgggggt gcgcggtacc   24060
agggcctcgt cgccctcgga ctcttcctct gactccaggc ggcggcggag acgcttcttt   24120
gggggcgcgc gcgtcagcgg cggcggagac ggggacgggg acgggacgg gacgccctcc   24180 acaggggtg gtcttcgcgc agacccgcgg ccgcgctcgg gggtcttttc gagctggtct   24240
tggtcccgac tggccattgt atcctcctcc tcctaggcag agagacataa ggagtctatc   24300
atgcaagtcg agaaggagga gagcttaacc accccctctg agaccgccga tgcgcccgcc   24360
gtcgccgtcg ccccgctgc cgccgacgcg cccgccacac cgagcgacac ccccgcggac   24420
cccccagccg acgcaccct gttcgaggaa gcggccgtgg agcaggaccc gggctttgtc   24480
tcggcagagg aggatttgcg agaggaggag gataaggaga agaagccctc agtgccaaaa   24540
gatgataaag agcaagacga gcacgacgca gatgcacacc agggtgaagt cgggcggggg   24600
gacggagggc atgacggcgc cgactaccta gacgaaggga acgacgtgct cttgaagcac   24660
ctgcatcgtc agtgcgccat cgtttgcgac gctctgcagg agcgcagcga agtgcccctc   24720
agcgtggcgg aggtcagcca cgcctacgag ctcagcctct tctcccccg ggtgcccccc   24780 cgccgccgcg aaaacggcac atgcgagccc aacccgcgcc tcaacttcta ccccgccttt   24840
gtggtgcccg aggtcctggc cacctatcac atcttctttc aaaattgcaa gatcccctc   24900 tcgtgccgcg ccaaccgtag ccgcgccgat aagatgctgg ccctgcgcca gggcgaccac   24960
atacctgata tcgccgcttt ggaagatgtg ccaaagatct tcgagggtct gggtcgcaac   25020
gagaagcggg cagcaaactc tctgcaacag gaaaacagcg aaaatgagag tcacaccggg   25080
gtactggtgg agctcgaggg cgacaacgcc cgcctggcgg tggtcaagcg cagcatcgag   25140
gtcacccact ttgcctaccc cgcgctcaac ctgccccca aagtcatgaa cgcggccatg   25200
gacgggctga tcatgcgccg cggccggccc ctcgctccag atgcaaactt gcatgaggag   25260
accgaggacg gccagcccgt ggtcagcgac gagcagctgg cgcgctggct ggagaccgcg   25320
gaccccgccg aactggagga gcggcgcaag atgatgatgg ccgcggtgct ggtcaccgta   25380
gagctggagt gtctgcagcg cttcttcggc gaccccgaga tgcagagaaa ggtcgaggag   25440
accctgcact acaccttccg ccagggctac gtgcgccagg cttgcaagat ctccaacgtg   25500
gagctcagca acctggtgtc ctacctgggc atcttgcatg agaaccgcct cgggcagagc   25560
gtgctgcact ccaccctgcg cggggaggcg cgccgcgact acgtgcgcga ctgcgtttac   25620
ctcttcctct gctacacctg gcagacggcc atggggtct ggcagcagtg cctggaggag   25680
cgcaacctca aggagctgga gaagctcctg cagcgcgcgc tcaaagacct ctggacgggc   25740
tacaacgagc gctcggtggc cgccgcgctg gccgacctca tcttccccga gcgcctgctc   25800
aaaaccctcc agcaggggct gcccgacttc accagccaaa gcatgttgca aaacttcagg   25860
aactttatcc tggagcgttc tggcatccta cccgccacct gctgcgccct gcccagcgac   25920
tttgtccccc tcgtgtaccg cgagtgcccc ccgccgctgt ggggtcactg ctacctgttc   25980
caactggcca actacctgtc ctaccacgcg gacctcatgg aggactccag cggcgagggg   26040
ctcatggagt gccactgccg ctgcaacctc tgcacgcccc accgctccct ggtctgcaac   26100
acccaactgc tcagcgagag tcagattatc ggtaccttcg agctacaggg tccgtcctcc   26160
tcagacgaga agtccgcggc tccgggggcta aaactcactc cggggctgtg gacttccgcc   26220
tacctgcgca aatttgtacc tgaagactac cacgcccacg agatcaggtt ttacgaagac   26280
```

```
caatcccgcc cgcccaaggc ggagctgacc gcctgcgtca tcacccaggg cgagatccta   26340
ggccaattgc aagccatcca aaaagcccgc caagattttt tgctgagaaa gggtcggggg   26400
gtgtatctgg accccagtc gggtgaggag ctcaacccgg ttccccgct gccgccgccg     26460
cgggaccttg cttcccagga taagcatcgc catggctccc agaaagaagc agcagcggcc   26520
gccactgccg ccaccccaca tgctggagga agaggaggaa tactgggaca gtcaggcaga   26580
ggaggtttcg gacgaggagg agccggagac ggagatggaa gagtgggagg aggacagctt   26640
agacgaggag gcttccgaag ccgaagaggc agacgcaaca ccgtcaccct cggccgcagc   26700
cccctcgcag gcgcccccga agtccgctcc cagcatcagc agcaacagca gcgctataac   26760
ctccgctcct ccaccgccgc gacccacggc cgaccgcaga cccaaccgta gatgggacac   26820
caccggaacc ggggccggta agtcctccgg gagaggcaag caagcgcagc gccaaggcta   26880
ccgctcgtgg cgcgctcaca agaacgccat agtcgcttgc ttgcaagact gcgggggaa    26940
catctccttc gcccgccgct tcctgctctt ccaccacggt gtggccttcc cccgtaacgt    27000
cctgcattac taccgtcatc tctacagccc ctactgcggc ggcagtgagc cagagacggt    27060
cggcggcggc ggcggcgccc gtttcggcgc ctaggaagac ccagggcaag acttcagcca    27120
agaaactcgc ggcggccgcg gcgaacgcgg tcgcgggggc cctgcgcctg acggtgaacg    27180
aaccctgtc gacccgcgaa ctgagaaacc gaatcttccc cactctctat gccatcttcc     27240
agcagagcag agggcaggat caggaactga agtaaaaaaa caggtctctg cgctccctca    27300
cccgcagctg tctgtatcac aagagcgaag accagcttcg gcgcacgctg gaggacgctg    27360
aggcactctt cagcaaatac tgcgcgctca ctcttaagga ctagctccgc gcccttctcg    27420
aatttaggcg ggaacgccta cgtcatcgca gcgccgccgt catgagcaag gacattccca    27480
cgccatacat gtggagctat cagccgcaga tgggactcgc ggcgggcgcc tcccaagact    27540
actccacccg catgaactgg ctcagtgccg gcccacacat gatctcacag gttaatgata    27600
tccgcaccca tcgaaaccaa atattggtgg agcaggcggc aattaccacc acgccccgca    27660
ataatcccaa ccccagggag tggcccgcgt ccctggtgta tcaggaaatt cccggcccca    27720
ccaccgtact acttccgcgt gattcccagg ccgaagtcca aatgactaac tcaggggcgc    27780
agctcgcggg cggctgtcgt cacagggtgc ggcctcctcg ccagggtata actcacctgg    27840
agatccgagg cagaggtatt cagctcaacg acgagtcggt gagctcctcg ctcggtctaa    27900
gacctgacgg gaccttccag atagccggag ccggccgatc ttccttcacg ccccgccagg    27960
cgtacctgac tctgcagagc tcgtcctcgg cgccgcgctc gggcggcatc gggactctcc    28020
agttcgtgca ggagtttgtg ccctcggtct acttcaaccc cttctcgggc tctcccggtc    28080
gctacccgga ccagttcatc tcgaactttg acgccgcgag ggactcggtg gacggctacg    28140
actgaatgtc gggtggaccc ggtgcagagc aacttcgcct gaagcacctc gaccactgcc    28200
gccgccctca gtgctttgcc cgctgtcaga ccggtgagtt ccagtacttt tccctgcccg    28260
actcgcaccc ggacggcccg gcgcacgggg tgcgcttttt catcccgagt caggtgcgct    28320
ctacccctaat cagggagttt accgcccgtc ccctactggc ggagttggaa aaggggcctt    28380
ctatcctaac cattgcctgc atctgctcta accctggatt gcaccaagat ctttgctgtc    28440
atttgtgtgc tgagtataat aaaggctgag atcagaatct actcgggctc ctgtcgccat    28500
cctgtcaacg ccaccgtcca agcccggccc gatcagcccg aggtgaacct cacctgcggt    28560
ctgcaccggc gcctgaggaa atacctagct tggtactaca acagcactcc ctttgtggtt    28620
```

```
tacaacagct ttgaccagga cggggtctca ctgagggata acctctcgaa cctgagctac  28680
tccatcagga agaacagcac cctcgagcta cttcctcctt acctgcccgg gacttaccag  28740
tgtgtcaccg gtccctgcac ccacacccac ctgttgatcg taaacgactc tcttccgaga  28800
acagacctca ataactcctc ttcgcagttc cccagaacag gaggtgagct caggaaaccc  28860
cgggtaaaga agggtggaca agagttaaca cttgtggggt ttctggtgta tgtgacgctg  28920
gtggtggctc ttttgattaa ggcttttcct tccatgtctg aactctccct cttttatgaa  28980
caactcgact agtgctaacg ggaccctacc caacgaatcg ggattgaata tcggtaacca  29040
ggttgcagtt tcacttttga ttaccttcat agtcctcttc ctgctagtgc tgtcgcttct  29100
gtgcctgcgg atcgggggct gctgcatcca cgtttatatc tggtgctggc tgtttagaag  29160
gttcggagac catcgcaggt agaataaaca tgctgctgct taccctcttt gtcctggcgc  29220
tggccgccag ctgccaagcc ttttccgagg ctgactttat agagcccag tgtaacgtga  29280 cttttaaagc ccatgcacag cgttgtcata ctataatcaa atgtgccacc gaacacgatg  29340
aatacctatt ccagtataaa gataaatcac acaaagtggc acttgttgac atctggaaac  29400
ccgaagaccc tttggaatac aatgtgaccg ttttccaggg tgacctcttc aaaatttaca  29460
attacacttt cccatttgac cagatgtgtg actttgtcat gtacatggaa aagcagcaca  29520
agctgtggcc tccgactccc cagggctgtg tggaaaatcc aggctctttc tgcatgatct  29580
ctctctgtgt aactgtgctg gcactaatac tcacgctttt gtatatcaga tttaaatcaa  29640
ggcaaagctt catcgatgaa aagaaaatgc cttaaacgct ttcacgcttg attgctaaca  29700
ccgggttttt atccgcagaa tgattggaat caccctacta atcacctccc tccttgcgat  29760
tgcccatggg ttggaacgaa tcgaagcccc tgtgggggcc aatgttaccc tggtggggcc  29820
tgtcggcaat gctacattaa tgtgggaaaa atatactaaa aatcaatggg tctcttactg  29880
cactaacaaa aacagccaca agcccagagc catctgcgat gggcaaaatc taaccttgat  29940
tgatgttcaa atgctggatg cgggctacta ttatgggcag ctgggtacaa tgattaatta  30000
ctggagaccc cacaaagatt acatgctcca cgtagtaaag ggtcccctta gcagcccacc  30060
cactaccacc tctactaccc ccactaccac cactactccc accaccagca ctgccgccca  30120
gcctcctcat agcagaacaa ccactttat caattccaag tcccactccc cccacattgc  30180
cggcgggccc tccgcctcag actccgagac caccgagatc tgcttctgca aatgctctga  30240
cgcctttgct gaggatttgg aagaccacga ggaagatgag catgacttcg cagatgcatg  30300
ccaggcatca gaggcagaag cgctgccggt ggccctcaaa cagtatgcag accccacac  30360 caccccaac cttcctccac cttcccagaa gccaagtttc ctgggggaaa atgaaactct  30420
gcctctctcc atactcgctc tgacatctgt tgctatgttg accgctctgc tggtgcttct  30480
atgctctata tgctacctga tctgctgcag aaagaaaaaa tctcacggcc atgctcacca  30540
gcccctcatg cacttccctt accctccaga gctgggcgac cacaaacttt aagtctgcag  30600
taactatctg cccatcccctt gtcagtcgac agcgatgagc cccactaatc taacggcctc  30660
tggacttaca acatcgtctc ttaatgagac caccgctcct caagacctgt acgatggtgt  30720
ctccgcgctg gttaaccagt gggatcacct gggcatatgg tggctcctca taggagcagt  30780
gaccctgtgc ctaatcctgg tctggatcat ctgctgcatc aaaagcagaa gacccaggcg  30840
gcggcccatc tacaggccct ttgtcatcac acctgaagat gatgatgaca ccacttccag  30900
gctgcagagg ctaaagcagc tactcttctc ttttacagca tggtaaattg aatcatgcct  30960 cgcatttca tctacttgtc tctccttcca cttttttctgg gctcttctac attggccgct  31020
```

```
gtgtcccaca tcgaggtaga ctgcctcacg cccttcacag tctacctgct tttcggcttt    31080
gtcatctgca cctttgtctg cagcgttatc actgtagtga tctgcttcat acagtgcatc    31140
gactacgtct gcgtgcgggt ggcttacttt agacaccacc cccagtatcg caacagggac    31200
atagcggctc tcctaagact tgtttaaaat catggccaaa ttaactgtga ttggtcttct    31260
gatcatctgc tgcgtcctag ccgcgattgg gactcaagct cctaccacca ccagcgctcc    31320
cagaaagaga catgtatcct gcagcttcaa gcgtccctgg aatataccc aatgctttac     31380 tgatgaacct gaaatctctt tggcttggta cttcagcgtc accgcccttc ttatcttctg    31440
cagtacggtt attgcccttg ccatctaccc ttcccttgac ctgggctgga atgctgtcaa    31500
ctctatggaa tatcccacct tcccagaacc agacctgcca gacctggttg ttctaaacgc    31560
gtttcctcct cctgctcccg ttcaaaatca gtttcgccct ccgtccccca cgcccactga    31620
ggtcagctac tttaatctaa caggcggaga tgactgaaaa cctagaccta gaaatggacg    31680
gtctctgcag cgagcaacgc acactagaga ggcgccggca aaaagagctc gagcgtctta    31740
aacaagagct ccaagacgcg gtggccatac accagtgcaa aaaaggtgtc ttctgtctgg    31800
taaaacaggc cacgctcacc tatgaaaaaa caggtgacac ccaccgccta ggatacaagc    31860
tgcccacaca gcgccagaag ttcgccctca tgataggcga caacccatc accgtgaccc     31920 agcactccgt ggagacagaa ggctgcatac acgctccctg taggggcgct gactgcctct    31980
acaccttgat caaaaccctc tgcggtctca gagacctcat ccctttaat taatcataac     32040 tgtaatcaat aaaaaatcac ttacttgaaa tctgatagca agcctctgtc caattttttc    32100
agcaacactt ccttcccctc ctcccaactc tggtactcta ggcgcctcct agctgcaaac    32160
ttcctccaca gtctgaaggg aatgtcagat tcctcctcct gtccctccgc acccacgatc    32220
ttcatgttgt tgcagatgaa acgcgcgaga tcgtctgacg agaccttcaa ccccgtgtac    32280
ccctacgata ccgagatcgc tccgacttct gtccctttcc ttaccctcc ctttgtgtca     32340 tccgcaggaa tgcaagaaaa tccagctggg gtgctgtccc tgcacttgtc agagcccctt    32400
accacccaca atgggccct gactctaaaa atgggggcg gcctgaccct ggacaaggaa      32460
gggaatctca cttcccaaaa catcaccagt gtcgatcccc ctctcaaaaa aagcaagaac    32520
aacatcagcc ttcagaccgc cgcaccccctc gccgtcagct ccggggccct aacactttt    32580 gccactcccc ccctagcggt cagtggtgac aaccttactg tgcagtctca ggcccctctc    32640
actttggaag actcaaaact aactctggcc accaaaggac ccctaactgt gtccgaaggc    32700
aaacttgtcc tagaaacaga ggctcccctg catgcaagtg acagcagcag cctgggcctt    32760
agcgttacgg ccccacttag cattaacaat gacagcctag gactagacat gcaagcgccc    32820
attagctctc gagatggaaa actggctcta acagtggcgg ccccctaac tgtggtcgag    32880 ggtatcaatg ctttggcagt agccacaggt aagggtattg ggctaaatga aaccaacaca    32940
cacctgcagg caaaactggt cgcacccctca ggctttgata ccaacggcaa cattaagcta   33000
agcgttgcag gaggcatgag gctaaacaat aacacactga tactagatgt aaactaccca    33060
tttgaggctc aaggccaact gagcctaaga gtgggctcgg gcccactata tgtagattct    33120
agtagtcata acctaaccat tagatgcctt aggggattgt atataacatc ttctaacaac    33180
caaaacggtc tagaagccaa cattaaacta acaagaggcc ttgtgtatga cggaaatgcc    33240
atagcagtta atgttggcaa agggctggaa tacagcccta ctgacacaac agaaaaacct    33300
atacagacta aaataggtct aggcatggag tatgataccg agggagccat gatgacaaaa    33360
```

```
ctaggctctg gactaagctt tgacaattca ggagccattg tagtgggaaa caaaaatgat    33420
gacaggctta ctttgtggac cacaccggac ccatcgccca actgtcagat ctactctgaa    33480
aaagatgcta aactaacctt ggtactgact aaatgtggca gtcaggttgt aggcacagta    33540
tctattgccg ctcttaaagg tagcctcgtg ccaatcacta gtgcaatcag tgtggttcag    33600
gtatacctaa ggtttgatga aaatggggta ctaatgagta actcttcact taatggcgaa    33660
tactggaatt ttagaaacgg agactcaact aatggcacac catatacaaa cgcagtgggt    33720
ttcatgccta atctactggc ctatcctaaa ggtcaaacta caactgcaaa agtaacatt    33780 gtcagccagg tctacatgaa tggggacgat actaaaccca tgacatttac aatcaacttc    33840
aatggcctta gtgaaacagg ggatacccct gttagtaaat attccatgac attctcatgg    33900
aggtggccaa atgaagcta catagggcac aattttgtaa caaactcctt taccttctcc    33960
tacatcgccc aagaataaag aaagcacaga gatgcttgtt tttgatttca aaattgtgtg    34020 ctttttattta ttttcagctt acagtatttc cagtagtcat tcaaataaag cttaatcaaa    34080
ctgcatgaga accccttccac atagcttaaa ttagcaccag tgcaaatgga gaaaaatcaa    34140 cataccttt tttatccaga tatcagagaa ctctagtggt cagttttccc ccaccctccc    34200
agctcacaga atacacagtc cttttccccccc ggctggcttt aaacaacact atctcattgg    34260
taacagacat attcttaggt gtaataatcc acacggtctc ttggcgggcc aaacgctggt    34320
cggtgatgtt aataaactcc ccaggcagct ctttcaagtt cacgtcgctg tccaactgct    34380
gaagcgctcg cggctccgac tgcgcctcta gcggaggcaa cggcaacacc cgatccttga    34440
tctataaagg agtagagtca taatcccca taagaatagg gcggtgatgc agcaacaagg    34500
cgcgcagcaa ctcctgccgc cgcctctccg tacggcagga atgcaacggc gtggtggtct    34560
cctccgtgat aatccgcacc gctcgcagca tcagcatcct cgtcctccgg gcacagcagc    34620
gcatcctgat ctcactgaga tcggcgcagt aagtgcagca caaaaccaag atgttattta    34680
agatcccaca gtgcaaagca ctgtacccaa agctcatggc gggaaggaca gcccccacgt    34740
gaccatcata ccagatcctc aggtaaatca aatgacgacc tctcataaac acgctggaca    34800
tgtacatcac ctccttgggc atgtgctgat tcaccacctc tcgataccac aagcatcgct    34860
gattaattaa agaccctcg agcaccatcc taaaccagga agccagcacc tgacccccg    34920 ccaggcactg cagggacccc ggtgaatcgc agtggcagtg aagactccag cgctcgtagc    34980
cgtgaaccat agagctggtc attatatcca cattggcaca acacagacac actttcatac    35040 acttttttcat gattagcagc tcctctctag tcaggaccat atcccaagga atcacccact    35100
cttgaatcaa ggtaaatccc acacagcagg gcaggcctct cacataactc acgttatgca    35160
tagtgagcgt gtcgcaatct ggaaataccg gatgatcttc catcaccgaa gcccgggtct    35220
ccgtctcaaa gggaggtaaa cggtccctcg tgtagggaca gtggcgggat aatcgagatc    35280
gtgttgaacg tagagtcatg ccaaagggaa cagcggacgt actcatattt cctccagcag    35340
aaccaagtgc gcgcgtggca gctatccctg cgtcttctgt ctcgccgcct gccccgttcg    35400
gtgtagtagt tgtaatacag ccactccctg agaccgtcaa ggcgctccct ggcgtccgga    35460
tctatgacaa caccgtcctg cagcgccgcc ctgatgacat ccaccaccgt agagtatgcc    35520
aagcccagcc aggaaatgca ttcactttga cagcgagaga taggaggagc ggggagagat    35580
ggaagaacca tgatagtaaa gagaactttt attccaatcg atcttctaag atatcaaagt    35640
ggagatctat aagatgacac tggtctcctc cgctgagtcg atcaaaaata acagctaaac    35700
cacaaacaac acgattggtc aaatgctcca caagggcctg cagcataaaa ttgcctcgga    35760
```

```
actccaccgc aagcataaca tcaaagccac cgcctctatc gtgatcaaga ataaaaaccc    35820
cacagctatc caccagaccc atatagtttt catctctcca tcgtgaaaaa agatttacaa    35880
gctcctcctt taaatcacct ccaaccaatt gaaaaagttg aaccagaccg ccctccacct    35940
tcattttcag caagcgtatc atgattgcaa aaattcaggc tcctcagaca cctgtataag    36000
attgagaagc ggaacgttaa catcgatgtt tcgctcgcgt aaatcacgcc tcagtgcaag    36060
cataatataa tcccacaggt cggagcggat cagcgaggac acctccccgc caggaaccaa    36120
ctcaacggag cctatgctga ttataatacg catattcgga gctatgctaa ccagcacggc    36180
ccccaaatag gcgtactgca taggcggcga caaaaagtga acagtttggg ttaaaaaatc    36240
aggcaaacac tcgcgcaaaa aagcaagaac atcataacca tgctcatgca aatagatgca    36300
agtaagctca ggaacaacca cagaaaaatg cacaattttt ctctcaaaca tgactgcgag    36360
ccctgcaaaa aataaaaaag aaacattaca caagagtagc ctgtcttacg atgggataga    36420
ctactctaac caacataaga cgggccacaa catcgcccgc gtggccataa aaaaaattgt    36480
ccgtgtgatt aaaaagaagc acagatagct ggccagtcat atccggagtc atcacgtgtg    36540
aacccgtgta gaccccgggg ttggacacat cggccaaaga agaaagcgg ccaatgtacc    36600
caggaggaat tataacacta agacgaagat acaacagaat aaccccatga ggggaataa    36660
caaagttagt aggtgaataa aaacgataaa caccgaaac tccctcctgc gtaggcaaaa    36720
tagcacccct cccttccaaa acaacatata gcgcttccac agcagccatg acaaaagact    36780
caaaacactc aaaagactca gtcttaccag gaaaatataaa gcactctcac agcaccagca    36840
ctaatcagag tgtgaagagg gccaagtgcc gaacgagtat atataggaat aaaaaatgac    36900
gtaaatgtgt aaaggtcaga aaacgcccag aaaaatacac agaccaacgc ccgaaacgaa    36960
aacccgcgaa aaaataccca gaacttcctc aacaaccgcc acttccgctt tctcacggta    37020
cgtcacttcc gcaagaaaag caaaactaca tttcccacat gtgtaaaaac gaaaccccgc    37080
cccttgtaac cgcccacaac ttacatcatc aaaacgtaaa ctcctacgtc acccgccccg    37140
cctctccccg cccacctcat tatcatattg gccacaatcc aaaataaggt atattat       37197
```

<210> SEQ ID NO 25
<211> LENGTH: 34075
<212> TYPE: DNA
<213> ORGANISM: Gorilla beringei graueri

<400> SEQUENCE: 25

```
catcatcaat aatataccct attttggatt gtggccaata tgataatgag gtgggcgggg     60
agaggcgggg cggtgacgt aggacgcgcg agtagggttg ggaggtgtgg cggaagtgtg    120
gcatttgcaa gtgggaggag ctcacatgca agcttccgtc gcggaaaatg tgacgttttt    180
gatgagcgcc gcctacctcc ggaagtgcca attttcgcgc gcttttcacc ggatatcgta    240
gtaattttgg gcgggaccat gtaagatttg gccattttcg cgcgaaaagt gaacggggga    300
agtgaaaact gaataatagg gcgttagtca tagtgcgtaa tatttaccga gggccgaggg    360
actttgaccg attacgtgga ggactcgccc aggtgttttt tacgtgaatt tccgcgttcc    420
gggtcaaagt ctccgttta ttgtcaccgt catttgacgc ttaggcctga ccatctggtg    480
ctggcctgca ccagggccga gtttgggtct agcgatgagg ataccgattg aggtgggtaa    540
ggtgggcgtg gctagaaggg tggggcgtgt ataaattggg ggtctaaggg tctctctgtt    600
ttgtcttgca acagccgccg ccatgagcga caccggcaac agctttgatg gaagcatctt    660
```

```
tagccccctat ctgacagtgc gcatgcctca ctgggctgga gtgcgtcaga atgtgatggg    720
ttccaacgtg gatggacgcc ccgttctgcc ttcaaattcg tctacaatgg cctacgcgac    780
cgtgggagga actccgctgg acgccgcgac ctccgccgcc gcctccgccg ccgccgcgac    840
cgcgcgcagc atggctacgg acctttacag ctctttggtg gcgagcggcg cggcctctcg    900
cgcgtctgct cgggatgaga aactgaccgc tctgctgctt aaactggaag acttgacccg    960
ggagctggct caactgaccc agcaggtctc cagcttgcgt gagagcagcc ttgcctcccc   1020
ctaatggccc ataatataaa taaaagccag tctgtttgga ttaagcaagt gtatgttctt   1080
tatttaactc tccgcgcgcg gtaagcccgg gaccagcggt ctcggtcgtt tagggtgcgg   1140
tggattcttt ccaacacgtg gtacaggtgg ctctggatgt ttagatacat gggcatgagt   1200
ccatccctgg ggtggaggta gcaccactgc agagcttcgt gctcggtggt ggtgttgtat   1260
atgatccagt cgtagcagga gcgctgggcg tggtgctgaa aaatgtcctt aagcaagagg   1320
cttatagcta gggggaggcc cttggtgtaa gtgtttacaa atctgctcag ttgggagggg   1380
tgcatccggg gggatataat gtgcatcttg gactggattt ttaggttggc tatgttccca   1440
cccagatccc ttctgggatt catgttgtgc aggaccacca gcacggtata tccagtacac   1500
ttgggaaatt tatcgtggag cttagacggg aatgcatgga agaacttgga gacgcccttg   1560
tggcctccca gattttccat acattcgtcc atgatgatgg caatgggccc gtgggaagct   1620
gcctgagcaa aaatgtttct gggatcgctc acatcgtagt tatgttccag ggtgaggtca   1680
tcataggaca tctttacaaa tcgggggcgg agggtcccgg actgggggat gatggtgccc   1740
tcgggccccg gggcgtagtt cccctcacag atctgcatct cccaggcttt catttcagag   1800
ggagggatca tatccacctg cggagcgatg aaaaacacag tttctggcgc aggggagatt   1860
aactgggatg agagcaggtt tctgagcagc tgtgactttc cacagccggt gggcccatat   1920
atcacgccta tcaccggctg cagctggtag ttaagagagc tgcagctgcc gtcctcccgg   1980 agcaggggg ccacctcgtt cagcatatcc ctgacgtgga tgttctccct gaccaattcc    2040
gccagaaggc gctcgccgcc cagcgaaagc agctcttgca aggaagcaaa atttttcagc   2100
ggttttaggc cgtcggccgt gggcatgttt ttcagcgtct gggtcagcag ttccagtctg   2160
tcccacagct cggtgatgtg ctctacggca tctcgatcca gcagatctcc tcgtttcgcg   2220
ggttggggcg gctttcgctg tagggcacca gccgatgggc gtccagcggg ccagagtca    2280 tgtccttcca tgggcgcagg gtcctcgtca gggtggtctg ggtcacggtg aagggtgcg    2340 ctccgggttg ggcgctggcc agggtgcgct tgaggctggt tctgctggtg ctgaatcgct   2400
gccgctcttc gccctgcgcg tcggccaggt agcatttgac catggtctcg tagtcgagac   2460
cctcggcggc gtgccccttg gcgcggagct ttcccttgga ggtggcgccg cacgagggc    2520 actgcaggct cttcagggcg tagagcttgg gagcgagaaa cacggactct ggggagtagg   2580
cgtccgcgcc gcaggaagcg cagaccgtct cgcattccac cagccaagtg agctccgggc   2640
ggtcagggtc aaaaaccagg ttgccccat gctttttgat gcgtttctta cctcggctct    2700
ccatgaggcg gtgtcccttc tcggtgacga agaggctgtc cgtgtctccg tagaccgact   2760 tcagggcct gtcttccagc ggagtgcctc tgtcctcctc gtagagaaac tctgaccact    2820
ctgagacgaa ggcccgcgtc caggccagga cgaaggaggc cacgtgggag gggtagcggt   2880
cgttgtccac tagcgggtcc accttctcca gggtgtgcag gcacatgtcc ccctcctccg   2940
cgtccagaaa agtgattggc ttgtaggtgt aggacacgtg accgggggtt cccgacgggg   3000
gggtataaaa gggggtgggc acccttcat cttcactctc ttccgcatcg ctgtctgcga    3060
```

```
gagccagctg ctggggtaag tattccctct cgaaggcggg catgacctca gcgctcaggt    3120
tgtcagtttc taaaaatgag gaggatttga tgttcacctg tccggaggtg atacctttga    3180
gggtacctgg gtccatctgg tcagaaaaca ctattttttt gttgtcaagc ttggtggcga    3240
acgacccgta gagggcgttg gagagcagct tggcgatgga gcgcagggtc tggttttgt     3300 cgcggtcggc tcgctccttg gccgcgatgt tgagttgcac gtactcgcgg gccacgcact    3360
tccactcggg gaagacggtg gtgcgctcgt ctgggatcag gcgcaccctc cagcctcggt    3420
tgtgcagggt gaccatgtcg acgctggtgg cgacctcgcc gcgcaggcgc tcgttggtcc    3480
agcagaggcg gccgcccttg cgcgagcaga agggggtag gggtccagc tggtcctcgt      3540 ttgggggtc cgcgtcgatg gtgaagaccc cggggagcaa gcgcgggtca agtagtcga     3600 tcttgcaagc ttgcatgtcc agagcccgct gccattcgcg ggcggcgagc gcgcgctcgt    3660
aggggttgag gggcgggccc cagggcatgg ggtgggtgag cgcggaggcg tacatgccgc    3720
agatgtcata cacgtacagg ggttccctga ggatgccgag gtaggtgggg tagcagcgcc    3780
ccccgcggat gctggcgcgc acgtagtcat agagctcgtg ggaggggccc agcatgttgg    3840
gcccgaggtt ggtgcgctgg gggcgctcgg cgcggaaggc gatctgcctg aagatggcat    3900
gggagttgga ggagatggtg ggccgctgga agacgttgaa gcttgcttct tgcaagccca    3960
ccgagtccct gacgaagcag gcgtaggact cgcgcagctt gtgcaccagc tcggcggtga    4020
cctggacgtc gagcgcgcag tagtcgaggg tctcgcggat gatgtcatac ttatcctccc    4080
ccttcttttt ccacagctcg cggttgagga cgaactcttc gcggtctttc cagtactctt    4140 ggagggaaa cccgtccgtg tccgaacggt aagagcctag catgtagaac tggttgacgg     4200
cctggtaggg gcaacagccc ttctccacgg gcagcgcgta ggcctgcgcc gccttgcgga    4260
gggaggtgtg ggtgagggcg aaagtgtccc tgaccatgac tttgaggtat tgatgtttga    4320
agtctgtgtc atcgcagccg ccctgttccc acagggtgta gtccgtgcgc tttttggagc    4380
gcgggttggg caggagaag gtgaggtcat tgaagaggat cttccccgct cgaggcatga     4440
agtttctggt gatgcgaaag ggccctggga ccgaggagcg gttgttgatg acctgggcgg    4500
ccaggacgat ctcgtcaaag ccgtttatgt tgtggcccac gatgtagagc tccaaaaagc    4560
ggggctggcc cttgatggag gggagctttt tgagttcctc gtaggtgagc tcctcgggcg    4620
attccaggcc gtgctcctcc agggcccagt cttgcaagtg agggttggcc gccaggaagg    4680
atcgccagag gtcgcgggcc atgagggtct gcaggcggtc gcggaaggtt ctgaactgtc    4740
gccccacggc catcttttcg ggggtgatgc agtagaaggt gaggggtct ttctcccagg     4800 ggtcccatct gagctctcgg gcgaggtcgc gcgcggcggc gaccagagcc tcgttgcccc    4860
ccagtttcat gaccagcatg aagggcacga gctgcttgcc aaaggctccc atccaagtgt    4920
aggtctctac atcgtaggtg acaaagaggc gctccgtgcg aggatgagag ccgatcggga    4980
agaactggat ctcccgccac cagttggagg attggctgtt gatgtggtga agtagaagt     5040 cccgtctgcg ggccgagcac tcgtgctggc ttttgtaaaa gcgaccgcag tactggcagc    5100
gctgcacggg ttgtatatct tgcacgaggt gaacctggcg acctctgacg aggaagcgca    5160
gcgggaatct aagtccccg cctgggtcc cgtgtggctg gtgtcttct actttggttg       5220 tctggccgcc agcatctgtc tcctggaggg cgatggtgga gcagaccacc acgccgcgag    5280
agccgcaggt ccagatctcg gcgctcggcg ggcggagttt gatgacgaca tcgcgcacat    5340
tggagctgtc catggtctcc agctcccgcg gcggcaggtc agctgggagt tcctggaggt    5400
```

```
tcacctcgca gagacgggtc aaggcgcggg cagtgttgag atggtatctg atttcaaggg   5460
gcgtgttggc ggcggagtcg atggcttgca ggaggccgca gccccggggg gccacgatgg   5520
ttccccgcgg ggcgcgaggg gaggcggaag ctgggggtgt gttcagaagc ggtgacgcgg   5580
gcgggccccc ggaggtaggg ggggttccgg ccccacaggc atgggcggca ggggcacgtc   5640
ttcgccgcgc gcgggcaggg gctggtgctg gctccgaaga gcgcttgcgt gcgcgacgac   5700
gcgacggttg gtgtcctgta tctgacgcct ctgagtgaag accacgggtc ccgtgacctt   5760
gaacctgaaa gagagttcga cagaatcaat ctcggcatcg ttgacagcgg cctggcgcag   5820
gatctcctgc acgtcgcccg agttgtcctg gtaggcgatc tctgccatga actgctcgat   5880
ctcttcttcc tggagatctc ctcgtccggc gcgctccacg gtggccgcca ggtcgttgga   5940
gatgcgaccc atgagctgcg agaaggcgtt gagcccgccc tcgttccaga cccggctgta   6000
gaccacgccc ccctcggcgt tgcgggcgcg catgaccacc tgggccaggt tgagctccac   6060
gtgtcgcgtg aagacggcgt agttgcgcag gcgctggaaa aggtagttca gggtggtggc   6120
ggtgtgctcg gcgacgaaga agtacatgac ccagcgccgc aacgtggatt cattgatgtc   6180
ccccaaggcc tccaggcgct ccatggcctc gtagaagtcc acggcgaagt tgaaaaactg   6240
ggagttgcga gcggacacgg tcaactcctc ctccagaaga cggatgagct cggcgacagt   6300
gtcgcgcacc tcgcgctcga aggccacggg gggcgcttct tcctcttcca cctcttcttc   6360
catgatcgct tcttcttctt cctcagccgg gacggggggg ggcggcggcg gcgggggagg   6420
ggcgcggcgg cggcggcggc gcaccgggag gcggtcgatg aagcgctcga tcatctcccc   6480
ccgcatgcgg cgcatggtct cggtgacggc gcggccgttc tcccgggggc gcagctcgaa   6540
gacgccgcct ctcatctcgc cgcggggcgg gcggccgtga ggtagcgaga cggcgctgac   6600
tatgcatctt aacaattgct gtgtaggtac accgccgagg gacctgattg agtccagatc   6660
caccggatcc gaaaaccttt ggaggaaagc gtctatccag tcgcagtcgc aaggtaggct   6720
gagcaccgtg gcgggcgggg gcgggtctgg agagttcctg gcggagatgc tgctgatgat   6780
gtaattaaag taggcggtct tgagaaggcg gatggtggac aggagcacca tgtctttggg   6840
tccggcctgt tggatgcgga ggcggtcggc catgccccag gcctcgttct gacaccggcg   6900
caggtctttg tagtagtctt gcatgagtct ttccaccggc acctcttctc cttcctcttc   6960
tccatctcgc cggtggtttc tcgcgccgcc catgcgcgtg accccaaagc ccctgagcgg   7020
ctgcagcagg gccaggtcgg cgaccacgcg ctcggccaag atggcctgct gcacctgagt   7080
gagggtcctc tcgaagtcat ccatgtccac gaagcggtgg taggcgcccg tgttgatggt   7140
gtaggtgcag ttggccatga cggaccagtt gacggtctgg tgtcccggct gcgagagctc   7200
cgtgtaccgc aggcgcgaga aggcgcggga atcgaacacg tagtcgttgc aagtccgcac   7260
cagatactgg tagcccacca ggaagtgcgg cggaggttgg cgatagaggg gccagcgctg   7320
ggtggcgggg gcgccgggcg ccaggttttc cagcatgagg cggtggtatc cgtagatgta   7380
cctggacatc caggtgatgc cggcggcggt ggtggtggcg cgcgcgtagt cgcggacccg   7440
gttccagatg tttcgcaggg gcgagaagtg ttccatggtc ggcacgctct ggccggtgag   7500
gcgcgcgcag tcgttgacgc tctatacaca cacaaaaacg aaagcgttta cagggctttc   7560
gttctgtagc ctggaggaaa gtaaatgggt tgggttgcgg tgtgccccgg ttcgagacca   7620
agctgagctc ggccggctga agccgcagct aacgtggtat tggcagtccc gtctcgaccc   7680
aggccctgta tcctccagga tacgtcgag agccctttg ctttcttggc caagcgcccg   7740
tggcgcgatc tgggatagat ggtcgcgatg agaggacaaa agcggctcgc ttccgtagtc   7800
```

-continued

```
tggagaaaca atcgccaggg ttgcgttgcg gcgtaccccg gttcgagccc ctatggcggc    7860
ttgaatcggc cggaaccgcg gctaacgagg gccgtggcag ccccgtcctc aggacccccgc   7920 cagccgactt ctccagttac gggagcgagc ccctttttgtt ttttattttt tagatgcatc   7980
ccgtgctgcg gcagatgcgc ccctcgcccc ggcccgatca gcagcagcaa cagcaggcat    8040
gcagaccccc ctctcccctt tccgcccccgg tcaccacggc cgcggcggcc gtgtcgggcg   8100 cgggggggcgc gctggagtca gatgagccac cgcggcggcg acctaggcag tatctggact   8160
tggaagaggg cgagggactg gcgcggctgg gggcgaactc tccagagcgc cacccgcggg    8220
tgcagttgaa aagggacgcg cgcgaggcgt acctgccgcg gcagaacctg tttcgcgacc    8280 gcggggggcga ggagcccgag gagatgcgag actgcaggtt ccaagcgggg cgcgagctgc    8340
ggcgcgggct ggacagacag cgcctgctgc gcgaggagga cttttgagccc gacacgcaga    8400 cgggcatcag ccccgcgcgc gcgcacgtag ccgcggccga cctggtgacc gcctacgagc    8460
agacggtgaa ccaggagcgc aacttccaaa agagcttcaa caaccacgtg cgcacgctgg    8520
tggcgcgcga ggaggtgacc ctgggtctca tgcatctgtg ggacctggtg gaggcgatcg    8580
tgcagaaccc cagcagcaag cccctgaccg cgcagctgtt cctggtggtg cagcacagca    8640
gggacaacga ggccttcagg gaggcgctgc tgaacatcac cgagccggag gggcgctggc    8700
tcctggacct gataaacatc ctgcagagca tagtggtgca ggagcgcagc ctgagcctgg    8760
ccgagaaggt ggcggccatc aactactcta tgctgagcct gggcaagttc tacgcccgca    8820
agatctacaa gacccctac gtgcccatag acaaggaggt gaagatagac agcttctaca    8880
tgcgcatggc gctgaaggtg ctgaccctga gcgacgacct gggagtgtac cgcaacgagc    8940
gcatccacaa ggccgtgagc gccagccggc ggcgcgagct gagcgaccgc gagctgatgc    9000
acagtctgca gcgcgcgctg accggcgcgg gcgagggcga cagggaggtc gagtcctact    9060
tcgacatggg ggccgacctg cactggcagc cgagccgccg cgccctggag gcggcggggg    9120
cgtacggcgg ccccctggcg gccgatgacc aggaagagga ggactatgag ctagaggagg    9180
gcgagtacct ggaggactga cctggctggt ggtgttttgg tatagatgca agatccgaac    9240
gtggcggacc cggcggtccg ggcggcgctg caaagccagc cgtccggcat taactcctct    9300
gacgactggg ccgcggccat gggtcgcatc atggccctga ccgcgcgcaa ccccgaggct    9360
ttcaggcagc agcctcaggc caaccggctg gcggccatct tggaagcggt agtgcccgcg    9420
cgctccaacc ccacccacga gaaggtgctg gccatagtca acgcgctggc ggagagcagg    9480
gccatccgcg cggacgaggc cggactggtg tacgatgcgc tgctgcagcg ggtggcgcgg    9540
tacaacagcg gcaacgtgca gaccaacctg gaccgcctgg tgacggacgt gcgcgaggcc    9600
gtggcgcagc gcgagcgctt gcatcaggac ggtaacctgg gctcgctggt ggcgctaaac    9660
gccttcctca gcacccagcc ggccaacgta ccgcggggc aggaggacta caccaacttt    9720
ttgagcgcgc tgcggctgat ggtgaccgag gtccctcaga gcgaggtgta ccagtcgggg    9780
cccgactact tcttccagac cagcagacag ggcttgcaaa ccgtgaacct gagccaggct    9840
ttcaagaacc tgcgggggct gtggggagtg aaggcgccca ccggcgaccg ggctacggtg    9900
tccagcctgc taacccccaa ctcgcgcctg ctgctgctgc tgatcgcgcc cttcacggac    9960
agcgggagcg tctcgcggga gacctatctg ggccacctgc tgacgctgta ccgcgaggcc   10020
atcgggcagg cgcaggtgga cgagcacacc ttccaagaga tcaccagcgt gagccacgcg   10080
ctggggcagg aggacacggg cagcctgcag gcgacccctga actacctgct gaccaacagg   10140
```

```
cggcagaaga ttcccacgct gcacagcctg acccaggagg aggagcgcat cttgcgctac   10200
gtgcagcaga gcgtgagcct gaacctgatg cgcgacggcg tgacgcccag cgtggcgctg   10260
gacatgaccg cgcgcaacat ggaaccgggc atgtacgcct cccaccggcc gttcatcaac   10320
cgcctgatgg actacttgca tcgggcggcg gccgtgaacc ccgagtactt cactaatgcc   10380
attctgaatc cccactggat gccccctccg ggtttctaca acgggacttt tgaggtgccc   10440
gaggtcaacg acgggttcct ctgggatgac atggatgaca gtgtgttctc acccaacccg   10500
ctgcgcgccg cgtctctgcg attgaaggag ggctctgaca gggaaggacc gagaagtctg   10560
gcctcctccc tggctctggg agcggtgggc gccacgggcg cggcggcgcg gggcagtagc   10620
cccttcccca gcctggcaga ctctctgaac agcgggcggg tgagcaggcc ccgcttgcta   10680
ggcgaggagg agtatctgaa caactccctg ctgcagcccg cgaggacaa gaacgctcag   10740 cggcagcagt ttcccaacaa tgggatagag agcctggtgg acaagatgtc cagatggaag   10800
acgtatgcgc aggagtacaa ggagtgggag gaccgccagc cgcggccctt gccgccccct   10860
aggcagcgct ggcagcggcg cgcgtccaac cgccgctgga ggcaggggcc cgaggacgat   10920
gatgactctg cagatgacag cagcgtgttg gacctgggcg ggagcgggaa ccccttttcg   10980
cacctgcgcc cacgcctggg caagatgttt taaaagaaaa aaaaaaaata aaactcacca   11040
aggccatggc gacgagcgtt ggttttttgt tcccttcctt agtatgcggc gcgcggcgat   11100
gttcgaggag gggcctcccc cctcttacga gagcgcgatg gggatttctc ctgcggcgcc   11160
cctgcagcct ccctacgtgc ctcctcggta cctgcaacct acaggggga gaaatagcat   11220 ctgttactct gagctgcagc ccctgtacga taccaccaga ctgtacctgg tggacaacaa   11280
gtccgcggac gtggcctccc tgaactacca gaacgaccac agcgattttt tgaccacggt   11340
gatccaaaac aacgacttca ccccaaccga ggccagcact cagaccataa acctggataa   11400
caggtcgaac tggggcggcg acctgaagac catcttgcac accaacatgc caacgtgaa   11460 cgagttcatg ttcaccaact cttttaaggc gcggtgatg gtggcgcgcg agcaggggga   11520
ggcgaagtac gagtgggtgg acttcacgct gcccgagggc aactactcag agaccatgac   11580
tctcgacctg atgaacaatg cgatcgtgga acactatctg aaagtgggca ggcagaacgg   11640
ggtgaaggaa agcgatatcg gggtcaagtt tgacaccaga aacttccgtc tgggctggga   11700
ccccgtgacc gggctggtca tgccgggggt ctacaccaac gaggcctttc atcccgacat   11760
agtgcttctg cccggctgtg gggtggactt cacccagagc cggctgagca acctgctggg   11820
cattcgcaag cggcagcctt tccaggaggg tttcaagatc acctatgagg atctgaaggg   11880
gggcaacatt cccgcgctcc ttgatctgga cgcctacgag gagagcttga acccgaggga   11940
gagcgctggc gacagcggcg agagtggcga ggagcaagcc ggcggcggtg gcggcgcgtc   12000
ggtagaaaac gaaagtacgc ccgcagtggc ggcggacgct gcggaggtcg agccggaggc   12060
catgcagcag gacgcagagg agggcgcgca ggagggcgcg cagaaggaca tgaacgatgg   12120
ggagatcagg ggagacacat tcgccacccg gggcgaagaa aaagaggcag aggcggcggc   12180
ggcggcgacg gcggaggccg aaaccgaggt tgaggcagag gcagagcccg agaccgaagt   12240
tatggaagac atgaatgatg gagaacgtag gggcgacacg ttcgccaccc ggggcgaaga   12300
gaaggcggcg gaggcagaag ccgcggctga ggaggcggct gcggctgcgg ccaagactga   12360
ggctgcggct aaggctgagg tcgaagccaa tgttgcggtt gaggctcagg ctgaggagga   12420
ggcggcggct gaagcagtta aggaaaaggc ccaggcagag caggaagaga aaaacctgt   12480 cattcaaccct ctaaaagaag atagcaaaaa gcgcagttac aacgtcatcg agggcagcac   12540
```

```
ctttacccag taccgcagct ggtacctggc gtacaactac ggcgacccgg tcaaggggt   12600
gcgctcgtgg accctgctct gcacgccgga cgtcacctgc ggctccgagc agatgtactg   12660
gtcgctgccg aacatgatgc aagacccggt gaccttccgc tccacgcggc aggttagcaa   12720
cttcccggtg gtgggcgccg aactgctgcc cgtgcactcc aagagttttt acaacgagca   12780
ggccgtctac tcccagctga tccgccaggc cacctctctg acccacgtgt tcaatcgctt   12840
tcccgagaac cagattttgg cgcgcccgcc ggccccacc atcaccaccg tgagtgaaaa    12900
cgttcctgcc ctcacagatc acgggacgct accgctgcgc aacagcatct caggagtcca   12960
gcgagtgacc attactgacg ccagacgccg gacctgcccc tacgtttaca aggccttggg   13020
catagtctcg ccgcgcgtcc tctccagtcg cactttttaa aacacatcta cccacacgtt   13080
ccaaaatcat gtccgtactc atctcaccca gcaacaacac cggctggggg ctgcgcgcgc   13140
ccagcaagat gtttggaggg gcgaggaagc gctccgacca gcaccctgtg cgcgtgcgcg   13200
gccactaccg cgcgccctgg ggagcgcaca agcgcgggcg cacagggcgc accactgtgg   13260
acgacgtcat tgactccgta gtggagcaag cgcgccacta cacacccggc gcgccgaccg   13320
cccccgccgt gtccaccgtg gaccaggcga tcgaaagcgt ggtacagggc gcgcggcact   13380
atgccaacct taaaagtcgc cgccgccgcg tggcccgccg ccatcgccgg agaccccggg   13440
ccaccgccgc cgcgcgcctt actaaggctc tgctcaggcg cgccaggcga actggccacc   13500
gggccgccat gagggccgca cggcgggctg ccgctgccgc aagcgccgtg gccccgcggg   13560
cacgaaggcg cgcggccgcc gccgccgccg ccgccattc cagcttggcc tcgacgcggc   13620
gcggtaacat atactgggtg cgcgactcgg taaccggcac gcgggtaccc gtgcgctttc   13680
gccccccgcg gaattagcac aagacaacat acacactgag tctcctgctg ttgtgtatcc   13740
cagcggcgac cgtcagcagc ggcgacatgt ccaagcgcaa aattaaagaa gagatgctcc   13800
aggtcatcgc gccggagatc tatgggcccc cgaagaagga ggaggatgat tacaagcccc   13860
gcaagctaaa gcgggtcaaa aagaaaaaga aagatgatga tgatgacgag gcggtggagt   13920
ttgtccgccg catggcaccc aggcgccccg tgcagtggaa gggccggcgc gtgcagcgcg   13980
ttttgcgccc cggcaccgcg gtggtcttca cgccggcga gcgctccacg cgcactttca   14040
agcgggtgta cgatgaggtg tacggcgacg aggacctgtt ggagcaggcc aaccagcgct   14100
ttgggggagtt tgcatatggg aaacggcccc gcgagagtct aaaagaggac ctgctggcgc   14160
taccgctgga cgagggcaat cccacccga gtctgaagcc ggtaaccctg caacaggtgc    14220
tgcctttgag cgcgcccagc gagcataagc gagggttgaa gcgcgaaggc ggggacctgg   14280
cgcccaccgt gcagttgatg gtgcccaagc ggcagaagct ggaggacgtg ctggagaaaa   14340
tgaaagtaga gccgggatc cagcccgaga tcaaggtccg ccccatcaag caggtggcgc    14400
ccggcgtggg agtccagacc gtggacgtta ggattcccac ggaggagatg gaaacccaaa   14460
ccgccactcc ctcttcggcg gccagcgcca ccaccggcac cgcttcggta gaggtgcaga   14520
cggacccctg gctacccgcc accgctgttg ccgccgccgc ccccgttcg cgcgggcgca    14580
agagaaatta ccagcggcc agcgcgctca tgcccagta cgcactgcat ccatccatcg   14640
cgcccacccc cggctaccgc gggtactcgt accgcccgcg cagatcagcc ggcactcgcg   14700
gccgccgccg ccgtgcgacc acaaccagcc gccgccgtcg ccgccgccgc cagccagtgc   14760
tgaccccgt gtctgtaagg aaggtggctc gctcggggag cacgctggtg gtgcccagag    14820
cgcgctacca ccccagcatc gtttaaagcc ggtctctgta tggttcttgc agatatggcc   14880
```

-continued

```
ctcacttgtc gcctccgctt cccggtgccg ggataccgag gaagaactca ccgccgcaga    14940
ggcatggcgg gcagcggtct ccgcggcggc cgtcgccatc gccggcgcgc aaaaagcagg    15000
cgcatgcgcg gcggtgtgct gcctctgcta atcccgctaa tcgccgcggc gatcggtgcc    15060
gtacccggga tcgcctccgt ggccctgcag gcgtcccaga acgttgact cttgcaacct     15120
tgcaagcttg cattttttgg aggaaaaata aaaaagtct agactctcac gctcgcttgg     15180
tcctgtgact attttgtaga aaaagatgg aagacatcaa ctttgcgtcg ctggccccgc     15240
gtcacggctc gcgcccgttc atgggagact ggacagatat cggcaccagc aatatgagcg    15300
gtggcgcctt cagctggggc agtctgtgga gcggccttaa aaattttggt tccaccatta    15360
agaactatgg caacaaagcg tggaacagca gcacgggcca gatgctgaga gacaagttga    15420
aagagcagaa cttccaggag aaggtggcgc agggcctggc ctctggcatc agcggggtgg    15480
tggacatagc taaccaggcc gtgcagaaaa agataaacag tcatctggac cccgtcctc     15540
aggtggagga aatgcctcca gcgatggaga cggtgtctcc cgagggcaaa ggcgaaaagc    15600
gcccgcggcc cgacagagaa gagaccctgg tgtcacacac cgaggagccg ccctcttacg    15660
aggaggcagt caaggccggc ctgcccacca ctcgccccat agcccccatg gccaccggtg    15720
tggtgggcca caggcaacac actcccgcaa cactagatct gccccgccg tccgagccgc     15780
cgcgccagcc aaaggcggcg acggtgcccg ctccctccac ttccgccgcc aacagagtgc    15840
ccctgcgccg cgccgcgagc ggcccccggg cctcgcgagt tagcggcaac tggcagagca    15900
cactgaacag catcgtgggc ctgggagtga ggagtgtgaa gcgccgccgt tgctactgaa    15960
tgagcaagct agctaacgtg ttgtatgtgt gtatgcgtcc tatgtcgccg ccagaggagc    16020
tgttgagccg ccggcgccgt ctgcactcca gcgaatttca agatggcgac cccatcgatg    16080
atgcctcagt ggtcgtacat gcacatctcg ggccaggacg cttcggagta cctgagcccc    16140
gggctggtgc agttcgcccg cgccacagac acctacttca acatgagtaa caagttcagg    16200
aaccccactg tggcgcccac ccacgatgtg accacggacc ggtcgcagcg cctgacgctg    16260
cggttcatcc ccgtggatcg ggaggacacc gcctactctt acaaggcgcg gttcacgctg    16320
gccgtgggcg acaaccgcgt gctggacatg gcctccactt actttgacat cagggggggtg    16380
ctggacaggg gccccacctt caagccctac tcgggtactg cctacaactc cctggccccc    16440
aagggcgctc ccaattcttg cgagtgggaa caagaggaaa atcaggtggt cgctgcagat    16500
gatgaacttg aagatgaaga agcgcaagct caagaggacg ccccagctaa aaaaattcat    16560
gtatatgccc aggcgcctct tgctggcgaa aagattacca aggatggttt gcaaataggt    16620
actgaagttg taggagatac atctaaggac acttttgcag acaaaacatt ccaacccgaa    16680
cctcagatag gcgagtctca gtggaacgag gctgatgcca cagtagcagg aggcagagtc    16740
ttgaaaaaaa ccacccctat gagaccttgc tatggatcct atgccaggcc tacaaatgcc    16800
aacgggggtc aaggaattat ggttgccaat gaacaaggag tgttggagtc taaagtggag    16860
atgcaatttt tttctaacac tacaaccctt aatgcgcggg atggagctgg caatcccgaa    16920
ccaaaggtgg tgttgtacag tgaagatgtc cacttggaat ctcctgacac tcatttgtct    16980
tacaagccca aaaaggatga tgttaatgct aaaattatgt tgggtcagca agctatggct    17040
aacaggccca acctcattgc ttttagagat aatttcattg gactcatgta ctacaacagc    17100
actggtaaca tggagtgct ggcgggtcag gcctctcagt tgaatgccgt ggtggacctg    17160
caggatagaa acacagaact gtcatatcag cttatgcttg attccattgg ggatagatcc    17220
agatacttct ccatgtggaa ccaggcagtg gatagctatg acccagatgt cagaatcatt    17280
```

```
gaaaaccatg gtgtcgagga cgagctaccc aactactgct tccctctggg cggcatagga   17340
attactgata cttatcaagg gatcaaaaat accaatggca atggtcagtg gaccaaagat   17400
gatcagttcg cggaccgtaa tgaaataggg gtgggaaaca acttcgccat ggagatcaac   17460
atccaggcca acctctggag gaacttcctc tatgcgaacg tggggctcta cctgccagac   17520
aagctcaagt acaaccccac caacgtggac atctctgaca accccaacac ctatgactac   17580
atgaacaagc gtgtggtggc tcccggcctg gtggactgct tgtcaatgt gggagccagg    17640
tggtccctgg actacatgga caacgtcaac cccttcaacc accacgcaa tgcgggtctg    17700
cgctaccgct ccatgatcct gggcaacggg cgctacgtgc ccttccacat tcaggtgccc   17760
cagaagttct tgccatcaa gaacctcctc ctcctgccgg gctcctacac ttacgagtgg    17820
aacttcagga aggatgtcaa catggtcctg cagagctctc tgggcaatga ccttagggtg   17880
gacggggcca gcatcaagtt tgacagcgtc accctctatg ctaccttctt ccccatggct   17940
cacaacaccg cctccacgct cgaggccatg ctgaggaacg acaccaacga ccagtccttc   18000
aatgactacc tctctggggc caacatgctc taccccatcc ccgccaaggc caccaacgtg   18060
cccatctcca ttccctctcg caactgggcc gccttcagag gctgggcctt tacccgcctt   18120
aagaccaagg aaaccccctc cctgggctcg ggttttgacc cctactttgt ctactcggga   18180
tccatcccct acctggatgg caccttctac ctcaaccaca cttttaagaa gatatccatc   18240
atgtatgact cctccgtcag ctggccgggc aatgaccgcc tgctcacccc caatgagttc   18300
gaggtcaagc gcgccgtgga cggcgagggc tacaacgtgg cccagtgcaa catgaccaag   18360
gactggttcc tggtgcagat gctggccaac tacaacatag gctaccaggg cttctacatc   18420
ccagagagct acaaggacag gatgtactcc ttcttcagaa atttccaacc catgagcagg   18480
caggtggtgg acgagaccaa atacaaggac tatcaggcca ttggcatcac tcaccagcac   18540
aacaactcgg gattcgtggg ctacctggct cccaccatgc gcgaggggca ggcctacccc   18600
gccaacttcc cctacccgtt gataggcaag accgcggtcg acagcgtcac ccagaaaaag   18660
ttcctctgcg accgcaccct ctggcgcatc cccttctcta gcaacttcat gtccatgggt   18720
gcgctcacgg acctgggcca gaacctgctc tatgccaact ccgcccatgc gctggacatg   18780
acttttgagg tggaccccat ggacgagccc acccttctct atattgtgtt tgaagtgttc   18840
gacgtggtca gagtgcacca gccgcaccgc ggtgtcatcg agaccgtgta cctgcgcacg   18900
cccttctcgg ccggcaacgc caccacctaa ggagacagcg ccgccgcctg catgacgggt   18960
tccaccgagc aagagctcag ggccatcgcc agagacctgg gatgcggacc ctatttttg    19020
ggcacctatg acaaacgctt cccgggcttc atctcccgag acaagctcgc ctgcgccatc   19080
gtcaacacgg ccgcgcgcga gaccggggc gtgcactggc tggcctttgg ctgggacccg    19140
cgctccaaaa cctgctacct cttcgacccc tttggcttct ccgatcagcg cctcagacag   19200
atctatgagt ttgagtacga ggggctgctg cgccgcagcg cgcttgcctc ctcgcccgac   19260
cgctgcatca cccttgagaa gtccaccgag accgtgcagg ggccccactc ggccgcctgc   19320
ggtctcttct gctgcatgtt tttgcacgcc tttgtgcgct ggccccagag tcccatggat   19380
cgcaacccca ccatgaactt gctcaaggga gtgcccaacg ccatgctcca gagccccag    19440
gtccagccca ccctgcgcca aaccaggaa cagctctacc gcttcctgga gcgccactcc    19500
ccctacttcc gcagtcacag cgcgcacatc cgggggggcca cctctttctg ccacttgcaa   19560
caaaacatgc aagacggaaa atgatgtaca gctcgctttt taataaatgt aaagactgtg   19620
```

-continued

```
cactttattt atacacgggc tctttctggt tatttattca acaccgccgt cgccatctag  19680
aaatcgaaag ggttctgccg cgcgtcgccg tgcgccacgg gcagagacac gttgcgatac  19740
tggaagcggc tcgcccactt gaactcgggc accaccatgc ggggcagtgg ctcctcgggg  19800
aagttctcgc cccacagggt gcgggtcagc tgcagcgcgc tcaggaggtc gggagccgag  19860
atcttgaagt cgcagttggg gccggaaccc tgcgcgcgcg agttgcggta cacggggttg  19920
cagcactgga acaccagcag ggccggatta cgcacgctgg ccagcaggct ctcgtcgctg  19980
atcatgtcgc tgtccagatc ctccgcgttg ctcagggcga atggggtcat cttgcagacc  20040
tgcctgccca ggaaaggcgg cagcccgggc ttgccgttgc agtcgcagcg caggggcatc  20100
agcaggtgcc cgtggcccgt ctgcgcctgc gggtacagcg cgcgcatgaa ggcttcgatc  20160
tgcctgaaag ccacctgcgt cttggctccc tccgaaaaga acatcccaca ggacttgctg  20220
gagaactggt tcgcgggaca gctggcatcg tgcaggcagc agcgcgcgtc ggtgttggcg  20280
atctgcacca cgttgcgacc ccaccggttc ttcactatct tggccttgga agcctgctcc  20340
ttcagcgcgc gctggccgtt ctcgctggtc acatccatct ctatcacctg ctccttgttg  20400
atcatgtttg tcccgtgcag acacttcagg tcgccctccg tctgggtgca gcggtgctcc  20460
cacagcgcgc aaccggtggg ctcccaattt ttgtgggtca ccccgcgta ggcctgcagg  20520 taggcctgca agaagcgccc catcatggcc acaaaggtct tctggctcgt aaaggtcagc  20580
tgcaggccga tgctcttc gttcagccag gtcttgcaga tggcggccag cgcctcggtc  20640
tgctcgggca gcatcctaaa atttgtcttc aggtcgttat ccacgtggta cttgtccatc  20700
atggcgcgcg ccgcctccat gcccttctcc caggcggaca ccatgggcag gcttaggggg  20760
tttatcactt ccaccggcga ggacaccgta ctttcgattt cttcttcctc cccctcttcc  20820
cggcgcgcgc ccacgctgct gcgcgctctc accgcctgca ccaaggggtc gtcttcaggc  20880
aagcgccgca ccgagcgctt gccgcccttg acctgcttaa tcagcaccgg cgggttgctg  20940
aagcccacca tggtcagctc cgcctgctct tcttcgtctt cgctgtctac cactatctct  21000
ggggaagggc ttctccgctc tgcggcggtg cgcttctttt ttttcttggg agcagccgtg  21060
acggagtccg ccacggcgac ggaggtcgag ggcgtggggc tggggtgcg cggtaccagg  21120 gcctcgtcgc cctcggactc ttcctctgac tccaggcggc ggcggagacg cttctttggg  21180
ggcgcgcgcg tcagcggcgg cggagacggg gacggggacg gggacgggac gccctccaca  21240
gggggtggtc ttcgcgcaga cccgcggccg cgctcggggg tcttttcgag ctggtcttgg  21300
tcccgactgg ccattgtatc ctcctcctcc taggcagaga gacataagga gtctatcatg  21360
caagtcgaga aggaggagag cttaaccacc ccctctgaga ccgccgatgc gcccgccgtc  21420
gccgtcgccc ccgctgccgc cgacgcgccc gccacaccga gcgacacccc gcggaccccc  21480
ccagccgacg caccctgtt cgaggaagcg gccgtggagc aggacccggg ctttgtctcg  21540
gcagaggagg atttgcgaga ggaggaggat aaggagaaga gccctcagt gccaaaagat  21600 gataaagagc aagacgagca cgacgcagat gcacaccagg gtgaagtcgg gcgggggggac  21660 ggagggcatg acggcgccga ctacctagac gaagggaacg acgtgctctt gaagcacctg  21720
catcgtcagt gcgccatcgt ttgcgacgct ctgcaggagc gcagcgaagt gcccctcagc  21780
gtggcggagg tcagccacgc ctacgagctc agcctcttct cccccgggt gcccccccgc  21840 cgccgcgaaa acggcacatg cgagcccaac ccgcgcctca acttctaccc cgcctttgtg  21900
gtgcccgagg tcctgccac ctatcacatc ttcttcaaa attgcaagat ccccctctcg  21960
tgccgcgcca accgtagccg cgccgataag atgctggccc tgcgccaggg cgaccacata  22020
```

```
cctgatatcg ccgctttgga agatgtgcca aagatcttcg agggtctggg tcgcaacgag    22080
aagcgggcag caaactctct gcaacaggaa aacagcgaaa atgagagtca caccggggta    22140
ctggtggagc tcgagggcga caacgcccgc ctggcggtgg tcaagcgcag catcgaggtc    22200
acccactttg cctaccccgc gctcaacctg cccccaaag tcatgaacgc ggccatggac     22260
gggctgatca tgcgccgcgg ccggcccctc gctccagatg caaacttgca tgaggagacc    22320
gaggacggcc agcccgtggt cagcgacgag cagctggcgc gctggctgga gaccgcggac    22380
cccgccgaac tggaggagcg gcgcaagatg atgatggccg cggtgctggt caccgtagag    22440
ctggagtgtc tgcagcgctt cttcggcgac cccgagatgc agagaaaggt cgaggagacc    22500
ctgcactaca ccttccgcca gggctacgtg cgccaggctt gcaagatctc caacgtggag    22560
ctcagcaacc tggtgtccta cctgggcatc ttgcatgaga accgcctcgg gcagagcgtg    22620
ctgcactcca ccctgcgcgg ggaggcgcgc cgcgactacg tgcgcgactg cgtttacctc    22680
ttcctctgct acacctggca gacgccatg ggggtctggc agcagtgcct ggaggagcgc     22740
aacctcaagg agctggagaa gctcctgcag cgcgcgctca aagacctctg gacgggctac    22800
aacgagcgct cggtggccgc cgcgctggcc gacctcatct cccccgagcg cctgctcaaa    22860
accctccagc aggggctgcc cgacttcacc agccaaagca tgttgcaaaa cttcaggaac    22920
tttatcctgg agcgttctgg catcctaccc gccacctgct cgccctgcc cagcgacttt     22980
gtcccctcg tgtaccgcga gtgccccccg ccgctgtggg gtcactgcta cctgttccaa     23040
ctggccaact acctgtccta ccacgcggac ctcatggagg actccagcgg cgagggctc     23100
atggagtgcc actgccgctg caacctctgc acgccccacc gctccctggt ctgcaacacc    23160
caactgctca gcgagagtca gattatcggt accttcgagc tacagggtcc gtcctcctca    23220
gacgagaagt ccgcggctcc ggggctaaaa ctcactccgg ggctgtggac ttccgcctac    23280
ctgcgcaaat ttgtacctga agactaccac gcccacgaga tcaggtttta cgaagaccaa    23340
tcccgcccgc ccaaggcgga gctgaccgcc tgcgtcatca cccagggcga gatcctaggc    23400
caattgcaag ccatccaaaa agcccgccaa gattttttgc tgagaaaggg tcgggggtg     23460
tatctggacc cccagtcggg tgaggagctc aacccggttc ccccgctgcc gccgccgcgg    23520
gaccttgctt cccaggataa gcatcgccat ggctcccaga agaagcagc agcggccgcc    23580
actgccgcca cccacatgc tggaggaaga ggaggaatac tgggacagtc aggcagagga    23640
ggtttcggac gaggaggagc cggagacgga gatggaagag tgggaggagg acagcttaga    23700
cgaggaggct tccgaagccg aagaggcaga cgcaacaccg tcaccctcgg ccgcagcccc    23760
ctcgcaggcg ccccgaagt ccgctcccag catcagcagc aacagcagcg ctataacctc     23820
cgctcctcca ccgccgcgac ccacggccga ccgcagaccc aaccgtagat gggacaccac    23880
cggaaccggg gccggtaagt cctccgggag aggcaagcaa gcgcagcgcc aaggctaccg    23940
ctcgtggcgc gctcacaaga acgccatagt cgcttgcttg caagactgcg gggggaacat    24000
ctccttcgcc cgccgcttcc tgctcttcca ccacggtgtg gccttccccc gtaacgtcct    24060
gcattactac cgtcatctct acagccccta ctgcggcggc agtgagccag agacggtcgg    24120
cggcggcggc ggcgcccgtt tcggcgccta ggaagaccca gggcaagact tcagccaaga    24180
aactcgcggc ggccgcggcg aacgcggtcg cgggggccct gcgcctgacg gtgaacgaac    24240
ccctgtcgac ccgcgaactg agaaaccgaa tcttccccac tctctatgcc atcttccagc    24300
agagcagagg gcaggatcag gaactgaaag taaaaaacag gtctctgcgc tccctcaccc    24360
```

```
gcagctgtct gtatcacaag agcgaagacc agcttcggcg cacgctggag gacgctgagg   24420
cactcttcag caaatactgc gcgctcactc ttaaggacta gctccgcgcc cttctcgaat   24480
ttaggcggga acgcctacgt catcgcagcg ccgccgtcat gagcaaggac attcccacgc   24540
catacatgtg gagctatcag ccgcagatgg gactcgcggc gggcgcctcc caagactact   24600
ccacccgcat gaactggctc agtgccggcc cacacatgat ctcacaggtt aatgatatcc   24660
gcacccatcg aaaccaaata ttggtggagc aggcggcaat taccaccacg ccccgcaata   24720
atcccaaccc cagggagtgg cccgcgtccc tggtgtatca ggaaattccc ggccccacca   24780
ccgtactact tccgcgtgat tcccaggccg aagtccaaat gactaactca ggggcgcagc   24840
tcgcgggcgg ctgtcgtcac agggtgcggc ctcctcgcca gggtataact cacctggaga   24900
tccgaggcag aggtattcag ctcaacgacg agtcggtgag ctcctcgctc ggtctaagac   24960
ctgacgggac cttccagata gccggagccg gccgatcttc cttcacgccc cgccaggcgt   25020
acctgactct gcagagctcg tcctcggcgc cgcgctcggg cggcatcggg actctccagt   25080
tcgtgcagga gtttgtgccc tcggtctact tcaaccccct tccgggctct cccggtcgct   25140
acccggacca gttcatctcg aactttgacg ccgcgaggga ctcggtggac ggctacgact   25200
gaatgtcggg tggacccggt gcagagcaac ttcgcctgaa gcacctcgac cactgccgcc   25260
gccctcagtg cttttgcccgc tgtcagaccg gtgagttcca gtacttttcc ctgcccgact   25320
cgcacccgga cggcccggcg cacggggtgc gcttttttcat cccgagtcag gtgcgctcta   25380
ccctaatcag ggagtttacc gcccgtcccc tactggcgga gttggaaaag gggccttcta   25440
tcctaaccat tgcctgcatc tgctctaacc ctggattgca ccaagatctt tgctgtcatt   25500
tgtgtgctga gtataataaa ggctgagatc agaatctact cgggctcctg tcgccatcct   25560
gtcaacgcca ccgtccaagc ccggcccgat cagcccgagg tgaacctcac ctgcggtctg   25620
caccggcgcc tgaggaaata cctagcttgg tactacaaca gcactcccttt tgtggtttac   25680
aacagctttg accaggacgg ggtctcactg agggataacc tctcgaacct gagctactcc   25740
atcaggaaga acagcaccct cgagctactt cctccttacc tgcccgggac ttaccagtgt   25800
gtcaccggtc cctgcaccca cacccacctg ttgatcgtaa acgactctct tccgagaaca   25860
gacctcaata actcctcttc gcagttcccc agaacaggag gtgagctcag gaaacccccgg   25920
gtaaagaagg gtggacaaga gttaacactt gtggggtttc tggtgtatgt gacgctggtg   25980
gtggctcttt tgattaaggc ttttccttcc atgtctgaac tctccctctt ttatgaacaa   26040
ctcgactagt gctaacggga ccctacccaa cgaatcggga ttgaatatcg gtaaccaggt   26100
tgcagtttca cttttgatta ccttcatagt cctcttcctg ctagtgctgt cgcttctgtg   26160
cctgcggatc gggggctgct gcatccacgt ttatatctgg tgctggctgt ttagaaggtt   26220
cggagaccat cgcaggtaga ataaacatgc tgctgcttac cctcttttgtc ctggcgctgg   26280
ccgccagctg ccaagccttt tccgaggctg actttatagac gccccagtgt aacgtgactt   26340
ttaaagccca tgcacagcgt tgtcatacta taatcaaatg tgccaccgaa cacgatgaat   26400
accttatcca gtataaagat aaatcacaca agtggcact tgttgacatc tggaaacccg   26460
aagacccttt ggaatacaat gtgaccgttt tccagggtga cctcttcaaa atttacaatt   26520
acactttccc atttgaccag atgtgtgact ttgtcatgta catggaaaag cagcacaagc   26580
tgtggcctcc gactcccag ggctgtgtgg aaaatccagg ctctttctgc atgatctctc   26640
tctgtgtaac tgtgctggca ctaatactca cgcttttgta tatcagattt aaatcaaggc   26700
aaagcttcat cgatgaaaag aaaatgcctt aaacgctttc acgcttgatt gctaacaccg   26760
```

```
ggttttatc cgcagaatga ttggaatcac cctactaatc acctccctcc ttgcgattgc   26820
ccatgggttg gaacgaatcg aagcccctgt gggggccaat gttaccctgg tggggcctgt   26880
cggcaatgct acattaatgt gggaaaaata tactaaaaat caatgggtct cttactgcac   26940
taacaaaaac agccacaagc ccagagccat ctgcgatggg caaaatctaa ccttgattga   27000
tgttcaaatg ctggatgcgg gctactatta tgggcagctg ggtacaatga ttaattactg   27060
gagaccccac aaagattaca tgctccacgt agtaaagggt cccttagca gcccacccac   27120 taccacctct actacccca ctaccaccac tactcccacc accagcactg ccgcccagcc   27180
tcctcatagc agaacaacca cttttatcaa ttccaagtcc cactccccc acattgccgg   27240 cgggccctcc gcctcagact ccgagaccac cgagatctgc ttctgcaaat gctctgacgc   27300
ctttgctgag gatttggaag accacgagga agatgagcat gacttcgcag atgcatgcca   27360
ggcatcagag gcagaagcgc tgccggtggc cctcaaacag tatgcagacc cccacaccac   27420
ccccaacctt cctccaccct cccagaagcc aagtttcctg ggggaaaatg aaactctgcc   27480
tctctccata ctcgctctga catctgttgc tatgttgacc gctctgctgg tgcttctatg   27540
ctctatatgc tacctgatct gctgcagaaa gaaaaaatct cacggccatg ctcaccagcc   27600
cctcatgcac ttcccttacc ctccagagct gggcgaccac aaactttaag tctgcagtaa   27660
ctatctgccc atcccttgtc agtcgacagc gatgagcccc actaatctaa cggcctctgg   27720
acttacaaca tcgtctctta atgagaccac cgctcctcaa gacctgtacg atggtgtctc   27780
cgcgctggtt aaccagtggg atcacctggg catatggtgg ctcctcatag gagcagtgac   27840
cctgtgccta atcctggtct ggatcatctg ctgcatcaaa agcagaagac ccaggcggcg   27900
gcccatctac aggcccttg tcatcacacc tgaagatgat gatgacacca cttccaggct   27960
gcagaggcta aagcagctac tcttctcttt tacagcatgg taaattgaat catgcctcgc   28020
attttcatct acttgtctct ccttccactt tttctgggct cttctacatt ggccgctgtg   28080
tcccacatcg aggtagactg cctcacgccc ttcacagtct acctgctttt cggctttgtc   28140
atctgcacct ttgtctgcag cgttatcact gtagtgatct gcttcataca gtgcatcgac   28200
tacgtctgcg tgcgggtggc ttactttaga caccacccc agtatcgcaa cagggacata   28260
gcggctctcc taagacttgt ttaaaatcat ggccaaatta actgtgattg gtcttctgat   28320
catctgctgc gtcctagccg cgattgggac tcaagctcct accaccacca gcgctcccag   28380
aaagagacat gtatcctgca gcttcaagcg tccctggaat ataccccaat gctttactga   28440
tgaacctgaa atctctttgg cttggtactt cagcgtcacc gcccttctta tcttctgcag   28500
tacggttatt gcccttgcca tctacccttc ccttgacctg gctggaatg ctgtcaactc   28560 tatggaatat cccaccttcc cagaaccaga cctgccagac ctggttgttc taaacgcgtt   28620
tcctcctcct gctcccgttc aaaatcagtt tcgccctccg tcccccacgc ccactgaggt   28680
cagctacttt aatctaacag gcggagatga ctgaaaacct agacctagaa atggacggtc   28740
tctgcagcga gcaacgcaca ctagagaggc gccggcaaaa agagctcgag cgtcttaaac   28800
aagagctcca agacgcggtg gccatacacc agtgcaaaaa aggtgtcttc tgtctggtaa   28860
aacaggccac gctcacctat gaaaaaacag gtgacaccca ccgcctagga tacaagctgc   28920
ccacacagcg ccagaagttc gccctcatga taggcgaaca acccatcacc gtgacccagc   28980
actccgtgga gacagaaggc tgcatacacg ctccctgtag gggcgctgac tgcctctaca   29040
ccttgatcaa aaccctctgc ggtctcagag acctcatccc ttttaattaa tcataactgt   29100
```

```
aatcaataaa aaatcactta cttgaaatct gatagcaagc ctctgtccaa tttttttcagc  29160 aacacttcct tcccctcctc ccaactctgg tactctaggc gcctcctagc tgcaaacttc  29220
ctccacagtc tgaagggaat gtcagattcc tcctcctgtc cctccgcacc cacgatcttc  29280
atgttgttgc agatgaaacg cgcgagatcg tctgacgaga ccttcaaccc cgtgtacccc  29340
tacgataccg agatcgctcc gacttctgtc cctttcctta cccctcccttt tgtgtcatcc  29400 gcaggaatgc aagaaaatcc agctggggtg ctgtccctgc acttgtcaga gcccttacc  29460 acccacaatg gggccctgac tctaaaaatg ggggcggcc tgaccctgga caaggaaggg  29520
aatctcactt cccaaaacat caccagtgtc gatcccctc tcaaaaaaag caagaacaac  29580
atcagccttc agaccgccgc acccctcgcc gtcagctccg ggccctaac acttttttgcc  29640 actcccccc tagcggtcag tggtgacaac cttactgtgc agtctcaggc ccctctcact  29700
ttggaagact caaaactaac tctggccacc aaaggacccc taactgtgtc cgaaggcaaa  29760
cttgtcctag aaacagaggc tcccctgcat gcaagtgaca gcagcagcct gggccttagc  29820
gttacggccc cacttagcat taacaatgac agcctaggac tagacatgca agcgcccatt  29880
agctctcgag atggaaaact ggctctaaca gtggcggccc ccctaactgt ggtcgagggt  29940
atcaatgctt tggcagtagc cacaggtaag ggtattgggc taaatgaaac caacacacac  30000
ctgcaggcaa aactggtcgc acccctaggc tttgatacca acggcaacat taagctaagc  30060
gttgcaggag gcatgaggct aaacaataac acactgatac tagatgtaaa ctacccattt  30120
gaggctcaag gccaactgag cctaagagtg ggctcgggcc cactatatgt agattctagt  30180
agtcataacc taaccattag atgccttagg ggattgtata taacatcttc taacaaccaa  30240
aacggtctag aagccaacat taaactaaca agaggccttg tgtatgacgg aaatgccata  30300
gcagttaatg ttggcaaagg gctggaatac agccctactg acacaacaga aaaacctata  30360
cagactaaaa taggtctagg catggagtat gataccgagg gagccatgat gacaaaacta  30420
ggctctggac taagctttga caattcagga gccattgtag tgggaaacaa aaatgatgac  30480
aggcttactt tgtggaccac accggaccca tcgcccaact gtcagatcta ctctgaaaaa  30540
gatgctaaac taaccttggt actgactaaa tgtggcagtc aggttgtagg cacagtatct  30600
attgccgctc ttaaaggtag cctcgtgcca atcactagtg caatcagtgt ggttcaggta  30660
tacctaaggt ttgatgaaaa tggggtacta atgagtaact cttcacttaa tggcgaatac  30720
tggaatttta gaaacggaga ctcaactaat ggcacaccat atacaaacgc agtgggtttc  30780
atgcctaatc tactgcccta tcctaaaggt caaactacaa ctgcaaaaag taacattgtc  30840
agccaggtct acatgaatgg ggacgatact aaacccatga catttacaat caacttcaat  30900
ggccttagtg aaacagggga tacccctgtt agtaaatatt ccatgacatt ctcatggagg  30960
tggccaaatg gaagctacat agggcacaat tttgtaacaa actcctttac cttctcctac  31020
atcgcccaag aataaagaaa gcacagagat gcttgttttt gatttcaaaa ttgtgtgctt  31080
ttatttattt tcagcttaca gtatttccag tagtcattca aataaagctt aatcaaactg  31140
catgagaacc cttccacata gcttaaatta gcaccagtgc aaatggagaa aacaattgac  31200
ggccgggatc ggtgatcacc gatccagaca tgataagata cattgatgag tttggacaaa  31260
ccacaactag aatgcagtga aaaaaatgct ttatttgtga aatttgtgat gctattgctt  31320
tatttgtaac cattataagc tgcaataaac aagttcccgg atcgcgatcc ggcccgaggc  31380
tgtagccgac gatggtgcgc caggagagtt gttgattcat tgtttgcctc cctgctgcgg  31440
tttttcaccg aagttcatgc cagtccagcg tttttgcagc agaaaagccg ccgacttcgg  31500
```

```
tttgcggtcg cgagtgaaga tccctttctt gttaccgcca acgcgcaata tgccttgcga   31560
ggtcgcaaaa tcggcgaaat tccatacctg ttcaccgacg acggcgctga cgcgatcaaa   31620
gacgcggtga tacatatcca gccatgcaca ctgatactct tcactccaca tgtcggtgta   31680
cattgagtgc agcccggcta acgtatccac gccgtattcg gtgatgataa tcggctgatg   31740
cagtttctcc tgccaggcca gaagttcttt ttccagtacc ttctctgccg tttccaaatc   31800
gccgctttgg acataccatc cgtaataacg gttcaggcac agcacatcaa agagatcgct   31860
gatggtatcg gtgtgagcgt cgcagaacat tacattgacg caggtgatcg gacgcgtcgg   31920
gtcgagttta cgcgttgctt ccgccagtgg cgcgaaatat tcccgtgcac cttgcggacg   31980
ggtatccggt tcgttggcaa tactccacat caccacgctt gggtggtttt tgtcacgcgc   32040
tatcagctct ttaatcgcct gtaagtgcgc ttgctgagtt tccccgttga ctgcctcttc   32100
gctgtacagt tctttcggct tgttgcccgc ttcgaaacca atgcctaaag agaggttaaa   32160
gccgacagca gcagtttcat caatcaccac gatgccatgt tcatctgccc agtcgagcat   32220
ctcttcagcg taagggtaat gcgaggtacg gtaggagttg gccccaatcc agtccattaa   32280
tgcgtggtcg tgcaccatca gcacgttatc gaatcctttg ccacgcaagt ccgcatcttc   32340
atgacgacca aagccagtaa agtagaacgg tttgtggtta atcaggaact gttcgccctt   32400
cactgccact gaccggatgc cgacgcgaag cgggtagata tcacactctg tctggctttt   32460
ggctgtgacg cacagttcat agagataacc ttcacccggt tgccagaggt gcggattcac   32520
cacttgcaaa gtcccgctag tgccttgtcc agttgcaacc acctgttgat ccgcatcacg   32580
cagttcaacg ctgacatcac cattggccac cacctgccag tcaacagacg cgtggttaca   32640
gtcttgcgcg acatgcgtca ccacggtgat atcgtccacc caggtgttcg gcgtggtgta   32700
gagcattacg ctgcgatgga ttccggcata gttaaagaaa tcatggaagt aagactgctt   32760
tttcttgccg ttttcgtcgg taatcaccat tcccggcggg atagtctgcc agttcagttc   32820
gttgttcaca caaacggtga tacgtacact tttcccggca ataacatacg gcgtgacatc   32880
ggcttcaaat ggcgtatagc cgccctgatg ctccatcact tcctgattat tgacccacac   32940
tttgccgtaa tgagtgaccg catcgaaacg cagcacgata cgctggcctg cccaaccttt   33000
cggtataaag acttcgcgct gataccagac gttgcccgca taattacgaa tatctgcatc   33060
ggcgaactga tcgttaaaac tgcctggcac agcaattgcc cggcttttctt gtaacgcgct   33120 ttcccaccaa cgctgatcaa ttccacagtt ttcgcgatcc agactgaatg cccacaggcc   33180
gtcgagtttt tgatttcac gggttgggt ttctacagga cggaccatgc gttcgacctt   33240
tctcttcttt tttgggccca tgatggcaga tccgtatagt gagtcgtatt agctggttct   33300
ttccgcctca gaagccatag agcccaccgc atccccagca tgcctgctat tgtcttccca   33360
atcctccccc ttgctgtcct gccccacccc accccccaga atagaatgac acctactcag   33420
acaatgcgat gcaatttcct cattttatta ggaaaggaca gtgggagtgg caccttccag   33480
ggtcaaggaa ggcacgggg aggggcaaac aacagatggc tggcaactag aaggcacagt   33540
cgaggctgat cagcgagctc tagatgcatg ctcgagcggc cgccagtgtg atggatatct   33600
gcagaattcc agcacactgg cggccgttac tagtggatcc gagctcggta ccaacgcgtc   33660
gtaactataa cggtcctaag gtagcgaaaa gcactctcac agcaccagca ctaatcagag   33720
tgtgaagagg gccaagtgcc gaacgagtat atataggaat aaaaaatgac gtaaatgtgt   33780
aaaggtcaga aaacgcccag aaaaatacac agaccaacgc ccgaaacgaa acccgcgaa   33840
```

```
aaaatacccca gaacttcctc aacaaccgcc acttccgctt tctcacggta cgtcacttcc    33900
gcaagaaaag caaaactaca tttcccacat gtgtaaaaac gaaacccgc cccttgtaac     33960 cgcccacaac ttacatcatc aaaacgtaaa ctcctacgtc acccgccccg cctctccccg    34020
cccacctcat tatcatattg gccacaatcc aaaataaggt atattattga tgatg         34075
```

<210> SEQ ID NO 26
<211> LENGTH: 34071
<212> TYPE: DNA
<213> ORGANISM: Gorilla beringei graueri

<400> SEQUENCE: 26

```
catcatcaat aatataccttt attttggatt gtggccaata tgataatgag gtgggcgggg     60
agaggcgggg cggtgacgt aggacgcgcg agtagggttg ggaggtgtgg cggaagtgtg    120
gcatttgcaa gtgggaggag ctcacatgca agcttccgtc gcggaaaatg tgacgttttt    180
gatgagcgcc gcctacctcc ggaagtgcca atttttcgcgc gcttttcacc ggatatcgta    240
gtaattttgg gcgggaccat gtaagatttg gccattttcg cgcgaaaagt gaaacgggga    300
agtgaaaact gaataatagg gcgttagtca tagtgcgtaa tatttaccga gggccgaggg    360
actttgaccg attacgtgga ggactcgccc aggtgttttt tacgtgaatt ccgcgttcc    420 gggtcaaagt ctccgtttta ttgtcaccgt catttgacag gcctgaccat ctggtgctgg    480
cctgcaccag ggccgagttt gggtctagcg atgaggatac cgattgaggt gggtaaggtg    540
ggcgtggcta aagggtggg gcgtgtataa attggggggtc taagggtctc tctgttttgt    600
cttgcaacag ccgccgccat gagcgacacc ggcaacagct ttgatggaag catctttagc    660
ccctatctga cagtgcgcat gcctcactgg gctggagtgc gtcagaatgt gatgggttcc    720
aacgtggatg gacgcccgt tctgccttca aattcgtcta caatggccta cgcgaccgtg    780
ggaggaactc cgctggacgc cgcgacctcc gccgccgcct ccgccgccgc cgcgaccgcg    840
cgcagcatgg ctacggacct ttacagctct ttggtggcga gcgcgcggc ctctcgcgcg    900 tctgctcggg atgagaaact gaccgctctg ctgcttaaac tggaagactt gacccgggag    960
ctggctcaac tgacccagca ggtctccagc ttgcgtgaga gcagccttgc ctcccccta    1020 tggcccataa tataaataaa agccagtctg tttggattaa gcaagtgtat gttctttatt    1080
taactctccg cgcgcggtaa gcccgggacc agcggtctcg gtcgtttagg gtgcggtgga    1140 ttcttttccaa cacgtggtac aggtggctct ggatgtttag atacatgggc atgagtccat    1200
ccctggggtg gaggtagcac cactgcagag cttcgtgctc gggggtggtg ttgtatatga    1260
tccagtcgta gcaggagcgc tgggcgtggt gctgaaaaat gtccttaagc aagaggctta    1320
tagctagggg gaggcccttg gtgtaagtgt ttacaaatct gctcagttgg gaggggtgca    1380
tccgggggga tataatgtgc atcttggact ggattttag gttggctatg ttcccaccca    1440
gatcccttct gggattcatg ttgtgcagga ccaccagcac ggtatatcca gtacacttgg    1500
gaaatttatc gtggagctta gacgggaatg catggaagaa cttggagacg cccttgtggc    1560
ctcccagatt ttccatacat tcgtccatga tgatggcaat gggcccgtgg gaagctgcct    1620
gagcaaaaat gttctcggga tcgctcacat cgtagttatg ttccagggtg aggtcatcat    1680
aggacatctt tacaaatcgg gggcggaggg tccggactg ggggatgatg gtgccctcgg    1740
gccccggggc gtagttcccc tcacagatct gcatctccca ggctttcatt tcagagggag    1800
ggatcatatc cacctgcgga gcgatgaaaa acacagtttc tggcgcaggg gagattaact    1860
gggatgagag caggtttctg agcagctgtg acttccacaa gccggtgggc ccatatatca    1920
```

-continued

```
cgcctatcac cggctgcagc tggtagttaa gagagctgca gctgccgtcc tcccggagca    1980
gggggggccac ctcgttcagc atatccctga cgtggatgtt ctccctgacc aattccgcca    2040
gaaggcgctc gccgcccagc gaaagcagct cttgcaagga agcaaaattt ttcagcggtt    2100
ttaggccgtc ggccgtgggc atgttttttca gcgtctgggt cagcagttcc agtctgtccc    2160
acagctcggt gatgtgctct acggcatctc gatccagcag atctcctcgt ttcgcgggtt    2220
ggggcggctt tcgctgtagg gcaccagccg atgggcgtcc agcggggcca gagtcatgtc    2280
cttccatggg cgcagggtcc tcgtcagggt ggtctgggtc acggtgaagg ggtgcgctcc    2340
gggttgggcg ctggccaggg tgcgcttgag gctggttctg ctggtgctga atcgctgccg    2400
ctcttcgccc tgcgcgtcgg ccaggtagca tttgaccatg gtctcgtagt cgagaccctc    2460
ggcggcgtgc cccttggcgc ggagcttttcc cttggaggtg gcgccgcacg aggggcactg    2520
caggctcttc agggcgtaga gcttgggagc gagaaacacg gactctgggg agtaggcgtc    2580
cgcgccgcag gaagcgcaga ccgtctcgca ttccaccagc caagtgagct ccgggcggtc    2640
agggtcaaaa accaggttgc ccccatgctt tttgatgcgt ttcttacctc ggctctccat    2700
gaggcggtgt cccttctcgg tgacgaagag gctgtccgtg tctccgtaga ccgacttcag    2760
gggcctgtct tccagcggag tgcctctgtc ctcctcgtag agaaactctg accactctga    2820
gacgaaggcc cgcgtccagg ccaggacgaa ggaggccacg tgggaggggt agcggtcgtt    2880
gtccactagc gggtccacct tctccagggt gtgcaggcac atgtccccct cctccgcgtc    2940
cagaaaagtg attggcttgt aggtgtagga cacgtgaccg ggggttcccg acggggggggt    3000
ataaaggggg gtgggcaccc tttcatcttc actctcttcc gcatcgctgt ctgcgagagc    3060
cagctgctgg ggtaagtatt ccctctcgaa ggcgggcatg acctcagcgc tcaggttgtc    3120
agtttctaaa aatgaggagg atttgatgtt cacctgtccg gaggtgatac ctttgagggt    3180
acctgggtcc atctggtcag aaaacactat tttttgttg tcaagcttgg tggcgaacga    3240
cccgtagagg gcgttggaga gcagcttggc gatggagcgc agggtctggt ttttgtcgcg    3300
gtcggctcgc tccttggccg cgatgttgag ttgcacgtac tcgcgggcca cgcacttcca    3360
ctcggggaag acgtggtgc gctcgtctgg gatcaggcgc accctccagc ctcggttgtg    3420
cagggtgacc atgtcgacgc tggtggcgac ctcgccgcgc aggcgctcgt ggtccagca    3480
gaggcggccg cccttgcgcg agcagaaggg gggtaggggg tccagctggt cctcgtttgg    3540
ggggtccgcg tcgatggtga agaccccggg gagcaagcgc gggtcaaagt agtcgatctt    3600
gcaagcttgc atgtccagag cccgctgcca ttcgcgggcg gcgagcgcgc gctcgtaggg    3660
gttgaggggc gggccccagg gcatgggggtg ggtgagcgcg gaggcgtaca tgccgcagat    3720
gtcatacacg tacaggggtt ccctgaggat gccgaggtag gtggggtagc agcgcccccc    3780
gcggatgctg gcgcgcacgt agtcatagag ctcgtgggag ggggccagca tgttgggccc    3840
gaggttggtg cgctggggggc gctcggcgcg gaaggcgatc tgcctgaaga tggcatggga    3900
gttggaggag atggtgggcc gctggaagac gttgaagctt gcttcttgca agcccaccga    3960
gtccctgacg aagcaggcgt aggactcgcg cagcttgtgc accagctcgg cggtgacctg    4020
gacgtcgagc gcgcagtagt cgagggtctc gcggatgatg tcatacttat cctccccctt    4080
cttttttccac agctcgcggt tgaggacgaa ctcttcgcgg tctttccagt actcttggag    4140
gggaaacccg tccgtgtccg aacggtaaga gcctagcatg tagaactggt tgacggcctg    4200
gtaggggcaa cagcccttct ccacgggcag cgcgtaggcc tgcgccgcct tgcggaggga    4260
```

```
ggtgtgggtg agggcgaaag tgtccctgac catgactttg aggtattgat gtttgaagtc    4320
tgtgtcatcg cagccgccct gttcccacag ggtgtagtcc gtgcgctttt tggagcgcgg    4380
gttgggcagg gagaaggtga ggtcattgaa gaggatcttc cccgctcgag gcatgaagtt    4440
tctggtgatg cgaaagggcc ctgggaccga ggagcggttg ttgatgacct gggcggccag    4500
gacgatctcg tcaaagccgt ttatgttgtg gcccacgatg tagagctcca aaaagcgggg    4560
ctggcccttg atggagggga gcttttttgag ttcctcgtag gtgagctcct cgggcgattc    4620
caggccgtgc tcctccaggg cccagtcttg caagtgaggg ttggccgcca ggaaggatcg    4680
ccagaggtcg cgggccatga gggtctgcag gcggtcgcgg aaggttctga actgtcgccc    4740
cacggccatc ttttcggggg tgatgcagta aaggtgagg gggtcttttct cccagggtc    4800 ccatctgagc tctcgggcga ggtcgcgcgc ggcggcgacc agagcctcgt tgcccccag    4860 tttcatgacc agcatgaagg gcacgagctg cttgccaaag gctcccatcc aagtgtaggt    4920
ctctacatcg taggtgacaa agaggcgctc cgtgcgagga tgagagccga tcgggaagaa    4980
ctggatctcc cgccaccagt tggaggattg gctgttgatg tggtgaaagt agaagtcccg    5040
tctgcgggcc gagcactcgt gctggctttt gtaaaagcga ccgcagtact ggcagcgctg    5100 cacggggttgt atatcttgca cgaggtgaac ctggcgacct ctgacgagga agcgcagcgg    5160
gaatctaagt cccccgcctg gggtcccgtg tggctggtgg tcttctactt tggttgtctg    5220
gccgccagca tctgtctcct ggagggcgat ggtggagcag accaccacgc cgcgagagcc    5280
gcaggtccag atctcggcgc tcggcgggcg gagtttgatg acgacatcgc gcacattgga    5340
gctgtccatg gtctccagct cccgcggcgg caggtcagct gggagttcct ggaggttcac    5400
ctcgcagaga cgggtcaagg cgcgggcagt gttgagatgg tatctgattt caaggggcgt    5460
gttggcggcg gagtcgatgg cttgcaggag gccgcagccc cgggggggcca cgatggttcc    5520 ccgcggggcg cgaggggagg cggaagctgg gggtgtgttc agaagcggtg acgcgggcgg    5580
gcccccggag gtagggggg ttccggcccc acaggcatgg gcggcagggg cacgtcttcg    5640
ccgcgcgcgg gcaggggctg gtgctggctc cgaagagcgc ttgcgtgcgc gacgacgcga    5700
cggttggtgt cctgtatctg acgcctctga gtgaagacca cggtcccgt gaccttgaac    5760 ctgaaagaga gttcgacaga atcaatctcg gcatcgttga cagcggcctg gcgcaggatc    5820
tcctgcacgt cgcccgagtt gtcctggtag gcgatctctg ccatgaactg ctcgatctct    5880
tcttcctgga gatctcctcg tccggcgcgc tccacggtgg ccgccaggtc gttggagatg    5940
cgacccatga gctgcgagaa ggcgttgagc ccgccctcgt tccagacccg gctgtagacc    6000
acgcccccct cggcgttgcg ggcgcgcatg accacctggg ccaggttgag ctccacgtgt    6060
cgcgtgaaga cggcgtagtt gcgcaggcgc tggaaaaggt agttcagggt ggtggcggtg    6120
tgctcggcga cgaagaagta catgacccag cgccgcaacg tggattcatt gatgtccccc    6180
aaggcctcca gcgctccat ggcctcgtag aagtccacgg cgaagttgaa aaactgggag    6240
ttgcgagcgg acacggtcaa ctcctcctcc agaagacgga tgagctcggc gacagtgtcg    6300
cgcacctcgc gctcgaaggc cacgggggc gcttcttcct cttccacctc ttcttccatg    6360
atcgcttctt cttcttcctc agccgggacg ggaggggggcg gcggcggcgg gggagggggcg    6420 cggcggcggc ggcggcgcac cgggaggcgg tcgatgaagc gctcgatcat ctcccccgc    6480 atgcggcgca tggtctcggt gacgcgcgcg ccgttctccc gggggcgcag ctcgaagacg    6540
ccgcctctca tctcgccgcg gggcgggcgg ccgtgaggta gcgagacggc gctgactatg    6600
cctcttaaca attgctgtgt aggtacaccg ccgagggacc tgattgagtc cagatccacc    6660
```

```
ggatccgaaa acctttggag gaaagcgtct atccagtcgc agtcgcaagg taggctgagc   6720
accgtggcgg gcggggcgg gtctggagag ttcctggcgg agatgctgct gatgatgtaa   6780
ttaaagtagg cggtcttgag aaggcggatg gtggacagga gcaccatgtc tttgggtccg   6840
gcctgttgga tgcggaggcg gtcggccatg ccccaggcct cgttctgaca ccggcgcagg   6900
tctttgtagt agtcttgcat gagtcttttc accggcacct cttctccttc ctcttctcca   6960
tctcgccggt ggtttctcgc gccgcccatg cgcgtgaccc caaagcccct gagcggctgc   7020
agcagggcca ggtcggcgac cacgcgctcg gccaagatgg cctgctgcac ctgagtgagg   7080
gtcctctcga agtcatccat gtccacgaag cggtggtagg cgcccgtgtt gatggtgtag   7140
gtgcagttgg ccatgacgga ccagttgacg gtctggtgtc ccggctgcga gagctccgtg   7200
taccgcaggc gcgagaaggc gcgggaatcg aacacgtagt cgttgcaagt ccgcaccaga   7260
tactggtagc ccaccaggaa gtgcggcgga ggttggcgat agaggggcca gcgctgggtg   7320
gcgggggcgc cgggcgccag gttttccagc atgaggcggg gtatccgta gatgtacctg    7380 gacatccagg tgatgccggc ggcggtggtg gtggcgcgcg cgtagtcgcg acccggttc    7440 cagatgtttc gcaggggcga gaagtgttcc atggtcggca cgctctggcc ggtgaggcgc   7500
gcgcagtcgt tgacgctcta tacacacaca aaaacgaaag cgtttacagg gctttcgttc    7560
tgtagcctgg aggaaagtaa atgggttggg ttgcggtgtg ccccggttcg agaccaagct   7620
gagctcggcc ggctgaagcc gcagctaacg tggtattggc agtcccgtct cgacccaggc   7680
cctgtatcct ccaggatacg gtcgagagcc cttttgcttt cttggccaag cgcccgtggc   7740
gcgatctggg atagatggtc gcgatgagag gacaaaagcg gctcgcttcc gtagtctgga   7800
gaaacaatcg ccagggttgc gttgcggcgt accccggttc gagcccctat gcggcttga    7860 atcggccgga accgcggcta acgagggccg tggcagcccc gtcctcagga ccccgccagc   7920
cgacttctcc agttacggga gcgagcccct tttgttttttt attttttaga tgcatcccgt   7980
gctgcggcag atgcgcccct cgcccgggcc cgatcagcag cagcaacagc aggcatgcag   8040
acccccctct ccccttttccg ccccggtcac cacggccgcg gcggccgtgt cgggcgcggg    8100
gggcgcgctg gagtcagatg agccaccgcg gcggcgacct aggcagtatc tggacttgga   8160
agagggcgag ggactggcgc ggctgggggc gaactctcca gagcgccacc cgcgggtgca   8220
gttgaaaagg gacgcgcgcg aggcgtacct gccgcggcag aacctgtttc gcgaccgcgg   8280
gggcgaggag cccgaggaga tgcgagactg caggttccaa gcggggcgcg agctgcggcg   8340
cgggctggac agacagcgcc tgctgcgcga ggaggacttt gagcccgaca cgcagacggg   8400
catcagcccc gcgcgcgcgc acgtagccgc ggccgacctg gtgaccgcct acgagcagac   8460
ggtgaaccag gagcgcaact tccaaaagag cttcaacaac cacgtgcgca cgctggtggc   8520
gcgcgaggag gtgaccctgg gtctcatgca tctgtgggac ctggtggagg cgatcgtgca   8580
gaaccccagc agcaagcccc tgaccgcgca gctgttcctg gtggtgcagc acagcaggga   8640
caacgaggcc ttcagggagg cgctgctgaa catcaccgag ccggagggc gctggctcct    8700 ggacctgata aacatcctgc agagcatagt ggtgcaggag cgcagcctga gcctggccga   8760
gaaggtggcg gccatcaact actctatgct gagcctgggc aagttctacg cccgcaagat   8820
ctacaagacc ccctacgtgc ccatagacaa ggaggtgaag atagacagct tctacatgcg   8880
catggcgctg aaggtgctga ccctgagcga cgacctggga gtgtaccgca acgagcgcat   8940
ccacaaggcc gtgagcgcca gccggcggcg cgagctgagc gaccgcgagc tgatgcacag   9000
```

```
tctgcagcgc gcgctgaccg gcgcgggcga gggcgacagg gaggtcgagt cctacttcga      9060
catgggggcc gacctgcact ggcagccgag ccgccgcgcc ctggaggcgg cgggggcgta      9120
cggcggcccc ctggcggccg atgaccagga agaggaggac tatgagctag aggagggcga      9180
gtacctggag gactgacctg gctggtggtg ttttggtata gatgcaagat ccgaacgtgg      9240
cggacccggc ggtccgggcg gcgctgcaaa gccagccgtc cggcattaac tcctctgacg      9300
actgggccgc ggccatgggt cgcatcatgg ccctgaccgc gcgcaacccc gaggctttca      9360
ggcagcagcc tcaggccaac cggctggcgg ccatcttgga agcggtagtg cccgcgcgct      9420
ccaaccccac ccacgagaag gtgctggcca tagtcaacgc gctggcggag agcagggcca      9480
tccgcgcgga cgaggccgga ctggtgtacg atgcgctgct gcagcgggtg gcgcggtaca      9540
acagcggcaa cgtgcagacc aacctggacc gcctggtgac ggacgtgcgc gaggccgtgg      9600
cgcagcgcga gcgcttgcat caggacggta acctgggctc gctggtggcg ctaaacgcct      9660
tcctcagcac ccagccggcc aacgtaccgc gggggcagga ggactacacc aacttttttga     9720
gcgcgctgcg gctgatggtg accgaggtcc ctcagagcga ggtgtaccag tcggggcccg      9780
actacttctt ccagaccagc agacagggct tgcaaaccgt gaacctgagc caggcttttca     9840
agaacctgcg ggggctgtgg ggagtgaagg cgcccaccgg cgaccgggct acggtgtcca      9900
gcctgctaac ccccaactcg cgcctgctgc tgctgctgat cgcgcccttc acggacagcg      9960
ggagcgtctc gcgggagacc tatctggccc acctgctgac gctgtaccgc gaggccatcg     10020
ggcaggcgca ggtggacgag cacaccttcc aagagatcac cagcgtgagc cacgcgctgg     10080
ggcaggagga cacgggcagc ctgcaggcga ccctgaacta cctgctgacc aacaggcggc     10140
agaagattcc cacgctgcac agcctgaccc aggaggagga gcgcatcttg cgctacgtgc     10200
agcagagcgt gagcctgaac ctgatgcgcg acggcgtgac gcccagcgtg gcgctggaca     10260
tgaccgcgcg caacatggaa ccgggcatgt acgcctccca ccggccgttc atcaaccgcc     10320
tgatggacta cttgcatcgg gcggcggccg tgaaccccga gtacttcact aatgccattc     10380
tgaatcccca ctggatgccc cctccgggtt tctacaacgg ggactttgag gtgcccgagg     10440
tcaacgacgg gttcctctgg gatgacatgg atgacagtgt gttctcaccc aacccgctgc     10500
gcgccgcgtc tctgcgattg aaggagggct ctgacaggga aggaccgaga agtctggcct     10560
cctccctggc tctgggagcg gtgggcgcca cggcgcgggc ggcgcggggc agtagccccct    10620
tccccagcct ggcagactct ctgaacagcg ggcgggtgag caggccccgc ttgctaggcg     10680
aggaggagta tctgaacaac tccctgctgc agcccgcgag ggacaagaac gctcagcggc     10740
agcagtttcc caacaatggg atagagagcc tggtggacaa gatgtccaga tggaagacgt     10800
atgcgcagga gtacaaggag tgggaggacc gccagccgcg gcccttgccg ccccctaggc     10860
agcgctggca gcggcgcgcg tccaaccgcc gctggaggca ggggcccgag gacgatgatg     10920
actctgcaga tgacagcagc gtgttggacc tgggcgggag cggaaccccc ttttcgcacc     10980
tgcgcccacg cctgggcaag atgttttaaa agaaaaaaaa aaaataaaac tcaccaaggc     11040
catggcgacg agcgttggtt ttttgttccc ttccttagta tgcggcgcgc ggcgatgttc     11100
gaggaggggc ctcccccctc ttacgagagc gcgatgggga tttctcctgc ggcgccctg      11160
cagcctccct acgtgcctcc tcggtacctg caacctacag ggggagaaa tagcatctgt      11220
tactctgagc tgcagcccct gtacgatacc accagactgt acctggtgga caacaagtcc     11280
gcggacgtgg cctccctgaa ctaccagaac gaccacagcg attttttgac cacggtgatc     11340
caaaacaacg acttcacccc aaccgaggcc agcactcaga ccataaacct ggataacagg     11400
```

```
tcgaactggg gcggcgacct gaagaccatc ttgcacacca acatgcccaa cgtgaacgag    11460
ttcatgttca ccaactcttt taaggcgcgg gtgatggtgg cgcgcgagca gggggaggcg    11520
aagtacgagt gggtggactt cacgctgccc gagggcaact actcagagac catgactctc    11580
gacctgatga acaatgcgat cgtggaacac tatctgaaag tgggcaggca gaacggggtg    11640
aaggaaagcg atatcggggt caagtttgac accagaaact ccgtctgggc tgggaccccc    11700
gtgaccgggc tggtcatgcc gggggtctac accaacgagg cctttcatcc cgacatagtg    11760
cttctgcccg gctgtggggt ggacttcacc cagagccggc tgagcaacct gctgggcatt    11820
cgcaagcggc agccttttcc aggagggttt aagatcacct atgaggatct gaaggggggc    11880
aacattcccg cgctccttga tctggacgcc tacgaggaga gcttgaaacc cgaggagagc    11940
gctggcgaca gcgcgagag tggcgaggag caagccggcg gcgtggcgg cgcgtcggta     12000
gaaaacgaaa gtacgcccgc agtggcggcg gacgctgcgg aggtcgagcc ggaggccatg    12060
cagcaggacg cagaggaggg cgcacaggag ggcgcgcaga aggacatgaa cgatggggag    12120
atcaggggag acacattcgc cacccggggc gaagaaaaag aggcagaggc ggcggcggcg    12180
gcgacggcgg aggccgaaac cgaggttgag gcagaggcag agcccgagac cgaagttatg    12240
gaagacatga atgatggaga acgtaggggc gacacgttcg ccacccgggg cgaagagaag    12300
gcggcggagc cagaagccgc ggctgaggag gcggctgcgg ctgcggccaa gactgaggct    12360
gcggctaagg ctgaggtcga agccaatgtt gcggttgagg ctcaggctga ggaggaggcg    12420
gcggctgaag cagttaagga aaaggcccag gcagagcagg aagagaaaaa acctgtcatt    12480
caacctctaa aagaagatag caaaaagcgc agttacaacg tcatcgaggg cagcaccttt    12540
acccagtacc gcagctggta cctggcgtac aactacggcg acccggtcaa gggggtgcgc    12600
tcgtggaccc tgctctgcac gccggacgtc acctgcggct ccgagcagat gtactggtcg    12660
ctgccgaaca tgatgcaaga cccggtgacc ttccgctcca cgcggcaggt tagcaacttc    12720
ccggtggtgg gcgccgaact gctgcccgtg cactccaaga gttttttacaa cgagcaggcc    12780
gtctactccc agctgatccg ccaggccacc tctctgaccc acgtgttcaa tcgctttccc    12840
gagaaccaga ttttggcgcg cccgccggcc cccaccatca ccaccgtgag tgaaaacgtt    12900
cctgccctca cagatcacgg gacgctaccg ctgcgcaaca gcatctcagg agtccagcga    12960
gtgaccatta ctgacgccag acgccggacc tgccctacg tttacaaggc cttgggcata    13020
gtctcgccgc gcgtcctctc cagtcgcact ttttaaaaca catctaccca cacgttccaa    13080
aatcatgtcc gtactcatct cacccagcaa caacaccggc tggggctgc gcgcgcccag    13140
caagatgttt ggagggggcga ggaagcgctc cgaccagcac cctgtgcgcg tgcgcggcca    13200
ctaccgcgcg ccctggggag cgcacaagcg cgggcgcaca gggcgcacca ctgtggacga    13260
cgtcattgac tccgtagtgg agcaagcgcg ccactacaca cccggcgcgc cgaccgcccc    13320
cgccgtgtcc accgtggacc aggcgatcga aagcgtggta cagggcgcgc ggcactatgc    13380
caaccttaaa agtcgccgcc gccgcgtggc ccgccgccat cgccggagac cccgggccac    13440
cgccgccgcg cgccttacta aggctctgct caggcgcgcc aggcgaactg gccaccgggc    13500
cgccatgagg gccgcacggc gggctgccgc tgccgcaagc gccgtggccc gcgggcacg    13560
aaggcgcgcg gccgccgccg ccgccgccgc catttccagc ttggcctcga cgcggcgcgg    13620
taacatatac tgggtgcgcg actcggtaac cggcacgcgg gtaccgtgc gctttcgccc    13680
cccgcggaat tagcacaaga caacatacac actgagtctc ctgctgttgt gtatcccagc    13740
```

```
ggcgaccgtc agcagcggcg acatgtccaa gcgcaaaatt aaagaagaga tgctccaggt   13800
catcgcgccg gagatctatg gccccccgaa gaaggaggag gatgattaca agccccgcaa   13860
gctaaagcgg gtcaaaaaga aaaagaaaga tgatgatgat gacgaggcgg tggagtttgt   13920
ccgccgcatg gcacccaggc gccccgtgca gtggaagggc cggcgcgtgc agcgcgtttt   13980
gcgccccggc accgcggtgg tcttcacgcc cggcgagcgc tccacgcgca ctttcaagcg   14040
ggtgtacgat gaggtgtacg gcgacgagga cctgttggag caggccaacc agcgctttgg   14100
ggagtttgca tatgggaaac ggccccgcga gagtctaaaa gaggacctgc tggcgctacc   14160
gctggacgag ggcaatccca ccccgagtct gaagccggta accctgcaac aggtgctgcc   14220
tttgagcgcg cccagcgagc ataagcgagg gttgaagcgc gaaggcgggg acctggcgcc   14280
caccgtgcag ttgatggtgc ccaagcggca gaagctggag gacgtgctgg agaaaatgaa   14340
agtagagccc gggatccagc ccgagatcaa ggtccgcccc atcaagcagg tggcgcccgg   14400
cgtgggagtc cagaccgtgg acgttaggat tcccacggag gagatggaaa cccaaaccgc   14460
cactccctct tcggcggcca gcgccaccac cggcaccgct tcggtagagg tgcagacgga   14520
cccctggcta cccgccaccg ctgttgccgc cgccgccccc cgttcgcgcg ggcgcaagag   14580
aaattatcca gcgccagcg cgctcatgcc ccagtacgca ctgcatccat ccatcgcgcc   14640 caccccggc taccgcgggt actcgtaccg cccgcgcaga tcagccggca ctcgcggccg   14700
ccgccgccgt gcgaccacaa ccagccgccg ccgtcgccgc cgccgccagc cagtgctgac   14760
ccccgtgtct gtaaggaagg tggctcgctc ggggagcacg ctggtggtgc ccagagcgcg   14820
ctaccacccc agcatcgttt aaagccggtc tctgtatggt tcttgcagat atggccctca   14880
cttgtcgcct ccgcttcccg gtgccgggat accgaggaag aactcaccgc cgcagaggca   14940
tggcgggcag cggtctccgc ggcggccgtc gccatcgccg gcgcgcaaaa agcaggcgca   15000
tgcgcggcgg tgtgctgcct ctgctaatcc cgctaatcgc cgcggcgatc ggtgccgtac   15060
ccgggatcgc ctccgtggcc ctgcaggcgt cccagaaacg ttgactcttg caaccttgca   15120
agcttgcatt ttttggagga aaaataaaaa aagtctagac tctcacgctc gcttggtcct   15180
gtgactattt tgtagaaaaa agatggaaga catcaacttt gcgtcgctgg ccccgcgtca   15240
cggctcgcgc ccgttcatgg gagactggac agatatcggc accagcaata tgagcggtgg   15300
cgccttcagc tggggcagtc tgtggagcgg ccttaaaaat tttggttcca ccattaagaa   15360
ctatggcaac aaagcgtgga acagcagcac gggccagatg ctgagagaca agttgaaaga   15420
gcagaacttc caggagaagg tggcgcaggg cctggcctct ggcatcagcg gggtggtgga   15480
catagctaac caggccgtgc agaaaaagat aaacagtcat ctggaccccc gtcctcaggt   15540
ggaggaaatg cctccagcga tggagacggt gtctcccgag ggcaaaggcg aaaagcgccc   15600
gcggcccgac agagaagaga ccctggtgtc acacaccgag gagccgccct cttacgagga   15660
ggcagtcaag gccggcctgc ccaccactcg ccccatagcc cccatggcca ccggtgtggt   15720
gggccacagg caacacactc ccgcaacact agatctgccc ccgccgtccg agccgccgcg   15780
ccagccaaag gcggcgacgg tgccgctcc ctccacttcc gccgccaaca gagtgcccct   15840
gcgccgcgcc gcgagcggcc cccggggcct gcgagttagc ggcaactggc agagcacact   15900
gaacagcatc gtgggcctgg gagtgaggag tgtgaagcgc cgccgttgct actgaatgag   15960
caagctagct aacgtgttgt atgtgtgtat gcgtcctatg tcgccgccag aggagctgtt   16020
gagccgccgc cgccgtctgc actccagcga atttcaagat ggcgacccca tcgatgatgc   16080
ctcagtggtc gtacatgcac atctcgggcc aggacgcttc ggagtacctg agccccgggc   16140
```

```
tggtgcagtt cgcccgcgcc acagacacct acttcaacat gagtaacaag ttcaggaacc   16200
ccactgtggc gcccacccac gatgtgacca cggaccggtc gcagcgcctg acgctgcggt   16260
tcatccccgt ggatcgggag gacaccgcct actcttacaa ggcgcggttc acgctggccg   16320
tgggcgacaa ccgcgtgctg gacatggcct ccacttactt tgacatcagg ggggtgctgg   16380
acagggcccc caccttcaag ccctactcgg gtactgccta caactccctg gcccccaagg   16440
gcgctcccaa ttcttgcgag tgggaacaag aggaaaatca ggtggtcgct gcagatgatg   16500
aacttgaaga tgaagaagcg caagctcaag aggacgcccc agctaaaaaa attcatgtat   16560
atgcccaggc gcctcttgct ggcgaaaaga ttaccaagga tggtttgcaa ataggtactg   16620
aagttgtagg agatacatct aaggacactt ttgcagacaa acattccaa cccgaacctc    16680
agataggcga gtctcagtgg aacgaggctg atgccacagt agcaggaggc agagtcttga   16740
aaaaaccac ccctatgaga ccttgctatg gatcctatgc caggcctaca aatgccaacg    16800
ggggtcaagg aattatggtt gccaatgaac aaggagtgtt ggagtctaaa gtggagatgc   16860
aatttttttc taacactaca acccttaatg cgcgggatgg agctggcaat cccgaaccaa   16920
aggtggtgtt gtacagtgaa gatgtccact tggaatctcc tgacactcat ttgtcttaca   16980
agcccaaaaa ggatgatgtt aatgctaaaa ttatgttggg tcagcaagct atggctaaca   17040
ggcccaacct cattgctttt agagataatt tcattggact catgtactac aacagcactg   17100
gtaacatggg agtgctggcg ggtcaggcct ctcagttgaa tgccgtggtg gacctgcagg   17160
atagaaacac agaactgtca tatcagctta tgcttgattc cattggggat agatccagat   17220
acttctccat gtggaaccag gcagtggata gctatgaccc agatgtcaga atcattgaaa   17280
accatggtgt cgaggacgag ctacccaact actgcttccc tctgggcggc ataggaatta   17340
ctgatactta tcaagggatc aaaaatacca atggcaatgg tcagtggacc aaagatgatc   17400
agttcgcgga ccgtaatgaa ataggggtgg gaaacaactt cgccatggag atcaacatcc   17460
aggccaacct ctggaggaac ttcctctatg cgaacgtggg gctctacctg ccagacaagc   17520
tcaagtacaa ccccaccaac gtggacatct ctgacaaccc caacacctat gactacatga   17580
acaagcgtgt ggtggctccc ggcctggtgg actgctttgt caatgtggga gccaggtggt   17640
ccctggacta catggacaac gtcaaccccc tcaaccacca ccgcaatgcg ggtctgcgct   17700
accgctccat gatcctgggc aacgggcgct acgtgccctt ccacattcag gtgccccaga   17760
agttctttgc catcaagaac ctcctcctcc tgccgggctc ctacacttac gagtggaact   17820
tcaggaagga tgtcaacatg gtcctgcaga gctctctggg caatgacctt agggtggacg   17880
gggccagcat caagtttgac agcgtcaccc tctatgctac cttcttcccc atggctcaca   17940
acaccgcctc cacgctcgag gccatgctga ggaacgacac caacgaccag tccttcaatg   18000
actacctctc tgggccaac atgctctacc ccatccccgc caaggccacc aacgtgccca   18060
tctccattcc ctctcgcaac tgggcgcct cagaggctg gcctttacc cgccttaaga     18120
ccaaggaaac cccctccctg ggctcgggtt ttgacccta ctttgtctac tcgggatcca    18180
tccccctacct ggatggcacc ttctacctca accacacttt taagaagata tccatcatgt   18240
atgactcctc cgtcagctgg ccgggcaatg accgcctgct cacccccaat gagttcgagg   18300
tcaagcgcgc cgtggacggc gagggctaca acgtggccca gtgcaacatg accaaggact   18360
ggttcctggt gcagatgctg gccaactaca acataggcta ccagggcttc tacatcccag   18420
agagctacaa ggacaggatg tactccttct tcagaaattt ccaacccatg agcaggcagg   18480
```

```
tggtggacga gaccaaatac aaggactatc aggccattgg catcactcac cagcacaaca   18540
actcgggatt cgtgggctac ctggctccca ccatgcgcga ggggcaggcc taccccgcca   18600
acttccccta cccgttgata ggcaagaccg cggtcgacag cgtcacccag aaaaagttcc   18660
tctgcgaccg caccctctgg cgcatcccct tctctagcaa cttcatgtcc atgggtgcgc   18720
tcacggacct gggccagaac ctgctctatg ccaactccgc ccatgcgctg acatgactt    18780
ttgaggtgga ccccatggac gagcccaccc ttctctatat tgtgtttgaa gtgttcgacg   18840
tggtcagagt gcaccagccg caccgcggtg tcatcgagac cgtgtacctg cgcacgccct   18900
tctcggccgg caacgccacc acctaaggag acagcgccgc cgcctgcatg acgggttcca   18960
ccgagcaaga gctcagggcc atcgccagag acctgggatg cggaccctat tttttgggca   19020
cctatgacaa acgcttcccg ggcttcatct cccgagacaa gctcgcctgc gccatcgtca   19080
acacggccgc gcgcgagacc gggggcgtgc actggctggc ctttggctgg gacccgcgct   19140
ccaaaacctg ctacctcttc gacccctttg gcttctccga tcagcgcctc agacagatct   19200
atgagtttga gtacgagggg ctgctgcgcc gcagcgcgct tgcctcctcg cccgaccgct   19260
gcatcaccct tgagaagtcc accgagaccg tgcaggggcc ccactcggcc gcctgcggtc   19320
tcttctgctg catgttttg cacgcctttg tgcgctggcc ccagagtccc atggatcgca   19380
accccaccat gaacttgctc aagggagtgc caacgccat gctccagagc ccccaggtcc    19440
agcccaccct gcgccacaac caggaacagc tctaccgctt cctggagcgc cactccccct   19500
acttccgcag tcacagcgcg cacatccggg gggccacctc tttctgccac ttgcaacaaa   19560
acatgcaaga cggaaaatga tgtacagctc gcttttttaat aaatgtaaag actgtgcact   19620
ttatttatac acgggctctt tctggttatt tattcaacac cgccgtcgcc atctagaaat   19680
cgaaagggtt ctgccgcgcg tcgccgtgcg ccacgggcag agacacgttg cgatactgga   19740
agcggctcgc ccacttgaac tcgggcacca ccatgcgggg cagtggctcc tcggggaagt   19800
tctcgcccca caggtgcgg gtcagctgca gcgcgctcag gaggtcggga gccgagatct    19860
tgaagtcgca gttggggccg gaaccctgcg cgcgcgagtt gcggtacacg gggttgcagc   19920
actggaacac cagcagggcc ggattacgca cgctggccag caggctctcg tcgctgatca   19980
tgtcgctgtc cagatcctcc gcgttgctca gggcgaatgg ggtcatcttg cagacctgcc   20040
tgcccaggaa aggcggcagc ccgggcttgc cgttgcagtc gcagcgcagg ggcatcagca   20100
ggtgcccgtg gcccgtctgc gcctgcgggt acagcgcgcg catgaaggct tcgatctgcc   20160
tgaaagccac ctgcgtcttg gctccctccg aaaagaacat cccacaggac ttgctggaga   20220
actggttcgc gggacagctg gcatcgtgca ggcagcagcg cgcgtcggtg ttggcgatct   20280
gcaccacgtt gcgaccccac cggttcttca ctatcttggc cttggaagcc tgctccttca   20340
gcgcgcgctg gccgttctcg ctggtcacat ccatctctat cacctgctcc ttgttgatca   20400
tgtttgtccc gtgcagacac ttcaggtcgc cctccgtctg ggtgcagcgg tgctcccaca   20460
gcgcgcaacc ggtgggctcc caattttgt gggtcacccc cgcgtaggcc tgcaggtagg   20520
cctgcaagaa gcgcccatc atggccacaa aggtcttctg gctcgtaaag gtcagctgca   20580
ggccgcgatg ctcttcgttc agccaggtct tgcagatggc ggccagcgcc tcggtctgct   20640
cgggcagcat cctaaaattt gtcttcaggt cgttatccac gtggtacttg tccatcatgg   20700
cgcgcgccgc ctccatgccc ttctcccagg cggacaccat gggcaggctt aggggggttta   20760
tcacttccac cggcgaggac accgtacttt cgatttcttc ttcctccccc tcttcccggc   20820
gcgcgcccac gctgctgcgc gctctcaccg cctgcaccaa ggggtcgtct tcaggcaagc   20880
```

```
gccgcaccga gcgcttgccg cccttgacct gcttaatcag caccggcggg ttgctgaagc   20940
ccaccatggt cagctccgcc tgctcttctt cgtcttcgct gtctaccact atctctgggg   21000
aagggcttct ccgctctgcg gcggtgcgct tcttttttt cttgggagca gccgtgacgg    21060
agtccgccac ggcgacggag gtcgagggcg tggggctggg ggtgcgcggt accagggcct   21120
cgtcgccctc ggactcttcc tctgactcca ggcggcggcg gagacgcttc tttggggcg   21180 cgcgcgtcag cggcggcgga gacggggacg ggacgggga cggacgccc tccacagggg     21240 gtggtcttcg cgcagacccg cggccgcgct cggggtcttt tcgagctgg tcttggtccc    21300 gactggccat tgtatcctcc tcctcctagg cagagagaca taaggagtct atcatgcaag   21360
tcgagaagga ggagagctta accacccct ctgagaccgc cgatgcgccc gccgtcgccg    21420
tcgcccccgc tgccgccgac gcgcccgcca caccgagcga caccccgcg acccccag     21480 ccgacgcacc cctgttcgag aagcggccg tgagcagga cccgggcttt gtctcggcag    21540
aggaggattt gcgagaggag gaggataagg agaagaagcc ctcagtgcca aaagatgata   21600
aagagcaaga cgagcacgac gcagatgcac accaggtgaa gtcgggcgg ggggacggag    21660 ggcatgacgg cgccgactac ctagacgaag ggaacgacgt gctcttgaag cacctgcatc   21720
gtcagtgcgc catcgtttgc gacgctctgc aggagcgcag cgaagtgccc ctcagcgtgg   21780
cggaggtcag ccacgcctac gagctcagcc tcttctcccc ccgggtgccc ccgccgcc     21840 gcgaaaacgg cacatgcgag cccaacccgc gcctcaactt ctaccccgcc tttgtggtgc   21900
ccgaggtcct ggccacctat cacatcttct ttcaaaattg caagatcccc ctctcgtgcc   21960
gcgccaaccg tagccgcgcc gataagatgc tggccctgcg ccagggcgac cacatacctg   22020
atatcgccgc tttggaagat gtgccaaaga tcttcgaggg tctgggtcgc aacgagaagc   22080
gggcagcaaa ctctctgcaa caggaaaaca gcgaaaatga gagtcacacc ggggtactgg   22140
tggagctcga gggcgacaac gcccgcctgg cggtggtcaa gcgcagcatc gaggtcaccc   22200
actttgccta ccccgcgctc aacctgcccc ccaaagtcat gaacgcggcc atggacgggc   22260
tgatcatgcg ccgcggccgg cccctcgctc cagatgcaaa cttgcatgag gagaccgagg   22320
acggccagcc cgtggtcagc gacgagcagc tggcgcgctg gctggagacc gcggaccccg   22380
ccgaactgga ggagcggcgc aagatgatga tggccgcggt gctggtcacc gtagagctgg   22440
agtgtctgca gcgcttcttc ggcgacccg agatgcagaa aaaggtcgag gagaccctgc   22500
actacacctt ccgccagggc tacgtgcgcc aggcttgcaa gatctccaac gtggagctca   22560
gcaacctggt gtcctacctg gcatcttgc atgagaaccg cctcgggcag agcgtgctgc    22620
actccaccct gcgcggggag gcgcgccgcg actacgtgcg cgactgcgtt tacctcttcc   22680
tctgctacac ctggcagacg gccatggggg tctggcagca gtgcctggag gagcgcaacc   22740
tcaaggagct ggagaagctc ctgcagcgcg cgctcaaaga cctctggacg ggctacaacg   22800
agcgctcggt ggccgccgcg ctggccgacc tcatcttccc cgagcgcctg ctcaaacccc   22860
tccagcaggg gctgcccgac ttcaccagcc aaagcatgtt gcaaaacttc aggaacttta   22920
tcctggagcg ttctggcatc ctacccgcca cctgctgcgc cctgcccagc gactttgtcc   22980
ccctcgtgta ccgcgagtgc ccccgccgc tgtggggtca ctgctacctg ttccaactgg    23040
ccaactacct gtcctaccac gcggacctca tggaggactc cagcggcgag gggctcatgg   23100
agtgccactg ccgctgcaac ctctgcacgc ccaccgctc cctggtctgc aacacccaac    23160
tgctcagcga gagtcagatt atcggtacct tcgagctaca gggtccgtcc tcctcagacg   23220
```

| | |
|---|---|
| agaagtccgc ggctccgggg ctaaaactca ctccggggct gtggacttcc gcctacctgc | 23280 |
| gcaaatttgt acctgaagac taccacgccc acgagatcag gttttacgaa gaccaatccc | 23340 |
| gcccgcccaa ggcggagctg accgcctgcg tcatcaccca gggcgagatc ctaggccaat | 23400 |
| tgcaagccat ccaaaaagcc cgccaagatt ttttgctgag aaagggtcgg ggggtgtatc | 23460 |
| tggaccccca gtcgggtgag gagctcaacc cggttccccc gctgccgccg ccgcgggacc | 23520 |
| ttgcttccca ggataagcat cgccatggct cccagaaaga agcagcagcg gccgccactg | 23580 |
| ccgccacccc acatgctgga ggaagaggag gaatactggg acagtcaggc agaggaggtt | 23640 |
| tcggacgagg aggagccgga gacggagatg gaagagtggg aggaggacag cttagacgag | 23700 |
| gaggcttccg aagccgaaga ggcagacgca acaccgtcac cctcggccgc agcccctcg | 23760 |
| caggcgcccc cgaagtccgc tcccagcatc agcagcaaca gcagcgctat aacctccgct | 23820 |
| cctccaccgc cgcgacccac ggccgaccgc agacccaacc gtagatggga caccaccgga | 23880 |
| accggggccg gtaagtcctc cgggagaggc aagcaagcgc agcgccaagg ctaccgctcg | 23940 |
| tggcgcgctc acaagaacgc catagtcgct tgcttgcaag actgcggggg gaacatctcc | 24000 |
| ttcgcccgcc gcttcctgct cttccaccac ggtgtggcct ccccccgtaa cgtcctgcat | 24060 |
| tactaccgtc atctctacag cccctactgc ggcggcagtg agccagagac ggtcggcggc | 24120 |
| ggcggcggcg cccgtttcgg cgcctaggaa gacccagggc aagacttcag ccaagaaact | 24180 |
| cgcggcggcc gcggcgaacg cggtcgcggg ggccctgcgc ctgacggtga acgaaccccc | 24240 |
| gtcgacccgc gaactgagaa accgaatctt ccccactctc tatgccatct ccagcagag | 24300 |
| cagagggcag gatcaggaac tgaaagtaaa aaacaggtct ctgcgctccc tcacccgcag | 24360 |
| ctgtctgtat cacaagagcg aagaccagct tcggcgcacg ctggaggacg ctgaggcact | 24420 |
| cttcagcaaa tactgcgcgc tcactcttaa ggactagctc cgcgcccttc tcgaatttag | 24480 |
| gcgggaacgc ctacgtcatc gcagcgccgc cgtcatgagc aaggacattc ccacgccata | 24540 |
| catgtggagc tatcagccgc agatgggact cgcggcgggc gcctcccaag actactccac | 24600 |
| ccgcatgaac tggctcagtg ccggcccaca catgatctca caggttaatg atatccgcac | 24660 |
| ccatcgaaac caaatattgg tggagcaggc ggcaattacc accacgcccc gcaataatcc | 24720 |
| caaccccagg gagtggcccg cgtccctggt gtatcaggaa attcccggcc ccaccaccgt | 24780 |
| actacttccg cgtgattccc aggccgaagt ccaaatgact aactcagggg cgcagctcgc | 24840 |
| gggcggctgt cgtcacaggg tgcggcctcc tcgccagggt ataactcacc tggagatccg | 24900 |
| aggcagaggt attcagctca cgacgagtc ggtgagctcc tcgctcggtc taagacctga | 24960 |
| cgggaccttc cagatagccg gagccggccg atcttccttc acgcccgcc aggcgtacct | 25020 |
| gactctgcag agctcgtcct cggcgccgcg ctcgggcggc atcgggactc tccagttcgt | 25080 |
| gcaggagttt gtgccctcgg tctacttcaa ccccttctcg gctctcccg gtcgctaccc | 25140 |
| ggaccagttc atctcgaact ttgacgccgc gagggactcg gtggacggct acgactgaat | 25200 |
| gtcgggtgga cccggtgcag agcaacttcg cctgaagcac ctcgaccact gccgccgccc | 25260 |
| tcagtgcttt gcccgctgtc agaccggtga gttccagtac ttttccctgc ccgactcgca | 25320 |
| cccgacggc ccggcgcacg gggtgcgctt tttcatcccg agtcaggtgc gctctaccct | 25380 |
| aatcagggag tttaccgccc gtcccctact ggcggagttg gaaaaggggc cttctatcct | 25440 |
| aaccattgcc tgcatctgct ctaaccctgg attgcaccaa gatctttgct gtcatttgtg | 25500 |
| tgctgagtat aataaaggct gagatcagaa tctactcggg ctcctgtcgc catcctgtca | 25560 |
| acgccaccgt ccaagcccgg cccgatcagc ccgaggtgaa cctcacctgc ggtctgcacc | 25620 |

```
ggcgcctgag gaaataccta gcttggtact acaacagcac tcccttttgtg gtttacaaca    25680
gctttgacca ggacggggtc tcactgaggg ataacctctc gaacctgagc tactccatca    25740
ggaagaacag cacctcgag ctacttcctc cttacctgcc cgggacttac cagtgtgtca     25800
ccggtccctg cacccacacc cacctgttga tcgtaaacga ctctcttccg agaacagacc    25860
tcaataactc ctcttcgcag ttccccagaa caggaggtga gctcaggaaa ccccgggtaa    25920
agaagggtgg acaagagtta acacttgtgg ggtttctggt gtatgtgacg ctggtggtgg    25980
ctcttttgat taaggctttt ccttccatgt ctgaactctc cctcttttat gaacaactcg    26040
actagtgcta acgggaccct acccaacgaa tcgggattga atatcggtaa ccaggttgca    26100
gtttcacttt tgattacctt catagtcctc ttcctgctag tgctgtcgct tctgtgcctg    26160
cggatcgggg gctgctgcat ccacgtttat atctggtgct ggctgtttag aaggttcgga    26220
gaccatcgca ggtagaataa acatgctgct gcttaccctc tttgtcctgg cgctggccgc    26280
cagctgccaa gccttttccg aggctgactt tatagagccc cagtgtaacg tgacttttaa    26340
agcccatgca cagcgttgtc atactataat caaatgtgcc accgaacacg atgaatacct    26400
tatccagtat aaagataaat cacacaaagt ggcacttgtt gacatctgga aacccgaaga    26460
cccctttggaa tacaatgtga ccgttttcca gggtgacctc ttcaaaattt acaattacac    26520
tttcccattt gaccagatgt gtgactttgt catgtacatg gaaaagcagc acaagctgtg    26580
gcctccgact ccccagggct gtgtggaaaa tccaggctct ttctgcatga tctctctctg    26640
tgtaactgtg ctggcactaa tactcacgct tttgtatatc agatttaaat caaggcaaag    26700
cttcatcgat gaaaagaaaa tgccttaaac gctttcacgc ttgattgcta acaccgggtt    26760
tttatccgca gaatgattgg aatcacccta ctaatcacct ccctccttgc gattgcccat    26820
gggttggaac gaatcgaagc ccctgtgggg gccaatgtta ccctggtggg gcctgtcggc    26880
aatgctacat taatgtggga aaaatatact aaaaatcaat gggtctctta ctgcactaac    26940
aaaaacagcc acaagcccag agccatctgc gatgggcaaa atctaaccttt gattgatgtt    27000
caaatgctgg atgcgggcta ctattatggg cagctgggta caatgattaa ttactggaga    27060
ccccacaaag attacatgct ccacgtagta aagggtcccc ttagcagccc acccactacc    27120
acctctacta ccccccactac caccactact cccaccacca gcactgccgc ccagcctcct    27180
catagcagaa caaccacttt tatcaattcc aagtcccact cccccacat tgccggcggg    27240
ccctccgcct cagactccga gaccaccgag atctgcttct gcaaatgctc tgacgccttt    27300
gctgaggatt tggaagacca cgaggaagat gagcatgact tcgcagatgc atgccaggca    27360
tcagaggcag aagcgctgcc ggtggccctc aaacagtatg cagaccccca caccacccc    27420
aaccttcctc caccttccca gaagccaagt ttcctggggg aaaatgaaac tctgcctctc    27480
tccatactcg ctctgacatc tgttgctatg ttgaccgctc tgctggtgct tctatgctct    27540
atatgctacc tgatctgctg cagaaagaaa aaatctcacg gccatgctca ccagcccctc    27600
atgcacttcc cttaccctcc agagctgggc gaccacaaac tttaagtctg cagtaactat    27660
ctgcccatcc cttgtcagtc gacagcgatg agccccacta atctaacggc ctctggactt    27720
acaacatcgt ctcttaatga gaccaccgct cctcaagacc tgtacgatgg tgtctccgcg    27780
ctggttaacc agtgggatca cctgggcata tggtggctcc tcataggagc agtgaccctg    27840
tgcctaatcc tggtctggat catctgctgc atcaaaagca gaagacccag gcggcggccc    27900
atctacaggc cctttgtcat cacacctgaa gatgatgatg acaccacttc caggctgcag    27960
```

-continued

```
aggctaaagc agctactctt ctcttttaca gcatggtaaa ttgaatcatg cctcgcattt  28020
tcatctactt gtctctcctt ccacttttc tgggctcttc tacattggcc gctgtgtccc   28080
acatcgaggt agactgcctc acgcccttca cagtctacct gcttttcggc tttgtcatct  28140
gcacctttgt ctgcagcgtt atcactgtag tgatctgctt catacagtgc atcgactacg  28200
tctgcgtgcg ggtggcttac tttagacacc accccagta tcgcaacagg acatagcgg    28260
ctctcctaag acttgtttaa aatcatggcc aaattaactg tgattggtct tctgatcatc   28320
tgctgcgtcc tagccgcgat tgggactcaa gctcctacca ccaccagcgc tcccagaaag   28380
agacatgtat cctgcagctt caagcgtccc tggaatatac cccaatgctt tactgatgaa   28440
cctgaaatct ctttggcttg gtacttcagc gtcaccgccc ttcttatctt ctgcagtacg   28500
gttattgccc ttgccatcta cccttcccctt gacctgggct ggaatgctgt caactctatg   28560
gaatatccca ccttcccaga accagacctg ccagacctgg ttgttctaaa cgcgtttcct   28620
cctcctgctc ccgttcaaaa tcagtttcgc cctccgtccc ccacgcccac tgaggtcagc   28680
tactttaatc taacaggcgg agatgactga aaacctagac ctagaaatgg acggtctctg   28740
cagcgagcaa cgcacactag agaggcgccg gcaaaaagag ctcgagcgtc ttaaacaaga   28800
gctccaagac gcggtggcca tacaccagtg caaaaaaggt gtcttctgtc tggtaaaaca   28860
ggccacgctc acctatgaaa aaacaggtga cacccaccgc ctaggataca agctgcccac   28920
acagcgccaa aagttcgccc tcatgatagg cgaacaaccc atcaccgtga cccagcactc   28980
cgtggagaca gaaggctgca tacacgctcc ctgtaggggc gctgactgcc tctacacctt   29040
gatcaaaacc ctctgcggtc tcagagacct catcccttt aattaatcat aactgtaatc   29100
aataaaaaat cacttacttg aaatctgata gcaagcctct gtccaatttt ttcagcaaca   29160
cttccttccc ctcctcccaa ctctggtact ctaggcgcct cctagctgca aacttcctcc   29220
acagtctgaa gggaatgtca gattcctcct cctgtccctc cgcacccacg atcttcatgt   29280
tgttgcagat gaaacgcgcg agatcgtctg acgagacctt caacccgtg tacccctacg    29340
ataccgagat cgctccgact tctgtccctt tccttaccc tccctttgtg tcatccgcag   29400
gaatgcaaga aaatccagct ggggtgctgt ccctgcactt gtcagagccc cttaccaccc   29460
acaatggggc cctgactcta aaaatggggg gcggcctgac cctggacaag gaagggaatc   29520
tcacttccca aaacatcacc agtgtcgatc ccctctcaa aaaagcaag aacaacatca    29580
gccttcagac cgccgcaccc ctcgccgtca gctccggggc cctaacactt tttgccactc   29640
ccccctagc ggtcagtggt gacaaccta ctgtgcagtc tcaggcccct ctcactttgg    29700
aagactcaaa actaactctg gccaccaaag gacccctaac tgtgtccgaa ggcaaacttg   29760
tcctagaaac agaggctccc ctgcatgcaa gtgacagcag cagcctgggc cttagcgtta   29820
cggcccccact tagcattaac aatgacagcc taggactaga catgcaagcg cccattagct   29880
ctcgagatgg aaaactggct ctaacagtgg cggcccccct aactgtggtc gagggtatca   29940
atgctttggc agtagccaca ggtaagggta ttgggctaaa tgaaaccaac acacacctgc   30000
aggcaaaact ggtcgcaccc ctaggctttg ataccaacgg caacattaag ctaagcgttg   30060
caggaggcat gaggctaaac aataacacac tgatactaga tgtaaactac ccatttgagg   30120
ctcaaggcca actgagccta agagtgggct cgggcccact atatgtagat tctagtagtc   30180
ataacctaac cattagatgc cttaggggat tgtatataac atcttctaac aaccaaaacg   30240
gtctagaagc caacattaaa ctaacaagag gccttgtgta tgacgaaat gccatagcag   30300
ttaatgttgg caaagggctg gaatacagcc ctactgacac aacagaaaaa cctatacaga   30360
```

```
ctaaaatagg tctaggcatg gagtatgata ccgagggagc catgatgaca aaactaggct   30420
ctggactaag ctttgacaat tcaggagcca ttgtagtggg aaacaaaaat gatgacaggc   30480
ttactttgtg gaccacaccg gacccatcgc ccaactgtca gatctactct gaaaaagatg   30540
ctaaactaac cttggtactg actaaatgtg gcagtcaggt tgtaggcaca gtatctattg   30600
ccgctcttaa aggtagcctc gtgccaatca ctagtgcaat cagtgtggtt caggtatacc   30660
taaggtttga tgaaaatggg gtactaatga gtaactcttc acttaatggc gaatactgga   30720
attttagaaa cggagactca actaatggca caccatatac aaacgcagtg ggtttcatgc   30780
ctaatctact ggcctatcct aaaggtcaaa ctacaactgc aaaaagtaac attgtcagcc   30840
aggtctacat gaatggggac gatactaaac ccatgacatt tacaatcaac ttcaatggcc   30900
ttagtgaaac aggggatacc cctgttagta aatattccat gacattctca tggaggtggc   30960
caaatggaag ctacataggg cacaattttg taacaaactc ctttaccttc tcctacatcg   31020
cccaagaata aagaaagcac agagatgctt gttttttgatt tcaaaattgt gtgcttttat   31080
ttattttcag cttacagtat ttccagtagt cattcaaata aagcttaatc aaactgcatg   31140
agaaccttc cacatagctt aaattagcac cagtgcaaat ggagaaaaca attgacggcc   31200
gggatcggtg atcaccgatc cagacatgat aagatacatt gatgagtttg acaaaccac   31260
aactagaatg cagtgaaaaa aatgctttat ttgtgaaatt tgtgatgcta ttgctttatt   31320
tgtaaccatt ataagctgca ataaacaagt tcccggatcg cgatccggcc cgaggctgta   31380
gccgacgatg gtgcgccagg agagttgttg attcattgtt tgcctccctg ctgcggtttt   31440
tcaccgaagt tcatgccagt ccagcgtttt tgcagcagaa aagccgccga cttcggtttg   31500
cggtcgcgag tgaagatccc tttcttgtta ccgccaacgc gcaatatgcc ttgcgaggtc   31560
gcaaaatcgg cgaaattcca tacctgttca ccgacgacgg cgctgacgcg atcaaagacg   31620
cggtgataca tatccagcca tgcacactga tactcttcac tccacatgtc ggtgtacatt   31680
gagtgcagcc cggctaacgt atccacgccg tattcggtga tgataatcgg ctgatgcagt   31740
ttctcctgcc aggccagaag ttctttttcc agtaccttct ctgccgtttc caaatcgccg   31800
ctttggacat accatccgta ataacggttc aggcacagca catcaaagag atcgctgatg   31860
gtatcggtgt gagcgtcgca gaacattaca ttgacgcagg tgatcggacg cgtcgggtcg   31920
agtttacgcg ttgcttccgc cagtggcgcg aaatattccc gtgcaccttg cggacgggta   31980
tccggttcgt tggcaatact ccacatcacc acgcttgggt ggttttttgtc acgcgctatc   32040
agctctttaa tcgcctgtaa gtgcgcttgc tgagtttccc cgttgactgc ctcttcgctg   32100
tacagttctt tcggcttgtt gcccgcttcg aaaccaatgc ctaaagagag gttaaagccg   32160
acagcagcag tttcatcaat caccacgatg ccatgttcat ctgcccagtc gagcatctct   32220
tcagcgtaag ggtaatgcga ggtacggtag gagttggccc caatccagtc cattaatgcg   32280
tggtcgtgca ccatcagcac gttatcgaat cctttgccac gcaagtccgc atcttcatga   32340
cgaccaaagc cagtaaagta gaacggtttg tggttaatca ggaactgttc gcccttcact   32400
gccactgacc ggatgccgac gcgaagcggg tagatatcac actctgtctg gcttttggct   32460
gtgacgcaca gttcatagag ataaccttca cccggttgcc agaggtgcgg attcaccact   32520
tgcaaagtcc cgctagtgcc ttgtccagtt gcaaccacct gttgatccgc atcacgcagt   32580
tcaacgctga catcaccatt ggccaccacc tgccagtcaa cagacgcgtg gttacagtct   32640
tgcgcgacat gcgtcaccac ggtgatatcg tccacccagg tgttcggcgt ggtgtagagc   32700
```

```
attacgctgc gatggattcc ggcatagtta aagaaatcat ggaagtaaga ctgcttttc    32760
ttgccgtttt cgtcggtaat caccattccc ggcgggatag tctgccagtt cagttcgttg   32820
ttcacacaaa cggtgatacg tacacttttc ccggcaataa catacggcgt gacatcggct   32880
tcaaatggcg tatagccgcc ctgatgctcc atcacttcct gattattgac ccacactttg   32940
ccgtaatgag tgaccgcatc gaaacgcagc acgatacgct ggcctgccca acctttcggt   33000
ataaagactt cgcgctgata ccagacgttg cccgcataat tacgaatatc tgcatcggcg   33060
aactgatcgt taaaactgcc tggcacagca attgcccggc tttcttgtaa cgcgctttcc   33120
caccaacgct gatcaattcc acagttttcg cgatccagac tgaatgccca caggccgtcg   33180
agttttttga tttcacgggt tggggtttct acaggacgga ccatgcgttc gacctttctc   33240
ttcttttttg ggcccatgat ggcagatccg tatagtgagt cgtattagct ggttctttcc   33300
gcctcagaag ccatagagcc caccgcatcc ccagcatgcc tgctattgtc ttcccaatcc   33360
tccccttgc tgtcctgccc caccccaccc cccagaatag aatgacacct actcagacaa   33420
tgcgatgcaa tttcctcatt ttattaggaa aggacagtgg gagtggcacc ttccaggtc    33480
aaggaaggca cggggagggg gcaaacaaca gatggctggc aactagaagg cacagtcgag   33540
gctgatcagc gagctctaga tgcatgctcg agcggccgcc agtgtgatgg atatctgcag   33600
aattccagca cactggcggc cgttactagt ggatccgagc tcggtaccaa cgcgtcgtaa   33660
ctataacggt cctaaggtag cgaaaagcac tctcacagca ccagcactaa tcagagtgtg   33720
aagagggcca agtgccgaac gagtatatat aggaataaaa aatgacgtaa atgtgtaaag   33780
gtcagaaaac gccagaaaaa atacacagac caacgcccga aacgaaaacc cgcgaaaaaa   33840
tacccagaac ttcctcaaca accgccactt ccgctttctc acggtacgtc acttccgcaa   33900
gaaaagcaaa actacatttc ccacatgtgt aaaaacgaaa ccccgcccct tgtaaccgcc   33960
cacaacttac atcatcaaaa cgtaaactcc tacgtcaccc gccccgcctc tccccgccca   34020
cctcattatc atattggcca caatccaaaa taaggtatat tattgatgat g            34071
```

<210> SEQ ID NO 27
<211> LENGTH: 33489
<212> TYPE: DNA
<213> ORGANISM: Gorilla beringei graueri

<400> SEQUENCE: 27

```
catcatcaat aatataccct attttggatt gtggccaata tgataatgag gtgggcgggg    60
agaggcgggg cgggtgacgt aggacgcgcg agtagggttg ggaggtgtgg cggaagtgtg   120
gcatttgcaa gtgggaggag ctcacatgca agcttccgtc gcggaaaatg tgacgttttt   180
gatgagcgcc gcctacctcc ggaagtgcca atttttcgcgc gcttttcacc ggatatcgta   240
gtaattttgg gcgggaccat gtaagatttg gccattttcg cgcgaaaagt gaaacgggga   300
agtgaaaact gaataatagg gcgttagtca tagtgcgtaa tatttaccga gggccgaggg   360
actttgaccg attacgtgga ggactcgccc aggtgttttt tacgtgaatt tccgcgttcc   420
gggtcaaagt ctccgttttta ttgtcaccgt catttgacgc ttaggcctga ccatctggtg   480
ctggcctgca ccagggccga gtttgggtct agcgatgagg ataccgattg aggtgggtaa   540
ggtgggcgtg gctagaaggg tggggcgtgt ataaattggg ggtctaaggg tctctctgtt   600
ttgtcttgca acagccgccg ccatgagcga caccggcaac agcttgatgg aagcatctt    660
tagcccctat ctgacagtgc gcatgcctca ctgggctgga gtgcgtcaga atgtgatggg   720
ttccaacgtg gatggacgcc ccgttctgcc ttcaaattcg tctacaatgg cctacgcgac   780
```

```
cgtgggagga actccgctgg acgccgcgac ctccgccgcc gcctccgccg ccgccgcgac    840
cgcgcgcagc atggctacgg acctttacag ctctttggtg gcgagcggcg cggcctctcg    900
cgcgtctgct cgggatgaga aactgaccgc tctgctgctt aaactggaag acttgacccg    960
ggagctggct caactgaccc agcaggtctc cagcttgcgt gagagcagcc ttgcctcccc   1020
ctaatggccc ataatataaa taaaagccag tctgtttgga ttaagcaagt gtatgttctt   1080
tatttaactc tccgcgcgcg gtaagccgg gaccagcggt ctcggtcgtt tagggtgcgg    1140
tggattcttt ccaacacgtg gtacaggtgg ctctggatgt ttagatacat gggcatgagt   1200
ccatccctgg ggtggaggta gcaccactgc agagcttcgt gctcggggt ggtgttgtat    1260 atgatccagt cgtagcagga gcgctgggcg tggtgctgaa aaatgtcctt aagcaagagg   1320
cttatagcta gggggaggcc cttggtgtaa gtgtttacaa atctgctcag ttgggagggg   1380
tgcatccggg gggatataat gtgcatcttg gactggattt ttaggttggc tatgttccca   1440
cccagatccc ttctgggatt catgttgtgc aggaccacca gcacggtata tccagtacac   1500
ttgggaaatt tatcgtggag cttagacggg aatgcatgga agaacttgga gacgcccttg   1560
tggcctccca gattttccat acattcgtcc atgatgatgg caatgggccc gtgggaagct   1620
gcctgagcaa aaatgtttct gggatcgctc acatcgtagt tatgttccag ggtgaggtca   1680
tcataggaca tctttacaaa tcggggcgg agggtcccgg actggggat gatggtgccc    1740 tcgggccccg gggcgtagtt cccctcacag atctgcatct cccaggcttt catttcagag   1800
ggagggatca tatccacctg cggagcgatg aaaaacacag tttctggcgc agggagatt    1860 aactgggatg agagcaggtt tctgagcagc tgtgactttc cacagccggt gggcccatat   1920
atcacgccta tcaccggctg cagctggtag ttaagagagc tgcagctgcc gtcctcccgg   1980
agcagggggg ccacctcgtt cagcatatcc ctgacgtgga tgttctccct gaccaattcc   2040
gccagaaggc gctcgccgcc cagcgaaagc agctcttgca aggaagcaaa attttttcagc  2100 ggttttaggc cgtcggccgt gggcatgttt ttcagcgtct gggtcagcag ttccagtctg   2160
tcccacagct cggtgatgtg ctctacggca tctcgatcca gcagatctcc tcgtttcgcg   2220
ggttggggcg gctttcgctg tagggcacca gccgatgggc gtccagcggg gccagagtca   2280
tgtccttcca tggcgcagg gtcctcgtca gggtggtctg ggtcacggtg aaggggtgcg    2340 ctccggggttg ggcgctggcc agggtgcgct tgaggctggt tctgctggtg ctgaatcgct   2400
gccgctcttc gccctgcgcg tcggccaggt agcatttgac catggtctcg tagtcgagac   2460
cctcggcggc gtgccccttg gcgcggagct ttcccttgga ggtggcgccg cacgaggggc   2520
actgcaggct cttcagggcg tagagcttgg gagcgagaaa cacggactct ggggagtagg   2580
cgtccgcgcc gcaggaagcg cagaccgtct cgcattccac cagccaagtg agctccgggc   2640
ggtcagggtc aaaaaccagg ttgcccccat gctttttgat gcgtttctta cctcggctct   2700
ccatgaggcg gtgtcccttc tcggtgacga agaggctgtc cgtgtctccg tagaccgact   2760 tcagggcct gtcttccagc ggagtgcctc tgtcctcctc gtagagaaac tctgaccact    2820
ctgagacgaa ggcccgcgtc caggccagga cgaaggaggc cacgtgggag gggtagcggt   2880
cgttgtccac tagcgggtcc accttctcca gggtgtgcag gcacatgtcc ccctcctccg   2940
cgtccagaaa agtgattggc ttgtaggtgt aggacacgtg accggggggtt cccgacgggg   3000 gggtataaaa gggggtgggc accctttcat cttcactctc ttccgcatcg ctgtctgcga   3060
gagccagctg ctggggtaag tattccctct cgaaggcggg catgacctca gcgctcaggt   3120
```

```
tgtcagtttc taaaaatgag gaggatttga tgttcacctg tccggaggtg atacctttga   3180
gggtacctgg gtccatctgg tcagaaaaca ctatttttt gttgtcaagc ttggtggcga    3240
acgacccgta gagggcgttg gagagcagct tggcgatgga gcgcagggtc tggttttgt    3300
cgcggtcggc tcgctccttg gccgcgatgt tgagttgcac gtactcgcgg ccacgcact    3360
tccactcggg gaagacggtg gtgcgctcgt ctgggatcag gcgcacctc cagcctcggt    3420
tgtgcagggt gaccatgtcg acgctggtgg cgacctcgcc gcgcaggcgc tcgttggtcc   3480
agcagaggcg gccgcccttg cgcgagcaga agggggtag ggggtccagc tggtcctcgt    3540
ttgggggtc cgcgtcgatg gtgaagaccc cggggagcaa gcgcgggtca aagtagtcga    3600
tcttgcaagc ttgcatgtcc agagcccgct gccattcgcg ggcggcgagc gcgcgctcgt   3660
aggggtttgag gggcgggccc cagggcatgg ggtgggtgag cgcggaggcg tacatgccgc   3720
agatgtcata cacgtacagg ggttccctga ggatgccgag gtaggtgggg tagcagcgcc   3780
ccccgcggat gctggcgcgc acgtagtcat agagctcgtg ggaggggcc agcatgttgg    3840
gcccgaggtt ggtgcgctgg gggcgctcgg cgcggaaggc gatctgcctg aagatggcat   3900
gggagttgga ggagatggtg ggccgctgga agacgttgaa gcttgcttct tgcaagccca   3960
ccgagtccct gacgaagcag gcgtaggact cgcgcagctt gtgcaccagc tcggcggtga   4020
cctggacgtc gagcgcgcag tagtcgaggg tctcgcggat gatgtcatac ttatcctccc   4080
ccttctttt ccacagctcg cggttgagga cgaactcttc gcggtctttc cagtactctt    4140
ggagggaaa cccgtccgtg tccgaacggt aagagcctag catgtagaac tggttgacgg    4200
cctggtaggg gcaacagccc ttctccacgg gcagcgcgta ggcctgcgcc gccttgcgga   4260
gggaggtgtg ggtgagggcg aaagtgtccc tgaccatgac tttgaggtat tgatgtttga   4320
agtctgtgtc atcgcagccg ccctgttccc acagggtgta gtccgtgcgc ttttggagc    4380
gcgggttggg caggagaag gtgaggtcat tgaagaggat cttccccgct cgaggcatga    4440
agtttctggt gatgcgaaag ggccctggga ccgaggagcg gttgttgatg acctgggcgg   4500
ccaggacgat ctcgtcaaag ccgtttatgt tgtggcccac gatgtagagc tccaaaaagc   4560
gggctggcc cttgatggag gggagctttt tgagttcctc gtaggtgagc tcctcgggcg    4620
attccaggcc gtgctcctcc agggcccagt cttgcaagtg agggttggcc gccaggaagg   4680
atcgccagag gtcgcgggcc atgagggtct gcaggcggtc gcggaaggtt ctgaactgtc   4740
gccccacggc catcttttcg ggggtgatgc agtagaaggt gaggggtct ttctcccagg    4800
ggtcccatct gagctctcgg gcgaggtcgc gcgcggcggc gaccagagcc tcgttgcccc   4860
ccagtttcat gaccagcatg aagggcacga gctgcttgcc aaaggctccc atccaagtgt   4920
aggtctctac atcgtaggtg acaaagaggc gctccgtgcg aggatgagag ccgatcggga   4980
agaactggat ctcccgccac cagttggagg attggctgtt gatgtggtga agtagaagt    5040
cccgtctgcg ggccgagcac tcgtgctggc ttttgtaaaa gcgaccgcag tactggcagc   5100
gctgcacggg ttgtatatct tgcacgaggt gaacctggcc acctctgacg aggaagcgca   5160
gcgggaatct aagtccccg cctggggtcc cgtgtggctg gtggtcttct actttggttg    5220
tctgccgcc agcatctgtc tcctggaggg cgatggtgga gcagaccacc acgccgcgag   5280
agccgcaggt ccagatctcg gcgctcggcg ggcggagttt gatgacgaca tcgcgcacat   5340
tggagctgtc catggtctcc agctcccgcg gcggcaggtc agctgggagt tcctggaggt   5400
tcacctcgca gagacgggtc aaggcgcggg cagtgttgag atggtatctg atttcaaggg   5460
gcgtgttggc ggcggagtcg atggcttgca ggaggccgca gccccggggg gccacgatgg   5520
```

```
ttccccgcgg ggcgcgaggg gaggcggaag ctgggggtgt gttcagaagc ggtgacgcgg    5580
gcgggccccc ggaggtaggg ggggttccgg ccccacaggc atgggcggca ggggcacgtc    5640
ttcgccgcgc gcgggcaggg gctggtgctg gctccgaaga gcgcttgcgt gcgcgacgac    5700
gcgacggttg gtgtcctgta tctgacgcct ctgagtgaag accacgggtc ccgtgacctt    5760
gaacctgaaa gagagttcga cagaatcaat ctcggcatcg ttgacagcgg cctggcgcag    5820
gatctcctgc acgtcgcccg agttgtcctg gtaggcgatc tctgccatga actgctcgat    5880
ctcttcttcc tggagatctc ctcgtccggc gcgctccacg gtggccgcca ggtcgttgga    5940
gatgcgaccc atgagctgcg agaaggcgtt gagcccgccc tcgttccaga cccggctgta    6000
gaccacgccc ccctcggcgt tgcgggcgcg catgaccacc tgggccaggt tgagctccac    6060
gtgtcgcgtg aagacggcgt agttgcgcag gcgctggaaa aggtagttca gggtggtggc    6120
ggtgtgctcg gcgacgaaga agtacatgac ccagcgccgc aacgtggatt cattgatgtc    6180
ccccaaggcc tccaggcgct ccatggcctc gtagaagtcc acggcgaagt tgaaaaactg    6240
ggagttgcga gcggacacgg tcaactcctc ctccagaaga cggatgagct cggcgacagt    6300
gtcgcgcacc tcgcgctcga aggccacggg gggcgcttct tcctcttcca cctcttcttc    6360
catgatcgct tcttcttctt cctcagccgg gacgggaggg ggcggcggcg gcggggagg     6420 ggcgcggcgg cggcggcggc gcaccgggag gcggtcgatg aagcgctcga tcatctcccc    6480
ccgcatgcgg cgcatggtct cggtgacggc gcggccgttc tcccggggc gcagctcgaa     6540 gacgccgcct ctcatctcgc cgcggggcgg gcggccgtga ggtagcgaga cggcgctgac    6600
tatgcatctt aacaattgct gtgtaggtac accgccgagg gacctgattg agtccagatc    6660
caccggatcc gaaaaccttt ggaggaaagc gtctatccag tcgcagtcgc aaggtaggct    6720
gagcaccgtg gcgggcgggg gcgggtctgg agagttcctg gcggagatgc tgctgatgat    6780
gtaattaaag taggcggtct tgagaaggcg gatggtggac aggagcacca tgtctttggg    6840
tccggcctgt tggatgcgga ggcggtcggc catgccccag gcctcgttct gacaccggcg    6900
caggtctttg tagtagtctt gcatgagtct ttccaccggc acctcttctc cttcctcttc    6960
tccatctcgc cggtggtttc tcgcgccgcc catgcgcgtg accccaaagc ccctgagcgg    7020
ctgcagcagg gccaggtcgg cgaccacgcg ctcggccaag atggcctgct gcacctgagt    7080
gagggtcctc tcgaagtcat ccatgtccac gaagcggtgg taggcgcccg tgttgatggt    7140
gtaggtgcag ttggccatga cggaccagtt gacggtctgg tgtcccggct gcgagagctc    7200
cgtgtaccgc aggcgcgaga aggcgcggga atcgaacacg tagtcgttgc aagtccgcac    7260
cagatactgg tagcccacca ggaagtgcgg cggaggttgg cgatagaggg gccagcgctg    7320
ggtggcgggg gcgccgggcg ccaggttttc cagcatgagg cggtggtatc cgtagatgta    7380
cctggacatc caggtgatgc cggcggcggt ggtggtggcg cgcgcgtagt cgcggacccg    7440
gttccagatg tttcgcaggg gcgagaagtg ttccatggtc ggcacgctct ggccggtgag    7500
gcgcgcgcag tcgttgacgc tctatacaca cacaaaaacg aaagcgttta cagggctttc    7560
gttctgtagc ctggaggaaa gtaaatgggt tgggttgcgg tgtgcccgg ttcgagacca     7620 agctgagctc ggccggctga agccgcagct aacgtggtat tggcagtccc gtctcgaccc    7680
aggccctgta tcctccagga tacggtcgag agccctttg cttcttggc caagcgcccg      7740 tggcgcgatc tgggatagat ggtcgcgatg agaggacaaa agcggctcgc ttccgtagtc    7800
tggagaaaca atcgccaggg ttgcgttgcg gcgtaccccg gttcgagccc ctatggcggc    7860
```

```
ttgaatcggc cggaaccgcg gctaacgagg gccgtggcag ccccgtcctc aggaccccgc  7920
cagccgactt ctccagttac gggagcgagc ccctttgtt ttttattttt tagatgcatc    7980
ccgtgctgcg gcagatgcgc ccctcgcccc ggcccgatca gcagcagcaa cagcaggcat  8040
gcagacccc ctctcccctt tccgcccgg tcaccacggc cgcggcggcc gtgtcgggcg    8100
cgggggggcgc gctggagtca gatgagccac cgcggcggcg acctaggcag tatctggact  8160
tggaagaggg cgagggactg gcgcggctgg gggcgaactc tccagagcgc cacccgcggg  8220
tgcagttgaa aagggacgcg cgcgaggcgt acctgccgcg gcagaacctg tttcgcgacc  8280
gcggggggcga ggagcccgag gagatgcgag actgcaggtt ccaagcgggg cgcgagctgc  8340
ggcgcgggct ggacagacag cgcctgctgc gcgaggagga ctttgagccc gacacgcaga  8400
cgggcatcag ccccgcgcgc gcgcacgtag ccgcggccga cctggtgacc gcctacgagc  8460
agacggtgaa ccaggagcgc aacttccaaa agagcttcaa caaccacgtg cgcacgctgg  8520
tggcgcgcga ggaggtgacc ctgggtctca tgcatctgtg ggacctggtg gaggcgatcg  8580
tgcagaaccc cagcagcaag cccctgaccg cgcagctgtt cctggtggtg cagcacagca  8640
gggacaacga ggccttcagg gaggcgctgc tgaacatcac cgagccggag gggcgctggc  8700
tcctggacct gataaacatc ctgcagagca tagtggtgca ggagcgcagc ctgagcctgg  8760
ccgagaaggt ggcggccatc aactactcta tgctgagcct gggcaagttc tacgcccgca  8820
agatctacaa gaccccctac gtgcccatag acaaggaggt gaagatagac agcttctaca  8880
tgcgcatggc gctgaaggtg ctgaccctga gcgacgacct gggagtgtac cgcaacgagc  8940
gcatccacaa ggccgtgagc gccagccggc ggcgcgagct gagcgaccgc gagctgatgc  9000
acagtctgca gcgcgcgctg accggcgcgg gcgagggcga cagggaggtc gagtcctact  9060
tcgacatggg ggccgacctg cactggcagc cgagccgccg cgccctggag gcggcgggg  9120
cgtacggcgg ccccctggcg gccgatgacc aggaagagga ggactatgag ctagaggagg  9180
gcgagtacct ggaggactga cctggctggt ggtgttttgg tatagatgca agatccgaac  9240
gtggcggacc cggcggtccg ggcggcgctg caaagccagc cgtccggcat taactcctct  9300
gacgactggg ccgcggccat gggtcgcatc atggccctga ccgcgcgcaa ccccgaggct  9360
ttcaggcagc agcctcaggc caaccggctg gcggccatct tggaagcggt agtgcccgcg  9420
cgctccaacc ccacccacga gaaggtgctg gccatagtca acgcgctggc ggagagcagg  9480
gccatccgcg cggacgaggc cggactggtg tacgatgcgc tgctgcagcg ggtggcgcgg  9540
tacaacagcg gcaacgtgca gaccaacctg gaccgcctgg tgacggacgt gcgcgaggcc  9600
gtggcgcagc gcgagcgctt gcatcaggac ggtaacctgg gctcgctggt ggcgctaaac  9660
gccttcctca gcacccagcc ggccaacgta ccgcggggc aggaggacta caccaacttt  9720
ttgagcgcgc tgcggctgat ggtgaccgag gtccctcaga gcgaggtgta ccagtcgggg  9780
cccgactact tcttccagac cagcagacag ggcttgcaaa ccgtgaacct gagccaggct  9840
ttcaagaacc tgcgggggct gtgggagtg aaggcgccca ccggcgaccg ggctacggtg  9900
tccagcctgc taaccccaa ctcgcgcctg ctgctgctgc tgatcgcgcc cttcacggac  9960
agcgggagcg tctcgcggga gacctatctg ggccacctgc tgacgctgta ccgcgaggcc  10020
atcgggcagg cgcaggtgga cgagcacacc ttccaagaga tcaccagcgt gagccacgcg  10080
ctggggcagg aggacacggg cagcctgcag gcgaccctga actacctgct gaccaacagg  10140
cggcagaaga ttcccacgct gcacagcctg acccaggagg aggagcgcat cttgcgctac  10200
gtgcagcaga gcgtgagcct gaacctgatg cgcgacggcg tgacgcccag cgtggcgctg  10260
```

```
gacatgaccg cgcgcaacat ggaaccgggc atgtacgcct cccaccggcc gttcatcaac   10320
cgcctgatgg actacttgca tcgggcggcg gccgtgaacc ccgagtactt cactaatgcc   10380
attctgaatc cccactggat gcccctccg ggtttctaca acggggactt tgaggtgccc   10440
gaggtcaacg acgggttcct ctgggatgac atggatgaca gtgtgttctc acccaacccg   10500
ctgcgcgccg cgtctctgcg attgaaggag ggctctgaca gggaaggacc gagaagtctg   10560
gcctcctccc tggctctggg agcggtgggc gccacgggcg cggcggcgcg gggcagtagc   10620 ccccttcccca gcctggcaga ctctctgaac agcgggcggg tgagcaggcc ccgcttgcta   10680
ggcgaggagg agtatctgaa caactccctg ctgcagcccg cgagggacaa gaacgctcag   10740
cggcagcagt ttcccaacaa tgggatagag agcctggtgg acaagatgtc cagatggaag   10800
acgtatgcgc aggagtacaa ggagtgggag gaccgccagc cgcggccctt gccgcccct   10860 aggcagcgct ggcagcggcg cgcgtccaac cgccgctgga ggcaggggcc cgaggacgat   10920
gatgactctg cagatgacag cagcgtgttg gacctgggcg ggagcgggaa ccccttttcg   10980
cacctgcgcc cacgcctggg caagatgttt taaaagaaaa aaaaaaata aaactcacca   11040 aggccatggc gacgagcgtt ggttttttgt tccctccctt agtatgcggc gcgcggcgat   11100
gttcgaggag gggcctcccc cctcttacga gagcgcgatg gggatttctc ctgcggcgcc   11160
cctgcagcct ccctacgtgc ctcctcggta cctgcaacct acaggggga gaaatagcat   11220 ctgttactct gagctgcagc ccctgtacga taccaccaga ctgtacctgg tggacaacaa   11280
gtccgcggac gtggcctccc tgaactacca gaacgaccac agcgattttt tgaccacggt   11340
gatccaaaac aacgacttca ccccaaccga ggccagcact cagaccataa acctggataa   11400
caggtcgaac tggggcggcg acctgaagac catcttgcac accaacatgc ccaacgtgaa   11460
cgagttcatg ttcaccaact cttttaaggc gcgggtgatg gtggcgcgcg agcaggggga   11520
ggcgaagtac gagtgggtgg acttcacgct gcccgagggc aactactcag agaccatgac   11580
tctcgacctg atgaacaatg cgatcgtgga acactatctg aaagtgggca ggcagaacgg   11640
ggtgaaggaa agcgatatcg gggtcaagtt tgacaccaga aacttccgtc tgggctggga   11700
ccccgtgacc gggctggtca tgccggggt ctacaccaac gaggccttc atcccgacat   11760 agtgcttctg cccggctgtg gggtggactt cacccagagc cggctgagca acctgctggg   11820
cattcgcaag cggcagcctt tccaggaggg tttcaagatc acctatgagg atctgaaggg   11880
gggcaacatt cccgcgctcc ttgatctgga cgcctacgag gagagcttga aacccgagga   11940
gagcgctggc gacagcggcg agagtggcga ggagcaagcc ggcggcggtg gcggcgcgtc   12000
ggtagaaaac gaaagtacgc ccgcagtggc ggcggacgct gcggaggtcg agccggaggc   12060
catgcagcag gacgcagagg agggcgcaca ggagggcgcg cagaaggaca tgaacgatgg   12120
ggagatcagg ggagacacat tcgccacccg gggcgaagaa aaagaggcag aggcggcggc   12180
ggcggcgacg gcgaggccg aaaccgaggt tgaggcagag gcagagcccg agaccgaagt   12240
tatggaagac atgaatgatg agaacgtag gggcgacacg ttcgccaccc ggggcgaaga   12300
gaaggcggcg gaggcagaag ccgcggctga ggaggcggct gcggctgcgg ccaagactga   12360
ggctgcggct aaggctgagg tcgaagccaa tgttgcggtt gaggtcagg ctgaggagga   12420 ggcggcggct gaagcagtta aggaaaaggc ccaggcagag caggaagaga aaaaacctgt   12480
cattcaacct ctaaagaag atagcaaaaa gcgcagttac aacgtcatcg agggcagcac   12540
ctttacccag taccgcagct ggtacctggc gtacaactac ggcgaccgg tcaaggggt   12600
```

-continued

```
gcgctcgtgg accctgctct gcacgccgga cgtcacctgc ggctccgagc agatgtactg    12660
gtcgctgccg aacatgatgc aagacccggt gaccttccgc tccacgcggc aggttagcaa    12720
cttcccggtg gtgggcgccg aactgctgcc cgtgcactcc aagagttttt acaacgagca    12780
ggccgtctac tcccagctga tccgccaggc cacctctctg acccacgtgt tcaatcgctt    12840
tcccgagaac cagattttgg cgcgcccgcc ggcccccacc atcaccaccg tgagtgaaaa    12900
cgttcctgcc ctcacagatc acgggacgct accgctgcgc aacagcatct caggagtcca    12960
gcgagtgacc attactgacg ccagacgccg gacctgcccc tacgtttaca aggccttggg    13020
catagtctcg ccgcgcgtcc tctccagtcg cacttttta aacacatcta cccacacgtt     13080
ccaaaatcat gtccgtactc atctcaccca gcaacaacac cggctggggg ctgcgcgcgc    13140
ccagcaagat gtttggaggg gcgaggaagc gctccgacca gcaccctgtg cgcgtgcgcg    13200
gccactaccg cgcgccctgg ggagcgcaca agcgcgggcg cacagggcgc accactgtgg    13260
acgacgtcat tgactccgta gtggagcaag cgcgccacta cacacccggc gcgccgaccg    13320
cccccgccgt gtccaccgtg gaccaggcga tcgaaagcgt ggtacagggc gcgcggcact    13380
atgccaacct taaaagtcgc cgccgccgcg tggcccgccg ccatcgccgg agacccgggg    13440
ccaccgccgc cgcgcgcctt actaaggctc tgctcaggcg cgccaggcga actggccacc    13500
gggccgccat gagggccgca cggcgggctg ccgctgccgc aagcgccgtg gccccgcggg    13560
cacgaaggcg cgcggccgcc gccgccgcg ccgccatttc cagcttggcc tcgacgcggc     13620
gcggtaacat atactgggtg cgcgactcgg taaccggcac gcgggtaccc gtgcgctttc    13680
gccccccgcg gaattagcac aagacaacat acacactgag tctcctgctg ttgtgtatcc    13740
cagcggcgac cgtcagcagc ggcgacatgt ccaagcgcaa aattaaagaa gagatgctcc    13800
aggtcatcgc gccggagatc tatgggcccc cgaagaagga ggaggatgat tacaagcccc    13860
gcaagctaaa gcgggtcaaa agaaaaaga agatgatga tgatgacgag gcggtggagt      13920
ttgtccgccg catggcaccc aggcgccccg tgcagtggaa gggccggcgc gtgcagcgcg    13980
ttttgcgccc cggcaccgcg gtggtcttca cgcccggcga gcgctccacg cgcactttca    14040
agcgggtgta cgatgaggtg tacgcgacg aggacctgtt ggagcaggcc aaccagcgct      14100
ttgggagtt tgcatatggg aaacggcccc gcgagagtct aaaagaggac ctgctggcgc     14160
taccgctgga cgagggcaat cccaccccga gtctgaagcc ggtaaccctg caacaggtgc    14220
tgcctttgag cgcgcccagc gagcataagc gagggttgaa gcgcgaaggc ggggacctgg    14280
cgcccaccgt gcagttgatg gtgcccaagc ggcagaagct ggaggacgtg ctggagaaaa    14340
tgaaagtaga gcccgggatc cagcccgaga tcaaggtccg ccccatcaag caggtggcgc    14400
ccggcgtggg agtccagacc gtggacgtta ggattccac ggaggagatg gaaacccaaa     14460
ccgccactcc ctcttcggcg ccagcgcca ccaccggcac cgcttcggta gaggtgcaga      14520
cggacccctg gctacccgcc accgctgttg ccgccgccgc ccccgttcg cgcgggcgca     14580
agagaaatta ccagcggcc agcgcgctca tgccccagta cgcactgcat ccatccatcg     14640
cgcccacccc cggctaccgc gggtactcgt accgcccgcg cagatcagcc ggcactcgcg    14700
gccgccgccg ccgtgcgacc acaaccagcc gccgccgtcg ccgccgccgc cagccagtgc    14760
tgaccccccgt gtctgtaagg aaggtggctc gctcggggag cacgctggtg gtgcccagag   14820
cgcgctacca ccccagcatc gtttaaagcc ggtctctgta tggttcttgc agatatggcc    14880
ctcacttgtc gcctccgctt cccggtgccg ggataccgag gaagaactca ccgccgcaga    14940
ggcatggcgg gcagcggtct ccgcggcggc cgtcgccatc gccggcgcgc aaaaagcagg    15000
```

```
cgcatgcgcg gcggtgtgct gcctctgcta atcccgctaa tcgccgcggc gatcggtgcc    15060
gtacccggga tcgcctccgt ggccctgcag gcgtcccaga acgttgact  cttgcaacct    15120 tgcaagcttg cattttttgg aggaaaaata aaaaagtct  agactctcac gctcgcttgg    15180
tcctgtgact attttgtaga aaaagatgg  aagacatcaa ctttgcgtcg ctggccccgc    15240
gtcacggctc gcgcccgttc atgggagact ggacagatat cggcaccagc aatatgagcg    15300
gtggcgcctt cagctggggc agtctgtgga gcggccttaa aaattttggt tccaccatta    15360
agaactatgg caacaaagcg tggaacagca gcacgggcca gatgctgaga gacaagttga    15420
aagagcagaa cttccaggag aaggtggcgc agggcctggc ctctggcatc agcggggtgg    15480
tggacatagc taaccaggcc gtgcagaaaa agataaacag tcatctggac ccccgtcctc    15540
aggtggagga aatgcctcca gcgatggaga cggtgtctcc cgagggcaaa ggcgaaaagc    15600
gcccgcggcc cgacagagaa gagaccctgg tgtcacacac cgaggagccg ccctcttacg    15660
aggaggcagt caaggccggc ctgcccacca ctcgccccat agcccccatg gccaccggtg    15720
tggtgggcca caggcaacac actcccgcaa cactagatct gcccccgccg tccgagccgc    15780
cgcgccagcc aaaggcggcg acggtgcccg ctccctccac ttccgccgcc aacagagtgc    15840
ccctgcgccg cgccgcgagc ggccccgggg cctcgcgagt tagcggcaac tggcagagca    15900
cactgaacag catcgtgggc ctgggagtga ggagtgtgaa gcgccgccgt tgctactgaa    15960
tgagcaagct agctaacgtg ttgtatgtgt gtatgcgtcc tatgtcgccg ccagaggagc    16020
tgttgagccg ccggcgccgt ctgcactcca gcgaatttca agatggcgac cccatcgatg    16080
atgcctcagt ggtcgtacat gcacatctcg ggccaggacg cttcggagta cctgagcccc    16140
gggctggtgc agttcgcccg cgccacagac acctacttca acatgagtaa caagttcagg    16200
aaccccactg tggcgcccac ccacgatgtg accacggacc ggtcgcagcg cctgacgctg    16260
cggttcatcc ccgtggatcg ggaggacacc gcctactctt acaaggcgcg gttcacgctg    16320
gccgtgggcg acaaccgcgt gctggacatg gcctccactt actttgacat caggggggtg    16380
ctggacaggg gccccacctt caagccctac tcgggtactg cctacaactc cctggccccc    16440
aagggcgctc ccaattcttg cgagtgggaa caagaggaaa atcaggtggt cgctgcagat    16500
gatgaacttg aagatgaaga agcgcaagct caagaggacg ccccagctaa aaaaattcat    16560
gtatatgccc aggcgcctct tgctggcgaa aagattacca aggatggttt gcaaataggt    16620
actgaagttg taggagatac atctaaggac acttttgcag acaaaacatt ccaacccgaa    16680
cctcagatag gcgagtctca gtggaacgag gctgatgcca cagtagcagg aggcagagtc    16740
ttgaaaaaaa ccaccccctat gagaccttgc tatggatcct atgccaggcc tacaaatgcc    16800
aacgggggtc aaggaattat ggttgccaat gaacaaggag tgttggagtc taaagtggag    16860
atgcaatttt tttctaacac tacacccctt aatgcgcggg atggagctgg caatcccgaa    16920 ccaaggtgg  tgttgtacag tgaagatgtc cacttggaat ctcctgacac tcatttgtct    16980
tacaagccca aaaaggatga tgttaatgct aaaattatgt tgggtcagca agctatggct    17040
aacaggccca acctcattgc ttttagagat aatttcattg gactcatgta ctacaacagc    17100
actggtaaca tgggagtgct ggcgggtcag gcctctcagt tgaatgccgt ggtggacctg    17160
caggatagaa acacagaact gtcatatcag cttatgcttg attccattgg ggatagatcc    17220
agatacttct ccatgtggaa ccaggcagtg gatagctatg acccagatgt cagaatcatt    17280
gaaaaccatg gtgtcgagga cgagctaccc aactactgct tccctctggg cggcatagga    17340
```

```
attactgata cttatcaagg gatcaaaaat accaatggca atggtcagtg gaccaaagat    17400
gatcagttcg cggaccgtaa tgaaataggg gtgggaaaca acttcgccat ggagatcaac    17460
atccaggcca acctctggag gaacttcctc tatgcgaacg tggggctcta cctgccagac    17520
aagctcaagt acaaccccac caacgtggac atctctgaca accccaacac ctatgactac    17580
atgaacaagc gtgtggtggc tcccggcctg gtggactgct tgtcaatgt gggagccagg     17640 tggtccctgg actacatgga caacgtcaac cccttcaacc accaccgcaa tgcgggtctg    17700
cgctaccgct ccatgatcct gggcaacggg cgctacgtgc ccttccacat tcaggtgccc    17760
cagaagttct tgccatcaa gaacctcctc ctcctgccgg gctcctacac ttacgagtgg    17820
aacttcagga aggatgtcaa catggtcctg cagagctctc tgggcaatga ccttagggtg    17880
gacggggcca gcatcaagtt tgacagcgtc accctctatg ctaccttctt ccccatggct    17940
cacaacaccg cctccacgct cgaggccatg ctgaggaacg acaccaacga ccagtccttc    18000
aatgactacc tctctggggc caacatgctc taccccatcc ccgccaaggc caccaacgtg    18060
cccatctcca ttccctctcg caactgggcc gccttcagag ctgggccttt acccgcctt    18120 aagaccaagg aaaccccctc cctgggctcg ggttttgacc cctactttgt ctactcggga    18180
tccatcccct acctggatgg caccttctac ctcaaccaca cttttaagaa gatatccatc    18240
atgtatgact cctccgtcag ctggccgggc aatgaccgcc tgctcacccc caatgagttc    18300
gaggtcaagc gcgccgtgga cggcgagggc tacaacgtgg cccagtgcaa catgaccaag    18360
gactggttcc tggtgcagat gctggccaac tacaacatag gctaccaggg cttctacatc    18420
ccagagagct acaaggacag gatgtactcc ttcttcagaa atttccaacc catgagcagg    18480
caggtggtgg acgagaccaa atacaaggac tatcaggcca ttggcatcac tcaccagcac    18540
aacaactcgg gattcgtggg ctacctggct cccaccatgc gcgaggggca ggcctacccc    18600
gccaacttcc cctacccgtt gataggcaag accgcggtcg acagcgtcac ccagaaaaag    18660
ttcctctgcg accgcaccct ctggcgcatc cccttctcta gcaacttcat gtccatgggt    18720
gcgctcacgg acctgggcca gaacctgctc tatgccaact ccgcccatgc gctggacatg    18780
acttttgagg tggaccccat ggacgagccc accttctctct atattgtgtt tgaagtgttc    18840
gacgtggtca gagtgcacca gccgcaccgc ggtgtcatcg agaccgtgta cctgcgcacg    18900
cccttctcgg ccggcaacgc caccacctaa ggagacagcg ccgccgcctg catgacgggt    18960
tccaccgagc aagagctcag ggccatcgcc agagacctgg gatgcggacc ctattttttg    19020
ggcacctatg acaaacgctt cccgggcttc atctcccgag acaagctcgc ctgcgccatc    19080
gtcaacacgg ccgcgcgcga gaccgggggc gtgcactggc tggcctttgg ctgggacccg    19140
cgctccaaaa cctgctacct cttcgacccc tttggcttct ccgatcagcg cctcagacag    19200
atctatgagt ttgagtacga ggggctgctg cgccgcagcg cgcttgcctc ctcgcccgac    19260
cgctgcatca cccttgagaa gtccaccgag accgtgcagg ggcccactc ggccgcctgc    19320 ggtctcttct gctgcatgtt tttgcacgcc tttgtgcgct ggccccagag tcccatggat    19380 cgcaaccca ccatgaactt gctcaaggga gtgcccaacg ccatgctcca gagcccccag    19440
gtccagccca ccctgcgcca caccaggaa cagctctacc gcttcctgga cgccactcc    19500 ccctacttcc gcagtcacag cgcgcacatc cgggggggcca cctcttcctg ccacttgcaa    19560
caaaacatgc aagacggaaa atgatgtaca gctcgctttt taataaatgt aaagactgtg    19620
cactttattt atacacgggc tctttctggt tatttattca acaccgccgt cgccatctag    19680
aaatcgaaag ggttctgccg cgcgtcgccg tgcgccacgg gcagagacac gttgcgatac    19740
```

```
tggaagcggc tcgcccactt gaactcgggc accaccatgc ggggcagtgg ctcctcgggg   19800
aagttctcgc cccacagggt gcgggtcagc tgcagcgcgc tcaggaggtc gggagccgag   19860
atcttgaagt cgcagttggg gccggaaccc tgcgcgcgcg agttgcggta cacggggttg   19920
cagcactgga acaccagcag ggccggatta cgcacgctgg ccagcaggct ctcgtcgctg   19980
atcatgtcgc tgtccagatc ctccgcgttg ctcagggcga atggggtcat cttgcagacc   20040
tgcctgccca ggaaaggcgg cagcccgggc ttgccgttgc agtcgcagcg caggggcatc   20100
agcaggtgcc cgtggcccgt ctgcgcctgc gggtacagcg cgcgcatgaa ggcttcgatc   20160
tgcctgaaag ccacctgcgt cttggctccc tccgaaaaga acatcccaca ggacttgctg   20220
gagaactggt tcgcgggaca gctggcatcg tgcaggcagc agcgcgcgtc ggtgttggcg   20280
atctgcacca cgttgcgacc ccaccggttc ttcactatct tggccttgga agcctgctcc   20340
ttcagcgcgc gctggccgtt ctcgctggtc acatccatct ctatcacctg ctccttgttg   20400
atcatgtttg tcccgtgcag acacttcagg tcgccctccg tctgggtgca gcggtgctcc   20460
cacagcgcgc aaccggtggg ctcccaattt ttgtgggtca cccccgcgta ggcctgcagg   20520
taggcctgca agaagcgccc catcatggcc acaaaggtct tctggctcgt aaaggtcagc   20580
tgcaggccgc gatgctcttc gttcagccag gtcttgcaga tggcggccag cgcctcggtc   20640
tgctcgggca gcatcctaaa atttgtcttc aggtcgttat ccacgtggta cttgtccatc   20700
atggcgcgcg ccgcctccat gcccttctcc caggcggaca ccatgggcag gcttaggggg   20760
tttatcactt ccaccggcga ggacaccgta ctttcgattt cttcttcctc cccctcttcc   20820
cggcgcgcgc ccacgctgct gcgcgctctc accgcctgca ccaaggggtc gtcttcaggc   20880
aagcgccgca ccgagcgctt gccgcccttg acctgcttaa tcagcaccgg cggggttgctg   20940 aagcccacca tggtcagctc cgcctgctct tcttcgtctt cgctgtctac cactatctct   21000
ggggaagggc ttctccgctc tgcggcggtg cgcttctttt ttttcttggg agcagccgtg   21060
acggagtccg ccacggcgac ggaggtcgag ggcgtggggc tggggtgcg cggtaccagg   21120 gcctcgtcgc cctcggactc ttcctctgac tccaggcggc ggcggagacg cttctttggg   21180
ggcgcgcgcg tcagcggcgg cggagacggg gacgggacg gggacgggac gccctccaca   21240
gggggtggtc ttcgcgcaga cccgcggccg cgctcggggg tcttttcgag ctggtcttgg   21300
tcccgactgg ccattgtatc ctcctcctcc taggcagaga gacataagga gtctatcatg   21360
caagtcgaga aggaggagag cttaaccacc ccctctgaga ccgccgatgc gcccgccgtc   21420
gccgtcgccc ccgctgccgc cgacgcgccc gccacaccga gcgacacccc cgcggacccc   21480
ccagccgacg cacccctgtt cgaggaagcg gccgtggagc aggacccggg ctttgtctcg   21540
gcagaggagg atttgcgaga ggaggaggat aaggagaaga agccctcagt gccaaaagat   21600
gataaagagc aagacgagca cgacgcagat gcacaccagg gtgaagtcgg gcggggggac   21660
ggagggcatg acgcgccga ctacctagac gaagggaacg acgtgctctt gaagcacctg   21720
catcgtcagt gcgccatcgt ttgcgacgct ctgcaggagc gcagcgaagt gcccctcagc   21780
gtggcggagg tcagccacgc ctacgagctc agcctcttct cccccggggt gcccccccgc   21840
cgccgcgaaa acggcacatg cgagcccaac ccgcgcctca acttctaccc cgcctttgtg   21900
gtgcccgagg tcctggccac ctatcacatc ttctttcaaa attgcaagat cccccctctcg   21960 tgccgcgcca accgtagccg cgccgataag atgctggccc tgcgccaggg cgaccacata   22020
cctgatatcg ccgctttgga agatgtgcca aagatcttcg agggtctggg tcgcaacgag   22080
```

```
aagcgggcag caaactctct gcaacaggaa aacagcgaaa atgagagtca caccggggta  22140
ctggtggagc tcgagggcga caacgcccgc ctggcggtgg tcaagcgcag catcgaggtc  22200
acccactttg cctaccccgc gctcaacctg cccccaaag tcatgaacgc ggccatggac  22260
gggctgatca tgcgccgcgg ccggcccctc gctccagatg caaacttgca tgaggagacc  22320
gaggacggcc agcccgtggt cagcgacgag cagctggcgc gctggctgga gaccgcggac  22380
cccgccgaac tggaggagcg gcgcaagatg atgatggccg cggtgctggt caccgtagag  22440
ctggagtgtc tgcagcgctt cttcggcgac cccgagatgc agagaaaggt cgaggagacc  22500
ctgcactaca ccttccgcca gggctacgtg cgccaggctt gcaagatctc caacgtggag  22560
ctcagcaacc tggtgtccta cctgggcatc ttgcatgaga accgcctcgg gcagagcgtg  22620
ctgcactcca ccctgcgcgg ggaggcgcgc cgcgactacg tgcgcgactg cgtttacctc  22680
ttcctctgct acacctggca gacggccatg ggggtctggc agcagtgcct ggaggagcgc  22740
aacctcaagg agctggagaa gctcctgcag cgcgcgctca agacctctg gacgggctac  22800
aacgagcgct cggtggccgc cgcgctggcc gacctcatct tccccgagcg cctgctcaaa  22860
accctccagc aggggctgcc cgacttcacc agccaaagca tgttgcaaaa cttcaggaac  22920
tttatcctgg agcgttctgg catcctaccc gccacctgct cgcccctgcc cagcgacttt  22980
gtcccctcg tgtaccgcga gtgccccccg ccgctgtggg gtcactgcta cctgttccaa  23040
ctggccaact acctgtccta ccacgcggac ctcatggagg actccagcgg cgaggggctc  23100
atggagtgcc actgccgctg caacctctgc acgccccacc gctccctggt ctgcaacacc  23160
caactgctca gcgagagtca gattatcggt accttcgagc tacagggtcc gtcctcctca  23220
gacgagaagt ccgcggctcc ggggctaaaa ctcactccgg ggctgtggac ttccgcctac  23280
ctgcgcaaat ttgtacctga agactaccac gcccacgaga tcaggtttta cgaagaccaa  23340
tcccgcccgc ccaaggcgga gctgaccgcc tgcgtcatca cccagggcga gatcctaggc  23400
caattgcaag ccatccaaaa agcccgccaa gattttttgc tgagaaaggg tcgggggtg  23460
tatctggacc cccagtcggg tgaggagctc aacccggttc cccgctgcc gccgccgcgg  23520
gaccttgctt cccaggataa gcatcgccat ggctcccaga agaagcagc agcggccgcc  23580
actgccgcca ccccacatgc tggaggaaga ggaggaatac tgggacagtc aggcagagga  23640
ggtttcggac gaggaggagc cggagacgga gatggaagag tgggaggagg acagcttaga  23700
cgaggaggct tccgaagccg aagaggcaga cgcaacaccg tcaccctcgg ccgcagcccc  23760
ctcgcaggcg ccccccgaagt ccgctcccag catcagcagc aacagcagcg ctataacctc  23820
cgctcctcca ccgccgcgac ccacggccga ccgcagaccc aaccgtagat gggacaccac  23880
cggaaccggg gccggtaagt cctccgggag aggcaagcaa gcgcagcgcc aaggctaccg  23940
ctcgtggcgc gctcacaaga acgccatagt cgcttgcttg caagactgcg gggggaacat  24000
ctccttcgcc cgccgcttcc tgctcttcca ccacggtgtg gccttccccc gtaacgtcct  24060
gcattactac cgtcatctct acagccccta ctgcggcggc agtgagccag agacggtcgg  24120
cggcggcggc ggcgcccgtt tcggcgccta ggaagaccca gggcaagact tcagccaaga  24180
aactcgcggc ggccgcggcg aacgcggtcg cgggggccct cgcgctgacg gtgaacgaac  24240
ccctgtcgac ccgcgaactg agaaaccgaa tcttccccac tctctatgcc atcttccagc  24300
agagcagagg gcaggatcag gaactgaaag taaaaaacag gtctctgcgc tccctcaccc  24360
gcagctgtct gtatcacaag agcgaagacc agcttcggcg cacgctggag gacgctgagg  24420
cactcttcag caaatactgc gcgctcactc ttaaggacta gctccgcgcc cttctcgaat  24480
```

```
ttaggcggga acgcctacgt catcgcagcg ccgccgtcat gagcaaggac attcccacgc  24540
catacatgtg gagctatcag ccgcagatgg gactcgcggc gggcgcctcc caagactact  24600
ccacccgcat gaactggctc agtgccggcc cacacatgat ctcacaggtt aatgatatcc  24660
gcacccatcg aaaccaaata ttggtggagc aggcggcaat taccaccacg ccccgcaata  24720
atcccaaccc cagggagtgg cccgcgtccc tggtgtatca ggaaattccc ggccccacca  24780
ccgtactact tccgcgtgat tcccaggccg aagtccaaat gactaactca ggggcgcagc  24840
tcgcgggcgg ctgtcgtcac agggtgcggc ctcctcgcca gggtataact cacctggaga  24900
tccgaggcag aggtattcag ctcaacgacg agtcggtgag ctcctcgctc ggtctaagac  24960
ctgacgggac cttccagata gccggagccg gccgatcttc cttcacgccc cgccaggcgt  25020
acctgactct gcagagctcg tcctcggcgc gcgctcggg cggcatcggg actctccagt  25080
tcgtgcagga gtttgtgccc tcggtctact tcaaccccct tctcgggctct cccggtcgct  25140 acccggacca gttcatctcg aactttgacg ccgcgaggga ctcggtggac ggctacgact  25200
gaatgtcggg tggacccggt gcagagcaac ttcgcctgaa gcacctcgac cactgccgcc  25260
gccctcagtg ctttgcccgc tgtcagaccg gtgagttcca gtacttttcc ctgcccgact  25320
cgcacccgga cggcccggcg cacggggtgc gcttttttcat cccgagtcag gtgcgctcta  25380
ccctaatcag ggagtttacc gcccgtcccc tactggcgga gttggaaaag gggccttcta  25440
tcctaaccat tgcctgcatc tgctctaacc ctggattgca ccaagatctt tgctgtcatt  25500
tgtgtgctga gtataataaa ggctgagatc agaatctact cgggctcctg tcgccatcct  25560
gtcaacgcca ccgtccaagc ccggcccgat cagcccgagg tgaacctcac ctgcggtctg  25620
caccggcgcc tgaggaaata cctagcttgg tactacaaca gcactccctt tgtggtttac  25680
aacagctttg accaggacgg ggtctcactg agggataacc tctcgaacct gagctactcc  25740
atcaggaaga acagcaccct cgagctactt cctccttacc tgcccgggac ttaccagtgt  25800
gtcaccggtc cctgcaccca cacccacctg ttgatcgtaa acgactctct tccgagaaca  25860
gacctcaata actcctcttc gcagttcccc agaacaggag gtgagctcag gaaaccccgg  25920
gtaaagaagg gtggacaaga gttaacactt gtggggtttc tggtgtatgt gacgctggtg  25980
gtggctcttt tgattaaggc ttttccttcc atgtctgaac tctccctctt ttatgaacaa  26040
ctcgactagt gctaacggga ccctacccaa cgaatcggga ttgaatatcg gtaaccaggt  26100
tgcagtttca cttttgatta ccttcatagt cctcttcctg ctagtgctgt cgcttctgtg  26160
cctgcggatc gggggctgct gcatccacgt ttatatctgg tgctggctgt ttagaaggtt  26220
cggagaccat cgcaggtaga ataaacatgc tgctgcttac cctctttgtc ctggcgctgg  26280
ccgccagctg ccaagccttt tccgaggctg actttataga gccccagtgt aacgtgactt  26340
ttaaagccca tgcacagcgt tgtcatacta taatcaaatg tgccaccgaa cacgatgaat  26400 acctatcca gtataaagat aaatcacaca agtggcact tgttgacatc tggaaacccg  26460 aagaccttt ggaatacaat gtgaccgttt tccagggtga cctcttcaaa atttacaatt  26520
acactttccc atttgaccag atgtgtgact ttgtcatgta catggaaaag cagcacaagc  26580
tgtggcctcc gactccccag ggctgtgtgg aaaatccagg ctctttctgc atgatctctc  26640
tctgtgtaac tgtgctggca ctaatactca cgcttttgta tatcagattt aaatcaaggc  26700
aaagcttcat cgatgaaaag aaaatgcctt aaacgctttc acgcttgatt gctaacaccg  26760 ggttttatc cgcagaatga ttggaatcac cctactaatc acctccctcc ttgcgattgc  26820
```

```
ccatggggttg gaacgaatcg aagccctgt gggggccaat gttaccctgg tggggcctgt    26880
cggcaatgct acattaatgt gggaaaaata tactaaaaat caatgggtct cttactgcac   26940
taacaaaaac agccacaagc ccagagccat ctgcgatggg caaaatctaa ccttgattga   27000
tgttcaaatg ctggatgcgg gctactatta tgggcagctg ggtacaatga ttaattactg   27060
gagaccccac aaagattaca tgctccacgt agtaaagggt cccttagca gcccacccac   27120
taccacctct actacccca ctaccaccac tactcccacc accagcactg ccgcccagcc   27180
tcctcatagc agaacaacca cttttatcaa ttccaagtcc cactccccc acattgccgg   27240
cgggccctcc gcctcagact ccagaccac cgagatctgc ttctgcaaat gctctgacgc   27300
ctttgctgag gatttggaag accacgagga agatgagcat gacttcgcag atgcatgcca   27360
ggcatcagag gcagaagcgc tgccggtggc cctcaaacag tatgcagacc cccacaccac   27420
ccccaacctt cctccaccctt cccagaagcc aagtttcctg ggggaaaatg aaactctgcc   27480
tctctccata ctcgctctga catctgttgc tatgttgacc gctctgctgg tgcttctatg   27540
ctctatatgc tacctgatct gctgcagaaa gaaaaaatct cacggccatg ctcaccagcc   27600
cctcatgcac ttcccttacc ctccagagct gggcgaccac aaactttaag tctgcagtaa   27660
ctatctgccc atccccttgtc agtcgacagc gatgagcccc actaatctaa cggcctctgg   27720
acttacaaca tcgtctctta atgagaccac cgctcctcaa gacctgtacg atggtgtctc   27780
cgcgctggtt aaccagtggg atcacctggg catatggtgg ctcctcatag gagcagtgac   27840
cctgtgccta atcctggtct ggatcatctg ctgcatcaaa agcagaagac ccaggcggcg   27900
gcccatctac aggccctttg tcatcacacc tgaagatgat gatgacacca cttccaggct   27960
gcagaggcta aagcagctac tcttctcttt tacagcatgg taaattgaat catgcctcgc   28020
attttcatct acttgtctct ccttccactt tttctgggct cttctacatt ggccgctgtg   28080
tcccacatcg aggtagactg cctcacgccc ttcacagtct acctgctttt cggcttttgtc   28140
atctgcacct ttgtctgcag cgttatcact gtagtgatct gcttcataca gtgcatcgac   28200
tacgtctgcg tgcgggtggc ttactttaga caccaccccc agtatcgcaa cagggacata   28260
gcggctctcc taagacttgt ttaaaatcat ggccaaatta actgtgattg gtcttctgat   28320
catctgctgc gtcctagccg cgattgggac tcaagctcct accaccacca gcgctcccag   28380
aaagagacat gtatcctgca gcttcaagcg tccctggaat ataccccaat gctttactga   28440
tgaacctgaa atctctttgg cttggtactt cagcgtcacc gccccttctta tcttctgcag   28500
tacggttatt gccccttgcca tctacccctc ccttgacctg gctggaatg ctgtcaactc   28560
tatggaatat cccaccttcc cagaaccaga cctgccagac ctggttgttc taaacgcgtt   28620
tcctcctcct gctcccgttc aaaatcagtt tcgccctccg tccccacgc ccactgaggt   28680
cagctacttt aatctaacag gcggagatga ctgaaaacct agacctagaa atggacggtc   28740
tctgcagcga gcaacgcaca ctagagaggc gccggcaaaa agagctcgag cgtcttaaac   28800
aagagctcca agacgcggtg gccatacacc agtgcaaaaa aggtgtcttc tgtctggtaa   28860
aacaggccac gctcacctat gaaaaaacag gtgacaccca ccgcctagga tacaagctgc   28920
ccacacagcg ccagaagttc gccctcatga taggcgaaca acccatcacc gtgacccagc   28980
actccgtgga gacagaaggc tgcatacacg ctccctgtag gggcgctgac tgcctctaca   29040
ccttgatcaa aacccctgc ggtctcagag acctcatccc ttttaattaa tcataactgt   29100
aatcaataaa aaatcactta cttgaaatct gatagcaagc ctctgtccaa ttttttcagc   29160
aacacttcct tcccctcctc ccaactctgg tactctaggc gcctcctagc tgcaaacttc   29220
```

```
ctccacagtc tgaagggaat gtcagattcc tcctcctgtc cctccgcacc cacgatcttc   29280
atgttgttgc agatgaaacg cgcgagatcg tctgacgaga ccttcaaccc cgtgtacccc   29340
tacgataccg agatcgctcc gacttctgtc cctttcctta cccctcccct tgtgtcatcc   29400
gcaggaatgc aagaaaatcc agctggggtg ctgtccctgc acttgtcaga gccccttacc   29460
acccacaatg gggccctgac tctaaaaatg ggggcggcc tgaccctgga caaggaaggg    29520
aatctcactt cccaaaacat caccagtgtc gatccccctc tcaaaaaaag caagaacaac   29580
atcagccttc agaccgccgc acccctcgcc gtcagctccg ggccctaac acttttttgcc   29640 actccccccc tagcggtcag tgtgacaac cttactgtgc agtctcaggc ccctctcact    29700
ttggaagact caaaactaac tctggccacc aaaggacccc taactgtgtc cgaaggcaaa   29760
cttgtcctag aaacagaggc tcccctgcat gcaagtgaca gcagcagcct gggccttagc   29820
gttacggccc cacttagcat taacaatgac agcctaggac tagacatgca agcgcccatt   29880
agctctcgag atggaaaact ggctctaaca gtggcggccc ccctaactgt ggtcgagggt   29940
atcaatgctt tggcagtagc cacaggtaag ggtattgggc taaatgaaac caacacacac   30000
ctgcaggcaa aactggtcgc acccctaggc tttgatacca acggcaacat taagctaagc   30060
gttgcaggag gcatgaggct aaacaataac acactgatac tagatgtaaa ctacccattt   30120
gaggctcaag gccaactgag cctaagagtg ggctcgggcc cactatatgt agattctagt   30180
agtcataacc taaccattag atgccttagg ggattgtata aacatcttc taacaaccaa    30240 aacggtctag aagccaacat taaactaaca agaggccttg tgtatgacgg aaatgccata   30300
gcagttaatg ttggcaaagg gctggaatac agccctactg acacaacaga aaaacctata   30360
cagactaaaa taggtctagg catggagtat gataccgagg gagccatgat gacaaaacta   30420
ggctctggac taagctttga caattcagga gccattgtag tgggaaacaa aaatgatgac   30480
aggcttactt tgtggaccac accggaccca tcgcccaact gtcagatcta ctctgaaaaa   30540
gatgctaaac taaccttggt actgactaaa tgtggcagtc aggttgtagg cacagtatct   30600
attgccgctc ttaaaggtag cctcgtgcca atcactagtg caatcagtgt ggttcaggta   30660
tacctaaggt ttgatgaaaa tggggtacta atgagtaact cttcacttaa tggcgaatac   30720
tggaatttta gaaacggaga ctcaactaat ggcacaccat atacaaacgc agtgggtttc   30780
atgcctaatc tactggccta tcctaaaggt caaactacaa ctgcaaaaag taacattgtc   30840
agccaggtct acatgaatgg ggacgatact aaacccatga catttacaat caacttcaat   30900
ggccttagtg aaacaggga taccctgtt agtaaatatt ccatgacatt ctcatggagg    30960
tggccaaatg gaagctacat agggcacaat tttgtaacaa actcctttac cttctcctac   31020
atcgcccaag aataaagaaa gcacagagat gcttgttttt gatttcaaaa ttgtgtgctt   31080
ttatttattt tcagcttaca gtatttccag tagtcattca aataaagctt aatcaaactg   31140
catgagaacc cttccacata gcttaaatta gcaccagtgc aaatggagaa aaatcaacat   31200 acctttttttt atccagatat cagagaactc tagtggtcag ttttcccca ccctcccagc    31260 tcacagaata cacagtcctt tccccccggc tggctttaaa caacactatc tcattggtaa   31320
cagacatatt cttaggtgta ataatccaca cggtctcttg gcgggccaaa cgctggtcgg   31380
tgatgttaat aaactcccca ggcagctctt tcaagttcac gtcgctgtcc aactgctgaa   31440
gcgctcgcgg ctccgactgc gcctctagcg gaggcaacgg caaacccga tccttgatca    31500 aagggaggta acggtccct cgtgtaggga cagtggcggg ataatcgaga tcgtgttgaa    31560
```

| | |
|---|---|
| cgtagagtca tgccaaaggg aacagcggac gtactcatat ttcctccagc agaaccaagt | 31620 |
| gcgcgcgtgg cagctatccc tgcgtcttct gtctcgccgc ctgccccgtt cggtgtagta | 31680 |
| gttgtaatac agccactccc tgagaccgtc aaggcgctcc ctggcgtccg gatctatgac | 31740 |
| aacaccgtcc tgcagcgccg ccctgatgac atccaccacc gtagagtatg ccaagcccag | 31800 |
| ccaggaaatg cattcacttt gacagcgaga gataggagga gcggggagag atggaagaac | 31860 |
| catgatagta aagagaactt ttattccaat cgatcttcta agatatcaaa gtggagatct | 31920 |
| ataagatgac actggtctta tcctccgctg agtcgatcaa aaataacagc taaaccacaa | 31980 |
| acaacacgat tggtcaaatg ctccacaagg gttacctgca gcagaaaatt gcctcggaac | 32040 |
| tccaccgcaa gcagaacagc aaagccaccg cctctatcgt gatcaagaat aaaaacccca | 32100 |
| cagctatcca cttacagacc cagatagttt tcagctctcc atcgtgaaaa agatttaca | 32160 |
| agctcctcct ttaaatcacc tccaaccaat tgaaaaagtt gaaccagacc gccctccacc | 32220 |
| ttcagtttca gcaagcgttt aattatgatt gcaaaaattc aggctcctca gacacctgta | 32280 |
| taagattgag aagcggaacg ttaacatcga tgtttcgctc gcgtaaatca cgcctcagtg | 32340 |
| caagcataat ataatcccac aggtcggagc ggatcagcga ggacacctcc ccgccaggaa | 32400 |
| ccaactcaac ggagcctatg ctgattataa tacgcatatt cggagctatg ctaaccagca | 32460 |
| cggcccccaa ataggcgtac tgcataggcg gcgacaaaaa gtgaacagtt tgggttaaaa | 32520 |
| aatcaggcaa acactcgcgc aaaaaagcaa gaacatcata accatgctca tgcaaataga | 32580 |
| tgcaagtaag ctcaggaaca accacagaaa aatgcacaat ttttctctca aacatgactg | 32640 |
| cgagccctgc aaaaaataaa aagaaacat tacacaagag tagcctgtct tacgatggga | 32700 |
| tagactactc taaccaacat aagacgggcc acaacatcgc ccgcgtggcc ataaaaaaaa | 32760 |
| ttgtccgtgt gattaaaaag aagcacagat agctggccag tcatatccgg agtcatcacg | 32820 |
| tgtgaacccg tgtagacccc cgggttggac acatcggcca agaaagaaa gcggccaatg | 32880 |
| tacccaggag gaattataac actaagacga agatacaaca gaataacccc atgaggggga | 32940 |
| ataacaaagt tagtaggtga ataaaaacga taaacacccg aaactccctc ctgcgtaggc | 33000 |
| aaaatagcac cctccccttc caaaacaaca tatagcgctt ccacagcagc catgacaaaa | 33060 |
| gactcaaaac actcaaaaga ctcagtctta ccaggaaaat aaaagcactc tcacagcacc | 33120 |
| agcactaatc agagtgtgaa gagggccaag tgccgaacga gtatatatag gaataaaaaa | 33180 |
| tgacgtaaat gtgtaaaggt cagaaaacgc ccagaaaaat acacagacca acgcccgaaa | 33240 |
| cgaaaacccg cgaaaaaata cccagaactt cctcaacaac cgccacttcc gctttctcac | 33300 |
| ggtacgtcac ttccgcaaga aaagcaaaac tacatttccc acatgtgtaa aaacgaaacc | 33360 |
| ccgccccttg taaccgccca caacttacat catcaaaacg taaactccta cgtcacccgc | 33420 |
| cccgcctctc cccgcccacc tcattatcat attggccaca atccaaaata aggtatatta | 33480 |
| ttgatgatg | 33489 |

<210> SEQ ID NO 28
<211> LENGTH: 33485
<212> TYPE: DNA
<213> ORGANISM: Gorilla beringei graueri

<400> SEQUENCE: 28

| | |
|---|---|
| catcatcaat aatataccttt attttggatt gtggccaata tgataatgag gtgggcgggg | 60 |
| agaggcgggg cgggtgacgt aggacgcgcg agtaggggttg ggaggtgtgg cggaagtgtg | 120 |
| gcatttgcaa gtgggaggag ctcacatgca agcttccgtc gcggaaaatg tgacgttttt | 180 |

| | |
|---|---|
| gatgagcgcc gcctacctcc ggaagtgcca attttcgcgc gcttttcacc ggatatcgta | 240 |
| gtaattttgg gcgggaccat gtaagatttg gccattttcg cgcgaaaagt gaaacgggga | 300 |
| agtgaaaact gaataatagg gcgttagtca tagtgcgtaa tatttaccga gggccgaggg | 360 |
| actttgaccg attacgtgga ggactcgccc aggtgttttt tacgtgaatt ccgcgttcc | 420 |
| gggtcaaagt ctccgtttta ttgtcaccgt catttgacag gcctgaccat ctggtgctgg | 480 |
| cctgcaccag ggccgagttt gggtctagcg atgaggatac cgattgaggt gggtaaggtg | 540 |
| ggcgtggcta aagggtggg gcgtgtataa attggggtc taagggtctc tctgttttgt | 600 |
| cttgcaacag ccgccgccat gagcgacacc ggcaacagct ttgatggaag catctttagc | 660 |
| ccctatctga cagtgcgcat gcctcactgg gctggagtgc gtcagaatgt gatgggttcc | 720 |
| aacgtggatg gacgcccgt tctgccttca aattcgtcta caatggccta cgcgaccgtg | 780 |
| ggaggaactc cgctggacgc cgcgacctcc gccgccgcct ccgccgccgc cgcgaccgcg | 840 |
| cgcagcatgg ctacggacct ttacagtctc ttggtggcga gcggcgcggc ctctcgcgcg | 900 |
| tctgctcggg atgagaaact gaccgctctg ctgcttaaac tggaagactt gacccgggag | 960 |
| ctggctcaac tgacccagca ggtctccagc ttgcgtgaga gcagccttgc ctccccctaa | 1020 |
| tggcccataa tataaataaa agccagtctg tttggattaa gcaagtgtat gttctttatt | 1080 |
| taactctccg cgcgcggtaa gcccgggacc agcggtctcg gtcgtttagg gtgcggtgga | 1140 |
| ttctttccaa cacgtggtac aggtggctct ggatgtttag atacatgggc atgagtccat | 1200 |
| ccctggggtg gaggtagcac cactgcagag cttcgtgctc gggggtggtg ttgtatatga | 1260 |
| tccagtcgta gcaggagcgc tgggcgtggt gctgaaaaat gtccttaagc aagaggctta | 1320 |
| tagctagggg gaggcccttg gtgtaagtgt ttacaaatct gctcagttgg gaggggtgca | 1380 |
| tccggggga tataatgtgc atcttggact ggattttttag gttggctatg ttcccaccca | 1440 |
| gatcccttct gggattcatg ttgtgcagga ccaccagcac ggtatatcca gtacacttgg | 1500 |
| gaaatttatc gtggagctta gacgggaatg catggaagaa cttggagacg cccttgtggc | 1560 |
| ctcccagatt ttccatacat tcgtccatga tgatggcaat gggcccgtgg aagctgcct | 1620 |
| gagcaaaaat gtttctggga tcgctcacat cgtagttatg ttccagggtg aggtcatcat | 1680 |
| aggacatctt tacaaatcgg gggcggaggg tcccggactg ggggatgatg gtgccctcgg | 1740 |
| gccccggggc gtagttcccc tcacagatct gcatctccca ggctttcatt tcagagggag | 1800 |
| ggatcatatc cacctgcgga gcgatgaaaa acacagtttc tggcgcaggg gagattaact | 1860 |
| gggatgagag caggttctg agcagctgtg actttccaca gccggtgggc ccatatatca | 1920 |
| cgcctatcac cggctgcagc tggtagttaa gagagctgca gctgccgtcc tcccggagca | 1980 |
| gggggggccac ctcgttcagc atatccctga cgtggatgtt ctccctgacc aattccgcca | 2040 |
| gaaggcgctc gccgcccagc gaaagcagct cttgcaagga agcaaaattt ttcagcggtt | 2100 |
| ttaggccgtc ggccgtgggc atgttttca gcgtctgggt cagcagttcc agtctgtccc | 2160 |
| acagctcggt gatgtgctct acggcatctc gatccagcag atctcctcgt ttcgcgggtt | 2220 |
| ggggcggctt tcgctgtagg gcaccagccg atgggcgtcc agcggggcca gagtcatgtc | 2280 |
| cttccatggg cgcagggtcc tcgtcagggt ggtctgggtc acgtgaagg ggtgcgctcc | 2340 |
| gggttgggcg ctggccaggg tgcgcttgag gctggttctg ctggtgctga atcgctgccg | 2400 |
| ctcttcgccc tgcgcgtcgg ccaggtagca tttgaccatg gtctcgtagt cgagaccctc | 2460 |
| ggcggcgtgc cccttggcgc ggagctttcc cttggaggtg gcgccgcacg aggggcactg | 2520 |

```
caggctcttc agggcgtaga gcttgggagc gagaaacacg gactctgggg agtaggcgtc    2580
cgcgccgcag gaagcgcaga ccgtctcgca ttccaccagc caagtgagct ccgggcggtc    2640
agggtcaaaa accaggttgc ccccatgctt tttgatgcgt ttcttacctc ggctctccat    2700
gaggcggtgt cccttctcgg tgacgaagag gctgtccgtg tctccgtaga ccgacttcag    2760
gggcctgtct tccagcggag tgcctctgtc ctcctcgtag agaaactctg accactctga    2820
gacgaaggcc cgcgtccagg ccaggacgaa ggaggccacg tgggagggggt agcggtcgtt   2880
gtccactagc gggtccacct tctccagggt gtgcaggcac atgtccccct cctccgcgtc    2940
cagaaaagtg attggcttgt aggtgtagga cacgtgaccg ggggttcccg acgggggggt    3000
ataaaagggg gtgggcaccc tttcatcttc actctcttcc gcatcgctgt ctgcgagagc    3060
cagctgctgg ggtaagtatt ccctctcgaa ggcgggcatg acctcagcgc tcaggttgtc    3120
agtttctaaa aatgaggagg atttgatgtt cacctgtccg gaggtgatac ctttgagggt    3180
acctgggtcc atctggtcag aaaacactat tttttttgttg tcaagcttgg tggcgaacga    3240
cccgtagagg gcgttggaga gcagcttggc gatggagcgc agggtctggt ttttgtcgcg    3300
gtcggctcgc tccttggccg cgatgttgag ttgcacgtac tcgcgggcca cgcacttcca    3360
ctcggggaag acgtggtgc gctcgtctgg gatcaggcgc accctccagc ctcggttgtg     3420
cagggtgacc atgtcgacgc tggtggcgac ctcgccgcgc aggcgctcgt tggtccagca    3480
gaggcggccg cccttgcgcg agcagaaggg gggtaggggg tccagctggt cctcgtttgg    3540
ggggtccgcg tcgatggtga agaccccggg gagcaagcgc gggtcaaagt agtcgatctt    3600
gcaagcttgc atgtccagag cccgctgcca ttcgcgggcg gcgagcgcgc gctcgtaggg    3660
gttgaggggc gggccccagg gcatgggggtg ggtgagcgcg gaggcgtaca tgccgcagat   3720
gtcatacacg tacaggggtt ccctgaggat gccgaggtag gtggggtagc agcgcccccc    3780
gcggatgctg gcgcgcacgt agtcatagag ctcgtgggag ggggccagca tgttgggccc    3840
gaggttggtg cgctggggggc gctcggcgcg gaaggcgatc tgcctgaaga tggcatggga    3900
gttggaggag atggtgggcc gctggaagac gttgaagctt gcttcttgca agcccaccga    3960
gtccctgacg aagcaggcgt aggactcgcg cagcttgtgc accagctcgg cggtgacctg    4020
gacgtcgagc gcgcagtagt cgagggtctc gcggatgatg tcatacttat cctcccccctt    4080
ctttttccac agctcgcggt tgaggacgaa ctcttcgcgg tctttccagt actcttggag    4140
gggaaacccg tccgtgtccg aacggtaaga gcctagcatg tagaactggt tgacggcctg    4200
gtagggggcaa cagcccttct ccacgggcag cgcgtaggcc tgcgccgcct tgcggaggga    4260
ggtgtgggtg agggcgaaag tgtccctgac catgactttg aggtattgat gtttgaagtc    4320
tgtgtcatcg cagccgccct gttcccacag ggtgtagtcc gtgcgctttt tggagcgcgg    4380
gttgggcagg gagaaggtga ggtcattgaa gaggatcttc cccgctcgag gcatgaagtt    4440
tctggtgatg cgaaagggcc ctgggaccga ggagcggttg ttgatgacct gggcggccag    4500
gacgatctcg tcaaagccgt ttatgttgtg gcccacgatg tagagctcca aaaagcgggg    4560
ctggcccttg atggagggga gcttttttgag ttcctcgtag gtgagctcct cgggcgattc    4620
caggccgtgc tcctccaggg cccagtcttg caagtgaggg ttggccgcca ggaaggatcg    4680
ccagaggtcg cgggccatga gggtctgcag gcggtcgcgg aaggttctga actgtcgccc    4740
cacggccatc ttttcggggg tgatgcagta gaaggtgagg gggtctttct cccagggggtc    4800
ccatctgagc tctcgggcga ggtcgcgcgc ggcggcgacc agagcctcgt tgcccccccag    4860
tttcatgacc agcatgaagg gcacgagctg cttgccaaag gctcccatcc aagtgtaggt     4920
```

```
ctctacatcg taggtgacaa agaggcgctc cgtgcgagga tgagagccga tcgggaagaa    4980
ctggatctcc cgccaccagt tggaggattg gctgttgatg tggtgaaagt agaagtcccg    5040
tctgcgggcc gagcactcgt gctggctttt gtaaaagcga ccgcagtact ggcagcgctg    5100
cacgggttgt atatcttgca cgaggtgaac ctggcgacct ctgacgagga agcgcagcgg    5160
gaatctaagt cccccgcctg gggtcccgtg tggctggtgg tcttctactt tggttgtctg    5220
gccgccagca tctgtctcct ggagggcgat ggtggagcag accaccacgc cgcgagagcc    5280
gcaggtccag atctcggcgc tcggcgggcg agtttgatg acgacatcgc gcacattgga    5340
gctgtccatg gtctccagct cccgcggcgg caggtcagct gggagttcct ggaggttcac    5400
ctcgcagaga cgggtcaagg cgcgggcagt gttgagatgg tatctgattt caaggggcgt    5460
gttggcggcg gagtcgatgg cttgcaggag gccgcagccc cggggggcca cgatggttcc    5520
ccgcggggcg cgaggggagg cggaagctgg gggtgtgttc agaagcggtg acgcgggcgg    5580
gcccccggag gtaggggggg ttccggcccc acaggcatgg gcggcagggg cacgtcttcg    5640
ccgcgcgcgg gcaggggctg gtgctggctc cgaagagcgc ttgcgtgcgc gacgacgcga    5700
cggttggtgt cctgtatctg acgcctctga gtgaagacca cgggtcccgt gacctgaac     5760
ctgaaagaga gttcgacaga atcaatctcg gcatcgttga cagcggcctg gcgcaggatc    5820
tcctgcacgt cgcccgagtt gtcctggtag gcgatctctg ccatgaactg ctcgatctct    5880
tcttcctgga gatctcctcg tccggcgcgc tccacggtgg ccgccaggtc gttggagatg    5940
cgacccatga gctgcgagaa ggcgttgagc ccgccctcgt tccagacccg gctgtagacc    6000
acgcccccct cggcgttgcg ggcgcgcatg accacctggg ccaggttgag ctccacgtgt    6060
cgcgtgaaga cggcgtagtt gcgcaggcgc tggaaaaggt agttcagggt ggtggcggtg    6120
tgctcggcga cgaagaagta catgacccag cgccgcaacg tggattcatt gatgtccccc    6180
aaggcctcca ggcgctccat ggcctcgtag aagtccacgg cgaagttgaa aaactgggag    6240
ttgcgagcgg acacggtcaa ctcctcctcc agaagacgga tgagctcggc gacagtgtcg    6300
cgcacctcgc gctcgaaggc cacgggggc gcttcttcct cttccacctc ttcttccatg     6360
atcgcttctt cttcttcctc agccgggacg ggagggggcg gcggcggcgg gggaggggcg    6420
cggcggcggc ggcggcgcac cgggaggcgg tcgatgaagc gctcgatcat ctcccccgc     6480
atgcggcgca tggtctcggt gacggcgcgg ccgttctccc gggggcgcag ctcgaagacg    6540
ccgcctctca tctcgccgcg gggcgggcgg ccgtgaggta gcgagacggc gctgactatg    6600
catcttaaca attgctgtgt aggtacaccg ccgagggacc tgattgagtc cagatccacc    6660
ggatccgaaa acctttggag gaaagcgtct atccagtcgc agtcgcaagg taggctgagc    6720
accgtggcgg gcggggcgg gtctggagag ttcctggcgg agatgctgct gatgatgtaa     6780
ttaaagtagg cggtcttgag aaggcggatg gtggacagga gcaccatgtc tttgggtccg    6840
gcctgttgga tgcggaggcg gtcggccatg ccccaggcct cgttctgaca ccggcgcagg    6900
tctttgtagt agtcttgcat gagtctttcc accggcacct cttctccttc ctcttctcca    6960
tctcgccggt ggtttctcgc gccgccatg cgcgtgaccc caaagcccct gagcggctgc     7020
agcagggcca ggtcggcgac cacgcgctcg gccaagatgg cctgctgcac ctgagtgagg    7080
gtcctctcga agtcatccat gtccacgaag cggtggtagg cgccgtgtt gatggtgtag     7140
gtgcagttgg ccatgacgga ccagttgacg gtctggtgtc ccggctgcga gagctccgtg    7200
taccgcaggc gcgagaaggc gcgggaatcg aacacgtagt cgttgcaagt ccgcaccaga    7260
```

```
tactggtagc ccaccaggaa gtgcggcgga ggttggcgat agaggggcca gcgctgggtg      7320
gcggggcgc cgggcgccag gttttccagc atgaggcggt ggtatccgta gatgtacctg       7380
gacatccagg tgatgccggc ggcggtggtg gtggcgcgcg cgtagtcgcg gacccggttc      7440
cagatgtttc gcaggggcga gaagtgttcc atggtcggca cgctctggcc ggtgaggcgc      7500
gcgcagtcgt tgacgctcta tacacacaca aaaacgaaag cgtttacagg gctttcgttc     7560
tgtagcctgg aggaaagtaa atgggttggg ttgcggtgtg ccccggttcg agaccaagct     7620
gagctcggcc ggctgaagcc gcagctaacg tggtattggc agtcccgtct cgacccaggc     7680
cctgtatcct ccaggatacg gtcgagagcc cttttgcttt cttggccaag cgcccgtggc    7740
gcgatctggg atagatggtc gcgatgagag gacaaagcg gctcgcttcc gtagtctgga      7800
gaaacaatcg ccagggttgc gttgcggcgt accccggttc gagcccctat ggcggcttga    7860
atcggccgga accgcggcta acgagggccg tggcagcccc gtcctcagga ccccgccagc    7920
cgacttctcc agttacggga gcgagcccct tttgttttt attttttaga tgcatcccgt       7980
gctgcggcag atgcgcccct cgccccggcc cgatcagcag cagcaacagc aggcatgcag      8040
accccctct ccccttttccg ccccggtcac cacggccgcg gcggccgtgt cgggcgcggg      8100
gggcgcgctg gagtcagatg agccaccgcg gcggcgacct aggcagtatc tggacttgga    8160
agagggcgag ggactggcgc ggctgggggc gaactctcca gagcgccacc cgcgggtgca    8220
gttgaaaagg gacgcgcgcg aggcgtacct gccgcggcag aacctgtttc gcgaccgcgg    8280
gggcgaggag cccgaggaga tgcgagactg caggttccaa gcggggcgcg agctgcggcg    8340
cgggctggac agacagcgcc tgctgcgcga ggaggacttt gagcccgaca cgcagacggg    8400
catcagcccc gcgcgcgcgc acgtagccgc ggccgacctg gtgaccgcct acgagcagac     8460
ggtgaaccag gagcgcaact tccaaaagag cttcaacaac cacgtgcgca cgctggtggc    8520
gcgcgaggag gtgaccctgg gtctcatgca tctgtgggac ctggtggagg cgatcgtgca    8580
gaaccccagc agcaagcccc tgaccgcgca gctgttcctg gtggtgcagc acagcaggga    8640
caacgaggcc ttcagggagg cgctgctgaa catcaccgag ccggaggggc gctggctcct    8700
ggacctgata aacatcctgc agagcatagt ggtgcaggag cgcagcctga gcctggccga    8760
gaaggtggcg gccatcaact actctatgct gagcctgggc aagttctacg cccgcaagat    8820
ctacaagacc ccctacgtgc ccatagacaa ggaggtgaag atagacagct tctacatgcg    8880
catggcgctg aaggtgctga ccctgagcga cgacctggga gtgtaccgca acgagcgcat    8940
ccacaaggcc gtgagcgcca gccggcgcg cgagctgagc gaccgcgagc tgatgcacag     9000
tctgcagcgc gcgctgaccg gcgcgggcga gggcgacagg gaggtcgagt cctacttcga    9060
catgggggcc gacctgcact ggcagccgag ccgccgcgcc ctggaggcgg cggggcgta     9120
cggcggcccc ctggcggccg atgaccagga agaggaggac tatgagctag gaggggcga    9180
gtacctggag gactgacctg gctggtggtg ttttggtata gatgcaagat ccgaacgtgg    9240
cggacccggc ggtccgggcg gcgctgcaaa gccagccgtc cggcattaac tcctctgacg    9300
actgggccgc ggccatgggt cgcatcatgg ccctgaccgc gcgcaacccc gaggctttca    9360
ggcagcagcc tcaggccaac cggctggcgg ccatcttgga agcggtagtg cccgcgcgct     9420
ccaacccac ccacgagaag gtgctggcca tagtcaacgc gctggcggag agcagggcca    9480
tccgcgcgga cgaggccgga ctggtgtacg atgcgctgct gcagcggggtg gcgcggtaca     9540
acagcggcaa cgtgcagacc aacctggacc gcctggtgac ggacgtgcgc gaggccgtgg    9600
cgcagcgcga gcgcttgcat caggacggta acctgggctc gctggtggcg ctaaacgcct    9660
```

```
tcctcagcac ccagccggcc aacgtaccgc gggggcagga ggactacacc aacttttttga   9720
gcgcgctgcg gctgatggtg accgaggtcc ctcagagcga ggtgtaccag tcggggcccg   9780
actacttctt ccagaccagc agacagggct tgcaaaccgt gaacctgagc caggctttca   9840
agaacctgcg ggggctgtgg ggagtgaagg cgcccaccgg cgaccgggct acggtgtcca   9900
gcctgctaac ccccaactcg cgcctgctgc tgctgctgat cgcgcccttc acggacagcg   9960
ggagcgtctc gcgggagacc tatctgggcc acctgctgac gctgtaccgc gaggccatcg  10020
ggcaggcgca ggtggacgag cacaccttcc aagagatcac cagcgtgagc cacgcgctgg  10080
ggcaggagga cacgggcagc ctgcaggcga ccctgaacta cctgctgacc aacaggcggc  10140
agaagattcc cacgctgcac agcctgaccc aggaggagga gcgcatcttg cgctacgtgc  10200
agcagagcgt gagcctgaac ctgatgcgcg acggcgtgac gcccagcgtg gcgctggaca  10260
tgaccgcgcg caacatggaa ccgggcatgt acgcctccca ccggccgttc atcaaccgcc  10320
tgatggacta cttgcatcgg gcggcggccg tgaaccccga gtacttcact aatgccattc  10380
tgaatcccca ctggatgccc cctccgggtt tctacaacgg ggactttgag gtgcccgagg  10440
tcaacgacgg gttcctctgg gatgacatgg atgacagtgt gttctcaccc aacccgctgc  10500
gcgccgcgtc tctgcgattg aaggagggct ctgacaggga aggaccgaga agtctggcct  10560
cctccctggc tctgggagcg gtgggcgcca cgggcgcggc ggcgcggggc agtagcccct  10620
tccccagcct ggcagactct ctgaacagcg ggcgggtgag caggccccgc ttgctaggcg  10680
aggaggagta tctgaacaac tccctgctgc agcccgcgag ggacaagaac gctcagcggc  10740
agcagtttcc caacaatggg atagagagcc tggtggacaa gatgtccaga tggaagacgt  10800
atgcgcagga gtacaaggag tgggaggacc gccagccgcg gcccttgccg cccccctaggc  10860
agcgctggca gcggcgcgcg tccaaccgcc gctggaggca ggggcccgag gacgatgatg  10920
actctgcaga tgacagcagc gtgttggacc tgggcgggag cgggaacccc ttttcgcacc  10980
tgcgcccacg cctgggcaag atgttttaaa agaaaaaaaa aaaataaaac tcaccaaggc  11040
catggcgacg agcgttggtt ttttgttccc ttccttagta tgcggcgcgc ggcgatgttc  11100
gaggaggggc ctcccccctc ttacgagagc gcgatgggga tttctcctgc ggcgcccctg  11160
cagcctccct acgtgcctcc tcggtacctg caacctacag gggggagaaa tagcatctgt  11220
tactctgagc tgcagcccct gtacgatacc accagactgt acctggtgga caacaagtcc  11280
gcggacgtgg cctccctgaa ctaccagaac gaccacagcg atttttttgac cacggtgatc  11340
caaaacaacg acttcacccc aaccgaggcc agcactcaga ccataaacct ggataacagg  11400
tcgaactggg gcggcgacct gaagaccatc ttgcacacca acatgcccaa cgtgaacgag  11460
ttcatgttca ccaactcttt taaggcgcgg gtgatggtgg cgcgcgagca gggggaggcg  11520
aagtacgagt gggtggactt cacgctgccc gagggcaact actcagagac catgactctc  11580
gacctgatga caatgcgat cgtgaacac tatctgaaag tgggcaggca gaacggggtg  11640
aaggaaagcg atatcggggt caagtttgac accagaaact tccgtctggg ctgggacccc  11700
gtgaccgggc tggtcatgcc gggggtctac accaacgagg cctttcatcc cgacatagtg  11760
cttctgcccg gctgtggggt ggacttcacc cagagccggc tgagcaacct gctgggcatt  11820
cgcaagcggc agccttttcca ggagggtttc aagatcacct atgaggatct gaaggggggc  11880
aacattcccg cgctccttga tctgacgcc tacgaggaga gcttgaaacc cgaggagagc  11940
gctggcgaca gcggcgagag tggcgaggag caagccggcg gcggtggcgg cgcgtcggta  12000
```

```
gaaaacgaaa gtacgcccgc agtggcggcg gacgctgcgg aggtcgagcc ggaggccatg   12060
cagcaggacg cagaggaggg cgcacaggag ggcgcgcaga aggacatgaa cgatggggag   12120
atcaggggag acacattcgc cacccggggc gaagaaaaag aggcagaggc ggcggcggcg   12180 gcgacggcg  aggccgaaac cgaggttgag gcagaggcag agcccgagac cgaagttatg   12240
gaagacatga atgatggaga acgtaggggc gacacgttcg ccacccgggg cgaagagaag   12300
gcggcggagg cagaagccgc ggctgaggag gcggctgcgg ctgcggccaa gactgaggct   12360
gcggctaagg ctgaggtcga agccaatgtt gcggttgagg ctcaggctga ggaggaggcg   12420
gcggctgaag cagttaagga aaaggcccag gcagagcagg aagagaaaaa acctgtcatt   12480
caacctctaa aagaagatag caaaaagcgc agttacaacg tcatcgaggg cagcaccttt   12540
acccagtacc gcagctggta cctggcgtac aactacggcg acccggtcaa gggggtgcgc   12600
tcgtggaccc tgctctgcac gccggacgtc acctgcggct ccgagcagat gtactggtcg   12660
ctgccgaaca tgatgcaaga cccggtgacc ttccgctcca cgcggcaggt tagcaacttc   12720
ccggtggtgg gcgccgaact gctgcccgtg cactccaaga gttttacaa cgagcaggcc   12780 gtctactccc agctgatccg ccaggccacc tctctgaccc acgtgttcaa tcgctttccc   12840
gagaaccaga ttttggcgcg cccgccgcc  cccaccatca ccaccgtgag tgaaaacgtt   12900
cctgccctca cagatcacgg gacgctaccg ctgcgcaaca gcatctcagg agtccagcga   12960
gtgaccatta ctgacgccag acgccggacc tgccctacg tttacaaggc cttgggcata   13020
gtctcgccgc gcgtcctctc cagtcgcact ttttaaaaca catctaccca cacgttccaa   13080
aatcatgtcc gtactcatct cacccagcaa caacaccggc tgggggctgc gcgcgcccag   13140
caagatgttt ggaggggcga ggaagcgctc cgaccagcac cctgtgcgcg tgcgcggcca   13200
ctaccgcgcg ccctggggag cgcacaagcg cgggcgcaca gggcgcacca ctgtggacga   13260
cgtcattgac tccgtagtgg agcaagcgcg ccactacaca cccggcgcgc cgaccgcccc   13320
cgccgtgtcc accgtggacc aggcgatcga aagcgtggta cagggcgcgc ggcactatgc   13380
caaccttaaa agtcgccgcc gccgcgtggc ccgccgccat cgccggagac cccgggccac   13440
cgccgccgcg cgccttacta aggctctgct caggcgcgcc aggcgaactg gccaccgggc   13500
cgccatgagg gccgcacggc gggctgccgc tgccgcaagc gccgtggccc cgcgggcacg   13560
aaggcgcgcg gccgccgccg ccgccgccgc catttccagc ttggcctcga cgcggcgcgg   13620
taacatatac tgggtgcgcg actcggtaac cggcacgcgg gtacccgtgc gctttcgccc   13680
cccgcggaat tagcacaaga caacatacac actgagtctc ctgctgttgt gtatcccagc   13740
ggcgaccgtc agcagcggcg acatgtccaa gcgcaaaatt aaagaagaga tgctccaggt   13800
catcgcgccg gagatctatg gccccccgaa gaaggaggag gatgattaca agccccgcaa   13860
gctaaagcgg gtcaaaaaga aaagaaaga  tgatgatgat gacgaggcgg tggagtttgt   13920
ccgccgcatg gcacccaggc gcccgtgca  gtggaagggc cggcgcgtgc agcgcgtttt   13980
gcgccccggc accgcggtgg tcttcacgcc cggcgagcgc tccacgcgca ctttcaagcg   14040
ggtgtacgat gaggtgtacg gcgacgagga cctgttggag caggccaacc agcgctttgg   14100
ggagtttgca tatgggaaac ggccccgcga gagtctaaaa gaggacctgc tggcgctacc   14160
gctggacgag ggcaatccca ccccgagtct gaagccggta accctgcaac aggtgctgcc   14220
tttgagcgcg cccagcgagc ataagcgagg gttgaagcgc gaaggcgggg acctggcgcc   14280
caccgtgcag ttgatggtgc ccaagcggca gaagctggag gacgtgctgg agaaaatgaa   14340
agtagagccc gggatccagc ccgagatcaa ggtccgcccc atcaagcagg tggcgcccgg   14400
```

```
cgtgggagtc cagaccgtgg acgttaggat tcccacggag gagatggaaa cccaaaccgc   14460
cactccctct tcggcggcca gcgccaccac cggcaccgct tcggtagagg tgcagacgga   14520
cccctggcta cccgccaccg ctgttgccgc cgccgccccc cgttcgcgcg ggcgcaagag   14580
aaattatcca gcgccagcg cgctcatgcc ccagtacgca ctgcatccat ccatcgcgcc    14640 caccccggc taccgcgggt actcgtaccg cccgcgcaga tcagccggca ctcgcggccg    14700
ccgccgccgt gcgaccacaa ccagccgccg ccgtcgccgc cgccgccagc cagtgctgac   14760
ccccgtgtct gtaaggaagg tggctcgctc ggggagcacg ctggtggtgc ccagagcgcg   14820
ctaccacccc agcatcgttt aaagccggtc tctgtatggt tcttgcagat atggccctca   14880
cttgtcgcct ccgcttcccg gtgccgggat accgaggaag aactcaccgc cgcagaggca   14940
tggcgggcag cggtctccgc ggcggccgtc gccatcgccg gcgcgcaaaa agcaggcgca   15000
tgcgcggcgg tgtgctgcct ctgctaatcc cgctaatcgc cgcggcgatc ggtgccgtac   15060
ccgggatcgc ctccgtggcc ctgcaggcgt cccagaaacg ttgactcttg caaccttgca   15120
agcttgcatt ttttggagga aaaataaaaa aagtctagac tctcacgctc gcttggtcct   15180
gtgactattt tgtagaaaaa agatggaaga catcaacttt gcgtcgctgg ccccgcgtca   15240
cggctcgcgc ccgttcatgg gagactggac agatatcggc accagcaata tgagcggtgg   15300
cgccttcagc tggggcagtc tgtggagcgg ccttaaaaat tttggttcca ccattaagaa   15360
ctatggcaac aaagcgtgga acagcagcac gggccagatg ctgagagaca agttgaaaga   15420
gcagaacttc caggagaagg tggcgcaggg cctggcctct ggcatcagcg gggtggtgga   15480
catagctaac caggccgtgc agaaaaagat aaacagtcat ctggaccccc gtcctcaggt   15540
ggaggaaatg cctccagcga tggagacggt gtctcccgag ggcaaaggcg aaaagcgccc   15600
gcggcccgac agagaagaga ccctggtgtc acacaccgag gagccgccct cttacgagga   15660
ggcagtcaag gccggcctgc ccaccactcg ccccatagcc cccatggcca ccggtgtggt   15720
gggccacagg caacacactc ccgcaacact agatctgccc ccgccgtccg agccgccgcg   15780
ccagccaaag gcggcgacgg tgcccgctcc ctccacttcc gccgccaaca gagtgccccct  15840 gcgccgcgcc gcgagcggcc cccgggcctc gcgagttagc ggcaactggc agagcacact   15900
gaacagcatc gtgggcctgg gagtgaggag tgtgaagcgc cgccgttgct actgaatgag   15960
caagctagct aacgtgttgt atgtgtgtat gcgtcctatg tcgccgccag aggagctgtt   16020
gagccgccgg cgccgtctgc actccagcga atttcaagat ggcgacccca tcgatgatgc   16080
ctcagtggtc gtacatgcac atctcgggcc aggacgcttc ggagtacctg agccccgggc   16140
tggtgcagtt cgcccgcgcc acagacacct acttcaacat gagtaacaag ttcaggaacc   16200
ccactgtggc gcccacccac gatgtgacca cggaccggtc gcagcgcctg acgctgcggt   16260
tcatccccgt ggatcgggag gacaccgcct actcttacaa ggcgcggttc acgctggccg   16320
tgggcgacaa ccgcgtgctg gacatggcct ccacttactt tgacatcagg ggggtgctgg   16380
acagggcccc caccttcaag ccctactcgg gtactgccta caactccctg gcccccaagg   16440
gcgctcccaa ttcttgcgag tgggaacaag aggaaaatca ggtggtcgct gcagatgatg   16500
aacttgaaga tgaagaagcg caagctcaag aggacgcccc agctaaaaaa attcatgtat   16560
atgcccaggc gcctcttgct ggcgaaaaga ttaccaagga tggtttgcaa ataggtactg   16620
aagttgtagg agatacatct aaggacactt ttgcagacaa aacattccaa cccgaacctc   16680
agataggcga gtctcagtgg aacgaggctg atgccacagt agcaggaggc agagtcttga   16740
```

```
aaaaaaccac ccctatgaga ccttgctatg gatcctatgc caggcctaca aatgccaacg   16800
ggggtcaagg aattatggtt gccaatgaac aaggagtgtt ggagtctaaa gtggagatgc   16860
aatttttttc taacactaca acccttaatg cgcgggatgg agctggcaat cccgaaccaa   16920
aggtggtgtt gtacagtgaa gatgtccact tggaatctcc tgacactcat ttgtcttaca   16980
agcccaaaaa ggatgatgtt aatgctaaaa ttatgttggg tcagcaagct atggctaaca   17040
ggcccaacct cattgctttt agagataatt tcattggact catgtactac aacagcactg   17100
gtaacatggg agtgctggcg ggtcaggcct ctcagttgaa tgccgtggtg gacctgcagg   17160
atagaaacac agaactgtca tatcagctta tgcttgattc cattggggat agatccagat   17220
acttctccat gtggaaccag gcagtggata gctatgaccc agatgtcaga atcattgaaa   17280
accatggtgt cgaggacgag ctacccaact actgcttccc tctgggcggc ataggaatta   17340
ctgatactta tcaagggatc aaaaatacca atggcaatgg tcagtggacc aaagatgatc   17400
agttcgcgga ccgtaatgaa ataggggtgg gaaacaactt cgccatggag atcaacatcc   17460
aggccaacct ctggaggaac ttcctctatg cgaacgtggg gctctacctg ccagacaagc   17520
tcaagtacaa ccccaccaac gtggacatct ctgacaaccc caacacctat gactacatga   17580
acaagcgtgt ggtggctccc ggcctggtgg actgctttgt caatgtggga gccaggtggt   17640
ccctggacta catggacaac gtcaaccccT tcaaccacca ccgcaatgcg ggtctgcgct   17700
accgctccat gatcctgggc aacgggcgct acgtgcccct tccacattcag gtgccccaga   17760
agttctttgc catcaagaac ctcctcctcc tgccgggctc ctacacttac gagtggaact   17820
tcaggaagga tgtcaacatg gtcctgcaga gctctctggg caatgacctt agggtggacg   17880
gggccagcat caagtttgac agcgtcaccc tctatgctac cttcttcccc atggctcaca   17940
acaccgcctc cacgctcgag gccatgctga ggaacgacac caacgaccag tccttcaatg   18000
actacctctc tgggccaac atgctctacc ccatccccgc caaggccacc aacgtgccca   18060
tctccattcc ctctcgcaac tgggccgcct tcagaggctg gccttttacc cgccttaaga   18120
ccaaggaaac cccctccctg gctcgggtt ttgaccccta cttttgtctac tcgggatcca   18180
tccctacct ggatggcacc ttctacctca accacacttt taagaagata tccatcatgt   18240
atgactcctc cgtcagctgg ccgggcaatg accgcctgct caccccaat gagttcgagg   18300
tcaagcgcgc cgtggacggc gagggctaca acgtggccca gtgcaacatg accaaggact   18360
ggttcctggt gcagatgctg ccaactaca acataggcta ccagggcttc tacatcccag   18420
agagctacaa ggacaggatg tactccttct tcagaaattt ccaacccatg agcaggcagg   18480
tggtggacga gaccaaatac aaggactatc aggccattgg catcactcac cagcacaaca   18540
actcgggatt cgtgggctac ctggctccca ccatgcgcga ggggcaggcc taccccgcca   18600
acttccccta cccgttgata ggcaagaccg cggtcgacag cgtcacccag aaaaagttcc   18660
tctgcgaccg cacccctctgg cgcatcccct tctctagcaa cttcatgtcc atgggtgcgc   18720
tcacggacct gggccagaac ctgctctatg ccaactccgc ccatgcgctg acatgacttt   18780
ttgaggtgga ccccatggac gagcccaccc ttctctatat tgtgtttgaa gtgttcgacg   18840
tggtcagagt gcaccagccg caccgcgtgt tcatcgagac cgtgtacctg cgcacgcct   18900
tctcggccgg caacgccacc acctaaggag acagcgccgc cgcctgcatg acgggttcca   18960
ccgagcaaga gctcagggcc atcgccagag acctggatg cggaccctat ttttggggca   19020
cctatgacaa acgcttcccg ggcttcatct cccgagacaa gctcgcctgc gccatcgtca   19080
acacggccgc gcgcgagacc gggggcgtgc actggctggc cttttggctgg gacccgcgct   19140
```

```
ccaaaacctg ctacctcttc gacccctttg gcttctccga tcagcgcctc agacagatct   19200
atgagtttga gtacgagggg ctgctgcgcc gcagcgcgct tgcctcctcg cccgaccgct   19260
gcatcaccct tgagaagtcc accgagaccg tgcaggggcc ccactcggcc gcctgcggtc   19320
tcttctgctg catgttttg cacgcctttg tgcgctggcc ccagagtccc atggatcgca   19380
accccaccat gaacttgctc aagggagtgc ccaacgccat gctccagagc cccaggtcc   19440 agcccaccct gcgccacaac caggaacagc tctaccgctt cctggagcgc cactcccct   19500 acttccgcag tcacagcgcg cacatccggg gggccacctc tttctgccac ttgcaacaaa   19560
acatgcaaga cggaaaatga tgtacagctc gcttttttaat aaatgtaaag actgtgcact   19620
ttatttatac acgggctctt tctggttatt tattcaacac cgccgtcgcc atctagaaat   19680
cgaaagggtt ctgccgcgcg tcgccgtgcg ccacgggcag agacacgttg cgatactgga   19740
agcggctcgc ccacttgaac tcgggcacca ccatgcgggg cagtggctcc tcggggaagt   19800
tctcgcccca cagggtgcgg gtcagctgca gcgcgctcag gaggtcggga gccgagatct   19860
tgaagtcgca gttggggccg gaaccctgcg cgcgcgagtt gcggtacacg gggttgcagc   19920
actggaacac cagcagggcc ggattacgca cgctggccag caggctctcg tcgctgatca   19980
tgtcgctgtc cagatcctcc gcgttgctca gggcgaatgg ggtcatcttg cagacctgcc   20040
tgcccaggaa aggcggcagc ccgggcttgc cgttgcagtc gcagcgcagg ggcatcagca   20100
ggtgcccgtg gcccgtctgc gcctgcgggt acagcgcgcg catgaaggct tcgatctgcc   20160
tgaaagccac ctgcgtcttg gctccctccg aaaagaacat cccacaggac ttgctggaga   20220
actggttcgc gggacagctg gcatcgtgca ggcagcagcg cgcgtcggtg ttggcgatct   20280
gcaccacgtt gcgaccccac cggttcttca ctatcttggc cttggaagcc tgctccttca   20340
gcgcgcgctg gccgttctcg ctggtcacat ccatctctat cacctgctcc ttgttgatca   20400
tgtttgtccc gtgcagacac ttcaggtcgc cctccgtctg ggtgcagcgg tgctcccaca   20460
gcgcgcaacc ggtgggctcc caattttgt gggtcacccc cgcgtaggcc tgcaggtagg   20520
cctgcaagaa gcgccccatc atggccacaa aggtcttctg gctcgtaaag gtcagctgca   20580
ggccgcgatg ctcttcgttc agccaggtct tgcagatggc ggccagcgcc tcggtctgct   20640
cgggcagcat cctaaaattt gtcttcaggt cgttatccac gtggtacttg tccatcatgg   20700
cgcgcgccgc ctccatgccc ttctcccagg cggacaccat gggcaggctt aggggggtta   20760
tcacttccac cggcgaggac accgtacttt cgatttcttc ttcctccccc tcttcccggc   20820
gcgcgcccac gctgctgcgc gctctcaccg cctgcaccaa ggggtcgtct tcaggcaagc   20880
gccgcaccga gcgcttgccg cccttgacct gcttaatcag caccggcggg ttgctgaagc   20940
ccaccatggt cagctccgcc tgctcttctt cgtcttcgct gtctaccact atctctgggg   21000
aagggcttct ccgctctgcg gcggtgcgct tctttttttt cttgggagca gccgtgacgg   21060
agtccgccac ggcgacggag gtcgagggcg tggggctggg ggtgcgcggt acagggcct   21120 cgtcgccctc ggactcttcc tctgactcca ggcggcggcg gagacgcttc tttgggggcg   21180
cgcgcgtcag cggcggcgga gacggggacg gggacgggga cgggacgccc tccacagggg   21240
gtggtcttcg cgcagacccg cggccgcgct cggggggtctt ttcgagctgg tcttggtccc   21300
gactggccat tgtatcctcc tcctcctagg cagagagaca taaggagtct atcatgcaag   21360
tcgagaagga ggagagctta accacccct ctgagaccgc cgatgcgccc gccgtcgccg   21420
tcgcccccgc tgccgccgac gcgcccgcca caccgagcga caccccgcg gaccccccag   21480
```

```
ccgacgcacc cctgttcgag gaagcggccg tggagcagga cccgggcttt gtctcggcag    21540
aggaggattt gcgagaggag gaggataagg agaagaagcc ctcagtgcca aaagatgata    21600
aagagcaaga cgagcacgac gcagatgcac accagggtga agtcgggcgg ggggacggag    21660
ggcatgacgg cgccgactac ctagacgaag ggaacgacgt gctcttgaag cacctgcatc    21720
gtcagtgcgc catcgtttgc gacgctctgc aggagcgcag cgaagtgccc ctcagcgtgg    21780
cggaggtcag ccacgcctac gagctcagcc tcttctcccc ccgggtgccc cccgccgcc    21840 gcgaaaacgg cacatgcgag cccaacccgc gcctcaactt ctaccccgcc tttgtggtgc    21900
ccgaggtcct ggccacctat cacatcttct ttcaaaattg caagatcccc ctctcgtgcc    21960
gcgccaaccg tagccgcgcc gataagatgc tggccctgcg ccagggcgac cacatacctg    22020
atatcgccgc tttggaagat gtgccaaaga tcttcgaggg tctgggtcgc aacgagaagc    22080
gggcagcaaa ctctctgcaa caggaaaaca gcgaaaatga gagtcacacc ggggtactgg    22140
tggagctcga gggcgacaac gcccgcctgg cggtggtcaa gcgcagcatc gaggtcaccc    22200
actttgccta ccccgcgctc aacctgcccc ccaaagtcat gaacgcggcc atggacgggc    22260
tgatcatgcg ccgcggccgg cccctcgctc cagatgcaaa cttgcatgag gagaccgagg    22320
acggccagcc cgtggtcagc gacgagcagc tggcgcgctg gctggagacc gcggaccccg    22380
ccgaactgga ggagcggcgc aagatgatga tggccgcggt gctggtcacc gtagagctgg    22440
agtgtctgca gcgcttcttc ggcgacccccg agatgcagag aaaggtcgag gagacccctgc    22500 actaccctt ccgccagggc tacgtgcgcc aggcttgcaa gatctccaac gtggagctca    22560
gcaacctggt gtcctacctg gcatcttgc atgagaaccg cctcgggcag agcgtgctgc    22620
actccaccct gcgcggggag gcgcgccgcg actacgtgcg cgactgcgtt tacctcttcc    22680
tctgctacac ctggcagacg gccatggggg tctggcagca gtgcctggag gagcgcaacc    22740
tcaaggagct ggagaagctc ctgcagcgcg cgctcaaaga cctctggacg ggctacaacg    22800
agcgctcggt ggccgccgcg ctggccgacc tcatcttccc cgagcgcctg ctcaaaaccc    22860
tccagcaggg gctgcccgac ttcaccagcc aaagcatgtt gcaaaacttc aggaacttta    22920
tcctggagcg ttctggcatc ctacccgcca cctgctgcgc cctgcccagc gactttgtcc    22980
ccctcgtgta ccgcgagtgc ccccgccgc tgtggggtca ctgctacctg ttccaactgg    23040
ccaactacct gtcctaccac gcggacctca tggaggactc cagcggcgag gggctcatgg    23100
agtgccactg ccgctgcaac ctctgcacgc cccaccgctc cctggtctgc aacacccaac    23160
tgctcagcga gagtcagatt atcggtacct tcgagctaca gggtccgtcc tcctcagacg    23220
agaagtccgc ggctccgggg ctaaaactca ctccggggct gtggacttcc gcctacctgc    23280
gcaaatttgt acctgaagac taccacgccc acgagatcag gttttacgaa gaccaatccc    23340
gcccgcccaa ggcggagctg accgcctgcg tcatcaccca gggcgagatc ctaggccaat    23400
tgcaagccat ccaaaaagcc cgccaagatt ttttgctgag aaagggtcgg ggggtgtatc    23460
tggaccccca gtcgggtgag gagctcaacc cggttccccc gctgccgccg ccgcgggacc    23520
ttgcttccca ggataagcat cgccatggct cccagaaaga agcagcagcg gccgccactg    23580
ccgccacccc acatgctgga ggaagaggag gaatactggg acagtcaggc agaggaggtt    23640
tcggacgagg aggagccgga gacggagatg gaagagtggg aggaggacag cttagacgag    23700
gaggcttccg aagccgaaga ggcagacgca acaccgtcac cctcggccgc agcccctcg    23760 caggcgcccc gaagtccgc tcccagcatc agcagcaaca gcagcgctat aacctccgct    23820
cctccaccgc cgcgacccac ggccgaccgc agacccaacc gtagatggga caccaccgga    23880
```

```
accggggccg gtaagtcctc cgggagaggc aagcaagcgc agcgccaagg ctaccgctcg   23940
tggcgcgctc acaagaacgc catagtcgct tgcttgcaag actgcggggg gaacatctcc   24000
ttcgcccgcc gcttcctgct cttccaccac ggtgtggcct tcccccgtaa cgtcctgcat   24060
tactaccgtc atctctacag cccctactgc ggcggcagtg agccagagac ggtcggcggc   24120
ggcggcggcg cccgtttcgg cgcctaggaa gacccagggc aagacttcag ccaagaaact   24180
cgcggcggcc gcggcgaacg cggtcgcggg ggccctgcgc ctgacggtga acgaacccct   24240
gtcgacccgc gaactgagaa accgaatctt ccccactctc tatgccatct ccagcagag   24300
cagagggcag gatcaggaac tgaaagtaaa aaacaggtct ctgcgctccc tcacccgcag   24360
ctgtctgtat cacaagagcg aagaccagct tcggcgcacg ctggaggacg ctgaggcact   24420
cttcagcaaa tactgcgcgc tcactcttaa ggactagctc cgcgcccttc tcgaatttag   24480
gcgggaacgc ctacgtcatc gcagcgccgc cgtcatgagc aaggacattc ccacgccata   24540
catgtggagc tatcagccgc agatgggact cgcggcgggc gcctcccaag actactccac   24600
ccgcatgaac tggctcagtg ccggcccaca catgatctca caggttaatg atatccgcac   24660
ccatcgaaac caaatattgg tggagcaggc ggcaattacc accacgcccc gcaataatcc   24720
caaccccagg gagtggcccg cgtccctggt gtatcaggaa attcccggcc ccaccaccgt   24780
actacttccg cgtgattccc aggccgaagt ccaaatgact aactcagggg cgcagctcgc   24840
gggcggctgt cgtcacaggg tgcggcctcc tcgccagggt ataactcacc tggagatccg   24900
aggcagaggt attcagctca acgacgagtc ggtgagctcc tcgctcggtc taagacctga   24960
cgggaccttc cagatagccg gagccggccg atcttccttc acgcccgcc aggcgtacct   25020
gactctgcag agctcgtcct cggcgccgcg ctcgggcggc atcgggactc tccagttcgt   25080
gcaggagttt gtgccctcgg tctacttcaa ccccttctcg ggctctcccg gtcgctaccc   25140
ggaccagttc atctcgaact ttgacgccgc gagggactcg gtggacggct acgactgaat   25200
gtcgggtgga cccggtgcag agcaacttcg cctgaagcac ctcgaccact gccgccgccc   25260
tcagtgcttt gcccgctgtc agaccggtga gttccagtac ttttccctgc ccgactcgca   25320
cccggacggc ccggcgcacg gggtgcgctt tttcatcccg agtcaggtgc gctctaccct   25380
aatcagggag tttaccgccc gtcccctact ggcggagttg gaaaaggggc cttctatcct   25440
aaccattgcc tgcatctgct ctaaccctgg attgcaccaa gatctttgct gtcatttgtg   25500
tgctgagtat aataaaggct gagatcagaa tctactcggg ctcctgtcgc catcctgtca   25560
acgccaccgt ccaagcccgg cccgatcagc ccgaggtgaa cctcacctgc ggtctgcacc   25620
ggcgcctgag gaaataccta gcttggtact acaacagcac tccctttgtg gtttacaaca   25680
gctttgacca ggacggggtc tcactgaggg ataacctctc gaacctgagc tactccatca   25740
ggaagaacag cacccctcgag ctacttcctc cttacctgcc cgggacttac cagtgtgtca   25800
ccggtccctg cacccacacc cacctgttga tcgtaaacga ctctcttccg agaacagacc   25860
tcaataactc ctcttcgcag ttccccagaa caggaggtga gctcaggaaa cccggtaa   25920
agaagggtgg acaagagtta acacttgtgg ggtttctggt gtatgtgacg ctggtggtgg   25980
ctcttttgat taaggctttt ccttccatgt ctgaactctc cctcttttat gaacaactcg   26040
actagtgcta acgggaccct acccaacgaa tcgggattga atatcggtaa ccaggttgca   26100
gtttcacttt tgattacctt catagtcctc ttcctgctag tgctgtcgct tctgtgcctg   26160
cggatcgggg gctgctgcat ccacgtttat atctggtgct ggctgtttag aaggttcgga   26220
```

```
gaccatcgca ggtagaataa acatgctgct gcttaccctc tttgtcctgg cgctggccgc   26280
cagctgccaa gccttttccg aggctgactt tatagagccc cagtgtaacg tgactttttaa  26340 agcccatgca cagcgttgtc atactataat caaatgtgcc accgaacacg atgaatacct   26400
tatccagtat aaagataaat cacacaaagt ggcacttgtt gacatctgga aacccgaaga   26460
ccctttggaa tacaatgtga ccgttttcca gggtgacctc ttcaaaattt acaattacac   26520
tttcccattt gaccagatgt gtgactttgt catgtacatg gaaaagcagc acaagctgtg   26580
gcctccgact ccccagggct gtgtggaaaa tccaggctct ttctgcatga tctctctctg   26640
tgtaactgtg ctggcactaa tactcacgct tttgtatatc agatttaaat caaggcaaag   26700
cttcatcgat gaaaagaaaa tgccttaaac gctttcacgc ttgattgcta acaccgggtt   26760
tttatccgca gaatgattgg aatcacccta ctaatcacct ccctccttgc gattgcccat   26820
gggttggaac gaatcgaagc ccctgtgggg gccaatgtta ccctggtggg gcctgtcggc   26880
aatgctacat taatgtggga aaaatatact aaaaatcaat gggtctctta ctgcactaac   26940
aaaaacagcc acaagcccag agccatctgc gatgggcaaa atctaacctt gattgatgtt   27000
caaatgctgg atgcgggcta ctattatggg cagctgggta caatgattaa ttactggaga   27060
ccccacaaag attacatgct ccacgtagta aagggtcccc ttagcagccc acccactacc   27120
acctctacta ccccccactac caccactact cccaccacca gcactgccgc ccagcctcct   27180
catagcagaa caaccacttt tatcaattcc aagtcccact ccccccacat gccggcggg    27240 ccctccgcct cagactccga gaccaccgag atctgcttct gcaaatgctc tgacgccttt   27300
gctgaggatt tggaagacca cgaggaagat gagcatgact tcgcagatgc atgccaggca   27360
tcagaggcag aagcgctgcc ggtggccctc aaacagtatg cagacccccca caccacccc   27420 aaccttcctc caccttccca gaagccaagt ttcctggggg aaaatgaaac tctgcctctc   27480
tccatactcg ctctgacatc tgttgctatg ttgaccgctc tgctggtgct tctatgctct   27540
atatgctacc tgatctgctg cagaaagaaa aaatctcacg gccatgctca ccagcccctc   27600
atgcacttcc cttaccctcc agagctgggc gaccacaaac tttaagtctg cagtaactat   27660
ctgcccatcc cttgtcagtc gacagcgatg agccccacta atctaacggc ctctggactt   27720
acaacatcgt ctcttaatga gaccaccgct cctcaagacc tgtacgatgg tgtctccgcg   27780
ctggttaacc agtgggatca cctgggcata tggtggctcc tcataggagc agtgaccctg   27840
tgcctaatcc tggtctggat catctgctgc atcaaaagca gaagacccag gcggcggccc   27900
atctacaggc cctttgtcat cacacctgaa gatgatgatg acaccacttc caggctgcag   27960
aggctaaagc agctactctt ctcttttaca gcatggtaaa ttgaatcatg cctcgcattt   28020
tcatctactt gtctctcctt ccactttttc tgggctcttc tacattggcc gctgtgtccc   28080
acatcgaggt agactgcctc acgcccttca cagtctacct gcttttcggc tttgtcatct   28140
gcacctttgt ctgcagcgtt atcactgtag tgatctgctt catacagtgc atcgactacg   28200
tctgcgtgcg ggtggcttac tttagacacc acccccagta tcgcaacagg acatagcgg    28260 ctctcctaag acttgtttaa aatcatggcc aaattaactg tgattggtct tctgatcatc   28320
tgctgcgtcc tagccgcgat tgggactcaa gctcctacca ccaccagcgc tcccagaaag   28380
agacatgtat cctgcagctt caagcgtccc tggaatatac cccaatgctt tactgatgaa   28440
cctgaaatct ctttggcttg gtacttcagc gtcaccgccc ttcttatctt ctgcagtacg   28500
gttattgccc ttgccatcta cccttccctt gacctgggct ggaatgctgt caactctatg   28560
gaatatccca ccttcccaga accagacctg ccagacctgg ttgttctaaa cgcgtttcct   28620
```

```
cctcctgctc ccgttcaaaa tcagtttcgc cctccgtccc ccacgcccac tgaggtcagc    28680
tactttaatc taacaggcgg agatgactga aaacctagac ctagaaatgg acggtctctg    28740
cagcgagcaa cgcacactag agaggcgccg gcaaaaagag ctcgagcgtc ttaaacaaga    28800
gctccaagac gcggtggcca tacaccagtg caaaaaaggt gtcttctgtc tggtaaaaca    28860
ggccacgctc acctatgaaa aaacaggtga cacccaccgc ctaggataca agctgcccac    28920
acagcgccag aagttcgccc tcatgatagg cgaacaaccc atcaccgtga cccagcactc    28980
cgtggagaca gaaggctgca tacacgctcc ctgtaggggc gctgactgcc tctacacctt    29040
gatcaaaacc ctctgcggtc tcagagacct catcccttt aattaatcat aactgtaatc    29100 aataaaaat cacttacttg aaatctgata gcaagcctct gtccaattt ttcagcaaca     29160 cttccttccc ctcctcccaa ctctggtact ctaggcgcct cctagctgca aacttcctcc    29220
acagtctgaa gggaatgtca gattcctcct cctgtccctc cgcacccacg atcttcatgt    29280
tgttgcagat gaaacgcgcg agatcgtctg acgagacctt caaccccgtg taccctacg    29340 ataccgagat cgctccgact tctgtccctt tccttacccc tcccttgtg tcatccgcag     29400 gaatgcaaga aaatccagct gggtgctgt ccctgcactt gtcagagccc cttaccaccc     29460
acaatggggc cctgactcta aaaatggggg gcggcctgac cctggacaag aagggaatc     29520 tcacttccca aaacatcacc agtgtcgatc ccctctcaa aaaagcaag aacaacatca      29580 gccttcagac cgccgcaccc ctcgccgtca gctccggggc cctaacactt tttgccactc    29640
cccccctagc ggtcagtggt gacaacctta ctgtgcagtc tcaggccct ctcactttgg     29700 aagactcaaa actaactctg gccaccaaag gaccctaac tgtgtccgaa ggcaaacttg     29760
tcctagaaac agaggctccc ctgcatgcaa gtgacagcag cagcctgggc cttagcgtta    29820 cggcccact tagcattaac aatgacagcc taggactaga catgcaagcg cccattagct     29880
ctcgagatgg aaaactggct ctaacagtgg cggcccccct aactgtggtc gagggtatca    29940
atgctttggc agtagccaca ggtaagggta ttgggctaaa tgaaaccaac acacacctgc    30000
aggcaaaact ggtcgcaccc ctaggctttg ataccaacgg caacattaag ctaagcgttg    30060
caggaggcat gaggctaaac aataacacac tgatactaga tgtaaactac ccatttgagg    30120
ctcaaggcca actgagccta agagtgggct cgggcccact atatgtagat tctagtagtc    30180
ataacctaac cattagatgc cttaggggat tgtatataac atcttctaac aaccaaaacg    30240
gtctagaagc caacattaaa ctaacaagag gccttgtgta tgacggaaat gccatagcag    30300
ttaatgttgg caaagggctg gaatacagcc ctactgacac aacagaaaaa cctatacaga    30360
ctaaaatagg tctaggcatg gagtatgata ccgagggagc catgatgaca aaactaggct    30420
ctggactaag ctttgacaat tcaggagcca ttgtagtggg aaacaaaaat gatgacaggc    30480
ttactttgtg gaccacaccg gacccatcgc ccaactgtca gatctactct gaaaaagatg    30540
ctaaactaac cttggtactg actaaatgtg gcagtcaggt tgtaggcaca gtatctattg    30600
ccgctcttaa aggtagcctc gtgccaatca ctagtgcaat cagtgtggtt caggtatacc    30660
taaggtttga tgaaaatggg gtactaatga gtaactcttc acttaatggc gaatactgga    30720
attttagaaa cggagactca actaatgcca caccatatac aaacgcagtg ggtttcatgc    30780
ctaatctact ggcctatcct aaaggtcaaa ctacaactgc aaaaagtaac attgtcagcc    30840
aggtctacat gaatgggggac gatactaaac ccatgacatt tacaatcaac ttcaatggcc    30900
ttagtgaaac aggggatacc cctgttagta aatattccat gacattctca tggaggtggc    30960
```

```
caaatggaag ctacataggg cacaattttg taacaaactc ctttaccttc tcctacatcg   31020
cccaagaata aagaaagcac agagatgctt gttttttgatt tcaaaattgt gtgcttttat   31080
ttattttcag cttacagtat ttccagtagt cattcaaata aagcttaatc aaactgcatg   31140
agaacccttc cacatagctt aaattagcac cagtgcaaat ggagaaaaat caacataccT   31200 tttttttatcc agatatcaga gaactctagt ggtcagtttt cccccacccT cccagctcac   31260
agaatacaca gtcctttccc cccggctggc tttaaacaac actatctcat tggtaacaga   31320
catattctta ggtgtaataa tccacacggt ctcttggcgg gccaaacgct ggtcggtgat   31380
gttaataaac tccccaggca gctctttcaa gttcacgtcg ctgtccaact gctgaagcgc   31440
tcgcggctcc gactgcgcct ctagcggagg caacggcaac acccgatcct tgatcaaagg   31500
gaggtaaacg gtccctcgtg tagggacagt ggcgggataa tcgagatcgt gttgaacgta   31560
gagtcatgcc aaagggaaca gcggacgtac tcatatttcc tccagcagaa ccaagtgcgc   31620
gcgtggcagc tatccctgcg tcttctgtct cgccgcctgc cccgttcggt gtagtagttg   31680
taatacagcc actccctgag accgtcaagg cgctccctgg cgtccggatc tatgacaaca   31740
ccgtcctgca gcgccgccct gatgacatcc accaccgtag agtatgccaa gcccagccag   31800
gaaatgcatt cactttgaca gcgagagata ggaggagcgg ggagagatgg aagaaccatg   31860
atagtaaaga gaacttttat tccaatcgat cttctaagat atcaaagtgg agatctataa   31920
gatgacactg gtcttatcct ccgctgagtc gatcaaaaat aacagctaaa ccacaaacaa   31980
cacgattggt caaatgctcc acaagggtta cctgcagcag aaaattgcct cggaactcca   32040
ccgcaagcag aacagcaaag ccaccgcctc tatcgtgatc aagaataaaa accccacagc   32100
tatccactta cagacccaga tagttttcag ctctccatcg tgaaaaaga tttacaagct   32160 cctcctttaa atcacctcca accaattgaa aaagttgaac cagaccgccc tccaccttca   32220
gtttcagcaa gcgtttaatt atgattgcaa aaattcaggc tcctcagaca cctgtataag   32280
attgagaagc ggaacgttaa catcgatgtt tcgctcgcgt aaatcacgcc tcagtgcaag   32340
cataatataa tcccacaggt cggagcggat cagcgaggac acctccccgc caggaaccaa   32400
ctcaacggag cctatgctga ttataatacg catattcgga gctatgctaa ccagcacggc   32460
ccccaaatag gcgtactgca taggcggcga caaaaagtga acagtttggg ttaaaaaatc   32520
aggcaaacac tcgcgcaaaa aagcaagaac atcataacca tgctcatgca aatagatgca   32580
agtaagctca ggaacaacca cagaaaaatg cacaattttt ctctcaaaca tgactgcgag   32640
ccctgcaaaa aataaaaaag aaacattaca caagagtagc ctgtcttacg atgggataga   32700
ctactctaac caacataaga cgggccacaa catcgcccgc gtggccataa aaaaaattgt   32760
ccgtgtgatt aaaaagaagc acagatagct ggccagtcat atccggagtc atcacgtgtg   32820
aacccgtgta gaccccgggg ttggacacat cggccaaaga aagaaagcgg ccaatgtacc   32880
caggaggaat tataacacta agacgaagat acaacagaat aacccatga gggggaataa   32940 caaagttagt aggtgaataa aaacgataaa cacccgaaac tccctcctgc gtaggcaaaa   33000
tagcacccTc cccttccaaa acaacatata gcgcttccac agcagccatg acaaaagact   33060
caaaacactc aaaagactca gtcttaccag gaaaataaaa gcactctcac agcaccagca   33120
ctaatcagag tgtgaagagg gccaagtgcc gaacgagtat atataggaat aaaaaatgac   33180
gtaaatgtgt aaaggtcaga aaacgcccag aaaaatacac agaccaacgc cgaaacgaa   33240 aacccgcgaa aaaatacccca gaacttcctc aacaaccgcc acttccgctt tctcacggta   33300
cgtcacttcc gcaagaaaag caaaactaca tttcccacat gtgtaaaaac gaaacccgc   33360
```

```
cccttgtaac cgcccacaac ttacatcatc aaaacgtaaa ctcctacgtc acccgccccg    33420 cctctcccg cccacctcat tatcatattg gccacaatcc aaaataaggt atattattga    33480
tgatg                                                               33485
```

SIMIAN (GORILLA) ADENOVIRUS OR ADENOVIRAL VECTORS AND METHODS OF USE

CROSS-REFERENCE TO RELATED APPLICATIONS

This patent application claims the benefit of U.S. Provisional Patent Application No. 61/543,661, filed Oct. 5, 2011, which is incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 415,835 Byte ASCII (Text) file named "716448 ST25.txt," created on Mar. 28, 2014.

BACKGROUND OF THE INVENTION

In vivo delivery of proteins in biologically relevant forms and amounts has been an obstacle to drug and vaccine development for decades. One solution that has proven to be a successful alternative to traditional protein delivery approaches is the delivery of exogenous nucleic acid sequences for production of proteins in vivo. Gene transfer vectors ideally enter a wide variety of cell types, have the capacity to accept large nucleic acid sequences, are safe, and can be produced in quantities required for treating patients. Viral vectors are gene transfer vectors with these advantageous properties (see, e.g., Thomas et al., *Nature Review Genetics*, 4: 346-358 (2003)). Furthermore, while many viral vectors are engineered to infect a broad range of cell types, viral vectors also can be modified to target specific cell types, which can enhance the therapeutic efficacy of the vector (see, e.g., Kay et al., *Nature Medicine*, 7(1): 33-40 (2001).

Viral vectors that have been used with some success to deliver exogenous proteins to mammalian cells for therapeutic purposes include, for example, Retrovirus (see, e.g., Cavazzana-Calvo et al., *Science*, 288 (5466): 669-672 (2000)), Lentivirus (see, e.g., Cartier et al., *Science*, 326: 818-823 (2009)), Adeno-associated virus (AAV) (see, e.g., Mease et al., *Journal of Rheumatology*, 27(4): 692-703 (2010)), Herpes Simplex Virus (HSV) (see, e.g., Goins et al., *Gene Ther.*, 16(4): 558-569 (2009)), Vaccinia Virus (see, e.g., Mayrhofer et al., *J. Virol.*, 83(10): 5192-5203 (2009)), and Adenovirus (see, e.g., Lasaro and Ertl, *Molecular Therapy*, 17(8): 1333-1339 (2009)).

Despite their advantageous properties, widespread use of viral gene transfer vectors is hindered by several factors. In this respect, certain cells are not readily amenable to gene delivery by currently available viral vectors. For example, lymphocytes are impaired in the uptake of adenoviruses (Silver et al., *Virology*, 165: 377-387 (1988), and Horvath et al., *J. Virology*, 62(1): 341-345 (1988)). In addition, viral vectors that integrate into the host cell's genome (e.g., retroviral vectors) have the potential to cause insertion mutations in oncogenes (see, e.g., Cavazzana-Calvo et al., supra, and Hacein-Bey-Abina et al., *N. Engl. J. Med.*, 348: 255-256 (2003)).

The use of viral vectors for gene transfer also is impeded by the immunogenicity of viral vectors. A majority of the U.S. population has been exposed to wild-type forms of many of the viruses currently under development as gene transfer vectors (e.g., adenovirus). As a result, much of the U.S. population has developed pre-existing immunity to certain virus-based gene transfer vectors. Such vectors are quickly cleared from the bloodstream, thereby reducing the effectiveness of the vector in delivering biologically relevant amounts of a gene product. Moreover, the immunogenicity of certain viral vectors prevents efficient repeat dosing, which can be advantageous for "boosting" the immune system against pathogens when viral vectors are used in vaccine applications, thereby resulting in only a small fraction of a dose of the viral vector delivering its payload to host cells.

Thus, there remains a need for improved viral vectors that can be used to efficiently deliver genes to mammalian cells in vivo. The invention provides such viral vectors.

BRIEF SUMMARY OF THE INVENTION

The invention provides an adenovirus or adenoviral vector. The adenovirus or adenoviral vector comprises one or more of the nucleic acid sequences selected from the group consisting of (a) a nucleic acid sequence that is at least 97% identical to SEQ ID NO: 1, (b) a nucleic acid sequence that is at least 97.5% identical to SEQ ID NO: 2, (c) a nucleic acid sequence that is at least 80% identical to SEQ ID NO: 3, (d) a nucleic acid sequence that is at least 96% identical to SEQ ID NO: 4, and (e) a nucleic acid sequence that is at least 96% identical to SEQ ID NO: 5.

The invention provides an adenovirus or adenoviral vector comprising one or more of the nucleic acid sequences selected from the group consisting of (a) a nucleic acid sequence that is at least 98.4% identical to SEQ ID NO: 6, (b) a nucleic acid sequence that is at least 99.01% identical to SEQ ID NO: 7, (c) a nucleic acid sequence that is at least 97.08% identical to SEQ ID NO: 8, (d) a nucleic acid sequence that is at least 96.52% identical to SEQ ID NO: 9, and (e) a nucleic acid sequence that is at least 98.49% identical to SEQ ID NO: 10.

The invention provides an adenovirus or adenoviral vector comprising one or more of the nucleic acid sequences selected from the group consisting of (a) a nucleic acid sequence comprising at least 121 contiguous nucleotides of SEQ ID NO: 6, (b) a nucleic acid sequence comprising at least 462 contiguous nucleotides of SEQ ID NO: 7, (c) a nucleic acid sequence comprising at least 234 contiguous nucleotides of SEQ ID NO: 8, (d) a nucleic acid sequence comprising at least 606 contiguous nucleotides of SEQ ID NO: 9, and (e) a nucleic acid sequence comprising at least 188 contiguous nucleotides of SEQ ID NO: 10.

The invention provides an adenovirus or adenoviral vector comprising one or more of the amino acid sequences selected from the group consisting of (a) an amino acid sequence that is at least 93% identical to SEQ ID NO: 11, (b) an amino acid sequence that is at least 80% identical to SEQ ID NO: 13, (c) an amino acid sequence that is at least 92% identical to SEQ ID NO: 14, and (d) an amino acid sequence that is at least 88% identical to SEQ ID NO: 15.

The invention provides an adenovirus or adenoviral vector comprising one or more of the nucleic acid sequences selected from the group consisting of (a) a nucleic acid sequence encoding an amino acid sequence that is at least 93% identical to SEQ ID NO: 11, (b) a nucleic acid sequence encoding an amino acid sequence that is at least 95% identical to SEQ ID NO: 12, (c) a nucleic acid sequence encoding an amino acid sequence that is at least 80% identical to SEQ ID NO: 13, (d) a nucleic acid sequence encoding an amino acid sequence that is at least 92% identical to SEQ ID NO: 14, and (e) a nucleic acid sequence encoding an amino acid sequence that is at least 88% identical to SEQ ID NO: 15.

The invention provides an adenovirus or adenoviral vector comprising one or more of the amino acid sequences selected from the group consisting of (a) an amino acid sequence that is at least 99% identical to SEQ ID NO: 16, (b) an amino acid sequence that is at least 97.8% identical to SEQ ID NO: 18, (c) an amino acid sequence that is at least 99.1% identical to SEQ ID NO: 19, and (d) an amino acid sequence that is at least 99.2% identical to SEQ ID NO: 20.

The invention provides an adenovirus or adenoviral vector comprising one or more of the nucleic acid sequences selected from the group consisting of (a) a nucleic acid sequence encoding an amino acid sequence that is at least 99% identical to SEQ ID NO: 16, (b) a nucleic acid sequence encoding an amino acid sequence that is at least 99.5% identical to SEQ ID NO: 17, (c) a nucleic acid sequence encoding an amino acid sequence that is at least 97.8% identical to SEQ ID NO: 18, (d) a nucleic acid sequence encoding an amino acid sequence that is at least 99.1% identical to SEQ ID NO: 19, and (e) a nucleic acid sequence encoding an amino acid sequence that is at least 99.2% identical to SEQ ID NO: 20.

The invention provides an adenovirus or adenoviral vector comprising one or more of the amino acid sequences selected from the group consisting of (a) an amino acid sequence comprising at least 89 contiguous amino acid residues of SEQ ID NO: 16, (b) an amino acid sequence comprising at least 247 contiguous amino acid residues of SEQ ID NO: 18, (c) an amino acid sequence comprising at least 230 contiguous amino acid residues of SEQ ID NO: 19, and (d) an amino acid sequence comprising at least 231 contiguous amino acid residues of SEQ ID NO: 20.

The invention provides an adenovirus or adenoviral vector comprising one or more of the nucleic acid sequences selected from the group consisting of (a) a nucleic acid sequence encoding an amino acid sequence comprising at least 89 contiguous amino acid residues of SEQ ID NO: 16, (b) a nucleic acid sequence encoding an amino acid sequence comprising at least 286 contiguous amino acid residues of SEQ ID NO: 17, (c) a nucleic acid sequence encoding an amino acid sequence comprising at least 247 contiguous amino acid residues of SEQ ID NO: 18, (d) a nucleic acid sequence encoding an amino acid sequence comprising at least 230 contiguous amino acid residues of SEQ ID NO: 19, and (e) a nucleic acid sequence encoding an amino acid sequence comprising at least 231 contiguous amino acid residues of SEQ ID NO: 20.

DETAILED DESCRIPTION OF THE INVENTION

Adenoviruses are generally associated with benign pathologies in humans, and the genomes of adenoviruses isolated from a variety of species, including humans, have been extensively studied. Adenovirus is a medium-sized (90-100 nm), nonenveloped icosohedral virus containing approximately 36 kb of double-stranded DNA. The adenovirus capsid mediates the key interactions of the early stages of the infection of a cell by the virus, and is required for packaging adenovirus genomes at the end of the adenovirus life cycle. The capsid comprises 252 capsomeres, which includes 240 hexons, 12 penton base proteins, and 12 fibers (Ginsberg et al., *Virology*, 28: 782-83 (1966)). The hexon comprises three identical proteins, namely polypeptide II (Roberts et al., *Science*, 232: 1148-51 (1986)). The penton base comprises five identical proteins and the fiber comprises three identical proteins. Proteins IIIa, VI, and IX are present in the adenoviral coat and are believed to stabilize the viral capsid (Stewart et al., *Cell*, 67: 145-54 (1991), and Stewart et al., *EMBO J.*, 12(7): 2589-99 (1993)). The expression of the capsid proteins, with the exception of pIX, is dependent on the adenovirus polymerase protein. Therefore, major components of an adenovirus particle are expressed from the genome only when the polymerase protein gene is present and expressed.

Several features of adenoviruses make them ideal vehicles for transferring genetic material to cells for therapeutic applications (i.e. "gene therapy"), or for use as antigen delivery systems for vaccine applications. For example, adenoviruses can be produced in high titers (e.g., about $10^{13}$ particle units (pu)), and can transfer genetic material to nonreplicating and replicating cells. The adenoviral genome can be manipulated to carry a large amount of exogenous DNA (up to about 8 kb), and the adenoviral capsid can potentiate the transfer of even longer sequences (Curiel et al., *Hum. Gene Ther.*, 3: 147-154 (1992)). Additionally, adenoviruses generally do not integrate into the host cell chromosome, but rather are maintained as a linear episome, thereby minimizing the likelihood that a recombinant adenovirus will interfere with normal cell function.

The invention is predicated, at least in part, on the discovery and isolation of an adenovirus that has not previously been identified or isolated. The adenovirus described herein was isolated from a *gorilla*. There are four widely recognized *gorilla* subspecies within the two species of Eastern *Gorilla* (*Gorilla beringei*) and Western *Gorilla* (*Gorilla gorilla*). The Western *Gorilla* species includes the subspecies Western Lowland *Gorilla* (*Gorilla gorilla gorilla*) and Cross River *Gorilla* (*Gorilla gorilla diehli*). The Eastern *Gorilla* species includes the subspecies Mountain *Gorilla* (*Gorilla beringei beringei*) and Eastern Lowland *Gorilla* (*Gorilla beringei graueri*) (see, e.g., Wilson and Reeder, eds., *Mammalian Species of the World*, 3$^{rd}$ ed., Johns Hopkins University Press, Baltimore, Md. (2005)). The adenovirus of the invention was isolated from Eastern Lowland *Gorilla* (*Gorilla beringei graueri*).

The genomes of several such adenoviruses have been analyzed, and it has been determined that the adenovirus can have the nucleic acid sequence of, for example, SEQ ID NO: 21, SEQ ID NO: 22, SEQ ID NO: 23, SEQ ID NO: 24, SEQ ID NO: 25, SEQ ID NO: 26, SEQ ID NO: 27, or SEQ ID NO: 28, each of which includes a number of sub-sequences that serve to uniquely define the adenovirus, namely the nucleic acid sequences SEQ ID NOs: 1-10, and amino acid sequences SEQ ID NOs: 11-20. SEQ ID NOs: 6-10 encode the amino acid sequences of SEQ ID NOs: 16-20, respectively. SEQ ID NOs: 1-5 are a subset of the nucleic acid sequences of SEQ ID NOs: 6-10, respectively. SEQ ID NOs: 11-15 are a subset of the amino acid sequences of SEQ ID NOs: 16-20, respectively.

The adenovirus can be modified in the same manner as previously known adenoviruses to be used as an adenoviral vector, e.g., a gene delivery vehicle.

The term "adenovirus," as used herein, refers to an adenovirus that retains the ability to participate in the adenovirus life cycle and has not been physically inactivated by, for example, disruption (e.g., sonication), denaturing (e.g., using heat or solvents), or cross-linkage (e.g., via formalin cross-linking). The "adenovirus life cycle" includes (1) virus binding and entry into cells, (2) transcription of the adenoviral genome and translation of adenovirus proteins, (3) replication of the adenoviral genome, and (4)

viral particle assembly (see, e.g., Fields Virology, 5$^{th}$ ed., Knipe et al. (eds.), Lippincott Williams & Wilkins, Philadelphia, Pa. (2006)).

The term "adenoviral vector," as used herein, refers to an adenovirus in which the adenoviral genome has been manipulated to accommodate a nucleic acid sequence that is non-native with respect to the adenoviral genome. Typically, an adenoviral vector is generated by introducing one or more mutations (e.g., a deletion, insertion, or substitution) into the adenoviral genome of the adenovirus so as to accommodate the insertion of a non-native nucleic acid sequence, for example, for gene transfer, into the adenovirus.

The adenovirus and adenoviral vector can be replication-competent, conditionally replication-competent, or replication-deficient.

A replication-competent adenovirus or adenoviral vector can replicate in typical host cells, i.e., cells typically capable of being infected by an adenovirus. A replication-competent adenovirus or adenoviral vector can have one or more mutations as compared to the wild-type adenovirus (e.g., one or more deletions, insertions, and/or substitutions) in the adenoviral genome that do not inhibit viral replication in host cells. For example, the adenovirus or adenoviral vector can have a partial or entire deletion of the adenoviral early region known as the E3 region, which is not essential for propagation of the adenovirus or adenoviral genome.

A conditionally-replicating adenovirus or adenoviral vector is an adenovirus or adenoviral vector that has been engineered to replicate under pre-determined conditions. For example, replication-essential gene functions, e.g., gene functions encoded by the adenoviral early regions, can be operably linked to an inducible, repressible, or tissue-specific transcription control sequence, e.g., promoter. In such an embodiment, replication requires the presence or absence of specific factors that interact with the transcription control sequence. Conditionally-replicating adenoviral vectors are further described in U.S. Pat. No. 5,998,205.

A replication-deficient adenovirus or adenoviral vector is an adenovirus or adenoviral vector that requires complementation of one or more gene functions or regions of the adenoviral genome that are required for replication, as a result of, for example, a deficiency in one or more replication-essential gene function or regions, such that the adenovirus or adenoviral vector does not replicate in typical host cells, especially those in a human to be infected by the adenovirus or adenoviral vector.

A deficiency in a gene function or genomic region, as used herein, is defined as a disruption (e.g., deletion) of sufficient genetic material of the adenoviral genome to obliterate or impair the function of the gene (e.g., such that the function of the gene product is reduced by at least about 2-fold, 5-fold, 10-fold, 20-fold, 30-fold, or 50-fold) whose nucleic acid sequence was disrupted (e.g., deleted) in whole or in part. Deletion of an entire gene region often is not required for disruption of a replication-essential gene function. However, for the purpose of providing sufficient space in the adenoviral genome for one or more transgenes, removal of a majority of one or more gene regions may be desirable. While deletion of genetic material is preferred, mutation of genetic material by addition or substitution also is appropriate for disrupting gene function. Replication-essential gene functions are those gene functions that are required for adenovirus replication (e.g., propagation) and are encoded by, for example, the adenoviral early regions (e.g., the E1, E2, and E4 regions), late regions (e.g., the L1, L2, L3, L4, and L5 regions), genes involved in viral packaging (e.g., the IVa2 gene), and virus-associated RNAs (e.g., VA-RNA-1 and/or VA-RNA-2).

Whether the adenovirus or adenoviral vector is replication-competent or replication-deficient, the adenovirus or adenoviral vector retains at least a portion of the adenoviral genome. The adenovirus or adenoviral vector can comprise any portion of the adenoviral genome, including protein coding and non-protein coding regions. Desirably, the adenovirus or adenoviral vector comprises at least one nucleic acid sequence that encodes an adenovirus protein. The adenovirus or adenoviral vector can comprise a nucleic acid sequence that encodes any suitable adenovirus protein, such as, for example, a protein encoded by any one of the early region genes (i.e., E1A, E1B, E2A, E2B, E3, and/or E4 regions), or a protein encoded by any one of the late region genes, which encode the virus structural proteins (i.e., L1, L2, L3, L4, and L5 regions).

The adenovirus or adenoviral vector desirably comprises one or more nucleic acid sequences that encode the pIX protein, the DNA polymerase protein, the penton protein, the hexon protein, and/or the fiber protein. The adenovirus or adenoviral vector can comprise a full-length nucleic acid sequence that encodes a full-length amino acid sequence of an adenovirus protein. Alternatively, the adenovirus or adenoviral vector can comprise a portion of a full-length nucleic acid sequence that encodes a portion of a full-length amino acid sequence of an adenovirus protein.

A "portion" of a nucleic acid sequence comprises at least ten nucleotides (e.g., about 10 to about 5000 nucleotides). Preferably, a "portion" of a nucleic acid sequence comprises 10 or more (e.g., 15 or more, 20 or more, 25 or more, 30 or more, 35 or more, 40 or more, 45 or more, 50 or more, or 100 or more) nucleotides, but less than 5,000 (e.g., 4900 or less, 4000 or less, 3000 or less, 2000 or less, 1000 or less, 800 or less, 500 or less, 300 or less, or 100 or less) nucleotides. Preferably, a portion of a nucleic acid sequence is about 10 to about 3500 nucleotides (e.g., about 10, 20, 30, 50, 100, 300, 500, 700, 1000, 1500, 2000, 2500, or 3000 nucleotides), about 10 to about 1000 nucleotides (e.g., about 25, 55, 125, 325, 525, 725, or 925 nucleotides), or about 10 to about 500 nucleotides (e.g., about 15, 30, 40, 50, 60, 70, 80, 90, 150, 175, 250, 275, 350, 375, 450, 475, 480, 490, 495, or 499 nucleotides), or a range defined by any two of the foregoing values. More preferably, a "portion" of a nucleic acid sequence comprises no more than about 3200 nucleotides (e.g., about 10 to about 3200 nucleotides, about 10 to about 3000 nucleotides, or about 30 to about 500 nucleotides, or a range defined by any two of the foregoing values).

A "portion" of an amino acid sequence comprises at least three amino acids (e.g., about 3 to about 1,200 amino acids). Preferably, a "portion" of an amino acid sequence comprises 3 or more (e.g., 5 or more, 10 or more, 15 or more, 20 or more, 25 or more, 30 or more, 40 or more, or 50 or more) amino acids, but less than 1,200 (e.g., 1,000 or less, 800 or less, 700 or less, 600 or less, 500 or less, 400 or less, 300 or less, 200 or less, or 100 or less) amino acids. Preferably, a portion of an amino acid sequence is about 3 to about 500 amino acids (e.g., about 10, 100, 200, 300, 400, or 500 amino acids), about 3 to about 300 amino acids (e.g., about 20, 50, 75, 95, 150, 175, or 200 amino acids), or about 3 to about 100 amino acids (e.g., about 15, 25, 35, 40, 45, 60, 65, 70, 80, 85, 90, 95, or 99 amino acids), or a range defined by any two of the foregoing values. More preferably, a "portion" of an amino acid sequence comprises no more than about 500 amino acids (e.g., about 3 to about 400 amino acids, about 10 to about 250 amino acids, or about 50 to about 100 amino acids, or a range defined by any two of the foregoing values).

The adenovirus pIX protein is present in the adenovirus capsid, has been shown to strengthen hexon nonamer interactions, and is essential for the packaging of full-length genomes (see, e.g., Boulanger et al., *J. Gen. Virol.,* 44: 783-800 (1979); Horwitz M. S., "Adenoviridae and their replication" in *Virology,* 2$^{nd}$ ed., B. N. Fields et al. (eds.), Raven Press, Ltd., New York, pp. 1679-1721 (1990), Ghosh-Choudhury et al., *EMBO J.,* 6: 1733-1739 (1987), and van Oostrum et al, *J. Virol.,* 56: 439-448 (1985)). In addition to its contribution to adenovirus structure, pIX also has been shown to exhibit transcriptional properties, such as stimulation of adenovirus major late promoter (MLP) activity (see, e.g., Lutz et al., *J. Virol.,* 71(7): 5102-5109 (1997)). Nucleic acid sequences that encode all or a portion of an adenovirus pIX protein include, for example, SEQ ID NO: 6 and SEQ ID NO: 1. Amino acid sequences that comprise a full-length pIX protein, or a portion thereof, include, for example, SEQ ID NO: 16 and SEQ ID NO: 11.

The adenovirus DNA polymerase protein is essential for viral DNA replication both in vitro and in vivo. The polymerase co-purifies in a complex with the precursor (pTP) of the terminal protein (TP), which is covalently attached to the 5' ends of adenovirus DNA (Field et al., *J. Biol. Chem.,* 259: 9487-9495 (1984)). Both the adenovirus DNA polymerase and pTP are encoded by the E2 region. The polymerase protein is required for the expression of all the structural proteins except for pIX. Without the gene sequence for polymerase protein, polymerase protein is not produced. As a result, the viral genome is not replicated, the Major Late Promoter is not activated, and the capsid proteins are not expressed. Nucleic acid sequences that encode all or a portion of an adenovirus DNA polymerase protein include, for example, SEQ ID NO: 7. SEQ ID NO: 2 is a subset of SEQ ID NO: 7. Amino acid sequences that comprise a full-length adenovirus DNA polymerase, or a portion thereof, include, for example, SEQ ID NO: 17 and SEQ ID NO: 12.

The adenovirus hexon protein is the largest and most abundant protein in the adenovirus capsid. The hexon protein is essential for virus capsid assembly, determination of the icosahedral symmetry of the capsid (which in turn defines the limits on capsid volume and DNA packaging size), and integrity of the capsid. In addition, hexon is a primary target for modification in order to reduce neutralization of adenoviral vectors (see, e.g., Gall et al., *J. Virol.,* 72: 10260-264 (1998), and Rux et al., *J. Virol.,* 77(17): 9553-9566 (2003)). The major structural features of the hexon protein are shared by adenoviruses across serotypes, but the hexon protein differs in size and immunological properties between serotypes (Jornvall et al., *J. Biol. Chem.,* 256(12): 6181-6186 (1981)). A comparison of 15 adenovirus hexon proteins revealed that the predominant antigenic and serotype-specific regions of the hexon appear to be in loops 1 and 2 (i.e., LI or l1, and LII or l2, respectively), within which are seven discrete hypervariable regions (HVR1 to HVR7) varying in length and sequence between adenoviral serotypes (Crawford-Miksza et al., *J. Virol.,* 70(3): 1836-1844 (1996)). Nucleic acid sequences that encode all or a portion of an adenovirus hexon protein include, for example, SEQ ID NO: 9 and SEQ ID NO: 4. Amino acid sequences that comprise a full-length adenovirus hexon protein, or a portion thereof, include, for example, SEQ ID NO: 19 and SEQ ID NO: 14.

The adenovirus fiber protein is a homotrimer of the adenoviral polypeptide IV that has three domains: the tail, shaft, and knob. (Devaux et al., *J. Molec. Biol.,* 215: 567-88 (1990), Yeh et al., *Virus Res.,* 33: 179-98 (1991)). The fiber protein mediates primary viral binding to receptors on the cell surface via the knob and the shaft domains (Henry et al., *J. Virol.,* 68(8): 5239-46 (1994)). The amino acid sequences for trimerization are located in the knob, which appears necessary for the amino terminus of the fiber (the tail) to properly associate with the penton base (Novelli et al., *Virology,* 185: 365-76 (1991)). In addition to recognizing cell receptors and binding the penton base, the fiber contributes to serotype identity. Fiber proteins from different adenoviral serotypes differ considerably (see, e.g., Green et al., *EMBO J.,* 2: 1357-65 (1983), Chroboczek et al., *Virology,* 186: 280-85 (1992), and Signas et al., *J. Virol.,* 53: 672-78 (1985)). Thus, the fiber protein has multiple functions key to the life cycle of adenovirus. Nucleic acid sequences that encode all or a portion of an adenovirus fiber protein include, for example, SEQ ID NO: 10. SEQ ID NO: 5 is a subset of SEQ ID NO: 10. Amino acid sequences that comprise a full-length adenovirus fiber protein, or a portion thereof, include, for example, SEQ ID NO: 20 and SEQ ID NO: 15.

The adenovirus penton base protein is located at the vertices of the icosahedral capsid and comprises five identical monomers. The penton base protein provides a structure for bridging the hexon proteins on multiple facets of the icosahedral capsid, and provides the essential interface for the fiber protein to be incorporated in the capsid. Each monomer of the penton base contains an RGD tripeptide motif (Neumann et al., *Gene,* 69: 153-157 (1988)). The RGD tripeptide mediates binding to αv integrins and adenoviruses that have point mutations in the RGD sequence of the penton base are restricted in their ability to infect cells (Bai et al., *J. Virol.,* 67: 5198-5205 (1993)). Thus, the penton base protein is essential for the architecture of the capsid and for maximum efficiency of virus-cell interaction. Nucleic acid sequences that encode all or a portion of an adenovirus penton base protein include, for example, SEQ ID NO: 8 and SEQ ID NO: 3. Amino acid sequences that comprise a full-length adenovirus penton base protein, or a portion thereof, include, for example, SEQ ID NO: 18 and SEQ ID NO: 13.

Nucleic acid or amino acid sequence "identity," as described herein, can be determined by comparing a nucleic acid or amino acid sequence of interest to a reference nucleic acid or amino acid sequence. The number of nucleotides or amino acid residues that have been changed and/or modified (such as, e.g., by point mutations, insertions, or deletions) in the reference sequence so as to result in the sequence of interest are counted. The total number of such changes is subtracted from the total length of the sequence of interest, and the difference is divided by the length of the sequence of interest and expressed as a percentage. A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FASTM, and SSEARCH) (for sequence alignment and sequence similarity searches). Sequence alignment algorithms also are disclosed in, for example, Altschul et al., *J. Molecular Biol.,* 215(3): 403-410 (1990), Beigert et al., *Proc. Natl. Acad. Sci.*

USA, 106(10): 3770-3775 (2009), Durbin et al., eds., *Biological Sequence Analysis: Probalistic Models of Proteins and Nucleic Acids*, Cambridge University Press, Cambridge, UK (2009), Soding, *Bioinformatics*, 21(7): 951-960 (2005), Altschul et al., *Nucleic Acids Res.*, 25(17): 3389-3402 (1997), and Gusfield, *Algorithms on Strings, Trees and Sequences*, Cambridge University Press, Cambridge UK (1997)).

In one embodiment, the adenovirus or adenoviral vector comprises one or more of the following nucleic acid sequences: (a) a nucleic acid sequence that is at least 97% identical (e.g., at least 98.20%, at least 99.41%, or 100% identical) to SEQ ID NO: 1, (b) a nucleic acid sequence that is at least 97.5% identical (e.g., at least 98.5%, at least 99.5%, or 100% identical) to SEQ ID NO: 2, (c) a nucleic acid sequence that is at least 80% identical (e.g., at least 82.22%, at least 84.44%, at least 86.67%, at least 88.89%, at least 91.11%, at least 93.33%, at least 95.56%, at least 97.78%, or 100% identical) to SEQ ID NO: 3, (d) a nucleic acid sequence that is at least 96% identical (e.g., at least 96.9%, at least 97.8%, at least 98.7%, at least 99.6%, or 100% identical) to SEQ ID NO: 4, and (e) a nucleic acid sequence that is at least 96% identical (e.g., at least 96.83% or 100% identical) to SEQ ID NO: 5.

The adenovirus or adenoviral vector can comprise one, two, three, four, or all five of the aforementioned sequences alone or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences. For example, the adenovirus or adenoviral vector can comprise a nucleic acid sequence that is at least 97% identical to SEQ ID NO: 1. The adenovirus or adenoviral vector can comprise a nucleic acid sequence that is at least 97.5% identical to SEQ ID NO: 2 and a nucleic acid sequence that is at least 80% identical to SEQ ID NO: 3. The adenovirus or adenoviral vector can comprise a nucleic acid sequence that is at least 97% identical to SEQ ID NO: 1; a nucleic acid sequence that is at least 80% identical to SEQ ID NO: 3, and a nucleic acid sequence that is at least 96% identical to SEQ ID NO: 5. The adenovirus or adenoviral vector can comprise (a) the nucleic acid sequence of SEQ ID NO: 1, (b) the nucleic acid sequence SEQ ID NO: 2, (c) the nucleic acid sequence of SEQ ID NO: 3, (d) the nucleic acid sequence of SEQ ID NO: 4, or (e) the nucleic acid sequence of SEQ ID NO: 5. The adenovirus or adenoviral vector can comprise (a) a nucleic acid sequence that is at least 97% identical to SEQ ID NO: 1, (b) a nucleic acid sequence that is at least 97.5% identical to SEQ ID NO: 2, (c) a nucleic acid sequence that is at least 80% identical to SEQ ID NO: 3, (d) a nucleic acid sequence that is at least 96% identical to SEQ ID NO: 4, and (e) a nucleic acid sequence that is at least 96% identical to SEQ ID NO: 5. The adenovirus or adenoviral vector can comprise (a) the nucleic acid sequence of SEQ ID NO: 1, (b) the nucleic acid sequence SEQ ID NO: 2, (c) the nucleic acid sequence of SEQ ID NO: 3, (d) the nucleic acid sequence of SEQ ID NO: 4, and (e) the nucleic acid sequence of SEQ ID NO: 5.

In another embodiment, the adenovirus or adenoviral vector comprises one or more of the following nucleic acid sequences: (a) a nucleic acid sequence that is at least 98.4% identical (e.g., at least 98.65%, at least 98.9%, at least 99.15%, at least 99.4%, at least 99.65%, at least 99.9%, or 100% identical) to SEQ ID NO: 6, (b) a nucleic acid sequence that is at least 99.01% identical (e.g., at least 99.04%, at least 99.07%, at least 99.10%, at least 99.14%, at least 99.17%, at least 99.20%, at least 99.23%, at least 99.26%, at least 99.29%, at least 99.33%, at least 99.36%, at least 99.39%, at least 99.42%, at least 99.45%, at least 99.48%, at least 99.52%, at least 99.55%, at least 99.58%, at least 99.61%, at least 99.64%, at least 99.67%, at least 99.70%, at least 99.74%, at least 99.77%, at least 99.80%, at least 99.83%, at least 99.86%, at least 99.89%, at least 99.93%, at least 99.96%, at least 99.99%, or 100% identical) to SEQ ID NO: 7, (c) a nucleic acid sequence that is at least 97.08% identical (e.g., at least 97.13%, at least 97.18%, at least 97.23%, at least 97.28%, at least 97.33%, at least 97.38%, at least 97.43%, at least 97.49%, at least 97.54%, at least 97.59%, at least 97.64%, at least 97.69%, at least 97.74%, at least 97.79%, at least 97.84%, at least 97.89%, at least 97.94%, at least 97.99%, at least 98.04%, at least 98.09%, at least 98.14%, at least 98.19%, at least 98.25%, at least 98.30%, at least 98.35%, at least 98.40%, at least 98.45%, at least 98.50%, at least 98.55%, at least 98.60%, at least 98.65%, at least 98.70%, at least 98.75%, at least 98.80%, at least 98.85%, at least 98.90%, at least 98.95%, at least 99.01%, at least 99.06%, at least 99.11%, at least 99.16%, at least 99.21%, at least 99.26%, at least 99.31%, at least 99.36%, at least 99.41%, at least 99.46%, at least 99.5%1, at least 99.56%, at least 99.61%, at least 99.66%, at least 99.71%, at least 99.76%, at least 99.82%, at least 99.87%, at least 99.92%, at least 99.97%, or 100% identical) to SEQ ID NO: 8, (d) a nucleic acid sequence that is at least 96.52% identical (e.g., at least 96.55%, at least 96.59%, at least 96.62%, at least 96.66%, at least 96.69%, at least 96.73%, at least 96.76%, at least 96.80%, at least 96.83%, at least 96.87%, at least 96.90%, at least 96.94%, at least 96.97%, at least 97.01%, at least 97.04%, at least 97.08%, at least 97.11%, at least 97.15%, at least 97.18%, at least 97.22%, at least 97.25%, at least 97.29%, at least 97.32%, at least 97.36%, at least 97.39%, at least 97.43%, at least 97.46%, at least 97.50%, at least 97.53%, at least 97.57%, at least 97.60%, at least 97.64%, at least 97.67%, at least 97.71%, at least 97.74%, at least 97.78%, at least 97.81%, at least 97.85%, at least 97.88%, at least 97.92%, at least 97.95%, at least 97.99%, at least 98.02%, at least 98.06%, at least 98.09%, at least 98.13%, at least 98.16%, at least at least 98.20%, at least 98.23%, at least 98.27%, at least 98.30%, at least 98.34%, at least 98.37%, at least at least 98.40%, at least 98.44%, at least 98.47%, at least 98.51%, at least 98.54%, at least 98.58%, at least 98.61%, at least 98.65%, at least 98.68%, at least 98.72%, at least 98.75%, at least 98.79%, at least 98.82%, at least 98.86%, at least 98.89%, at least 98.93%, at least 98.96%, at least 99.00%, at least 99.03%, at least 99.07%, at least 99.10%, at least 99.14%, at least 99.17%, at least 99.21%, at least 99.24%, at least 99.28%, at least 99.31%, at least 99.35%, at least 99.38%, at least 99.42%, at least 99.45%, at least 99.49%, at least 99.52%, at least 99.56%, at least 99.59%, at least 99.63%, at least 99.66%, at least 99.70%, at least 99.73%, at least 99.77%, at least 99.80%, at least 99.84%, at least 99.87%, at least 99.91%, at least 99.94%, at least 99.98%, or 100% identical) to SEQ ID NO: 9, and (e) a nucleic acid sequence that is at least 98.49% identical (e.g., at least 98.55%, at least 98.60%, at least 98.66%, at least 98.72%, at least 98.78%, at least 98.83%, at least 98.89%, at least 98.95%, at least 99.01%, at least 99.06%, at least 99.12%, at least 99.18%, at least 99.24%, at least 99.29%, at least 99.35%, at least 99.41%, at least 99.47%, at least 99.52%, at least 99.58%, at least 99.64%, at least 99.70%, at least 99.75%, at least 99.81%, at least 99.87%, at least 99.93%, at least 99.98%, or 100% identical) to SEQ ID NO: 10.

The adenovirus or adenoviral vector can comprise one, two, three, four, or all five of the aforementioned sequences alone or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences. For example, the adenovirus or adenoviral vector can comprise a nucleic acid sequence that is at least 98.4% identical to SEQ ID NO: 6. The adenovirus or adenoviral vector can comprise a nucleic acid sequence that is at least 99.01% identical to SEQ ID NO: 7 and a nucleic acid sequence that is at least 97.08% identical to SEQ ID NO: 8. The adenovirus or adenoviral vector can comprise a nucleic acid sequence that is at least 97.08% identical to SEQ ID NO: 8, a nucleic acid sequence that is at least 96.52% identical to SEQ ID NO: 9, and a nucleic acid sequence that is at least 98.49% identical to SEQ ID NO: 10. The adenovirus or adenoviral vector can comprise (a) the nucleic acid sequence of SEQ ID NO: 6, (b) the nucleic acid sequence SEQ ID NO: 7, (c) the nucleic acid sequence of SEQ ID NO: 8, (d) the nucleic acid sequence of SEQ ID NO: 9, or (e) the nucleic acid sequence of SEQ ID NO: 10. The adenovirus or adenoviral vector can comprise (a) a nucleic acid sequence that is at least 98.4% identical to SEQ ID NO: 6, (b) a nucleic acid sequence that is at least 99.01% identical to SEQ ID NO: 7, (c) a nucleic acid sequence that is at least 97.08% identical to SEQ ID NO: 8, (d) a nucleic acid sequence that is at least 96.52% identical to SEQ ID NO: 9, and (e) a nucleic acid sequence that is at least 98.49% identical to SEQ ID NO: 10. The adenovirus or adenoviral vector can comprise (a) the nucleic acid sequence of SEQ ID NO: 6, (b) the nucleic acid sequence SEQ ID NO: 7, (c) the nucleic acid sequence of SEQ ID NO: 8, (d) the nucleic acid sequence of SEQ ID NO: 9, and (e) the nucleic acid sequence of SEQ ID NO: 10.

In another embodiment, the adenovirus or adenoviral vector comprises one or more of the following nucleic acid sequences: (a) a nucleic acid sequence comprising at least 121 contiguous nucleotides of SEQ ID NO: 6, (b) a nucleic acid sequence comprising at least 462 contiguous nucleotides of SEQ ID NO: 7, (c) a nucleic acid sequence comprising at least 234 contiguous nucleotides of SEQ ID NO: 8, (d) a nucleic acid sequence comprising at least 606 contiguous nucleotides of SEQ ID NO: 9, or (e) a nucleic acid sequence comprising at least 188 contiguous nucleotides of SEQ ID NO: 10.

The adenovirus or adenoviral vector can comprise a nucleic acid sequence comprising at least 121 (e.g., 125 or more, 130 or more, 150 or more, 200 or more, 250 or more, or 300 or more) contiguous nucleotides of SEQ ID NO: 6, but no more than 399 (e.g., 398 or less, 350 or less, or 275 or less) contiguous nucleotides of SEQ ID NO: 6. Preferably, the adenovirus or adenoviral vector comprises a nucleic acid sequence comprising 121 to 300 contiguous nucleotides (e.g., 125, 150, 175, 200, 250, or 275 contiguous nucleotides), 121 to 200 contiguous nucleotides (e.g., 130, 140, 145, 160, 165, 170, 180, 185, 190, 195, or 199 contiguous nucleotides), or 121 to 150 contiguous nucleotides (e.g., 122, 123, 124, 125, 126, 127, 128, 129, 130, 131, 132, 133, 134, 135, 136, 137, 138, 139, 140, 141, 142, 143, 144, 145, 146, 147, 148, or 149 contiguous nucleotides) of SEQ ID NO: 6, or a range defined by any two of the foregoing values.

The adenovirus or adenoviral vector can comprise a nucleic acid sequence comprising at least 462 (e.g., 470 or more, 500 or more, 600 or more, 700 or more, 800 or more, 900 or more, or 1,000 or more) contiguous nucleotides of SEQ ID NO: 7, but no more than 3168 (e.g., 3,100 or less, 3,000 or less, 2,500 or less, 2,000 or less, or 1,500 or less) contiguous nucleotides of SEQ ID NO: 7. Preferably, the adenovirus or adenoviral vector comprises a nucleic acid sequence comprising 462 to 2,000 contiguous nucleotides (e.g., 475, 500, 700, 1,000, 1,200, 1,500, or 1,700 contiguous nucleotides), 462 to 1,000 contiguous nucleotides (e.g., 490, 525, 575, 600, 650, 675, 725, 750, 800, 850, 900, or 950 contiguous nucleotides), or 462 to 800 contiguous nucleotides (e.g., 480, 485, 490, 495, 499, 510, 515, 530, 540, 550, 560, 565, 570, 580, 585, 590, 595, 615, 625, 630, 640, 660, 665, 670, 680, 685, 690, 695, 705, 715, 730, 740, 755, 760, 765, 770, 775, 780, 785, 790, 795, or 799 contiguous nucleotides) of SEQ ID NO: 7, or a range defined by any two of the foregoing values.

The adenovirus or adenoviral vector can comprise a nucleic acid sequence comprising at least 234 (e.g., 235 or more, 250 or more, 300 or more, 350 or more, 400 or more, 450 or more, or 500 or more) contiguous nucleotides of SEQ ID NO: 8, but no more than 1,974 (e.g., 1,900 or less, 1,800 or less, 1,500 or less, 1,200 or less, 1,000 or less, 850 or less, 800 or less, 750 or less, or 700 or less) contiguous nucleotides of SEQ ID NO: 8. Preferably, the adenovirus or adenoviral vector comprises a nucleic acid sequence comprising 234 to 1,500 contiguous nucleotides (e.g., 290, 300, 400, 500, 600, 700, 800, 900, 1,000, or 1,200 contiguous nucleotides), 234 to 1,000 contiguous nucleotides (e.g., 295, 350, 450, 550, 650, 750, 850, or 950 contiguous nucleotides), or 234 to 500 contiguous nucleotides (e.g., 290, 305, 310, 315, 325, 340, 345, 360, 365, 370, 375, 380, 385, 390, 395, 405, 425, 430, 440, 455, 460, 465, 470, 475, 480, 485, 490, 495, or 499 contiguous nucleotides) of SEQ ID NO: 8, or a range defined by any two of the foregoing values.

The adenovirus or adenoviral vector can comprise a nucleic acid sequence comprising at least 606 (e.g., 610 or more, 650 or more, 700 or more, 800 or more, or 1,000 or more) contiguous nucleotides of SEQ ID NO: 9, but no more than 2865 (2,800 or less, 2,500 or less, 2,000 or less, 1,800 or less, or 1,500 or less) contiguous nucleotides of SEQ ID NO: 9. Preferably, the adenovirus or adenoviral vector comprises a nucleic acid sequence comprising 606 to 2,000 contiguous nucleotides (e.g., 615, 650, 700, 800, 900, 1,000, 1,200, 1,500, 1,700, or 1,900 contiguous nucleotides), 606 to 1,000 contiguous nucleotides (e.g., 630, 645, 665, 675, 725, 750, 775, 825, 850, 875, 925, 950, or 975 contiguous nucleotides), or 606 to 800 contiguous nucleotides (e.g., 620, 635, 640, 655, 660, 670, 680, 685, 690, 695, 699, 705, 715, 730, 735, 740, 745, 755, 760, 765, 770, 785, 790, 795, or 799 contiguous nucleotides) of SEQ ID NO: 9, or a range defined by any two of the foregoing values.

The adenovirus or adenoviral vector can comprise a nucleic acid sequence comprising at least 188 (e.g., 189 or more, 200 or more, 300 or more, 500 or more, 700 or more, or 900 or more) contiguous nucleotides of SEQ ID NO: 10, but no more than 1,740 (1,700 or less, 1,500 or less, 1,200 or less, or 1,000 or less) contiguous nucleotides of SEQ ID NO: 10. Preferably, the adenovirus or adenoviral vector comprises a nucleic acid sequence comprising 188 to 1,500 contiguous nucleotides (e.g., 200, 400, 600, 800, 1,000, 1,200, or 1,400 contiguous nucleotides), 188 to 1,000 contiguous nucleotides (e.g., 195, 250, 350, 450, 550, 650, 750, 850, or 950 contiguous nucleotides), or 188 to 500 contiguous nucleotides (e.g., 190, 225, 230, 240, 255, 260, 265, 270, 275, 315, 325, 330, 340, 355, 360, 365, 370, 375, 380, 385, 390, 395, 415, 425, 430, 440, 455, 460, 465, 470, 475, 480, 485, 490, 495, or 499 contiguous nucleotides) of SEQ ID NO: 10, or a range defined by any two of the foregoing values.

The adenovirus or adenoviral vector can comprise one, two, three, four, or all five of the aforementioned sequences alone, or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences. For example, the adenovirus or adenoviral vector can comprise a nucleic acid sequence comprising at least 121 contiguous nucleotides of SEQ ID NO: 6. The adenovirus or adenoviral vector can comprise a nucleic acid sequence comprising at least 234 contiguous nucleotides of SEQ ID NO: 8, and a nucleic acid sequence comprising at least 188 contiguous nucleotides of SEQ ID NO: 10. The adenovirus or adenoviral vector can comprise a nucleic acid sequence comprising at least 462 contiguous nucleotides of SEQ ID NO: 7, a nucleic acid sequence comprising at least 606 contiguous nucleotides of SEQ ID NO: 9, and a nucleic acid sequence comprising at least 188 contiguous nucleotides of SEQ ID NO: 10. The adenovirus or adenoviral vector can comprise a nucleic acid sequence comprising at least 121 contiguous nucleotides of SEQ ID NO: 6, a nucleic acid sequence comprising at least 462 contiguous nucleotides of SEQ ID NO: 7, a nucleic acid sequence comprising at least 234 contiguous nucleotides of SEQ ID NO: 8, and a nucleic acid sequence comprising at least 606 contiguous nucleotides of SEQ ID NO: 9. The adenovirus or adenoviral vector can comprise (a) a nucleic acid sequence comprising at least 121 contiguous nucleotides of SEQ ID NO: 6, (b) a nucleic acid sequence comprising at least 462 contiguous nucleotides of SEQ ID NO: 7, (c) a nucleic acid sequence comprising at least 234 contiguous nucleotides of SEQ ID NO: 8, (d) a nucleic acid sequence comprising at least 606 contiguous nucleotides of SEQ ID NO: 9, and (e) a nucleic acid sequence comprising at least 188 contiguous nucleotides of SEQ ID NO: 10.

In another embodiment, the adenovirus or adenoviral vector comprises one or more of the following amino acid sequences: (a) an amino acid sequence that is at least 93% identical (e.g., at least 96.57% or 100% identical) to SEQ ID NO: 11, (b) an amino acid sequence that is at least 80% identical (e.g., at least 86.67%, at least 93.33%, or 100% identical) to SEQ ID NO: 13, (c) an amino acid sequence that is at least 92% identical (e.g., at least 97.56% or 100% identical) to SEQ ID NO: 14, and (d) an amino acid sequence that is at least 88% identical (e.g., at least 94.67% or 100% identical) to SEQ ID NO: 15.

The adenovirus or adenoviral vector can comprise one, two, three, or all four of the aforementioned amino acid sequences alone or in any combination. In this respect, the adenovirus or adenoviral vector can comprise any combination of any two of the aforementioned sequences, any combination of any three of the aforementioned sequences, or all four of the aforementioned sequences. For example, the adenovirus or adenoviral vector can comprise an amino acid sequence that is at least 93% identical to SEQ ID NO: 11. The adenovirus or adenoviral vector can comprise an amino acid sequence that is at least 93% identical to SEQ ID NO: 11, and an amino acid sequence that is at least 80% identical to SEQ ID NO: 13. The adenovirus or adenoviral vector can comprise an amino acid sequence that is at least 93% identical to SEQ ID NO: 11, an amino acid sequence that is at least 80% identical to SEQ ID NO: 13, and an amino acid sequence that is at least 88% identical to SEQ ID NO: 15. The adenovirus or adenoviral vector can comprise (a) the amino acid sequence of SEQ ID NO: 11, (b) the amino acid sequence of SEQ ID NO: 13, (c) the amino acid sequence of SEQ ID NO: 14, or (d) the amino acid sequence of SEQ ID NO: 15. The adenovirus or adenoviral vector can comprise (a) an amino acid sequence that is at least 93% identical to SEQ ID NO: 11, (b) an amino acid sequence that is at least 80% identical to SEQ ID NO: 13, (c) an amino acid sequence that is at least 92% identical to SEQ ID NO: 14, and (d) an amino acid sequence that is at least 88% identical to SEQ ID NO: 15. The adenovirus or adenoviral vector can comprise (a) the amino acid sequence of SEQ ID NO: 11, (b) the amino acid sequence of SEQ ID NO: 13, (c) the amino acid sequence of SEQ ID NO: 14, and (d) the amino acid sequence of SEQ ID NO: 15.

In another embodiment, the adenovirus or adenoviral vector comprises one or more of the following amino acid sequences: (a) an amino acid sequence that is at least 99% identical (e.g., at least 99.75% or 100% identical) to SEQ ID NO: 16, (b) an amino acid sequence that is at least 97.8% identical (e.g., at least 97.95%, at least 98.10%, at least 98.26%, at least 98.41%, at least 98.56%, at least 98.71%, at least 98.86%, at least 99.02%, at least 99.17%, at least 99.32%, at least 99.47%, at least 99.62%, at least 99.78%, at least 99.93%, or 100% identical) to SEQ ID NO: 18, (c) an amino acid sequence that is at least 99.1% identical (e.g., at least 99.20%, at least 99.31%, at least 99.41%, at least 99.52%, at least 99.62%, at least 99.73%, at least 99.83%, at least 99.94%, or 100% identical) to SEQ ID NO: 19, and (d) an amino acid sequence that is at least 99.2% identical (e.g., at least 99.37%, at least 99.54%, at least 99.72%, at least 99.89%, or 100% identical) to SEQ ID NO: 20.

The adenovirus or adenoviral vector can comprise one, two, three, or all four of the aforementioned amino acid sequences alone or in any combination. In this respect, the adenovirus or adenoviral vector can comprise any combination of any two of the aforementioned sequences, any combination of any three of the aforementioned sequences, or all four of the aforementioned sequences. For example, the adenovirus or adenoviral vector can comprise an amino acid sequence that is at least 99% identical to SEQ ID NO: 16. The adenovirus or adenoviral vector can comprise an amino acid sequence that is at least 99% identical to SEQ ID NO: 16, and an amino acid sequence that is at least 99.1% identical to SEQ ID NO: 19. The adenovirus or adenoviral vector can comprise an amino acid sequence that is at least 99% identical to SEQ ID NO: 16, an amino acid sequence that is at least 99.1% identical to SEQ ID NO: 19, and an amino acid sequence that is at least 99.2% identical to SEQ ID NO: 20. The adenovirus or adenoviral vector can comprise (a) the amino acid sequence of SEQ ID NO: 16, (b) the amino acid sequence of SEQ ID NO: 18, (c) the amino acid sequence of SEQ ID NO: 19, or (d) the amino acid sequence of SEQ ID NO: 20. The adenovirus or adenoviral vector can comprise (a) an amino acid sequence that is at least 99% identical to SEQ ID NO: 16, (b) an amino acid sequence that is at least 97.8% identical to SEQ ID NO: 18, (c) an amino acid that is at least 99.1% identical to SEQ ID NO: 19, and (d) an amino acid sequence that is at least 99.2% identical to SEQ ID NO: 20. The adenovirus or adenoviral vector can comprise (a) the amino acid sequence of SEQ ID NO: 16, (b) the amino acid sequence of SEQ ID NO: 18, (c) the amino acid sequence of SEQ ID NO: 19, and (d) the amino acid sequence of SEQ ID NO: 20.

In another embodiment, the adenovirus or adenoviral vector comprises one or more of the following amino acid sequences: (a) an amino acid sequence comprising at least 89 contiguous amino acid residues of SEQ ID NO: 16, (b) an amino acid sequence comprising at least 247 contiguous amino acid residues of SEQ ID NO: 18, (c) an amino acid sequence comprising at least 230 contiguous amino acid residues of SEQ ID NO: 19, and (d) an amino acid sequence comprising at least 231 contiguous amino acid residues of SEQ ID NO: 20.

The adenovirus or adenoviral vector can comprise an amino acid sequence comprising at least 89 (e.g., 90 or more, 100 or more, or 110 or more) contiguous amino acid residues of SEQ ID NO: 16, but no more than 133 (e.g., 130 or less, 125 or less, 120 or less, or 115 or less) contiguous amino acid residues of SEQ ID NO: 16. Preferably, the adenovirus or adenoviral vector comprises an amino acid sequence comprising 89 to 130 contiguous amino acid residues (e.g., 90, 100, 110, 115, 120, or 125 contiguous amino acid residues) of SEQ ID NO: 16, 89 to 115 contiguous amino acid residues of SEQ ID NO: 16 (e.g., 95, 110, or 112 contiguous amino acid residues), or 89 to 100 contiguous amino acid residues (e.g., 89, 90, 91, 92, 93, 94, 95, 96, 97, 98, or 99 contiguous amino acid residues) of SEQ ID NO: 16, or a range defined by any two of the foregoing values.

The adenovirus or adenoviral vector can comprise an amino acid sequence comprising at least 247 (e.g., 250 or more, 275 or more, 300 or more, or 400 or more) contiguous amino acid residues of SEQ ID NO: 18, but no more than 658 (e.g., 650 or less, 550 or less, or 450 or less) contiguous amino acid residues of SEQ ID NO: 18. Preferably, the adenovirus or adenoviral vector comprises an acid sequence comprising 247 to 600 contiguous amino acid residues (e.g., 255, 275, 300, 400, or 500 contiguous amino acid residues) of SEQ ID NO: 18, 247 to 500 contiguous amino acid residues of SEQ ID NO: 18 (e.g., 325, 350, 375, 425, 450, or 475 contiguous amino acid residues), or 247 to 400 contiguous amino acid residues (e.g., 265, 280, 285, 290, 295, 360, 365, 380, 385, 390, 395, or 399 contiguous amino acid residues) of SEQ ID NO: 18, or a range defined by any two of the foregoing values.

The adenovirus or adenoviral vector can comprise an amino acid sequence comprising at least 230 (e.g., 250 or more, 300 or more, 350 or more, 400 or more, or 500 or more) contiguous amino acid residues of SEQ ID NO: 19, but no more than 955 (e.g., 950 or less, 900 or less, 800 or less, 700 or less, or 600 or less) contiguous amino acid residues of SEQ ID NO: 19. Preferably, the adenovirus or adenoviral vector comprises an acid sequence comprising 230 to 800 contiguous amino acid residues (e.g., 240, 260, 270, 280, 290, 300, 350, 390, 400, 500, 600, or 750 contiguous amino acid residues) of SEQ ID NO: 19, 230 to 600 contiguous amino acid residues (e.g., 255, 265, 275, 285, 295, 305, 325, 335, 345, 355, 365, 375, 385, 395, 425, 445, 450, 465, 475, 525, 545, 550, 565 or 575 contiguous amino acid residues) of SEQ ID NO: 19, or 230 to 500 contiguous amino acid residues (e.g., 235, 245, 299, 320, 330, 340, 360, 370, 385, 389, 395, 399, 415, 435, 440, 460, 470, 480, or 499 contiguous amino acid residues) of SEQ ID NO: 19, or a range defined by any two of the foregoing values.

The adenovirus or adenoviral vector can comprise an amino acid sequence comprising at least 231 (e.g., 250 or more, 300 or more, or 350 or more) contiguous amino acid residues of SEQ ID NO: 20, but no more than 580 (e.g., 575 or less, 550 or less, 500 or less, 450 or less, or 400 or less) contiguous amino acid residues of SEQ ID NO: 20. Preferably, the adenovirus or adenoviral vector comprises an acid sequence comprising 231 to 500 contiguous amino acid residues (e.g., 245, 255, 275, 300, 350, 375, or 400 contiguous amino acid residues) of SEQ ID NO: 20, 231 to 400 contiguous amino acid residues (e.g., 235, 265, 280, 285, 295, 305, 315, 325, 335, 345, 355, 365, 375, 385, 395, or 399 contiguous amino acid residues) of SEQ ID NO: 20, or 231 to 300 contiguous amino acid residues (e.g., 240, 250, 260, 270, or 299 contiguous amino acid residues) of SEQ ID NO: 20, or a range defined by any two of the foregoing values.

The adenovirus or adenoviral vector can comprise one, two, three, or all four of the aforementioned amino acid sequences alone or in any combination. In this respect, the adenovirus or adenoviral vector can comprise any combination of any two of the aforementioned sequences, any combination of any three of the aforementioned sequences, or all four of the aforementioned sequences. For example, the adenovirus or adenoviral vector can comprise an amino acid sequence comprising at least 89 contiguous amino acid residues of SEQ ID NO: 16. The adenovirus or adenoviral vector can comprise an amino acid sequence comprising at least 89 contiguous amino acid residues of SEQ ID NO: 16, and an amino acid sequence comprising at least 230 contiguous amino acid residues of SEQ ID NO: 19. The adenovirus or adenoviral vector can comprise an amino acid sequence comprising at least 89 contiguous amino acid residues of SEQ ID NO: 16, an amino acid sequence comprising at least 247 contiguous amino acid residues of SEQ ID NO: 18, and an amino acid sequence comprising at least 230 contiguous amino acid residues of SEQ ID NO: 19. The adenovirus or adenoviral vector can comprise an amino acid sequence comprising at least 89 contiguous amino acid residues of SEQ ID NO: 16, an amino acid sequence comprising at least 247 contiguous amino acid residues of SEQ ID NO: 18, and an amino acid sequence comprising at least 231 contiguous amino acid residues of SEQ ID NO: 20. The adenovirus or adenoviral vector can comprise (a) an amino acid sequence comprising at least 89 contiguous amino acid residues of SEQ ID NO: 16, (b) an amino acid sequence comprising at least 247 contiguous amino acid residues of SEQ ID NO: 18, (c) an amino acid sequence comprising at least 230 contiguous amino acid residues of SEQ ID NO: 19, and (d) an amino acid sequence comprising at least 231 contiguous amino acid residues of SEQ ID NO: 20.

In other embodiments, the adenovirus or adenoviral vector comprises one or more nucleic acid sequences that encode one or more of any of the aforementioned amino acid sequences, e.g., the amino acid sequences of any of SEQ ID NOs: 11-20 or any of the variants and/or portions thereof as described herein. For example, the adenovirus or adenoviral vector can comprise a nucleic acid sequence encoding an amino acid sequence that is at least 99.5% identical (e.g., at least 99.59%, at least 99.69%, at least 99.78%, at least 99.88%, at least 99.97%, or 100% identical) to SEQ ID NO: 17, or a nucleic acid sequence encoding an amino acid sequence that is at least 95% identical (e.g., at least 97.94% or 100% identical) to SEQ ID NO: 12.

The adenovirus or adenoviral vector can comprise the nucleic acid sequence of, for example, SEQ ID NO: 21, SEQ ID NO: 22, SEQ ID NO: 23, SEQ ID NO: 24, SEQ ID NO: 25, SEQ ID NO: 26, SEQ ID NO: 27, or SEQ ID NO: 28.

As discussed herein, the adenovirus or adenoviral vector can be replication-competent, conditionally-replicating, or replication-deficient. Preferably, the adenovirus or adenoviral vector is replication-deficient, such that the replication-deficient adenovirus or adenoviral vector requires complementation of at least one replication-essential gene function of one or more regions of the adenoviral genome for propagation (e.g., to form adenoviral vector particles).

The replication-deficient adenovirus or adenoviral vector can be modified in any suitable manner to cause the deficiencies in the one or more replication-essential gene functions in one or more regions of the adenoviral genome for propagation. The complementation of the deficiencies in the one or more replication-essential gene functions of one or more regions of the adenoviral genome refers to the use of exogenous means to provide the deficient replication-essential gene functions. Such complementation can be effected in any suitable manner, for example, by using complementing cells and/or exogenous DNA (e.g., helper adenovirus) encoding the disrupted replication-essential gene functions.

The adenovirus or adenoviral vector can be deficient in one or more replication-essential gene functions of only the early regions (i.e., E1-E4 regions) of the adenoviral genome, only the late regions (i.e., L1-L5 regions) of the adenoviral genome, both the early and late regions of the adenoviral genome, or all adenoviral genes (i.e., a high capacity adenovector (HC-Ad). See Morsy et al., Proc. Natl. Acad. Sci. USA, 95: 965-976 (1998); Chen et al., Proc. Natl. Acad. Sci. USA, 94: 1645-1650 (1997); and Kochanek et al., Hum. Gene Ther., 10: 2451-2459 (1999). Examples of replication-deficient adenoviral vectors are disclosed in U.S. Pat. Nos. 5,837,511; 5,851,806; 5,994,106; 6,127,175; 6,482,616; and 7,195,896, and International Patent Application Publications WO 1994/028152, WO 1995/002697, WO 1995/016772, WO 1995/034671, WO 1996/022378, WO 1997/012986, WO 1997/021826, and WO 2003/022311.

The early regions of the adenoviral genome include the E1, E2, E3, and E4 regions. The E1 region comprises the E1A and E1B subregions, and one or more deficiencies in replication-essential gene functions in the E1 region can include one or more deficiencies in replication-essential gene functions in either or both of the E1A and E1B subregions, thereby requiring complementation of the E1A subregion and/or the E1B subregion of the adenoviral genome for the adenovirus or adenoviral vector to propagate (e.g., to form adenoviral vector particles). The E2 region comprises the E2A and E2B subregions, and one or more deficiencies in replication-essential gene functions in the E2 region can include one or more deficiencies in replication-essential gene functions in either or both of the E2A and E2B subregions, thereby requiring complementation of the E2A subregion and/or the E2B subregion of the adenoviral genome for the adenovirus or adenoviral vector to propagate (e.g., to form adenoviral vector particles).

The E3 region does not include any replication-essential gene functions, such that a deletion of the E3 region in part or in whole does not require complementation of any gene functions in the E3 region for the adenovirus or adenoviral vector to propagate (e.g., to form adenoviral vector particles). In the context of the invention, the E3 region is defined as the region that initiates with the open reading frame that encodes a protein with high homology to the 12.5K protein from the E3 region of human adenovirus 5 (NCBI reference sequence AP_000218) and ends with the open reading frame that encodes a protein with high homology to the 14.7K protein from the E3 region of human adenovirus 5 (NCBI reference sequence AP_000224.1). The E3 region may be deleted in whole or in part, or retained in whole or in part. The size of the deletion may be tailored so as to retain an adenovirus or adenoviral vector whose genome closely matches the optimum genome packaging size. A larger deletion will accommodate the insertion of larger heterologous nucleic acid sequences in the adenovirus or adenoviral genome. In one embodiment of the invention, the L4 polyadenylation signal sequences, which reside in the E3 region, are retained.

The E4 region comprises multiple open reading frames (ORFs). An adenovirus or adenoviral vector with a deletion of all of the open reading frames of the E4 region except ORF6, and in some cases ORF3, does not require complementation of any gene functions in the E4 region for the adenovirus or adenoviral vector to propagate (e.g., to form adenoviral vector particles). Conversely, an adenovirus or adenoviral vector with a disruption or deletion of ORF6, and in some cases ORF3, of the E4 region (e.g., with a deficiency in a replication-essential gene function based in ORF6 and/or ORF3 of the E4 region), with or without a disruption or deletion of any of the other open reading frames of the E4 region or the native E4 promoter, polyadenylation sequence, and/or the right-side inverted terminal repeat (ITR), requires complementation of the E4 region (specifically, of ORF6 and/or ORF3 of the E4 region) for the adenovirus or adenoviral vector to propagate (e.g., to form adenoviral vector particles). The late regions of the adenoviral genome include the L1, L2, L3, L4, and L5 regions. The adenovirus or adenoviral vector also can have a mutation in the major late promoter (MLP), as discussed in International Patent Application Publication WO 2000/000628, which can render the adenovirus or adenoviral vector replication-deficient if desired.

The one or more regions of the adenoviral genome that contain one or more deficiencies in replication-essential gene functions desirably are one or more early regions of the adenoviral genome, i.e., the E1, E2, and/or E4 regions, optionally with the deletion in part or in whole of the E3 region.

The replication-deficient adenovirus or adenoviral vector also can have one or more mutations as compared to the wild-type adenovirus (e.g., one or more deletions, insertions, and/or substitutions) in the adenoviral genome that do not inhibit viral replication in host cells. Thus, in addition to one or more deficiencies in replication-essential gene functions, the adenovirus or adenoviral vector can be deficient in other respects that are not replication-essential. For example, the adenovirus or adenoviral vector can have a partial or entire deletion of the adenoviral early region known as the E3 region, which is not essential for propagation of the adenovirus or adenoviral genome.

In one embodiment, the adenovirus or adenoviral vector is replication-deficient and requires, at most, complementation of the E1 region or the E4 region of the adenoviral genome, for propagation (e.g., to form adenoviral vector particles). Thus, the replication-deficient adenovirus or adenoviral vector requires complementation of at least one replication-essential gene function of the E1A subregion and/or the E1B region of the adenoviral genome (denoted an E1-deficient adenoviral vector) or the E4 region of the adenoviral genome (denoted an E4-deficient adenoviral vector) for propagation (e.g., to form adenoviral vector particles). The adenovirus or adenoviral vector can be deficient in at least one replication-essential gene function (desirably all replication-essential gene functions) of the E1 region of the adenoviral genome and at least one gene function of the nonessential E3 region of the adenoviral genome (denoted an E1/E3-deficient adenoviral vector). The adenovirus or adenoviral vector can be deficient in at least one replication-essential gene function (desirably all replication-essential gene functions) of the E4 region of the adenoviral genome and at least one gene function of the nonessential E3 region of the adenoviral genome (denoted an E3/E4-deficient adenoviral vector).

In one embodiment, the adenovirus or adenoviral vector is replication-deficient and requires, at most, complementation of the E2 region, preferably the E2A subregion, of the adenoviral genome, for propagation (e.g., to form adenoviral vector particles). Thus, the replication-deficient adenovirus or adenoviral vector requires complementation of at least one replication-essential gene function of the E2A subregion of the adenoviral genome (denoted an E2A-deficient adenoviral vector) for propagation (e.g., to form adenoviral vector particles). The adenovirus or adenoviral vector can be deficient in at least one replication-essential gene function (desirably all replication-essential gene functions) of the E2A region of the adenoviral genome and at least one gene function of the nonessential E3 region of the adenoviral genome (denoted an E2A/E3-deficient adenoviral vector).

In one embodiment, the adenovirus or adenoviral vector is replication-deficient and requires, at most, complementation of the E1 and E4 regions of the adenoviral genome for propagation (e.g., to form adenoviral vector particles). Thus, the replication-deficient adenovirus or adenoviral vector requires complementation of at least one replication-essential gene function of both the E1 and E4 regions of the adenoviral genome (denoted an E1/E4-deficient adenoviral vector) for propagation (e.g., to form adenoviral vector particles). The adenovirus or adenoviral vector can be deficient in at least one replication-essential gene function (desirably all replication-essential gene functions) of the E1 region of the adenoviral genome, at least one replication-essential gene function of the E4 region of the adenoviral genome, and at least one gene function of the nonessential E3 region of the adenoviral genome (denoted an E1/E3/E4-deficient adenoviral vector). The adenovirus or adenoviral vector preferably requires, at most, complementation of the E1 region of the adenoviral genome for propagation, and does not require complementation of any other deficiency of the adenoviral genome for propagation. More preferably, the adenovirus or adenoviral vector requires, at most, complementation of the E1 and E4 regions of the adenoviral genome for propagation, and does not require complementation of any other deficiency of the adenoviral genome for propagation.

The adenovirus or adenoviral vector, when deficient in multiple replication-essential gene functions of the adenoviral genome (e.g., an E1/E4-deficient adenoviral vector), can include a spacer sequence to provide viral growth in a complementing cell line similar to that achieved by adenoviruses or adenoviral vectors deficient in a single replication-essential gene function (e.g., an E1-deficient adenoviral vector). The spacer sequence can contain any nucleotide sequence or sequences which are of a desired length, such as sequences at least about 15 base pairs (e.g., between about 15 nucleotides and about 12,000 nucleotides), preferably about 100 nucleotides to about 10,000 nucleotides, more preferably about 500 nucleotides to about 8,000 nucleotides, even more preferably about 1,500 nucleotides to about 6,000 nucleotides, and most preferably about 2,000 to about 3,000 nucleotides in length, or a range defined by any two of the foregoing values. The spacer sequence can be coding or non-coding and native or non-native with respect to the adenoviral genome, but does not restore the replication-essential function to the deficient region. The spacer also can contain an expression cassette. More preferably, the spacer comprises a polyadenylation sequence and/or a gene that is non-native with respect to the adenovirus or adenoviral vector. The use of a spacer in an adenoviral vector is further described in, for example, U.S. Pat. No. 5,851,806 and International Patent Application Publication WO 1997/021826.

By removing all or part of the adenoviral genome, for example, the E1, E3, and E4 regions of the adenoviral genome, the resulting adenovirus or adenoviral vector is able to accept inserts of exogenous nucleic acid sequences while retaining the ability to be packaged into adenoviral capsids. An exogenous nucleic acid sequence can be inserted at any position in the adenoviral genome so long as insertion in the position allows for the formation of adenovirus or the adenoviral vector particle. The exogenous nucleic acid sequence preferably is positioned in the E1 region, the E3 region, or the E4 region of the adenoviral genome.

The replication-deficient adenovirus or adenoviral vector of the invention can be produced in complementing cell lines that provide gene functions not present in the replication-deficient adenovirus or adenoviral vector, but required for viral propagation, at appropriate levels in order to generate high titers of viral vector stock. Such complementing cell lines are known and include, but are not limited to, 293 cells (described in, e.g., Graham et al., *J. Gen. Virol.,* 36: 59-72 (1977)), PER.C6 cells (described in, e.g., International Patent Application Publication WO 1997/000326, and U.S. Pat. Nos. 5,994,128 and 6,033,908), and 293-ORF6 cells (described in, e.g., International Patent Application Publication WO 95/34671 and Brough et al., *J. Virol.,* 71: 9206-9213 (1997)). Other suitable complementing cell lines to produce the replication-deficient adenovirus or adenoviral vector of the invention include complementing cells that have been generated to propagate adenoviral vectors encoding transgenes whose expression inhibits viral growth in host cells (see, e.g., U.S. Patent Application Publication No. 2008/0233650). Additional suitable complementing cells are described in, for example, U.S. Pat. Nos. 6,677,156 and 6,682,929, and International Patent Application Publication WO 2003/020879. In some instances, the cellular genome need not comprise nucleic acid sequences, the gene products of which complement for all of the deficiencies of a replication-deficient adenoviral vector. One or more replication-essential gene functions lacking in a replication-deficient adenoviral vector can be supplied by a helper virus, e.g., an adenoviral vector that supplies in trans one or more essential gene functions required for replication of the replication-deficient adenovirus or adenoviral vector. Alternatively, the inventive adenovirus or adenoviral vector can comprise a non-native replication-essential gene that complements for the one or more replication-essential gene functions lacking in the inventive replication-deficient adenovirus or adenoviral vector. For example, an E1/E4-deficient adenoviral vector can be engineered to contain a nucleic acid sequence encoding E4 ORF 6 that is obtained or derived from a different adenovirus (e.g., an adenovirus of a different serotype than the inventive adenovirus or adenoviral vector, or an adenovirus of a different species than the inventive adenovirus or adenoviral vector).

The adenovirus or adenoviral vector can further comprise a transgene. The ten "transgene" is defined herein as a non-native nucleic acid sequence that is operably linked to appropriate regulatory elements (e.g., a promoter), such that the non-native nucleic acid sequence can be expressed to produce a protein (e.g., peptide or polypeptide). The regulatory elements (e.g., promoter) can be native or non-native to the adenovirus or adenoviral vector.

A "non-native" nucleic acid sequence is any nucleic acid sequence (e.g., DNA, RNA, or cDNA sequence) that is not a naturally occurring nucleic acid sequence of an adenovirus in a naturally occurring position. Thus, the non-native nucleic acid sequence can be naturally found in an adenovirus, but located at a non-native position within the adenoviral genome and/or operably linked to a non-native promoter. The terms "non-native nucleic acid sequence," "heterologous nucleic acid sequence," and "exogenous nucleic acid sequence" are synonymous and can be used interchangeably in the context of the invention. The non-native nucleic acid sequence preferably is DNA and preferably encodes a protein (i.e., one or more nucleic acid sequences encoding one or more proteins).

The non-native nucleic acid sequence can encode a therapeutic protein that can be used to prophylactically or therapeutically treat a mammal for a disease. Examples of suitable therapeutic proteins include cytokines, toxins, tumor suppressor proteins, growth factors, hormones, receptors, mitogens, immunoglobulins, neuropeptides, neurotransmitters, and enzymes. Alternatively, the non-native nucleic acid sequence can encode an antigen of a pathogen (e.g., a bacterium or a virus), and the adenovirus or adenoviral vector can be used as a vaccine.

The invention provides a composition comprising the adenovirus or adenoviral vector described herein and a carrier therefor (e.g., a pharmaceutically acceptable carrier). The composition desirably is a physiologically acceptable (e.g., pharmaceutically acceptable) composition, which comprises a carrier, preferably a physiologically (e.g., pharmaceutically) acceptable carrier, and the adenovirus or adenoviral vector. Any suitable carrier can be used within the context of the invention, and such carriers are well known in the art. The choice of carrier will be determined, in part, by the particular use of the composition (e.g., administration to an animal) and the particular method used to administer the composition. Ideally, in the context of replication-deficient adenoviral vectors, the pharmaceutical composition preferably is free of replication-competent adenovirus. The pharmaceutical composition optionally can be sterile.

Suitable compositions include aqueous and non-aqueous isotonic sterile solutions, which can contain anti-oxidants, buffers, and bacteriostats, and aqueous and non-aqueous sterile suspensions that can include suspending agents, solubilizers, thickening agents, stabilizers, and preservatives. The composition can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the adenovirus or adenoviral vector is part of a composition formulated to protect the adenovirus or adenoviral vector from damage prior to administration. For example, the composition can be formulated to reduce loss of the adenovirus or adenoviral vector on devices used to prepare, store, or administer the adenovirus or adenoviral vector, such as glassware, syringes, or needles. The composition can be formulated to decrease the light sensitivity and/or temperature sensitivity of the adenovirus or adenoviral vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the adenovirus or adenoviral vector, and facilitate its administration. Formulations for adenovirus or adenoviral vector-containing compositions are further described in, for example, U.S. Pat. No. 6,225,289, U.S. Pat. No. 6,514,943, and International Patent Application Publication WO 2000/034444.

The composition also can be formulated to enhance transduction efficiency. In addition, one of ordinary skill in the art will appreciate that the adenovirus or adenoviral vector can be present in a composition with other therapeutic or biologically-active agents. For example, factors that control inflammation, such as ibuprofen or steroids, can be part of the composition to reduce swelling and inflammation associated with in vivo administration of the adenovirus or adenoviral vector. If the adenovirus or adenoviral vector is used to deliver an antigen-encoding nucleic acid sequence to a host, immune system stimulators or adjuvants, e.g., interleukins, lipopolysaccharide, or double-stranded RNA, can be administered to enhance or modify any immune response to the antigen. Antibiotics, i.e., microbicides and fungicides, can be present to treat existing infection and/or reduce the risk of future infection, such as infection associated with gene transfer procedures.

The following examples further illustrate the present invention and, of course, should not be construed as in any way limiting its scope.

Example 1

This example demonstrates the immunogenicity of an adenoviral vector encoding a Respiratory Syncytial Virus (RSV) F protein in cotton rats.

A *gorilla* adenovirus having the nucleic acid sequence of SEQ ID NO: 22 was modified by genetic engineering to (1) be rendered replication-deficient by deletion of the E1 region, and (2) express the human Respiratory Syncytial Virus (RSV) Fusion (F) glycoprotein. Because RSV replicates in the cytoplasm of cells, the gene encoding the F protein was modified for expression in a cell nucleus by removing RNA processing signals (e.g., RNA splicing sites), and was codon-optimized for expression in a mammalian cell. The expression of the F protein from the adenoviral vector was verified by infection of HEK-293 cells in vitro, and by a Western blot assay using protein extracts of infected cells and a commercially available anti-RSV polyclonal antibody (Pab7133P, Maine Biotechnology, Portland, Me.).

Cotton rats (*Sigmodon hispidus*) were injected in the tibialis muscle with a single administration of $10^7$ particle units (pu) of the E1-deleted adenoviral vector expressing the RSV F glycoprotein. The animals were then challenged 28 days later with live human RSV ($10^6$ particle forming units (pfu) administered intranasally). At 5 days post-challenge, the viral load of RSV in the lungs of the animals was measured. The animals that were immunized with the adenoviral vector expressing the F protein did not have detectable RSV in the lungs (limit of detection 70 pfu/gram of lung tissue).

The results of this example demonstrate that the inventive adenoviral vector encoding an RSV F protein is immunogenic in vivo and can confer complete protection against RSV infection in cotton rats.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An adenovirus or adenoviral vector comprising a non-native nucleic acid sequence and a nucleic acid sequence that is at least 96.52% identical to SEQ ID NO: 9.

2. The adenovirus or adenoviral vector of claim 1, which further comprises one or more of the nucleic acid sequences selected from the group consisting of:
   (a) a nucleic acid sequence that is at least 98.4% identical to SEQ ID NO: 6,
   (b) a nucleic acid sequence that is at least 99.01% identical to SEQ ID NO: 7,
   (c) a nucleic acid sequence that is at least 97.08% identical to SEQ ID NO: 8, and
   (d) a nucleic acid sequence that is at least 98.49% identical to SEQ ID NO: 10.

3. The adenovirus or adenoviral vector of claim 2, which comprises a nucleic acid sequence that is at least 98.4% identical to SEQ ID NO: 6.

4. The adenovirus or adenoviral vector of claim 3, which comprises the nucleic acid sequence of SEQ ID NO: 6.

5. The adenovirus or adenoviral vector of claim 2, which comprises a nucleic acid sequence that is at least 99.01% identical to SEQ ID NO: 7.

6. The adenovirus or adenoviral vector of claim 5, which comprises the nucleic acid sequence of SEQ ID NO: 7.

7. The adenovirus or adenoviral vector of claim 2, which comprises a nucleic acid sequence that is at least 97.08% identical to SEQ ID NO: 8.

8. The adenovirus or adenoviral vector of claim 7, which comprises the nucleic acid sequence of SEQ ID NO: 8.

9. The adenovirus or adenoviral vector of claim 1, which comprises the nucleic acid sequence of SEQ ID NO: 9.

10. The adenovirus or adenoviral vector of claim 2, which comprises a nucleic acid sequence that is at least 98.49% identical to SEQ ID NO: 10.

11. The adenovirus or adenoviral vector of claim 10, which comprises the nucleic acid sequence of SEQ ID NO: 10.

12. An adenovirus or adenoviral vector comprising a non-native nucleic acid sequence and a nucleic acid sequence comprising at least 606 contiguous nucleotides of SEQ ID NO: 9.

13. The adenovirus or adenoviral vector of claim 12, which further comprises one or more of the nucleic acid sequences selected from the group consisting of:
    (a) a nucleic acid sequence comprising at least 121 contiguous nucleotides of SEQ ID NO: 6,
    (b) a nucleic acid sequence comprising at least 462 contiguous nucleotides of SEQ ID NO: 7,
    (c) a nucleic acid sequence comprising at least 234 contiguous nucleotides of SEQ ID NO: 8, and
    (d) a nucleic acid sequence comprising at least 188 contiguous nucleotides of SEQ ID NO: 10.

14. The adenovirus or adenoviral vector of claim 13, which comprises a nucleic acid sequence comprising at least 121 contiguous nucleotides of SEQ ID NO: 6.

15. The adenovirus or adenoviral vector of claim 14, which comprises the nucleic acid sequence of SEQ ID NO: 6.

16. The adenovirus or adenoviral vector of claim 13, which comprises a nucleic acid sequence comprising at least 462 contiguous nucleotides of SEQ ID NO: 7.

17. The adenovirus or adenoviral vector of claim 16, which comprises the nucleic acid sequence of SEQ ID NO: 7.

18. The adenovirus or adenoviral vector of claim 13, which comprises a nucleic acid sequence comprising at least 234 contiguous nucleotides of SEQ ID NO: 8.

19. The adenovirus or adenoviral vector of claim 18, which comprises the nucleic acid sequence of SEQ ID NO: 8.

20. The adenovirus or adenoviral vector of claim 12, which comprises the nucleic acid sequence of SEQ ID NO: 9.

21. The adenovirus or adenoviral vector of claim 13, which comprises a nucleic acid sequence comprising at least 188 contiguous nucleotides of SEQ ID NO: 10.

22. The adenovirus or adenoviral vector of claim 21, which comprises the nucleic acid sequence of SEQ ID NO: 10.

23. The adenovirus or adenoviral vector of claim 12, wherein the adenovirus or adenoviral vector requires complementation of a deficiency in one or more early regions of the adenoviral genome for propagation and does not require complementation of any other deficiency of the adenoviral genome for propagation.

24. The adenovirus or adenoviral vector of claim 12, wherein the non-native nucleic acid sequence is a transgene.

25. A composition comprising the adenovirus or adenoviral vector of claim 1 and a pharmaceutically acceptable carrier.

26. The adenovirus or adenoviral vector of claim 1, wherein the adenovirus or adenoviral vector requires complementation of a deficiency in one or more early regions of the adenoviral genome for propagation and does not require complementation of any other deficiency of the adenoviral genome for propagation.

27. The adenovirus or adenoviral vector of claim 1, wherein the non-native nucleic acid sequence is a transgene.

28. A composition comprising the adenovirus or adenoviral vector of claim 1 and a pharmaceutically acceptable carrier.

29. The adenovirus or adenoviral vector of claim 1, wherein the non-native nucleic acid sequence is a transgene or a nucleic acid sequence naturally found in an adenovirus but located at a non-native position within the adenoviral genome.

30. The adenovirus or adenoviral vector of claim 12, wherein the non-native nucleic acid sequence is naturally found in an adenovirus but located at a non-native position within the adenoviral genome.

* * * * *